(12) United States Patent
Kishore et al.

(10) Patent No.: US 9,060,475 B2
(45) Date of Patent: *Jun. 23, 2015

(54) GENETIC MARKERS ASSOCIATED WITH DROUGHT TOLERANCE IN MAIZE

(71) Applicant: Syngenta Participations AG, Basel (CH)

(72) Inventors: Venkata Krishna Kishore, Bangalore (IN); Paul Altendorf, Research Triangle Park, NC (US); Thomas Joseph Prest, Slater, IA (US); Chris Zinselmeier, Slater, IA (US); Daolong Wang, Research Triangle Park, NC (US); William Briggs, Enkhuizen (NL); Sonali Gandhi, Banaglore (IN); David Foster, Ankeny, IA (US); Christine Chaulk-Grace, LaSalle, CO (US); Joseph Dallas Clarke, V, Research Triangle Park, NC (US); Allen Sessions, Raleigh, NC (US); Kari Denise Kust, Stanton, MN (US); Jon Aaron Tucker Reinders, Wilmington, DE (US); Libardo Andres Gutierrez Rojas, Santiago (CL); Meijuan Li, Silver Spring, MD (US); Todd Warner, Stanton, MN (US); Nicolas Martin, Slater, IA (US); Robert Lynn Miller, Iowa City, IA (US); John Arbuckle, Urbandale, IA (US); Dale Wayne Skalla, Research Triangle Park, NC (US); Molly Dunn, Raleigh, NC (US); Gayle Dace, Research Triangle Park, NC (US); Vance Cary Kramer, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/503,907

(22) Filed: Oct. 1, 2014

(65) Prior Publication Data

US 2015/0033406 A1   Jan. 29, 2015

Related U.S. Application Data

(62) Division of application No. 12/977,996, filed on Dec. 23, 2010, now Pat. No. 8,822,755.

(60) Provisional application No. 61/289,718, filed on Dec. 23, 2009, provisional application No. 61/369,999, filed on Aug. 2, 2010.

(51) Int. Cl.
*A01H 1/02* (2006.01)
*A01H 5/10* (2006.01)
*A01H 1/04* (2006.01)
*C12Q 1/68* (2006.01)
*C12N 15/82* (2006.01)

(52) U.S. Cl.
CPC .. *A01H 1/02* (2013.01); *A01H 1/04* (2013.01); *A01H 5/10* (2013.01); *C12Q 1/6895* (2013.01); *C12Q 2600/13* (2013.01); *C12Q 2600/156* (2013.01); *C12Q 2600/172* (2013.01); *C12N 15/8274* (2013.01); *C12N 15/8275* (2013.01); *C12N 15/8278* (2013.01); *C12N 15/8282* (2013.01)

(58) Field of Classification Search
None
See application file for complete search history.

(56) References Cited

U.S. PATENT DOCUMENTS

| | | | |
|---|---|---|---|
| 6,635,803 B1 | 10/2003 | Schroeder et al. | |
| 7,314,757 B2 | 1/2008 | Medrano et al. | |
| 7,332,651 B2 | 2/2008 | Xiang | |
| 7,432,416 B2 | 10/2008 | Van Winkle et al. | |
| 2004/0133951 A1 | 7/2004 | Eubanks | |

OTHER PUBLICATIONS

International Search Report and Written Opinion of the International Searching Authority, dated Aug. 4, 2011 for International Application No. PCT/US2010/062028.
Notification Concerning Transmittal of the International Preliminary Report on Patentability corresponding to International Application No. PCT/US2010/062028 dated Jul. 5, 2012.
Wilson et al., Genbank Accession No. AC214546.3, Zea mays chromosome 8 clone CH201-491C9. Washington University Genome Sequencing Center. Jul. 1, 2008. Retrieved from the Internet Jul. 26, 2011: <http://www.ncbi.nlm.nih.gov/nuccore/AC214546>.
Wilson et al. GenBank Accession No. AC212397.3. Zea mays chromosome 8 clone ZMMBBb-189G5. Washington University Genome Sequencing Center, Oct. 28, 2008. Retrieved from the Internet Jul. 26, 2011: <http://www.ncbi.nlm.nih.gov/nuccore/AC212397>.
Wilson et al. Genbank Accession No. AC193477. Zea mays chromosome 8 clone CH201-351L23. Washington University Genome Sequencing Center. May 19, 2007. Retrieved from the Internet Jul. 26, 2011: <http://www.ncbi.nlm.nih.gov/nuccore/AC193477>.
Springer et al. (Genome Research, 2007, 17: pp. 264-275.
Bruce et al. (2002), J Exp Botany 13-25.
Jeanneau et al, (2002) 84 Biochimie 1127-1135.
Kebede et al. (2001) 103 Theor Appl Genet 266-276.
Salekdeh et al, (2009) Trends in Plant Science 14: 488-496.
Turner et al. (2003) ICWSAWLR China.

*Primary Examiner* — David T Fox
*Assistant Examiner* — Jared Shapiro
(74) *Attorney, Agent, or Firm* — Kevin Markham

(57) ABSTRACT

The presently disclosed subject matter relates to methods and compositions for identifying, selecting, and/or producing drought tolerant maize plants or germplasm. Maize plants or germplasm that have been identified, selected, and/or produced by any of the methods of the presently disclosed subject matter are also provided.

11 Claims, 6 Drawing Sheets

Figure 1

| | Cateto homozygous - | Cateto homozygous + | Cateto- | Cateto+ |
|---|---|---|---|---|
| ALLELE 1 | GG | GG | G? | G? |
| ALLELE 4 | CC | aa | CA | aA |
| ALLELE 5 | AA | gg | AG | gG |
| ALLELE 8 | AA | AA | AC | AC |
| ALLELE 11 | CC | CC | CC | CC |
| ALLELE 13 | CC | CC | CT | CT |
| ALLELE 14 | AA | AA | AA | AA |
| ALLELE 19 | GG | GG | GG | GG |
| ALLELE 20 | CC | CC | CC | CC |
| ALLELE 27 | GG | GG | GA | GA |

Figure 4

SEQUENCE LISTING

```
<160> NUMBER OF SEQ ID NOS: 413

<210> SEQ ID NO 1
<211> LENGTH: 552
<212> TYPE: DNA
<213> ORGANISM: Zea mays
<220> FEATURE:
<221> NAME/KEY: misc_feature
<222> LOCATION: (75)..(508)
<223> OTHER INFORMATION: n is a, c, g, or t
<220> FEATURE:
<221> NAME/KEY: misc_feature
<222> LOCATION: (115)..(115)
<223> OTHER INFORMATION: s is c or g
<220> FEATURE:
<221> NAME/KEY: misc_feature
<222> LOCATION: (270)..(483)
<223> OTHER INFORMATION: r is a or g
<220> FEATURE:
<221> NAME/KEY: misc_feature
<222> LOCATION: (301)..(301)
<223> OTHER INFORMATION: y is c or t

<400> SEQUENCE: 1
tagggtcctg ctacaagaga tcgccacatt ttattgctac ggaagtccag ttgtgtctgt      60
ctgtttggtg gtcantggna tatggttcgg tttttactgc tgtaaaaagg gactsgggaa     120
nnaaaaatgc aaactgactt ggattttttg ttctgttctg catgaagatg aaatggtagg     180
gtcgtcggag gaggacgaag catgctcggg aggagacacg gaggcgacgg agccggggca     240
gcaggagcac agctcccgcc tggcggaccr tgagctgaag gagatgctgc tgaagaagta     300
yagcgggtgc ctgagccggc tgcggtccga gttcctgaag aagaggaaga aagggaagct     360
gcccaaggac gcgcggtcgg cgctcatgga ctggtggaac acgcactacc gctggccgta     420
ccctacggta accatgcatg catcctggca aacacgcagc agcagcatcg ctcgctggaa     480
tgrcagatct gtgaccagca tnnncngncg gtgcaggagg aggacaaggt gaggctggcg     540
gcggcgactg gg                                                         552

<210> SEQ ID NO 2
<211> LENGTH: 490
<212> TYPE: DNA
<213> ORGANISM: Zea mays
<220> FEATURE:
<221> NAME/KEY: misc_feature
<222> LOCATION: (100)..(100)
<223> OTHER INFORMATION: r is a or g
<220> FEATURE:
<221> NAME/KEY: misc_feature
<222> LOCATION: (264)..(271)
<223> OTHER INFORMATION: the sequence nnnnnnn is either caccaagg or is
      absent

<400> SEQUENCE: 2
tagccgtcct gcaaacctcc tggataaagt ttggacctta tttaggaaga gaagcaccct      60
ggacgagccg cgtggtatca attcttgccg ctctcctccr ctttcatctt cttctcccac     120
```

```
ctacgtttct ggtggaaaaa aagtttcaaa gcacgaacag agagatgagc cagttagatc    180
ttttttcaag ggatgccttc gttcaatcac tattacagct atcgttacat ttgatctgaa    240
aacacaaaca tggcatcttt gtgnnnnnnn ntcaatgcag gataaaaagc tggatcgctg    300
acaacagata tttgattgtc cgttggaaaa tattttttca atggccacag ttttagaaaa    360
tattttccca aaattatgtc attactatta ctagactagc aaagtagata atggcgagca    420
accatcagga aatcttgcca tcagtgcagc agaactgcag acccttatat tagcgcacca    480
gcagaatcta                                                          490

<210> SEQ ID NO 3
<211> LENGTH: 427
<212> TYPE: DNA
<213> ORGANISM: Zea mays
<220> FEATURE:
<221> NAME/KEY: misc_feature
<222> LOCATION: (18)..(18)
<223> OTHER INFORMATION: d is a or g or t
<220> FEATURE:
<221> NAME/KEY: misc_feature
<222> LOCATION: (49)..(416)
<223> OTHER INFORMATION: n is a, c, g, or t
<220> FEATURE:
<221> NAME/KEY: misc_feature
<222> LOCATION: (216)..(216)
<223> OTHER INFORMATION: k is g or t

<400> SEQUENCE: 3
cgagtggttt gaggttgdca cacaagtatt gaatattgat aaatcacana tacntnnaca     60
gggcggacaa aggtgacacc attaaagtgt caggngttta tcaccttgan gagaaacaga    120
aggcctcagc tgtggctgag ctaacccgga ggctctcaac aaatcagaac acactcacag    180
tcggnggact gtncacagtt gatccccaga cagctktgaa ggcaagactc aataacactg    240
gaacgcttgc cgcgcttctt cagcatgagc ttaaacccaa gtcgctcttg acnatctctg    300
gtgaattcga cacaaangcc ctggacagat ccccaaagtt tgggttggcg cttgcactga    360
agccctgatc agatcatccc atgttgattg atgattggtg gtgaatcttg aattcnttt    420 tttttt                                                              427

<210> SEQ ID NO 4
<211> LENGTH: 1020
<212> TYPE: DNA
<213> ORGANISM: Zea mays
<220> FEATURE:
<221> NAME/KEY: misc_feature
<222> LOCATION: (503)..(503)
<223> OTHER INFORMATION: r is a or g

<400> SEQUENCE: 4
cttaatatgt gagttttcta agttagtaat cttatatatt tgggcactgt atgcgactgt     60
tgttctgaca acccttaagc ttatttgata cctgtaatat ctttattgat ggttaattgc    120
aaatccctgc ttgatgcatc tcaacttcaa gttgttttgt agctggttta gtgcataaaa    180
ttagtcaaaa tattaatata ccggtcaccg tcatttcacc ttttctcact gacatttctc    240
aaatggagtt tgaaagaag gttttacttc acttatatac gtttgcaaca acatgagtt    300 tctaattcac tcagattata aaaaaactcg gccggggagg aaatgaccgt cttgctggta    360
ttatattaag aagagaccga aacaatggtc ctgccgagaa aatccttgaa ccctggcccc    420
catcactaac ggaccggtgt caaccgtcaa ctctgcaacg gcccaaccgg agggtggcgc    480
ataggacatc gtaacccgag acrgagagcg ggtggggcac agcgagggaa ttttttttaac    540
```

```
caagccgaaa aattcgcccc tgaggtgtta ctcggaagcc tttaatcact aggttagagg    600
ccctttcgca actcactcag attattgcat gtacagaaat tggtcaatgt aactgacttt    660
gctagtgttt ttagtttcac tgaaaaaagg atctcttgca gtaagctggt agcagcagta    720
tggctaatat taagctgtgc ctccagtaag ggtttggtgc tcagtatttt gttttctaa     780 ttgagtcaaa agtcttatgt ataatcttat attaaatgaa attgatgtca tagttcctca    840
acagatataa tcccattttt aaggacgttt aacgtcttat tattgcagtt acatccaaat    900
tttctgtaac ttatccaacc ttctcttgca ggaacaacaa gggagacaac cttactggag    960
cttactacca caaggtgagc gaattgacaa acacagctgt tggggcagag cttacccact   1020
```

<210> SEQ ID NO 5
<211> LENGTH: 910
<212> TYPE: DNA
<213> ORGANISM: Zea mays
<220> FEATURE:
<221> NAME/KEY: misc_feature
<222> LOCATION: (283)..(440)
<223> OTHER INFORMATION: n is a, c, g, or t
<220> FEATURE:
<221> NAME/KEY: misc_feature
<222> LOCATION: (818)..(821)
<223> OTHER INFORMATION: nnnn is cgcg or is absent
<220> FEATURE:
<221> NAME/KEY: misc_feature
<222> LOCATION: (860)..(872)
<223> OTHER INFORMATION: n is a, c, g, or t

<400> SEQUENCE: 5

```
acaactacaa ggacctcgaa gccgaggctg ctgcggcgac ggaccaggtg ccgccgtcca     60
tcgtcaaccc cctgctcagg acggggtacc acttccagcc ccccaagaac tggatcaatg    120
gtaatgtaaa gctactaact aatccaccac ccaacgtcgt ttgaaggtga tgtgtgtgtt    180
aagcatctcc tgaaatatat aagagagcga ggctagtaat cggcttgttg ttcagggttt    240
tggtttacca cttgtagcct caactaataa agctatatat atnngagagc gacgagagag    300
aagagacaaa acattcatga gtatggtcag acagactagc tagctagaca cggcagagaa    360
attacgagag ttaaaaaaaa ntgcgcttga agggtgaacc aaaacaaaac aactttagta    420
ctatgcgtca acaaannnnn gctgtgttca tgtgtcagct agcactagag tcatagtgcg    480
tggccagtga gctgttgtct agcaaccaac gcgaactgaa gtttgagagc gtactcgtgt    540
tctcgatctc ttgcagcgca aaggtcttcg tacgtgatca ggaatattgc accatttact    600
gcttaattaa ttaagtacgt acgtactgta cgtttggctc tacctcatct tctaatcttt    660
tcggtgctgt cttgtgctct ctcggctctg attgcatcga tcggcggcgg cgtgaacttt    720
gcaacggcgg cagatcccaa cggtaataag tcgttttccc cacccttttt atttcctcta    780
ataatgcatc aatattccaa ctgggtgcat atgcatgnnn ncagcgccca tgtactacaa    840
ggggtggtac catttcttcn taccaataca antcccaagg cgccgtatg gggcaacatc     900 gtgtgggcgc                                                            910
```

<210> SEQ ID NO 6
<211> LENGTH: 346
<212> TYPE: DNA
<213> ORGANISM: Zea mays
<220> FEATURE:
<221> NAME/KEY: misc_feature
<222> LOCATION: (98)..(99)
<223> OTHER INFORMATION: n is a, c, g, or t
<220> FEATURE:

```
<221> NAME/KEY: misc_feature
<222> LOCATION: (254)..(254)
<223> OTHER INFORMATION: r is a or g

<400> SEQUENCE: 6
gggcaggcgt gtacaagccg ccatacggag gattcgtgga cgtcgacgtt gaggagcacg      60
agaccatcaa tttgagaacc ctggtgagtt ttttttttnnc tttttacttt tttgctgctt    120
tgtccttcag cgatctgctc agttcgtttg taatttgcac agattgatca ctcggtggtg    180
gagagcttcg gagctgacgg gcggatgtgc atcacggctc gagtgtaccc tgagcacgcg    240
gagacgagca acarccacat gttcgtgttc aacaatggca caggcacggt ggaggtgtcc    300
aagctcgagg catgggagct cgcggcggcg accgtaaatt ccgttg                   346

<210> SEQ ID NO 7
<211> LENGTH: 7437
<212> TYPE: DNA
<213> ORGANISM: Zea mays
<220> FEATURE:
<221> NAME/KEY: misc_feature
<222> LOCATION: (4454)..(4474)
<223> OTHER INFORMATION: n is a, c, g, or t
<220> FEATURE:
<221> NAME/KEY: misc_feature
<222> LOCATION: (4497)..(4498)
<223> OTHER INFORMATION: nn is ga or both nucleotides are absent
<220> FEATURE:
<221> NAME/KEY: misc_feature
<222> LOCATION: (4505)..(4969)
<223> OTHER INFORMATION: k is g or t
<220> FEATURE:
<221> NAME/KEY: misc_feature
<222> LOCATION: (4505)..(4969)
<223> OTHER INFORMATION: m is a or c
<220> FEATURE:
<221> NAME/KEY: misc_feature
<222> LOCATION: (4505)..(4969)
<223> OTHER INFORMATION: w is a or t
<220> FEATURE:
<221> NAME/KEY: misc_feature
<222> LOCATION: (4505)..(4969)
<223> OTHER INFORMATION: y is c or t
<220> FEATURE:
<221> NAME/KEY: misc_feature
<222> LOCATION: (4536)..(5309)
<223> OTHER INFORMATION: n is a, c, g, or t
<220> FEATURE:
<221> NAME/KEY: misc_feature
<222> LOCATION: (4979)..(4981)
<223> OTHER INFORMATION: wcy is either act or tcc

<400> SEQUENCE: 7
aatgtcaagt atatccattt aaatatcatt aggtcccgtt tgtttccttt cattttaagg      60
aattggaatc ttactaataa ataagctat ttttttagaa tacgagattc caccactttc    120
caaagttatc agataagcct atctcaaatt catggggtga gagatggaaa ttgattctat    180
agatttacat gttattttcc cgatgtacaa cttatatcat actctcctaa ttgcttcgct    240
ataacataaa tgcactatat aactatctct cttatatgat ttaggataat atacaaatat    300
attacatata taaatatatt aacttaatta gttttgtcta aattataatt attaaaatgg    360
aattcaattc caacgaaaca aacgggccct tacaaaattt ctagtatcat ttaaccatct    420
attcaacaca ccaaagataa ttggataaaa tagcaacact aggacaaata ctacatagca    480
cattacatgt tccattatat ggtcattaaa ttgtcgttaa gccttctata acattatggc    540
ctaaaaggtt gttaaatagt aaaaaaagat ggatgactaa agtccaagtt catgcttggg    600
ctaagtttat attgggtatt ttataccacg ggttaacggg tatgggtgaa ggcggaacgt    660
```

```
tctgattccc gtttacttat tgggtgaaga ttttttgccta ataatagacc tacgggtgaa    720
tatttatccc acatatatat cctagtggag tcaatatcca tcggatatcg gtcgtgggta    780
cccattgcca tctctagatc gaagagtaga aatttacttc ctaaacctct ctctgtctca    840
tgcagcacaa tagacgcttt gtttcgttgc aacagcttgt ttctctttga cgtccaaatt    900
cgtctatcta cggacccacg gccgcccaga ttttgaaatt tcaaaacgga acacaccccg    960
gggttcggag tatctgctgc ccctgcggtc ctggaaagcc cggcccacct ctcacttgca   1020
ccaccagctc accggttccg gtcaacagtc tctcgcgggt gcctgtgccg gtggtcctcc   1080
gtcctggctc tggctgccac ccacctcccg attaccgttc tcgcctcgac ttcaaaacaa   1140
gagcccagat ctaaaccaag cacgcccatc tttgccacac cacaccccca gtattcgaat   1200
ctctcgtgcc cagatgcggc aaattaaaaa caacggacag acgcggaacc cctccggcca   1260
acggatctca ccctctgcgg catgggtccc actcacgctc gggtccactc gacagcgtgt   1320
agggcagaga ggcgagcggt accagtacca taggcctccc gacgcagtcc gggcagcggg   1380
ccccgcggat tggaccggtc aaaaggcgtg gcccaaccaa accccaaggg atccggcgct   1440
ttgtctgcac gtgaatggtg ccaagatcgc ctggttgaca ggtgggaccc gtgaggttgt   1500
agacccacat gtctgtggcg ttaaaggagg ggggagggat cggcgggcgg gtggtgcgcg   1560
cgggcaggcg ggcgtcgcgt ggtggtggtg gtggtgggtg ctttgactgc aggcctcggc   1620
agcaggcaga gaggactaga ggagtcgggg cctcggagga ggggagggag agggcgaaga   1680 gtaggggggaa ccaaatcttg aagggtaaac ggagagttct ttcgtggagg aggaagggg   1740 ggacagcagg aggagggtag aggtatgtgc gcacccatct gttcttgctc ctgatttggc   1800
tgtttgtttt ttctgtctgt tcttcgctgt tggtagtttg tgaccgtgaa tgggcgttcc   1860
tggtccatgt tcgcgtgcgc tgctgccgat tctgggagct ctctggtcgt ccgtctcgct   1920
gggatctgcc ttttccccgg tgagagccgc ggaacgttcg ccgccttttc ttactcgcgg   1980
gccagttatg gtttctggag cgttttctct gttcttggcg aggtggtcat cgctctgaga   2040
acgatgcgct ctttctccga gtttgtgctc aagttttcgt cagcctagag gctatagcgt   2100
ttgctgcgga tctcacgact tctctcttcc tcttctctat tggtgcatac gttttcatcc   2160
gaaatccatt agttagtgcc cgagccgtca attctttgtg gatttgcttg ttccccttcg   2220
ttacaggctc ggaaatgccc ctgaacagat tcacaggggt cctagattag gattatttc    2280 tatgactttc caagagtcag gagcacgatt gcttctctc ggctgtctgc ctggttcatg    2340
actcagccgg gtttgcaagc ctaggaagaa cttgctcacg tttcttacat ttatctagat   2400
tcgagggacg ggttgtactc gttaacaaag ttcacctcgt tagtcattaa agctccgctg   2460
ttgtgaatga tgctgccatt gcgatatctg gaatcatcgc tctgatcgat ttggttgtta   2520
atccacttac aggtagctca atagatctac tgctctcggg ggagttaatg caaagctgag   2580
ttgctgcacg ttggctttct tcagagatgg cttcagctgg tgtagcccca tctgggtaca   2640
aaaacagcag cagcactagc attggtgccg agaagttgca agatcagatg aacgagctaa   2700
agattagaga tgataaggtg aagatgcctt gatatcttgt ttcgggctta ctgtaatttc   2760
ctcaagatta tgtgaaaaat gggactgtga tgtaaccttt ggtgtgaatg ccaaatgcag   2820
gaagttgaag caaccataat taatgggaaa gggactgaaa ctgggcacat aattgtcacc   2880
actactggtg gcaagaatgg tcaaccaaaa caggtgagtg ctttactgca tttgatcatg   2940
atttatcaac tattctacat gtttttagtg catgtctgaa tctaataatt gagagtcaag   3000
```

```
accataattt aatgtccttc ttttgcatat tgccaatata tccatgttgc taacttataa    3060
gattgtggag ttgttctgat cagttttgtc agattctttt tgtataataa tgtgtattta    3120
ttggttgcat ttgcagacag tgagctacat ggctgagcgc attgtaggtc aaggttcttt    3180
tgggatcgtc ttccaggtta tttgcaataa cttgtgactg actttgatat gtactattat    3240
gtagccgcct gtggtgttgc tttccacggc gctgcacatg ttttagatct tcatatcttg    3300
cgtgctataa atcacctttc ttaatcagat gccatttcac ctgttcatag gctaagtgtt    3360
tggagacggg tgagactgtt gccataaaga aggttcttca ggataagcgt tacaagaacc    3420
gcgagttgca gaccatgcgc cttcttgacc accctaatgt tgttgctttg aagcattgct    3480
tcttttcaac taccgagaag gatgagcttt atctgaactt ggtccttgag tatgtgccgg    3540
agacagttca tcgagttgtg aagcatcaca acaagatgaa ccaacgcatg ccacttattt    3600
atgtgaagct gtatatgtac caggtaatgg tttgtcctgt tcctttttgc tgttgtttta    3660
attatacctt aaagcttatg ttttgggccc tgtttgatgt tgaaactaac aaacatattt    3720
catttcgcct aaatattgtc tgctccaatg aatgtgctag ttctttttca atatttgata    3780
ttatattgga ttttggcaga tatgtagggc attggcttac attcatggca ctattggtgt    3840
ctgccacaga gatattaagc cacaaaacct tctggtatgc tggaaaatct gctattttgc    3900
tactgtatct ttttgtaaag aaatgatttg tactttgaaa ttgatgttca aacttcacta    3960
caggtgaacc cacacaccca ccagcttaaa ctatgtgact tggcagtgc aaaagttctg    4020
gtcaaggggg aaccaaacat atcgtacatc tgctcccgat actataggc tccagagctc    4080
atatttggtg ccactgagta taccacgcg attgacattt ggtctgctgg atgtgttctt    4140
gctgagctta tgctagggca ggtaaggtgt ctcaaattt tattgccatt ttaaaaaggg   4200
ttttcaagcc aacaaggtcc tttcagttca cactgtctta caagaactat ttggacagcc    4260
tttgtttccg ggtgaaagtg gtgtggacca acttgttgaa atcatcaagg taattgtcgg    4320
ttctacaagc ttgtgaattg tcttctatag aagcataaaa tctgatcacc cctaaaatga    4380
ttttgtatgg caggtcctcg gtacgccaac aagggaagaa ataaatgca tgaacccaaa    4440
ttacacagag tttnaagttc ccnacaaatc aaangcacac ccatggcaca aggtgcnnaa    4500
atctktctac атттттgттac aatactctaa gaaaanctgt tactgttgnn nnnnnnnnn    4560
nnnnnnnnnn nnnnnnnnnn nnnnnnnnnn nnnnnnnnnn ntgttactwa tttactttt    4620
gtacatttta тcттттcaggт mttccacaaa aggatgccgc cagaagctgt tgatctggtc    4680
tctcggctac tccagtactc cccaaatctg aгатgcacтg ctgtaagtgc atgccattgt    4740
acattataca tgatggaaat acccctgttg actttggttt tctaagatct tyatgaatgt    4800
tttgtccaga tggaggcact tgttcaccca ttctttgatg agcytcgaga tcctaatact    4860
cgccttccaa atggtcgctt tttgccacca ctattcaatt tcaagcctca cggtatgttt    4920
catgcctaca taattcaaca tcgttatcat agctgctaca accaggtakc agtgtagtwc    4980
yaagtttgtt ctttgtatat caccacctta catgctcgcc acctctgttc tgcagaactt    5040
aaaggagtcc catcagacat tgtcgcgaaa ttgattccag aacatgcaaa gaagcaatgc    5100
tcctatgttg gnattgtgaa atgaccgcgc cttgagactg gaacctgtgg ttgcaattgt    5160
gaatttcccc tgggatgttt gacgatctga ggcnatgcga gcctgttgtt gaagatgcaa    5220
ggttacgtac ttgtacgaca atgtgacctg tgtagctgag tagtctatgt cgcagtgaca    5280
tgtaacggca ccccccnnnt tcctactaac tgacgcttac tcgagattgc catagttgat    5340
cттgтaатттт gttatagagc agtatgaatg tatttatggt agcttgaatc tatgtatgga    5400
```

```
ttcacttcgt ttttccatgt ttccttgtct ccagacccag attgctaccg tattgtttca    5460
gaattcctag ctacctgttg cctattgagt attgactacc agcttgcact tgtctgttat    5520
tgcactggct gtggaatcag ctgttgattt ttgccacaat attttagttc agatgtactc    5580
cctattctaa aaagaatgtg aaatcttact aatagaatag actactttt ttagaatttc     5640
tttccatttt gaggaattaa aatcttacta atagaataga ctactttttt ttagaatgtg    5700
acattacacc actttctaaa gttatcatat aagcctatct catttatggg gtgagagatg    5760
aaaattgatt atatagattt acatactgtt tttccgatgt acaatttata gcacacccttt   5820
ctacttgctt cgctataaca taaatgtagt atataactat ctctttcatg tgatttaaga    5880
taatatataa atatattaca tatataaata tatgaactta attagtttta tctaaattat    5940
aactattaaa ataaaattca atttcaacga aacaaacggg gccttgatta attataaaat    6000
gtattttgt aataagttga tttaaagcta taatgtaaat actatttact agaaacttgg     6060
ttaaatatga attagtttaa ctaacgagtt taattggcat accacttata gttatattct    6120
ttgagacgga gggacgagta cgttgttcga tcggtctgga agtatgctga cttgatcgtt    6180
cttaccagaa agttgcatta ttgcagcgtt tgagacgact gacgaggaaa tgtgacacgc    6240
agatgctact cagtgcttgg caggactgca ttccaagtgg tccttctggg gagagaggaa    6300
tcatagactg tagctccggt ttcttgaaaa aaaacggttc ccgtgaaatg gcaggtatgg    6360
ttctccggtt cctttgaaaa ctactctttg taaaatgaag tatgcttggc tctatcgaag    6420
ttagctgttg ttaacagcca taccagacag gttctttcag tgtccggtta gattttgagg    6480
cgtcgagggt tgtttggttg agaagtggag agttccttta gagtgtgttt agttgagaag    6540
tggaggaaaa tggatcgact atattcctat ttttttatg tttagtttcc aagaaaagcg      6600
gagcagagcg gctcctgaag tttagaaat ttaccataaa tagtttaaat gctcccgctc      6660
cgtcaaaacg aacatacacg agcgctctcc tccctctact tccttctaca accgtatgtc    6720
tttccaatca agcaaagaac ggagtagctc tgctctattc tactcttaac caaacaaaaa    6780
aatgaagtga ctctgttctg cttgtcaaat gcgaaataga atgattctat tctaaaaat     6840
tggaatagag ccgctccaac caaactaacc tcactcgagg gactaaagtt tagtctttac    6900
tctatttgat tccaaggact aaaagtattc ataacatatt aaatgacttg aaaactaaaa    6960
tgttcttaac attcttccgc cattagcata actaaaataa actagggata agtgaaatta    7020
atatggacta aaacaatttg gtcgctgttt tattcccata tttgacaatt tagaaattaa    7080
ataaaactaa aatagatgga ttaattttta gttcctcaaa caattttttc taacaatttt    7140
cgatggacta agtttagtca ttttcataa gaaattaata tggactaagg gcctgtttgt     7200
ttacccctca gattatataa tctggattaa ataatcctaa gaggcaaaca aacagtctag    7260
cttatttgtc gagattatat aatctaactc ctggattatg ataatccata agcaagtgag    7320
gaggtgctta tttcagatta ttttttttcca cttctccact acccctttcaa gtttcctaga  7380
aattacccac cattgccatt ataacccacc attggcattc ttgtcttcct catacaa       7437
```

<210> SEQ ID NO 8
<211> LENGTH: 570
<212> TYPE: DNA
<213> ORGANISM: Zea mays
<220> FEATURE:
<221> NAME/KEY: misc_feature
<222> LOCATION: (217)..(477)
<223> OTHER INFORMATION: r is a or g

<400> SEQUENCE: 8

```
aaggtgggaa aactgaaaaa gacaatcatg aaggtgtaaa ttctttacta tctgaggagt      60
tggaaaaact agctaatggg aatagcaagg tatgatatac cctccatgat tctgctttca     120
tttattcttt gttcatatgg tatggttatt taacagtgct atgtattgcc gtaaatgcag     180
attcctggta cattagatga gtatagaaag cttgtcrttc caataattga ggagtatttt     240
agtacaggag atgtggaatt ggcagcttct gagctgaagt gtcttggatc tgatcagttt     300
catcattact ttgtgaagaa gcttatatct atggcaatgg atcgccatga caaagaaaaa     360
gaaatggcat cgattctgtt atcatctttr tatgctgatc tactgagctc ctacaggatc     420
agtgaaggtt ttatgatgct tctggagtct acagaagatc taactgttga tataccrgat     480
gctactgatg tattggcagt ttttattgca cgggctattg ttgatgaaat tttgcctcct     540
gttttcctca ctcgagctag ggcactactt                                      570
```

<210> SEQ ID NO 9
<211> LENGTH: 501
<212> TYPE: DNA
<213> ORGANISM: Zea mays
<220> FEATURE:
<221> NAME/KEY: misc_feature
<222> LOCATION: (7)..(478)
<223> OTHER INFORMATION: n is a, c, g, or t
<220> FEATURE:
<221> NAME/KEY: misc_feature
<222> LOCATION: (292)..(292)
<223> OTHER INFORMATION: m is a or c

<400> SEQUENCE: 9

```
cggtttnnng gccnancnnc atatcccacg tttgctggnt gaattgtctg gccttgagaa      60
gttacttgnt gcaactggcc cagttccaga cccatggcat catttgcaga ccctgtcagc     120
atgttaggtg gtaagaacga aaangtgtca tcatatggtg cctggacatt ggnggatgaa     180
ctctgcagct gagatggatg tgttgcgctt tggtcgangc catacccctgc agaatcagtt     240
ccanctgaaa aaaattata gagagcactg cattcaaant tcaaaggctc amtatactga     300
agtagcatat ttacatatcn taaagccttg tatcaaacta aantatcnat atcaatgtac     360
ttacaacaac aattagggtt nnccagttna acataagcta caaactgaaa cnntcaagat     420
aatagagctn nnnntnnaat tgtatctgng cctcagatgc tgctcacctg atggtgangg     480
ccctggcatg ctcatcgaag a                                               501
```

<210> SEQ ID NO 10
<211> LENGTH: 1260
<212> TYPE: DNA
<213> ORGANISM: Zea mays
<220> FEATURE:
<221> NAME/KEY: misc_feature
<222> LOCATION: (166)..(166)
<223> OTHER INFORMATION: r is a or g
<220> FEATURE:
<221> NAME/KEY: misc_feature
<222> LOCATION: (205)..(1251)
<223> OTHER INFORMATION: n is a, c, g, or t

<400> SEQUENCE: 10

```
cacgccgact tcagtaggcg aggcagggtg tcgtcgcttc atgcatgcgc tggcattgct      60
tctcggagca ttcgcagcca ttcctacagg tatagactat acctatacgt gcatgcgcat     120
ccatccaccc ataatccgtg catgcatgca tgattattga cactartgtc cttattacta     180
aacaggagtc caatccatcg gcgtntgcta cggcgtgaac ggcgacaacc tgccccggc     240
```

```
gagcgacgtg gtgcagctgt accagtccaa cggcatcaac ctgatgcgca tctacttccc      300
ggacgcnaac gcgctgaacg cgntgagcgg caccagcatc gggctcatca tggacgtgcc      360
caacacggac ctngcctcgc tggcctccga cccgagcgcg gcggccgcct gggtgcagag      420
caacgtgcag gcgttcccgt cggtcagctt ccgctacatc gccgtgggca acgaggnctc      480
cggcggggac accggcagca tccttcccgc catgcagaac ctcaacgcgg cgctggccaa      540
cgccggcctg ggcggcagca tcaaggtgtc cacggcggtg cagagcgncg tcacccaggg      600
cttcccgccg tcncagggca ccttctcgca gggctacatg gcgcccatcg cgcagtacct      660
gcagagcacc ggcgccccnc tgctgtgcaa cgtctacccc tacttctcct acntcggcaa      720
cccggcccag atcgacctca gctacgcgct cttcacctcg ccgggcaccg tcgtgcagga      780
cggcagcaac gcgtaccaga acctcttcga gcgctcgtc gacaccttcg tctccgcgct      840
cnagaacgcc ggcgcnggca acgtcccngt cgtcgtgtcc gagagcggct ggccgtccgc      900 cggggggcgac gccgccaccg cggccaacgc gcagacctac aaccagaacc tcatcaacca      960
cgtcgnccag ggcacgccca agcgccctgg ccccatcgag acctacatct tcgccatgtt     1020
caacgaggac cagaagacgg gagccgagtc ggagaggcac ttcggnctct tcaacccgga     1080
caaatcgccg gcgtaccca tcaatttctc ctaattccta aacaagacgc cgaggtccat     1140
tccaagacat ttataaggca atacacacac atagatatat atatacacat acatacgggg     1200
gaaaactgaa taaataaacg cctgaagtat aagcatagag ccnnnnannn ntcggacccc     1260

<210> SEQ ID NO 11
<211> LENGTH: 522
<212> TYPE: DNA
<213> ORGANISM: Zea mays
<220> FEATURE:
<221> NAME/KEY: misc_feature
<222> LOCATION: (139)..(454)
<223> OTHER INFORMATION: n is a, c, g, or t
<220> FEATURE:
<221> NAME/KEY: misc_feature
<222> LOCATION: (148)..(148)
<223> OTHER INFORMATION: k is g or t

<400> SEQUENCE: 11
aaggactttg gaggagatac tctatgctct ggttgttcag aagttcgttg aagctggtgt       60
ctctctggtt ccagcactct cacgctccac cgatccttct ggaagagttg atcagtgggc      120
agaaactgtg gaagaaaanc ttcaacgkct gcactcgcan gaggcctatg aaatgatcga      180
gaatcacctc accctcatnc tggggcagcg tcaaggtgac gccactatcg cagccataag      240
taagctccgn gttggccagg tctatgctgc atctgtgatg tacggttatt tcctgaagag      300
agttgaccag aggttccagc tcgagaagac aatgaagggc ctcccttggg gntcagaaga      360
ggaagacagc gctttgaatc aagttatgat gaccgacttg atgccttcag ctcagacttc      420
tagctctcat ccagagatgg gctcgtggac cgcncctgcc ttcagcacag agggcccag      480 ccaatctatc aagccttgcc gccttaggtc gtatgtcatg tc                         522

<210> SEQ ID NO 12
<211> LENGTH: 157
<212> TYPE: DNA
<213> ORGANISM: Zea mays
<220> FEATURE:
<221> NAME/KEY: misc_feature
<222> LOCATION: (34)..(34)
<223> OTHER INFORMATION: n is a, c, g, or t
<220> FEATURE:
```

<221> NAME/KEY: misc_feature
<222> LOCATION: (94)..(94)
<223> OTHER INFORMATION: s is c or g

<400> SEQUENCE: 12

```
gtagtccttg agcgaccaga agctgatcag cgcngtggcc gccatggcga cgcagaccat    60
gaagttgctc gtcacccaca ccaccctcgg cccsaccttc cggcacatgg gctcgatcag   120
gaacgagctg aatcctagaa cgatctgcac gtacggt                            157
```

<210> SEQ ID NO 13
<211> LENGTH: 145
<212> TYPE: DNA
<213> ORGANISM: Zea mays
<220> FEATURE:
<221> NAME/KEY: misc_feature
<222> LOCATION: (35)..(35)
<223> OTHER INFORMATION: w is a or t
<220> FEATURE:
<221> NAME/KEY: misc_feature
<222> LOCATION: (86)..(86)
<223> OTHER INFORMATION: m is a or c
<220> FEATURE:
<221> NAME/KEY: misc_feature
<222> LOCATION: (89)..(89)
<223> OTHER INFORMATION: s is c or g
<220> FEATURE:
<221> NAME/KEY: misc_feature
<222> LOCATION: (116)..(120)
<223> OTHER INFORMATION: n is a, c, g, or t

<400> SEQUENCE: 13

```
atctcaccga gttgagcagc agcccgaacg agccwactct gacgccttcg tcgaacgcgg    60
tgtcgtagag gatgaacggg aaccamgasa gctgcatgga cgacacagtg catggnnnnn   120
cagcagcgtc agccgtcagt aaaga                                         145
```

<210> SEQ ID NO 14
<211> LENGTH: 736
<212> TYPE: DNA
<213> ORGANISM: Zea mays
<220> FEATURE:
<221> NAME/KEY: misc_feature
<222> LOCATION: (63)..(681)
<223> OTHER INFORMATION: n is a, c, g, or t
<220> FEATURE:
<221> NAME/KEY: misc_feature
<222> LOCATION: (432)..(432)
<223> OTHER INFORMATION: r is a or g

<400> SEQUENCE: 14

```
tgcaagaagc acactctcca caaggttact cagtacaaga agggtaagga tagcctgtct    60
gcncagggaa agcgccgtta tgaccgcaag cagtcaggat anggtggcca gaccaagcct   120
gtcttccaca agaaggtaat gaagtatacc tatgtgattg tactattgct ccatcaatcc   180
ttcatctttg tccgttttga tgctagcatg aaagactgaa ataacnnnc atttctaaat    240 gtctgttnnn nnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnnnnnnn    360
nnnnnnnggg tgcacagatt gggatatgac aaatgttgtg attttcaggc caagaccacc   420
aagaaaatcg trttgaagct gcagtgccag agctgcaagc actactcaca gcacgcaatt    480
aaggtgcagt gtctcatttt cctgtgttag gcttgctgtt gcacnaagta ttgtctcact    540
ttgatttagc tcactctttc ctgactgact cnccctgtgtc acagaggtgc aagcattttg   600
agattggtgg aganaagaag ggcaagggaa catctctctt ctaagtttct catcgcncat    660
```

```
ctcgatgttg gatcgaanct ntgggtctac tactgttcta aaaactcgtc aaatttcaat    720
gttactagta gttctg                                                    736
```

<210> SEQ ID NO 15
<211> LENGTH: 835
<212> TYPE: DNA
<213> ORGANISM: Zea mays
<220> FEATURE:
<221> NAME/KEY: misc_feature
<222> LOCATION: (27)..(826)
<223> OTHER INFORMATION: n is a, c, g, or t
<220> FEATURE:
<221> NAME/KEY: misc_feature
<222> LOCATION: (753)..(753)
<223> OTHER INFORMATION: r is a or g

<400> SEQUENCE: 15

```
gagaagacct gctccttctt tgtcggnatg gtggtgttcc tggggatgag cacagtcatg     60
acgcctccng ccgtctccag gccgagcgag agcggcgaga cgtcgagcag gagcagatcc    120
tgaaccttct cnttgccctc gccagtgagg atggcggcct ggacggccgc nccgtacgcg    180
acagcctcgt ctgggttgat gctcttgcac anctccttgc cgttgaagaa gtcctggagc    240
agctgctgca cgcggggat gcgagtggan ccgcccacga gaacgacgtc gtgcacgctg     300
ctcttgtcca tcttggcgtc gcggaggcac ttctccacgg gctccatgca cttgcggaag    360
aggtccatgt tgagctcctc gaaccgngca cgggtgatgg tcgtgtagaa gtcgatgccc    420
tcatagagcg agtcgatctc gatggtggtt tgggcggtgg aggagagcgt cctcttagcc    480
ctctcgcagg cggtcctcag ncgccggagc gccctggggt tgccagtgat ntccttcttg    540
ttcttcctct tgaactcctg gacgaagtgg ttcacgagcc ggttgtcgaa ntcctcgcct    600
cccagntggg tntcgccggc ggtggccttg acctcaaaga tgccctcctc gatggtgagg    660
agcgagacgt caaaggtacc gccgccgagg tcgaagatga ggacgttctt ctcgccgtcg    720
ctgctcgant tcttgtcgag cccgtatgcg atrgccgcgg cggtgggctc gttgatgatg    780
cgcatgacgt taggccggag atgacgccgg cgtccttggt ggncnngcgc tggga         835
```

<210> SEQ ID NO 16
<211> LENGTH: 1024
<212> TYPE: DNA
<213> ORGANISM: Zea mays
<220> FEATURE:
<221> NAME/KEY: misc_feature
<222> LOCATION: (23)..(967)
<223> OTHER INFORMATION: n is a, c, g, or t
<220> FEATURE:
<221> NAME/KEY: misc_feature
<222> LOCATION: (755)..(755)
<223> OTHER INFORMATION: y is c or t

<400> SEQUENCE: 16

```
tatagtacgt tttattcgac acnnnagcct ctgcatgcaa taatagtaca nccccgatt     60 taattaattg gactaatgca tgctgaggat ngatcagatg gagatgctgc tggggatgcc    120
cctcccggtg actcccggct tggagaaggg cttgagcagc tcgtacggca cgatcccggc    180
gccgcagcgg ttcttgaggt ccaggttgtt gttgcactcg tcgatgaacc cctcgatctc    240
cttcatcctg ccgccgaact tctcgaacgc cgccttcacc atgggctccg ccagccacga    300
nggctccgcg aactccccca tgtactcctc gtcgggcgag ngcgacgaga ggatgtccag    360
cgtcgtcatg accttgatgg cctgcatctg cgnggcagc atgtccagca gcgtcgtctc    420
```

| | |
|---|---|
| cggctgcttg aggaacttct ccatctccnc gcccgncccg ccctcctcca ccggcatgtt | 480 |
| cttccggatg gtggtcggcc ggttgggggaa gtagccggcg aagtggtact gnccgaagtt | 540 |
| gacggccgag tggtggccgg aggtgaccca catgatggtg gtcagcgtct ccaccaggct | 600 |
| gtcgcgggtc tccagcacgg gccaccacgg ctcgtccttc ttgtcgccgt gccccacgtt | 660 |
| gcgcacctcg tcccagaacg ccctcagctc ggggtcggcg gccacggcct cgtcggactt | 720 |
| gtagtagacg ttgacgtact cggacgccca ctgcytgatg gagtcccaga ccaggagccc | 780 |
| gtcgtgggcg taggggtagt ccttgatggt gagctccagc tccccgtcct ccccgcgcac | 840 |
| ggccagcccg cgcttganga ggtcgttggg cagcgcctcc gtgtcgaact gccacgtcgc | 900 |
| gccgtacgcc acggagctna gntcgacggc gtacttnccc ggccnnnang nnnncnnnnn | 960 |
| nnnnncntcg gcgttgatga gcgcctccct ggccagcgcg ttgatctcca tggtgtagcg | 1020 |
| gaag | 1024 |

<210> SEQ ID NO 17
<211> LENGTH: 499
<212> TYPE: DNA
<213> ORGANISM: Zea mays
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (431)..(431)
<223> OTHER INFORMATION: s is c or g

<400> SEQUENCE: 17

| | |
|---|---|
| gacaagctcg ccatactggg tctcccgatc tggattactg agttggatgt cacagcagag | 60 |
| aacgagcaca tacagctga tgatctagag gtgttcctcc gggaagcatt tgcacatcct | 120 |
| gctgtggggg gaatcatcct ctggggattc tgggagatgt ttatgtttcg agagcacgcc | 180 |
| catctggtcg atgctgatgg gacaatcaac gaggctggca gnaggtacct tgctctcaaa | 240 |
| caagagtggc tgacccgtat gaacggcagt gtcgatcacc aaggagagtt taagttcaga | 300 |
| ggataccatg gttcgtacac agtggaagtg aacacgcctt caggcaaggt agctagatcg | 360 |
| tttgttgttg acaaggatag cccggttcag gtgatcgctc tgaatgttta atgtgtggga | 420 |
| aatcatcgc stgtcctgta ttttagcgat gtactgaggt gttgaacaca gatagtttca | 480 |
| tagctgatgc cacgccttc | 499 |

<210> SEQ ID NO 18
<211> LENGTH: 886
<212> TYPE: DNA
<213> ORGANISM: Zea mays
<220> FEATURE:
<221> NAME/KEY: misc_feature
<222> LOCATION: (32)..(883)
<223> OTHER INFORMATION: n is a, c, g, or t
<220> FEATURE:
<221> NAME/KEY: misc_feature
<222> LOCATION: (518)..(518)
<223> OTHER INFORMATION: k is g or t

<400> SEQUENCE: 18

| | |
|---|---|
| gtcagtagtt catccatttg tcccattttt tnagcnngga agtttggttn cactnnnctt | 60 |
| ggtctaataa ctgagtagtc attttatnac gntgtttnga caagtcngta gctcatccat | 120 |
| ctgtcccatt tttttcngct aggaagtttg gttncactgg ncttggncta ataactgant | 180 |
| agtcatttta ttacnttgtt tcgacaagtc antagctcat ccatctgtcc cattttttcag | 240 |

```
ctaggaagtt cggttgcact gaatttgtga acccaaanga ccacaacaag ccngtgcagg      300
aggtctgtnt ctttacccaa gncaacaaaa ggttatcaca gcttatgctg aacttggcca      360
taacattcaa taattccttt atggtctagg tacttgctga gatgaccaac ggaggggtcg      420
accgcagngt ggaatgcact ggcaacatna atgctatgat ccaagctttc gaatgtgttc      480
atgatgtaag tatatgtata cactctcagc tactttcktt ctccaggttc ccttcatcca      540
gacatgcatg ttctaacngc cgcnctcgtg atccagggct ggggtgttgc ngtgctggtg      600
ggtgtgccnc ataaggacgc tgagttcaag acccacccga tgaacttcct gaacgaaagg      660
accctgaagg ggaccttctt tggcaactan aagccacgca ctgatctgcc aaatgtggtg      720
gagctgtaca tgaaaaaggt aaattgcaaa gtgcngttcc ttcngtttcc ttaccngccg      780
agcttttngc tgaaaaactg ttaagaatcg ttcctgcaat tctgnnnnnn nnnnacagga      840
gctggaggtg gagaagttca tcacgcacag cgtcccgttc gcngag                    886

<210> SEQ ID NO 19
<211> LENGTH: 904
<212> TYPE: DNA
<213> ORGANISM: Zea mays
<220> FEATURE:
<221> NAME/KEY: misc_feature
<222> LOCATION: (87)..(842)
<223> OTHER INFORMATION: n is a, c, g, or t
<220> FEATURE:
<221> NAME/KEY: misc_feature
<222> LOCATION: (182)..(330)
<223> OTHER INFORMATION: r is a or g
<220> FEATURE:
<221> NAME/KEY: misc_feature
<222> LOCATION: (463)..(463)
<223> OTHER INFORMATION: s is c or g

<400> SEQUENCE: 19
atgcgccctt gggtacatag caggagactg gaaaggtaac aaatggaata cggacacgta       60
gataaccatg gaggcccagc aatgttnnng aggnnnnntat tgtttggtca ctgcatagcc     120
gatgatgatc accacgcnct cgtgnatgcc tcatgtctta acagcagcca gatgatctct      180
grgcccggtt gccacctacc acatccacgg tatctggcac ataccttcaa gaacaaatcg      240
ataaggtcaa aaaaaanngg ggnacggctt ttacatagat aataaggac cagcacaggg       300 aaacaaatra aggaaatcna aaagtgattr atgattttac atagatataa cactgaaaac      360
gagaccagca gaagaagcta gtcttattgc agcagctaat gatgccaacc ctggtacacc      420
cccnagaaag aggatcaaca nnnngaanag nnnnnnnnnt ngsnncttat tttgctgatg      480
actaacaact ggangcaaaa agaccaacag aaggaccggt tgatattaaa aatgtaatta      540
cttttancag cnagcgnctc cggttttcta gtacttgcag caactaatgt cacataaaaa      600
cnnnnnntgt caaatgccaa tcaaacacac aaannnngaa acgaganatc annnagngnt      660
gtgcnttaca attcttcctc cnggttcatt ncnttcagag cattctttac aatacactgg      720
aaggcatctt ccacgttcgt tccatncctt agcagacgtc tcaaagtacg ggatgttccc      780
tttagaggcg caccatgcct ttgccntttt tctccgacac ctaaaaccaa agcagattat      840
antttctaag cagctcgtga tccagttcaa gagaagaatt tattcagaga acaaatcatg      900
tagc                                                                  904

<210> SEQ ID NO 20
<211> LENGTH: 815
<212> TYPE: DNA
```

```
<213> ORGANISM: Zea mays
<220> FEATURE:
<221> NAME/KEY: misc_feature
<222> LOCATION: (52)..(438)
<223> OTHER INFORMATION: k is g or t
<220> FEATURE:
<221> NAME/KEY: misc_feature
<222> LOCATION: (96)..(96)
<223> OTHER INFORMATION: r is a or g
<220> FEATURE:
<221> NAME/KEY: misc_feature
<222> LOCATION: (152)..(296)
<223> OTHER INFORMATION: y is c or t
<220> FEATURE:
<221> NAME/KEY: misc_feature
<222> LOCATION: (180)..(180)
<223> OTHER INFORMATION: w is a or t
<220> FEATURE:
<221> NAME/KEY: misc_feature
<222> LOCATION: (208)..(208)
<223> OTHER INFORMATION: m is a or c
<220> FEATURE:
<221> NAME/KEY: misc_feature
<222> LOCATION: (419)..(419)
<223> OTHER INFORMATION: s is c or g
<220> FEATURE:
<221> NAME/KEY: misc_feature
<222> LOCATION: (773)..(776)
<223> OTHER INFORMATION: nnnn is ctgg or gtgc

<400> SEQUENCE: 20
ggtttgtctg tttcatgaat aatgttctgt tgcgtcaaat taatagcaag tktctgatat      60
ttttttttct ccagcatgtt tttgaatact ttacaraaag aaccccaaga tcccatttcg     120
aacatcgkga aacatcattt gtgtggaact ayaagtatgc tggtaagtgt ttatcttccw     180
aacattcttt ttaagcragg tctgtgcmgt aacattttat ttccaccttc tatytcaaag     240
atgttgagtt yggaaggcta caagcaagag atatgctgca gcacytgkgg acrggyccga     300
tctcaaatgc agctgttgat gttkttcaag ggagtcgatc agttgaagtt cggtctgttg     360
gagttaccaa ggtaagtggt gctgtatgat ggtccatgac agtagatggt ttgrcctast     420
tgaggtttta aacatcaktt gtctccttcc tatagggtgc tgcaattgat cgtatttag      480 gggagatagt tcacagcgaa aacatgatta ctccaattga ctatgtcctg tgcatagggc     540
atttccttgg gaaggtaatt tccaattctt cacgttattg ttctgatctg gttttagttc     600
tgtggatagg atcaagaaac ttatgaatga agaratgraa gggtttagaa cattcaaaat     660
gcattgccaa ggaaaggaga aggatgtgga cttaattaga aaaatcacta tggtttactt     720
tatatgtttg gtctgtccct attcttttcg actttggtct gttttgtaac atnnnnttcc     780
tcgtgtttca gratgaggac atctacgtct tcttt                                815

<210> SEQ ID NO 21
<211> LENGTH: 426
<212> TYPE: DNA
<213> ORGANISM: Zea mays
<220> FEATURE:
<221> NAME/KEY: misc_feature
<222> LOCATION: (61)..(200)
<223> OTHER INFORMATION: y is c or t
<220> FEATURE:
<221> NAME/KEY: misc_feature
<222> LOCATION: (310)..(407)
<223> OTHER INFORMATION: n is a, c, g, or t
<220> FEATURE:
<221> NAME/KEY: misc_feature
<222> LOCATION: (316)..(324)
<223> OTHER INFORMATION: nnnnnnnnn is gcgtacgtg or is absent

<400> SEQUENCE: 21
```

```
tcttcagtct ccaccctgat tcaacaacag actctgacag cttgcacggt agctgccccg      60
ycatcgaagg ccagaagtgg tccgcgacta aatggatcca tgtgaggtca tttgacctca     120
ccgtcaagca gccgggtccc tctgatggat gtgaggacga caatgtcctc tgcccccagt     180
gggcggccgt gggcgagtgy gccaagaacc ctaactacat ggtggggacc aaggaagcac     240
ctggcttctg ccggaagagc tgcaaagtat gcgcagagta aggtatcggt cctctgcgtc     300
tgatgagtan tcgtgnnnnn nnnnttacgt agttgctgtc accatttnac cagggtttag     360
atacgaccga gtacagcatg tataagacag tacaancccg gaagnnngag tcgtaagagt     420
tagggg                                                                 426
```

<210> SEQ ID NO 22
<211> LENGTH: 432
<212> TYPE: DNA
<213> ORGANISM: Zea mays
<220> FEATURE:
<221> NAME/KEY: misc_feature
<222> LOCATION: (1)..(432)
<223> OTHER INFORMATION: b is c or g or t
<220> FEATURE:
<221> NAME/KEY: misc_feature
<222> LOCATION: (1)..(432)
<223> OTHER INFORMATION: k is g or t
<220> FEATURE:
<221> NAME/KEY: misc_feature
<222> LOCATION: (1)..(432)
<223> OTHER INFORMATION: m is a or c
<220> FEATURE:
<221> NAME/KEY: misc_feature
<222> LOCATION: (1)..(432)
<223> OTHER INFORMATION: r is a or g
<220> FEATURE:
<221> NAME/KEY: misc_feature
<222> LOCATION: (1)..(432)
<223> OTHER INFORMATION: s is c or g
<220> FEATURE:
<221> NAME/KEY: misc_feature
<222> LOCATION: (1)..(432)
<223> OTHER INFORMATION: y is c or t
<220> FEATURE:
<221> NAME/KEY: misc_feature
<222> LOCATION: (265)..(375)
<223> OTHER INFORMATION: n is a, c, g, or t

<400> SEQUENCE: 22

```
graagcgaac gaggaaagga agaacaagtt ggctycgaty gaaggckcra caactgccga      60
gtaccatctg cctgttctgg caatgacagc ygatgttatm caggcaactt aygaagagtg     120
cataaaatcg ggaatggayg grtacgtatc taaacccttc gacgaggagc agctatacca     180
agcagtctcc agattggtag tgggaacgac rgattcggct gtttgatgtt caaaatacga     240
tgsmmcbgac ttctcattcr tcgannnnag tgaagcatca ccatmttgcm tctgtccagc     300
tgactctann tcccttgaca atgggcctnn gacatggcct ctcacaagac tagatgaaaa     360
aannnngaag atnnngaaag tgccgtgagt tagstacgyr tcacacatga catgaagttg     420
ctgcggcagc cc                                                          432
```

<210> SEQ ID NO 23
<211> LENGTH: 880
<212> TYPE: DNA
<213> ORGANISM: Zea mays
<220> FEATURE:
<221> NAME/KEY: misc_feature
<222> LOCATION: (116)..(217)
<223> OTHER INFORMATION: r is a or g
<220> FEATURE:

<221> NAME/KEY: misc_feature
<222> LOCATION: (515)..(856)
<223> OTHER INFORMATION: n is a, c, g, or t

<400> SEQUENCE: 23

```
attttgatcc gtcattatct tgctcaaatt ctgtaacttt catcccaaag ttcgccagaa    60
ttcgtttctt ttttattttg ttaccagtag agcatctcct gatctacctc ttcgtrgtgt   120
ttggtaaaga ctattgagct caggtgtgtt gcgttgtgca gagcacaagt ggtgggatgg   180
ccaccagtct gcaactaccg caagaacacg atgactrcca cccagctgaa gggcagcaag   240
gaggatggtg atgccaagca gggtcagggg ttcctgtacg tcaaggtcag catggatggc   300
gcgccgtacc tcaggaagat cgacctcaag acttacaaga actacaagga cctgtcgacc   360
gcgcttgaga agatgttcag tggcttcagt actggtgaga tgtctcgggg ttactctctc   420
tctctctctc tctctctctc tcggatggcg cgacagagag taattatgtt tcgttttgat   480
gtggatggtg atagaagcac atcaagaagt ctttnaaaaa gcagcatact cctacttgat   540
tcctaggata agcaatagct tgaacttacc ccgatatatt ttgagtaatt gtgagattac   600
acacaatctg gcacgccttg ttttgttaat ttttgggaga actttatatt tctcccaaaa   660
caaataccct ggagattgtt cagatattgc atccgtatca agtctctctt agagagatgt   720
agttttctgt aaggcaaaat aagttgtgtc tccatctata tgaatatgcg aggatatctt   780
cgagctctga gtatnattcc atagagagct actaatctct atgagagtga cctccccnta   840
tatattcctg aaattnttgg agatctgcgg ccctgtatat                         880
```

<210> SEQ ID NO 24
<211> LENGTH: 921
<212> TYPE: DNA
<213> ORGANISM: Zea mays
<220> FEATURE:
<221> NAME/KEY: misc_feature
<222> LOCATION: (106)..(913)
<223> OTHER INFORMATION: n is a, c, g, or t
<220> FEATURE:
<221> NAME/KEY: misc_feature
<222> LOCATION: (746)..(746)
<223> OTHER INFORMATION: m is a or c

<400> SEQUENCE: 24

```
cgctgaatcc aacctaatgc tgtacagaat atcctttaca gccaagccgc caaccaagac    60
gctgagtcta atgccatgtc ctggtggatc caactatcca acaancaga tcaccccctt   120
tgagctgact gacgatcatg atgctgaaag tattggatgc tggtcgaagg cttcaccctc   180
ttgctggctg tgaagtggaa gacagagtca tgtaatcagt ttgcttgcct tcaaatcata   240
cacctggtgt aaagtacagt ttggtttgaa tataaacaag tatcataaag tacttcttta   300
aaattgtcca acgggggagt cagctgtctt ttgcacctca gggtgcttca cacgtagcta   360
tatgatggtc actggttaac tcatttacat agacaatttc agaagggata atctatgcaa   420
aatctaatga tattattatg accccctgatc catttagaac aacatgagct gtactcctcc   480
tagatatgat tacataagca tcttganntc tatcaggcct ttggtgagta ctcaacactc   540
aacagaaacc tactaactcc tatcgttctc tgattaaacg agtgaacagt tcaggacact   600
gcagaagatt ttttttttnct ataagccacc gctattcaac aatcaacggn ttttgctaat   660
cagatgtcac aaatgccaac atattgtcat ccgaggatat ccgtaaggt ggacaagata   720
gaaccagntt atctcagaaa aaaagmccat taaggatat ctggtaataa ctacatcacc   780
atccttctgt attcaagtat tagcagaaga ganttgataa tggaaggaaa tcatccctga   840
```

```
antaagcacc agtaatnggg natatggtca tgntatcaaa tgtaatttat taagcatcgc    900
aagttttaga atntagcaac c                                             921
```

<210> SEQ ID NO 25
<211> LENGTH: 831
<212> TYPE: DNA
<213> ORGANISM: Zea mays
<220> FEATURE:
<221> NAME/KEY: misc_feature
<222> LOCATION: (42)..(633)
<223> OTHER INFORMATION: n is a, c, g, or t
<220> FEATURE:
<221> NAME/KEY: misc_feature
<222> LOCATION: (562)..(562)
<223> OTHER INFORMATION: r is a or g

<400> SEQUENCE: 25

```
acaaaggaaa gggaagaaa atgacttcta ggttttcacg tnctccttttt ggttgaccaa    60 gaagagatgg tcggtagagt gaatggcctt gtgccatctc aattctttcg cgtggatcat   120
acattgtctc atctcttata gcctgaagaa tcgaatcagc aggacggtcc ctgtgcacat   180
atatgtaaac agaccaactc agtcaaatat cataaaacct tagttcaatg aattatttcc   240
aaactattgg aagataaagt agaatagctg gcacacatgc aggggcagaa ggaaccatgc   300
caatcaagtt atcggtatgt atgggttagt aatataggtt actggcatnn aggtaatacg   360
ctgaaaatgt aactggtgta gagtatgtgg cgttggtctt aggttctaac ctcgtgatca   420
gaatcctatg tagtgctttt aggatcgggc acatctcaac cggcgcaaca gatctgttgg   480
cttctggatg catgacactt aagctatcct gactaagaag ctcataaaac gcatcaactg   540
cagagacacc ctgaaatgga arggcaacag gntaattcat cacatgattc atttaggcat   600
attcatgcag ttcttttgaag tttcgttgtc gancaaaatt aaaagggcat acctgaatgg   660 tccctttttcc tttaatactg tcacccattt ctaatgtcaa ttcacccttta gctaacttct   720 gcccatacca tgcattacga cctttcaaca atgtgacata agtgtcagct aataagggtc   780
cagcaagttt ttcaggttct tcttccagaa ggtgtgtgat gtagatcatc t            831
```

<210> SEQ ID NO 26
<211> LENGTH: 1901
<212> TYPE: DNA
<213> ORGANISM: Zea mays
<220> FEATURE:
<221> NAME/KEY: misc_feature
<222> LOCATION: (687)..(1892)
<223> OTHER INFORMATION: n is a, c, g, or t
<220> FEATURE:
<221> NAME/KEY: misc_feature
<222> LOCATION: (1271)..(1271)
<223> OTHER INFORMATION: m is a or c

<400> SEQUENCE: 26

```
taccttgttt ccccaccaga gatagataga acatctgggg agtacttggt gaagaatggc    60
atccgcacct tgcttgcag gcaagtacta tctatttctc agcctttctc ttgatacttt   120
tttatttact tcaatatcgt aaaatcactt agttttctg agtcatctaa gtcagcatgc   180
tccatttatt ttgaatcaac attatcaagt gtacttcgta caatcttgta catacctgtg   240
aggagcactg accttctgga agatatcat ttttcacttc acagaacatc aggaattcaa   300
gattcactca gttaattgat attttaaata atttgaaaa ttgaaataca ggaaaatatg   360 tgttttttaag gcattacatt ttgcatataa atattcaatc tcactaaagg aaaatgtttt   420
```

-continued

```
aagaacattt ttctttagtg aaaaggaatc caaatgcttt cgaattctgt tgtgacttat      480
ctctattacc ttatactgca tccgtactag tatatttgac atctgtagag aagagttctt      540
ttttctaggg taatcttcta gctgcagtgc agtatgctga cattgtgcta acttaggctg      600
atatttggtt gcattgctct gcccatgatt tgtgccctaa tactgtatat tagggctgca      660
taatgttatt tttggattga ttcattnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn nnnnnnnnnn nnnnnnnnnn nnnnnnnnnn      960
nnnnnnnnnn nnnnnnnnnn nnnnnnnnnn nnnnnnnnnn nnnnnnnnnn nnnnnnnnnn     1020
nnnnnnnnnn nnnnnnnnnn nnnnnnnnnn nnnnnnnnnn nnnnnnnnnn nnnnnnnnnn     1080
nnnnnnnnnn naaatggtga catggttggt cacactggtg atattgaggc caccgtagnt     1140
tgcttgcnaa ggcagctgat gaagctgtta aggtgagagc accaatgaaa gttcgctgac     1200
atgtgtgttg tcttattatc tgcattggaa gttcgcttat acatcaataa aggttcttac     1260
agtagcacgc mtcataggcc tttgcctatt ttttaaccaa gtgttcttct gaacagatta     1320
ttttggatgc tgtcgagcaa gttggtggta tttaccttgt taccgccgat catggcaatg     1380
ctgaggatat ggtgaaaagg aacaagtctg gcaagccgtt gctcgacaag aatgaccgta     1440
tccagattct tacctcgcat acccttcagc cggtgagtgc aatgccattt gacccccatgt    1500 cttttggttn nctctcccag caaaatcata cccgtgttga ttgcttggat gctaatgcct     1560
ctgtaaaact tgcaggtccc ggttgccatt ggaggccctg gccttcaccc tggagtgaaa     1620
ttccggaacg acatccaaac ccctgggctc gccaacgtag ccgcaaccgt gatgaacctc     1680
cacggatttg aggctcctgc tgactacgag caaaccctca ttgaagtggc tgacaactaa     1740
acactggcca cctgtgtcca attttggtta tatgtagttc tgagaatgga cattcaataa     1800
tttatgtttg caagcacgtt gctcaaactc accaaaacat cgagggatgc cttttgactt     1860
tggcatttac agcattttcg tttggcttta anccttatcg g                        1901
```

<210> SEQ ID NO 27
<211> LENGTH: 595
<212> TYPE: DNA
<213> ORGANISM: Zea mays
<220> FEATURE:
<221> NAME/KEY: misc_feature
<222> LOCATION: (64)..(64)
<223> OTHER INFORMATION: s is c or g
<220> FEATURE:
<221> NAME/KEY: misc_feature
<222> LOCATION: (201)..(576)
<223> OTHER INFORMATION: n is a, c, g, or t
<220> FEATURE:
<221> NAME/KEY: misc_feature
<222> LOCATION: (254)..(254)
<223> OTHER INFORMATION: y is c or t

<400> SEQUENCE: 27

```
cgtccgcggc agcggccgcg tccaggtggt cgggcccgac ggggtgcgcg tcctggagac       60
gcgsgtcgag ggcggcttcc tcttcatcgt gccccgcttc cacgtcgtct ccaagatcgc      120
cgacgcgtcc ggcatggagt ggttctccca catcaccacc cccaagtaat tgttgtctc      180 gatcgatcga tccatcgatc nnnnttttt tattgcgaat tgcactggag atttgattgc      240
acgtgaatta atgyttgcat tgcattgcag cccgatcttc agccacctgg ccgggaagac     300
```

```
gtcggtgtgg aaggccatct cggcggaggt gctgcaggcg tcgttcaaca ccacgccgga    360
gatggagaag ctgttccggt ccaagaggct cgactcggag atcttcttcg ctcccccatc    420
caactgagaa aataggccgg aagcccacg gtggagtnnn ncctctcgtt aggtcgtcgt    480
gcttagatta ggttagctag cttgcctttta ataaaaagag agtggtggtc gtcggcgtcg    540
gcttcggcgg tctgcttctt cttcattcnn nnnnnnagtg cgtcggtcgg tttag         595
```

<210> SEQ ID NO 28
<211> LENGTH: 558
<212> TYPE: DNA
<213> ORGANISM: Zea mays
<220> FEATURE:
<221> NAME/KEY: misc_feature
<222> LOCATION: (39)..(550)
<223> OTHER INFORMATION: n is a, c, g, or t
<220> FEATURE:
<221> NAME/KEY: misc_feature
<222> LOCATION: (98)..(496)
<223> OTHER INFORMATION: y is c or t
<220> FEATURE:
<221> NAME/KEY: misc_feature
<222> LOCATION: (224)..(224)
<223> OTHER INFORMATION: m is a or c

<400> SEQUENCE: 28

```
ccgtgttggt tggatctatg gctcggtgac ggaggatgnt ggtcactggg taccggantn     60
gcacaanccg ggggttggaan gntcggtgta ctgtgtnyac caangcgtga ncgccnttcc   120
gcggcaccgc gcccatcnaa cctgacygan ccgtncntnc caccanggtg cntnccggtg   180
ggctanctgg nantcnagtg gagantcntt cnttncntnc ccgmaacnaa ncngcgctgc   240
tggcgangcc gcagnaantg naagnttctt gcagaggnan tcgcgtacct gnaacgtggg   300
tatctacccg ttcacgtcca ntncttccnt ngatncgtct actgcttncc tgccggcgct   360
gtcgctgttn ctcggggcag ttcatcgtga agnancgctg aancgtgacg ttncctgacg   420
tacctgctgg tngatcacgc tgacgcntgt gcctgctggc ggtgctngga gnantcnaag   480
tggtcgggga tcangyctgg aggangtngg tggcggaacg agcagnttnc tggctgatcg   540
gcggcacgan gcgcgcac                                                  558
```

<210> SEQ ID NO 29
<211> LENGTH: 937
<212> TYPE: DNA
<213> ORGANISM: Zea mays
<220> FEATURE:
<221> NAME/KEY: misc_feature
<222> LOCATION: (92)..(668)
<223> OTHER INFORMATION: n is a, c, g, or t
<220> FEATURE:
<221> NAME/KEY: misc_feature
<222> LOCATION: (258)..(258)
<223> OTHER INFORMATION: y is c or t

<400> SEQUENCE: 29

```
aatgtgatat catgatactc atgcacctgt accttagcca atgcaggagt ctgttaaagt     60
ctcaataaca ttttgtgatg ctcaccaaca gnttccttt tacaggattc atctggtata    120
ttctgggata atgacagttt agctggtctt ttggctattg aacttaaagc agatctcctt    180
gttctactaa gtgatgtaga tggtctatac agcggtccac caagcgaacc gggatcaaag   240
atcattcata cctacatyaa agataaacat tacagtggaa taacttttgg ggataagtca   300
cgtgtaggta gaggaggaat gacagctaaa gtganagngc tgcttttgtg gcttcgaaca   360
```

```
gtggcacacc tgttgttatt acaaggtatg tattgcattt ttcattcttt atncgagaat    420
taaaactgcc cttcgttgct catttatatg ttcccatgtg attgtgatct atcaaacttt    480
ccctgtgaca tgcaaccaat aataaggaat ttagacaaaa cagttgatag gtggtgtgat    540
taactacata tttggtgtat actacatttg actcaagtgt tttatttttg gnnnnnnngt    600
gtagactaca tttgactcga gtgtttctta catctttaat gatatgaaga attggttttc    660
agaagtgnaa atatttcctt agactttttt ctctctcgaa cgcgcaggag agctgcacat    720
cattatattt ccttagactg ttatgctgaa tcctcgcttg tgatgttcac ttattttct    780 atgttggatt ttatttacat ataataaggt ctgttggtca aatccaaata cgccatctgt    840
tttcaatgtt tgttcacggc cttaggaaaa tgtgttgcac attgtttgtc tattgaggat    900
atcaggagtg tagttattgc tatgtttcca ctctccc                            937
```

<210> SEQ ID NO 30
<211> LENGTH: 1193
<212> TYPE: DNA
<213> ORGANISM: Zea mays
<220> FEATURE:
<221> NAME/KEY: misc_feature
<222> LOCATION: (8)..(1108)
<223> OTHER INFORMATION: n is a, c, g, or t
<220> FEATURE:
<221> NAME/KEY: misc_feature
<222> LOCATION: (259)..(259)
<223> OTHER INFORMATION: y is c or t
<220> FEATURE:
<221> NAME/KEY: misc_feature
<222> LOCATION: (296)..(296)
<223> OTHER INFORMATION: w is a or t
<220> FEATURE:
<221> NAME/KEY: misc_feature
<222> LOCATION: (398)..(398)
<223> OTHER INFORMATION: r is a or g
<220> FEATURE:
<221> NAME/KEY: misc_feature
<222> LOCATION: (1057)..(1057)
<223> OTHER INFORMATION: s is c or g

<400> SEQUENCE: 30

```
gtgaatgnac agggngactc ctggnacagc ctactcggca ggaacaagca cgacgaccag     60
gagaagaaga accagcagnn nnnnnngncg gaggaggagn nnctggcgac cggcatggag    120
aagnnngtca cggtnggccg agcccgacca caaggaggag ggacacgagg ccgccgagaa    180
gaaggacagc cttctcgcca agctgcaccg caccagctcc agttccagct cggtgagtnn    240
nntcgtcgta aaacatgayc tgctgctagc tagtttaatt gactccgcct tcggawcagt    300
aagctaataa accggcttct cactgcgatc gtggtgcctg cgcgcatgca gtcgagncga    360
cgacnaggaa gaggaggtng atcgatgaga acggcgarat tgtcaagagg aagaagaaga    420
agaagggcct taaggagaag gtcaaggaga agctggcggc ccacaaggcn ccacgatgag    480
ggcgaccacc accagnnnnn nnacnngcc cnngcgccnn nnnngcccgt ggtggtggac    540
acgcatgctc accaccagga gggagagcac nnnnnnnnnt tcccgcgcc ggcgcctccc    600 ccgcacgtgg agacgcacca ccnnnccgtc gtcgtccaca agatcgagga cgacgacacg    660
aagattcagn accccaccac aggcaccgga ngaggagaag aaaggcctgc tggacaagat    720
caaggagaag cttcccggtg ccacaagaa gccggaagac gctgctgccg ccgccgccgc    780
gccggccgtc cacgcgccac cgccgnnngc gccgcacgcc gaggtcgacg tcagcagccc    840
ncgatgnngn caagaagggc ttgctgggca agatcatgga caagataccc cgctaccaca    900
agagctcggg tgaagaagac cgcaaggacg ccgccggcga gcacaagacc agctcctaag    960
```

```
gtcgcagnnn nnnnncgtgt gcgtgtccgt cgtacgttct ggccggccgg gccttnnngg      1020
gcgcgcgatc agaagcgttg cgttggcgtg tgtgtgsttc tggtttgctt taattttacc      1080
aangtttgtt tcaaggtgga tcgcgtgngt caaggtccgt gtgctttaaa gacccaccgg      1140
cactggcagt gagtgttgct gcttgtgtag gctttggtac gtatgggctt tat             1193
```

<210> SEQ ID NO 31
<211> LENGTH: 482
<212> TYPE: DNA
<213> ORGANISM: Zea mays
<220> FEATURE:
<221> NAME/KEY: misc_feature
<222> LOCATION: (121)..(471)
<223> OTHER INFORMATION: n is a, c, g, or t
<220> FEATURE:
<221> NAME/KEY: misc_feature
<222> LOCATION: (239)..(239)
<223> OTHER INFORMATION: r is a or g

<400> SEQUENCE: 31

```
gcaaaggtac agcgtaaaaa ctaagaggag agccagcaag ctagcatttt atttagtaaa        60
atcgttcact cgcaggtacc caatcttctc agctttacac actcgccatc ttgaggctgt       120
ngcccttctc ctgcaggctc acgagtaggc ngncaaagct cttcttgaag gagtccangc       180
cttccagctc aagctgcttt ccnacctcnn cccagncnat gccaagcttc tccaaggcrc       240
tgtatacacc ttccgcctca gacacnttng catcnactgt cctnganacn gtgccgtggt       300
ctatgaatgc ntgcaaagct tggtcgggca tcgtgttgac ctgaaangtg cancannnct       360
acagagttat tttttnnnnn atgataagaa acaangccan ttcaagtggn naactcgtcg       420
tgnnancatn ccgtgtcagg tccnatgaga ctgtcnannt aaagagtgtc nggataagct       480
gg                                                                    482
```

<210> SEQ ID NO 32
<211> LENGTH: 376
<212> TYPE: DNA
<213> ORGANISM: Zea mays
<220> FEATURE:
<221> NAME/KEY: misc_feature
<222> LOCATION: (12)..(355)
<223> OTHER INFORMATION: n is a, c, g, or t
<220> FEATURE:
<221> NAME/KEY: misc_feature
<222> LOCATION: (208)..(208)
<223> OTHER INFORMATION: r is a or g

<400> SEQUENCE: 32

```
ccaggcgacc anggggttca agaacaagat gctgctcggc nccggcggct tngggagggt        60
gtacaagggc gtgctcnccg ggtccaagct cnaggtcgcc gtgaagaggg tgtcgcacga       120
ctcgaagcag gggatgaagg agttcatcgc ggaggtggtg agcatcggcc acctccgcca       180
ccggaacctg gtgcagctgc tgggctartg ccggcggaag ggcgagctgc tgctggtgta       240
cgactacatg tccaacggca gcctggacaa gtacctctac gacgncagga ccgccaggcc       300
cgtcctggac tgggngcaga ggttccagat cgncagggggc gtcgccgccg gcctnctgta       360
cctgcacgag gactgg                                                     376
```

<210> SEQ ID NO 33
<211> LENGTH: 839
<212> TYPE: DNA
<213> ORGANISM: Zea mays
<220> FEATURE:

```
<221> NAME/KEY: misc_feature
<222> LOCATION: (346)..(837)
<223> OTHER INFORMATION: n is a, c, g, or t
<220> FEATURE:
<221> NAME/KEY: misc_feature
<222> LOCATION: (391)..(391)
<223> OTHER INFORMATION: r is a or g

<400> SEQUENCE: 33
aaacaacaac ttgttgttgt ccacaacagg ttaacagatc aaagaaggat aggtgagcgg      60
cactactcat ctcgtggctt ctggatctgg tgacagatga tcagcccacg aaggaaaaag    120
aaaaagggac tcgcttgatt tgcgttgctt tgctttccgc gcaaggccga aagcttaagg    180
tcggggcaac gagtacaccg agagcgacgg agatatatca cgctctgctg cttcatgata    240
gctggaagga catcagcatg acacgcatgc caataatgta gtagaagact agtttatttg    300
tcacctacta ggcagagagt gcggtggttc catgaaccaa ccattnnnnc gtgcgtgcgt    360
gcccaccgca cgaccacgag ggggcatgca rcatatactt tacaaaattc attcggttgt    420
tgacttggtt tcaattcatt gggttgggaa gacaaaacta acatggatgc gttgcgtact    480
cacaggaagg tgatggctca gactggtgag atccggtgcg ccatggatca catcctcgag    540
gccgagagga agggcgagat caaccacgac aacgtcctct acatcgtcga aacatcaac    600 gtcgcaggta tcgnnnnata atcgtcactg ctcagtgcaa tgaaacggaa acagagtatg    660
ctatgtctga agaaccaagt gagnacttat cattcaacta ctgcagtcca cgctactac    720 acaaacaaat agcactgcaa tatcggaaga tataataata taaggcacgt cttaatcaag    780
tctccgtcag ccaacttaat tccntcctta attaaccggc aacatactga gcctaangc    839

<210> SEQ ID NO 34
<211> LENGTH: 693
<212> TYPE: DNA
<213> ORGANISM: Zea mays
<220> FEATURE:
<221> NAME/KEY: misc_feature
<222> LOCATION: (145)..(146)
<223> OTHER INFORMATION: nn is ca or both nucleotides are absent
<220> FEATURE:
<221> NAME/KEY: misc_feature
<222> LOCATION: (169)..(169)
<223> OTHER INFORMATION: w is a or t
<220> FEATURE:
<221> NAME/KEY: misc_feature
<222> LOCATION: (174)..(590)
<223> OTHER INFORMATION: n is a, c, g, or t
<220> FEATURE:
<221> NAME/KEY: misc_feature
<222> LOCATION: (537)..(537)
<223> OTHER INFORMATION: w is a or t

<400> SEQUENCE: 34
tgacctacaa ctcaaacagg ctcgtcttca atggccacga gatctacccg tcagcagtcg      60
tgtctaaacc aagagtagag gttcaagggg gtgacttgcg gtcgttcttc acattggtta    120
gcaccagtcc aacactactc cacanngtta gctctccaag ttgttctawa tatnnnnnnn    180
tgtatccnnn nnnnncttcc tttccctaat ggccatagtt cctgaatntc caggttatga    240
cagacccaga cgtcccagga ccaagcgatc catatntnag ggagcacctt cactggtaac    300
atctggcatt tcctaccaan ncatctaggg gaatgctgtg tgactgnnat atgtccttta    360
catttgcagg atcgtgactg anatacctgg gacaactgat gcctcattcg gtagtnnnnn    420
cnccncnctc tgctttgtgg ttaattagtn gttccagttg ttcttgnanc tagtnaattn    480
nnancaggca tttnttttc agggagagaa gtcgtaagct atgagagccc gagaccwggc    540
```

| | |
|---|---|
| attggtatcc acaggttcat ctttgttctc ttcaagcaga nnnagcgcan gcagcagcag | 600 |
| actgtagcgg cggtgccatc ctccagcagg gaccatttca tcacgcgtca gttcgctgcg | 660 |
| gaaaacgatc ttggccaccc tgtagccgct gtg | 693 |

<210> SEQ ID NO 35
<211> LENGTH: 765
<212> TYPE: DNA
<213> ORGANISM: Zea mays
<220> FEATURE:
<221> NAME/KEY: misc_feature
<222> LOCATION: (76)..(76)
<223> OTHER INFORMATION: r is a or g
<220> FEATURE:
<221> NAME/KEY: misc_feature
<222> LOCATION: (97)..(625)
<223> OTHER INFORMATION: n is a, c, g, or t

<400> SEQUENCE: 35

| | |
|---|---|
| tatgcatgat ttatgcccgc caaacagaca gaaaacgcaa caaactacaa ccatttacag | 60 |
| accggagcca agtgarccta acttgttaac atcatangaa ggnacatcct aaacgagcaa | 120 |
| tgcttactca aatttactgc tatgctactt ctattgctgt taatgaggca gtcactcaca | 180 |
| ggctgctgct gactggaaag ccaggggaaa ttagcgttct ggcttcaggt cacgatcaat | 240 |
| gtactgcctc acagcctctt ggtttacntg gaaaataaac ctcatgtcct ttatctggaa | 300 |
| aggggnggna aaaggtagct aaattagtan agcatgaaga tacttaatta aatgcatcag | 360 |
| tgatatctca gtcaaataac aagggaagga ttgtcaggta tagcaaaggt taacttgtca | 420 |
| aaaagtaatt gtttcatgtc tgcttacana tcaccatagt atcattcgta ctgtttttag | 480 |
| atactctata aaccccaaa ataacataat ggcaagaagt aaancttcaa gcaccctcta | 540 |
| ccagtagaac cataaactat gacaggatca caggaatagt tacaaaaact gtgcattgac | 600 |
| taaccaccag gttacagatt cattnaaaaa tgaaggtata ctagaacggg gaagtattgg | 660 |
| tacctcgatt aatgagtctg agcttaggtt gatgcgtttg cagcttggta tttccttgct | 720 |
| attaacaaag attggacatt ttccagtgtt cttaatatga aaata | 765 |

<210> SEQ ID NO 36
<211> LENGTH: 774
<212> TYPE: DNA
<213> ORGANISM: Zea mays
<220> FEATURE:
<221> NAME/KEY: misc_feature
<222> LOCATION: (281)..(652)
<223> OTHER INFORMATION: n is a, c, g, or t
<220> FEATURE:
<221> NAME/KEY: misc_feature
<222> LOCATION: (500)..(698)
<223> OTHER INFORMATION: y is c or t
<220> FEATURE:
<221> NAME/KEY: misc_feature
<222> LOCATION: (568)..(568)
<223> OTHER INFORMATION: r is a or g

<400> SEQUENCE: 36

| | |
|---|---|
| agcatcatgg agtacggtca gcaggggcag cgcggccacg gcgccacggg ccatgtcgac | 60 |
| cagtacggca acccagtcgg cggcgtcgag cacggcaccg gcggcatgag gcacggcacg | 120 |
| ggaaccaccg gcggcatggg ccagctgggt gagcacggcg gcgctggcat gggtggcggg | 180 |
| cagttccagc ctgcgaggga ggagcacaag accggcggca tcctgcatcg ctccggcagc | 240 |
| tccagctcca gctcggtaat tacgactctg gatacttctt nnntcttttg tgtgcgcgct | 300 |

```
gcttcgtcct atatataata atacatgnag ttaggcttag taataatcaa ttaatttaat    360
ccgtgggttt cgtgtttaag tcggaggacg acggcatggg cggaaggagg aagaagggaa    420
tcaaggagaa gatcaaagag aagctgcccg gaggccacaa ggacgaccag cacgccacgg    480
cgacgaccgg cggcgcctay gggcagcagg acacaccgg cagcgcctac gggcagcagg     540
gacacaccgg cggcgcctac gccaccgrca ccgagggcac cggcgagaag aaaggcatta    600
tggacaagat caaggagaag ctgcccggac agcactgagc ggcgcctata cntggctgtg    660
ctgtgctgtg ctggcgcgtc aaagccgtac tcttcagygt tccatagata ataagataaa    720
cccatgaata agtgtcccta cccttttgatc atgtgacagg gacagggaca ggga         774
```

<210> SEQ ID NO 37
<211> LENGTH: 460
<212> TYPE: DNA
<213> ORGANISM: Zea mays
<220> FEATURE:
<221> NAME/KEY: misc_feature
<222> LOCATION: (53)..(449)
<223> OTHER INFORMATION: n is a, c, g, or t
<220> FEATURE:
<221> NAME/KEY: misc_feature
<222> LOCATION: (375)..(386)
<223> OTHER INFORMATION: r is a or g
<400> SEQUENCE: 37

```
aaggcaacat tctgaagatg cagcgcaagc agaagccatg cactcccctc ccntccaaca    60
ngcagagtcg gtactaccgg ccncgggtca aggtangcgn cagnanccga ctcctngagg    120
cnannttccc cgcagnggca agannnnnnn nnnnnnnnnn nnnnnnnnnn nntntcnnnn    180
tgnnnaagnn tnnctgnnnc tgnctgtctn tgtgtgttcn cgctttcnnn ngcagggag     240 gtttgtcagc aaggcttgtt tnctccagcg acagcaagcg ttagagaagg agagctagag    300
aangatggat cctgctccaa ggcgcatttc tgnggctctc ttggagaagc agcagagctt    360
ctccnttttc atctrtgcgg cggtaragtg cggcagatgt agagatgcct gtagagtggt    420
gcttgtnanc ctcaattctc agtttcttnt atccattcca                          460
```

<210> SEQ ID NO 38
<211> LENGTH: 553
<212> TYPE: DNA
<213> ORGANISM: Zea mays
<220> FEATURE:
<221> NAME/KEY: misc_feature
<222> LOCATION: (78)..(542)
<223> OTHER INFORMATION: n is a, c, g, or t
<220> FEATURE:
<221> NAME/KEY: misc_feature
<222> LOCATION: (309)..(309)
<223> OTHER INFORMATION: s is c or g
<220> FEATURE:
<221> NAME/KEY: misc_feature
<222> LOCATION: (342)..(342)
<223> OTHER INFORMATION: m is a or c
<400> SEQUENCE: 38

```
cacaaaagag aaggctctca aggtgaacta gaacagaatc tcccgacggc cggggctcaa    60
accagctcat cctcggcnat atctcgagga ttcctcacca gctcgagcat gctcacgacc    120
tcacccatgc caggccggtt cgacggcacc tganaggtgc anacaaggcc cagcttgatg    180
accggcaggg cctcgtccat ggggaactcg ccgcgcagnc gnggntcgac gcagtcctcn    240
ggcctgcctt cctccagcgc ncctctgacc aggtcacaca ggacaaccac gtcgtcttcc    300
aagtactcsa cgggcctcct gcccgtcaan ncctccagca gmagcacccc gaagccatag    360
```

```
acgtcgcatt tctcggtgat cttcaccgtc ttgcacgcaa actctggcgc catgtacccg    420
agcgcgctct ggaccttact gctcaggacg taccggtcca gcatcggcag cagcttggcg    480
aggccgtagt caccnacctt tggctcgccg ttgctgtcca gcagcacgtt gcttgacttg    540
anattgtagt gga                                                      553
```

```
<210> SEQ ID NO 39
<211> LENGTH: 622
<212> TYPE: DNA
<213> ORGANISM: Zea mays
<220> FEATURE:
<221> NAME/KEY: misc_feature
<222> LOCATION: (4)..(619)
<223> OTHER INFORMATION: n is a, c, g, or t
<220> FEATURE:
<221> NAME/KEY: misc_feature
<222> LOCATION: (445)..(445)
<223> OTHER INFORMATION: b is c or g or t

<400> SEQUENCE: 39
ttcnntngca ttcntngctg atgtttnnga ntgnctctta ggacaagtgt ggctacaccg     60
gagcatgtcg aagaggcatt cagactgttc aatgtntcca ccgttgatgc tgcaagatcn    120
ggaatcaatg agcatttgaa cctgtcaccg gagatcgcaa angaaatcaa ggttagtatt    180
tgcatcccag ggtnnncaaa atncagctnt tgaaccttgn atttttcctga acggcnttcn    240 ncatttttt gcnnatctgn cagcnagcgg aggcncaaat aaagagaaga atgggcatcg    300
gcagccacat atccnagcga cggctnatng atganctaaa ccggatgggg atgaatgaat    360
ccatcgtagg aaccctgtca tcgnatctta gaactgaaac tatggtttc  aagtaagacc    420 cgntcgtttt tctgacaata tcttbcacac tttgtttcag gtcagaagag cccttctgat    480
catgcatcaa agngacgagg tggagtacaa gagagagcgc cacgtgatcg tccgaaaggc    540
ttgaggtgga gagnngccag tcagattcac ggcatacaac gtacactgga ggnggtcctt    600
ccnnntcgna cgtgtgtana cc                                            622
```

```
<210> SEQ ID NO 40
<211> LENGTH: 664
<212> TYPE: DNA
<213> ORGANISM: Zea mays
<220> FEATURE:
<221> NAME/KEY: misc_feature
<222> LOCATION: (24)..(642)
<223> OTHER INFORMATION: n is a, c, g, or t
<220> FEATURE:
<221> NAME/KEY: misc_feature
<222> LOCATION: (602)..(602)
<223> OTHER INFORMATION: w is a or t

<400> SEQUENCE: 40
ttcctctata agtacccgcc ccanatctgc gccattttct catcgcagaa atcctccgca     60
acttcacagc gtatcatcgt tttncatcgc tcctactcct ancatccaga aaatctgagn    120
ggtattgatg gcgcccaagg cggagaagaa gccggcggcn aagaaggtgg cggaggagga    180
gccctcggag aaggcggctc cggcggagaa ggccccgcg  gggaagaagn ccaaggcgga    240
gaagcggctn ccngcgggca agtcngcngg caaggagggc ggcgacaaga agggnaggaa    300
gaaggcgaag aagagcgtgg agacctacaa gatctacatc ttcaaggtcc tgaagcaggt    360
gcaccccgac atcggcatct cctccaaggc catgtccatc atgaactcct tcatcaacga    420
catcttcgag aagctcgccn cggaggccgc caagctcgcc cgntacaaca agaagcccac    480
```

```
catcacctcc cgcgagatcc agacctccgt ccgcctcgtc ctccccggcg agctcgccaa      540
gcacgccgtc tcggagggta ccaaggccgt caccaagttc acctcgtcnt agccnccttg      600
twgtaggcgt cgttgtnnnc tgcttctcaa gcaagcactg tnatgtgccg cttctcatgg      660
cagt                                                                   664

<210> SEQ ID NO 41
<211> LENGTH: 722
<212> TYPE: DNA
<213> ORGANISM: Zea mays
<220> FEATURE:
<221> NAME/KEY: misc_feature
<222> LOCATION: (13)..(708)
<223> OTHER INFORMATION: n is a, c, g, or t
<220> FEATURE:
<221> NAME/KEY: misc_feature
<222> LOCATION: (190)..(190)
<223> OTHER INFORMATION: r is a or g
<220> FEATURE:
<221> NAME/KEY: misc_feature
<222> LOCATION: (580)..(580)
<223> OTHER INFORMATION: s is c or g

<400> SEQUENCE: 41
aaacaacaca gtnatctgat cgtnataaaa tgatatantc tgtctatacc gcacccaagt       60
gtttcagtct ttcagagnnc caaaacgttc gantcttttc tttanccnat cttcttcctc      120
ccgacgnnnc accgccgcng nnnnnnnnnc nnnnnnnncc gcgtntgagt tccaacactc      180
gagtgaggtr tannnnnnnn nnnnnnnnnn nnnnnnnnnn nannnnnnnc ttnccgaant      240
gntatnnnnn gtaatacatg acaaaacgac ggttaattct tgtgtaacaa tgcganacga      300
gcagggcnga tgtactacaa cgnnatgtac catctcttct accagtacaa cccgcacggc      360
gcgctctggg gcgtnggcaa cctctcctgg ggccactccg tntcnggcga cctcgtnaac      420
tgggccgcnc tggacacggc nctggacccg acgtcgccct tcgacgccaa cggctgctgg      480
tcgggctccg ccaccatnct ccccggcggc acccecgccca tcctctacac gggcatcgac      540
gccaacgggg agcaggtgca gnaacgtggc gttccccags gacccggcgg acccgctcct      600
tcgccggtgg gacaagcccg gctacaaccc cgtcatcccg ctccccgccg acgtcccggg      660
cgncaagttc cgggacccnt cgacggcgtg gctcggccgc gacgggcngt ggcgcgtcgc      720
gt                                                                     722

<210> SEQ ID NO 42
<211> LENGTH: 940
<212> TYPE: DNA
<213> ORGANISM: Zea mays
<220> FEATURE:
<221> NAME/KEY: misc_feature
<222> LOCATION: (195)..(730)
<223> OTHER INFORMATION: n is a, c, g, or t
<220> FEATURE:
<221> NAME/KEY: misc_feature
<222> LOCATION: (238)..(238)
<223> OTHER INFORMATION: r is a or g
<220> FEATURE:
<221> NAME/KEY: misc_feature
<222> LOCATION: (266)..(268)
<223> OTHER INFORMATION: nng is ttg or all three nucleotides are absent
<220> FEATURE:
<221> NAME/KEY: misc_feature
<222> LOCATION: (808)..(808)
<223> OTHER INFORMATION: s is c or g

<400> SEQUENCE: 42
ctgtcatcca tgtccaggag gtctgttgct gcacacccttt ggcatgatct ggagataggt       60
```

```
attgtacacg ctctagcttg acaaatggtc agccgttgat ctctgctatt tgcaaccaga    120
gcttaagttc atcttggatt catgcaggtc ctggtgctcc aaccatattc aactgcgtaa    180
ggccaccctg tcatnngctt gactggtcct cttgtgatat gttcatgtta atagcatrat    240
gtcttttgtt ctattggaaa ataaanngtc tccctggact ctaaaatcaa tgcctgtgaa    300
cacatgaact gtttgtgtca cccatgttcc tctgctcctt ggcactttct gatgcatgct    360
caaatgctta agaagactc atagaagcga ctcctattcc tatgccaggt cattgagata    420
ccaaggggca gcaaggttaa atatgaactt gacaagaaaa ctggactgat caaggtaaag    480
caatgttgtt ttcctcccgc tgaagtctta ttgtgaagct atatttcttg ccagttctaa    540
tatttactcc tttccgtttc aatctgtgtg catgtgcagg tggaccgtgt gctgtattca    600
tcagttgttt accctcacaa ctatggattc attcctcgca cgctttgtga agacagtgat    660
cctttggatg tactggttat aatgcaggta tgcttctttt ttatatatat cattggnnga    720
ttcacaaaan tggtacatca gtagtgatct gagtatcctt gggcataagt tgagctaatt    780
ttcaaatctt gtcattttcc atttctgsga atggtcgaga acatgtctat aaactgttac    840
ttccaagcat gtaggagcca gtcattttcc atttctgttt atagttgcct agtcgggaac    900
atgtatgtaa actgttactt ccgtgcatgc aggagcctgt                          940
```

<210> SEQ ID NO 43
<211> LENGTH: 805
<212> TYPE: DNA
<213> ORGANISM: Zea mays
<220> FEATURE:
<221> NAME/KEY: misc_feature
<222> LOCATION: (150)..(801)
<223> OTHER INFORMATION: n is a, c, g, or t
<220> FEATURE:
<221> NAME/KEY: misc_feature
<222> LOCATION: (708)..(708)
<223> OTHER INFORMATION: m is a or c

<400> SEQUENCE: 43

```
ggatccatac aaggtgcttt tttttcgatt tagaattctt tcttcatcga ttttgcccta     60
tgtgctagat cctcaaatca attccgcatc ttgtttccgc ccttgattga tgcattcgct    120
cgtctgactt gattgatgcg ctcgatctgn gggactcttc gttcttgcag caccgcccgt    180
ctagtgggag caactccagc ttctggacca ccaactccgg cgcccccgtc tgnaacaaca    240
actctgccct caccgtcgga cagcgaggtc agaccacaac ccctctctct gtttatcctg    300
tagctgacat gctgctgcct tcatttgtcn ngtctctcca tcccggtttc nttttccctt    360
gcacgatcct gtatgtactc actatgtatg nagcatatat gttcttgatt tgtgcgagac    420
ccatccgagg cataaatgat ctgtnctagc tttgctttga ggcctattat tgcaccgtgg    480
aagcnagagg atttcgnttc ccatncattc aaagcttgca tctngatgtg cttttaatta    540
atttccagtg actaattttg cctgctcngt acatgcgggt tgtcgttgat tnacctgtcc    600
naatatcgtc aatgaatttg agacttgccc aaaggactta ttccttgtat cagctgtaag    660
gtgaagcttt tgtcctgata tttttgccag tcgctgtcga accattamgt tacttaaggg    720
aaagaaagca cnttccnggt acgaaatgcc atcatggagt catagtgata atcctaggtg    780
agggacactt ggagagtagt naagt                                          805
```

<210> SEQ ID NO 44
<211> LENGTH: 860
<212> TYPE: DNA

```
<213> ORGANISM: Zea mays
<220> FEATURE:
<221> NAME/KEY: misc_feature
<222> LOCATION: (10)..(117)
<223> OTHER INFORMATION: n is a, c, g, or t
<220> FEATURE:
<221> NAME/KEY: misc_feature
<222> LOCATION: (266)..(266)
<223> OTHER INFORMATION: m is a or c

<400> SEQUENCE: 44
gtacctcctn nncttagtcn gctagcgaga gagannnaat cctggcctca catgagatcg      60
actggttcct gggttccttc tctcctcccc ccgttaagtt gcccgtcgga ggaggantcc     120
tgagcacatc gatcagtcgc gtgtctaggt ttcctctctc accatagcgc ccgctctgtc     180
gcccttcgtt cacctctcct tcctctcctc cctgcctgcc agggagaggg gaagtcagag     240
gcacggagtg gcgcagagca gacgcmcgtg aaccattgta gctgtccctg tcgtcgtcgt     300
catcgtcgtc aacgaatccg cacaaggaaa agatggagaa gaagccgacc atcctcatga     360
acaggtacga gctcgggcgc acgctcgggc agggcacctt cgccaaggtg taccacggcc     420
ggaacctcgc gtccggcgag agcgtggcca tcaaggtcat cgacaaggag aaggtgatgc     480
gcgtcggcat gatcgaccag atcaagcgcg agatctccgt catgcgcctc gtccgccacc     540
ccaacgtcgt gcagctgcac gaggtgatgg ccagcaagag caagatatac ttcgccatgg     600
agtacgtccg gggcggcgag ctcttcgccc gcgtcgcacg cggccggctc aaggaggacg     660
ccgcgagaag gtacttccac cagctcgtcg gcgccgtcga cttctgccac agccgcggcg     720
tctaccaccg cgacctcaag cccgagaacc tcctcgtcga cgagcacggc aacctcaagg     780
tctccgactt cggcctcagc gcgctcaagg agtgccagaa gcaggacggc ctgctgcaca     840
ccacctgcgg cacccccgcg                                                 860

<210> SEQ ID NO 45
<211> LENGTH: 676
<212> TYPE: DNA
<213> ORGANISM: Zea mays
<220> FEATURE:
<221> NAME/KEY: misc_feature
<222> LOCATION: (1)..(676)
<223> OTHER INFORMATION: k is g or t
<220> FEATURE:
<221> NAME/KEY: misc_feature
<222> LOCATION: (1)..(676)
<223> OTHER INFORMATION: m is a or c
<220> FEATURE:
<221> NAME/KEY: misc_feature
<222> LOCATION: (1)..(676)
<223> OTHER INFORMATION: r is a or g
<220> FEATURE:
<221> NAME/KEY: misc_feature
<222> LOCATION: (1)..(676)
<223> OTHER INFORMATION: s is c or g
<220> FEATURE:
<221> NAME/KEY: misc_feature
<222> LOCATION: (1)..(676)
<223> OTHER INFORMATION: v is a or c of g
<220> FEATURE:
<221> NAME/KEY: misc_feature
<222> LOCATION: (1)..(676)
<223> OTHER INFORMATION: w is a or t
<220> FEATURE:
<221> NAME/KEY: misc_feature
<222> LOCATION: (1)..(676)
<223> OTHER INFORMATION: y is c or t

<400> SEQUENCE: 45
catctggtcc tgcggcgtca tcctcttcgt gctcctcgcc ggctacctcc cgttccacga     60
```

```
cgccaacctg gtggagatgt accgcaagak sagmaragcc gacgtcaagt acccgcagtg    120
gttctcccct gagctscggc ggwtgmtgcc caagctcctc gaaccgaacc caaacaayag    180
grtcacratm ragaagctgg tckascaccc ytggttyawg aaggggtaca sgccgsccgt    240
catgctggca cagccgcacg gctccagcag cctcaaggat gtccaggtcg ccttcagcaa    300
ygcygaccac aaggacagca gcavcaaggt ggaacagccg gcggacagct ccttgaagcc    360
ggcgagcctg aacgcgttcg acatcwtctc ccactssrga gggttcgacc tgtcaagcct    420
gttcgaggtg gaccaagagc agaaggccag caactcgcgg ttcatgaccs araayccggc    480
gtcggcgata gtgtcaaagc tggagcagat cgctgagaca gagcgcttca tggtgaaraa    540
acaggacggg ctggtgaagc tgcagggggtc caagcaaggg aggaaggggc agctcgcgat    600
cgacgccgag atcttcgagg tgacaccggc ctttcacgtc gtcgaggtga agaagtcggc    660
aggcgacacg ctggag                                                    676

<210> SEQ ID NO 46
<211> LENGTH: 742
<212> TYPE: DNA
<213> ORGANISM: Zea mays
<220> FEATURE:
<221> NAME/KEY: misc_feature
<222> LOCATION: (386)..(386)
<223> OTHER INFORMATION: s is c or g
<220> FEATURE:
<221> NAME/KEY: misc_feature
<222> LOCATION: (516)..(516)
<223> OTHER INFORMATION: n is a, c, g, or t

<400> SEQUENCE: 46
gcaatgtgaa tgaatatatg acgcaccatt atgttatgtg tgacatattt tgatttctat     60
acttctaagt attctctgat catctgggac gtgtaaacat aaaaagataa taaactaact    120
gcattcgaga tcatgaccag taataacaaa caaatgtaat ctgcagtgag aacagataag    180
tggccacata accaaaacct tgagtctgca cagcatctta attgtcactt aacacaagaa    240
aacaatttag acagttataa gcaacatata acattgacca ttgatcattt aggttaacat    300
ggggacaaga cataattgat tgctaaatct atctgtaagc tttattaatc ttataattca    360
taattacaat gagttcattg caaccstcaa ggtgtaatgt tacagcaagt caaccacagc    420
agcacagaac aagaacatgt tgtagaccta aggttttagt ctcccttttga actctattac    480 tcagatatag agtatatatc taacaaaaat ggtacnggaa aagcataccct aagaaaccac    540 aagccacaga attgatgtag cttcgagctt caattgaatc cagacctagg acaattatgt    600
ggaactgact gtagaactct atctctttat cttcaatcct gcaaaaatga ggaactatgt    660
tcaccccatt aactcgctcc ataaccctct tcgctgctac ttcagccttg gacttcccaa    720
catcttgaac tctgtacagc ag                                             742

<210> SEQ ID NO 47
<211> LENGTH: 808
<212> TYPE: DNA
<213> ORGANISM: Zea mays
<220> FEATURE:
<221> NAME/KEY: misc_feature
<222> LOCATION: (87)..(87)
<223> OTHER INFORMATION: r is a or g
<220> FEATURE:
<221> NAME/KEY: misc_feature
<222> LOCATION: (182)..(762)
<223> OTHER INFORMATION: n is a, c, g, or t
```

<400> SEQUENCE: 47

```
gagaagcaac atgacggcaa gctcagtggc tacattcgaa taaggagcaa gacccaggga      60
attgcactca gcttagggga caagatract ctcaagcaga aaggtggcag ttaactgtga     120
caagtaatcg cagttgtatc atcatttttc gcatttagga aatccacgtg ccagagagag     180
anncccagtgc cgtggcattg aactgagtat aaatgctttt ttgtacaaaa ggatcgatca     240
aagagagaga ganntaagag gacagttatg aggaggaagt cacnnnnnnn nnnnnnnnnn     300
nnnnnggtgt tagagacccc tgagcgcgaa gttgtcggtc gaagatccat gttgctgtag     360
taacgatgct gttccaanct tccttgaaat agttgtgaag tttatgttga tttctcgaca     420
ggtagttcaa ttgtgatctt gtactattac nnngaatccc tcttgtttta atgttttatt     480
tgcctttta ttttagttgt ctggacttgg aaacagaagc ttggaggncg gtgttgtcac     540
gttattttg tagagatgaa ttggagctca ttttctgtta cgtatagatt tgccaattgt      600
gttaggttat ttttagcgtg gttatttgag aaatgaggta gtccattatc ttctcactca     660
ctttcttctt ttgtttgtgg aatgaaatga ggtaatcaaa ctgaacccg aaacgaagat     720
ggccttaggc tgacgatgag acccantaga acttccnnnn nnctactatt actctactag     780
ggcctaggaa gtgatcatga tatggttg                                        808
```

<210> SEQ ID NO 48
<211> LENGTH: 1088
<212> TYPE: DNA
<213> ORGANISM: Zea mays
<220> FEATURE:
<221> NAME/KEY: misc_feature
<222> LOCATION: (83)..(1064)
<223> OTHER INFORMATION: n is a, c, g, or t
<220> FEATURE:
<221> NAME/KEY: misc_feature
<222> LOCATION: (472)..(472)
<223> OTHER INFORMATION: r is a or g

<400> SEQUENCE: 48

```
atagtgcaaa tctgagtgtt aaccataata acacaaatct gagtgtcgca cagagaaaag      60
gataacgcat gtagcagatc aancatattt ataatcatag tgcatcgcag cccaatattg     120
aaacagataa aaatacatta accagtagag agttgtacca agagagaaca gaacttactt     180
cctgagcctg agctggggtg gcgactttgc cagttccaat agcccagact ggttcatagg     240
caagaacaac gttgctccag tccttgatct tctctgtaaa acaaacagcc atttgatcca     300
ttcagcctga ttttcgtat agggtcaaaa aaaacttggt aacttcaaag caaggcacta     360
aatgttcaca tgaacaaaac aaagggcaga cccagctccc acatgaatgt ggggtctttc     420
ccccacaaat gcggaaagga aaatccagca tgtaaattca tccaagcaac araaacaaaa     480
actcggccgg ggaaggaaac accgccctcc cggtattcta ttaagaagag accgaaacat     540
ggtcccggcc gaaaaaatcc ccgaacccta gcccccatc actagttggc cgtcatcgcc     600
cactctgcaa atgcccaacc ggagggtggg gntgcatgac ataacccgag agcgggcggg     660
gcacaacgaa gggattttt aaccaagccc gaaattcgcc ctcaagggg atcgaacccg      720
ggacctggag gtgctacttg gaagctttaa ccattacgct aaaggccctt tcgcagcgac     780
agaaacacac ataagttgat tcctaaacta agctgttac agaaaaacag taatgtccga     840
actccggata tgtagattat ctaacagaac tgatcaccag aagcaaaggg cctgttcagt     900
ttgggtttca gctgctgtgg ctagctgcag ctagcttata actacagtaa ctctactgtg     960
acacctgaga ggcagcagcc aacgactgca taaatgccaa ccgaacaatc tcaaccaaaa    1020
```

```
<210> SEQ ID NO 49
<211> LENGTH: 935
<212> TYPE: DNA
<213> ORGANISM: Zea mays
<220> FEATURE:
<221> NAME/KEY: misc_feature
<222> LOCATION: (84)..(804)
<223> OTHER INFORMATION: n is a, c, g, or t
<220> FEATURE:
<221> NAME/KEY: misc_feature
<222> LOCATION: (166)..(166)
<223> OTHER INFORMATION: s is c or g
<220> FEATURE:
<221> NAME/KEY: misc_feature
<222> LOCATION: (224)..(224)
<223> OTHER INFORMATION: w is a or t
<220> FEATURE:
<221> NAME/KEY: misc_feature
<222> LOCATION: (650)..(892)
<223> OTHER INFORMATION: r is a or g

<400> SEQUENCE: 49
```

| | | | | | |
|---|---|---|---|---|---|
| gatgtatagc | tacatttata | taatgaacca | acaaggcagc | aacncttcat | taccattaaa | 1080 |
| aaactaac | | | | | 1088 |

| | | | | | |
|---|---|---|---|---|---|
| atcaagagca | gcagctgctt | tgctgagaaa | caggctgacc | ccgcatttgc | acagttgcag | 60 |
| gcctactagc | accacttgca | gctnggttga | cttgccatcc | tatccaacaa | ggagaatgaa | 120 |
| gaatgattag | gtgctcccgt | atacagataa | acaatagcaa | acatastgat | catgggattc | 180 |
| atggcttatt | tttcactttg | aatcatatgc | aatattatnn | ngtwgcacag | tgttctttgt | 240 |
| ttgtactcag | tccctcaata | aaagagggcc | tccatatgtt | gacatactat | acttgatgac | 300 |
| tcnnnaagga | atgagaaaat | gctgccacaa | aaaagtctac | aacacaaatg | atctagttac | 360 |
| ctgttcttta | tctcccctgc | catggtcatg | aatgccttct | ccacatttgt | tgcatccttg | 420 |
| gcactagtct | caaggaatgg | tattccgatg | tcatcagcaa | gggcctatga | tgacaagcaa | 480 |
| catgcagcca | atttaactat | catcccggtt | gaaagaagca | tgtccagtaa | aagtaattaa | 540 |
| tgcagagaaa | tattaccttg | ccagcctcgt | aagaaactac | tctgttctca | gccaggtcac | 600 |
| acttgttccc | caccaaaagc | ttgttcacat | tttcactggc | atacctatcr | atttcattca | 660 |
| gccactgctt | gacattgtta | aagctctcct | ggtcagttac | atcatacaca | acctatagaa | 720 |
| atacaaaagt | ttaaacaaga | ctcagattaa | caaagatgag | ataatagcag | ataggaaaaa | 780 |
| aancgaaata | agaaaaagaa | agcntcacaa | taatgccatg | agctccacgg | tagtagctgc | 840 |
| ttgtgatggt | cctaaagcgt | tcttggccag | cagtatccca | ctaaatcaga | araatgtgga | 900 |
| gaaacataag | tgtcaaagct | tctaactgtt | aggaa | | | 935 |

```
<210> SEQ ID NO 50
<211> LENGTH: 579
<212> TYPE: DNA
<213> ORGANISM: Zea mays
<220> FEATURE:
<221> NAME/KEY: misc_feature
<222> LOCATION: (541)..(541)
<223> OTHER INFORMATION: w is a or t
<220> FEATURE:
<221> NAME/KEY: misc_feature
<222> LOCATION: (556)..(556)
<223> OTHER INFORMATION: n is a, c, g, or t

<400> SEQUENCE: 50
```

| | | | | | |
|---|---|---|---|---|---|
| cgacgaggag | attctcgggc | ttgaggtcgc | ggtggaagac | gccgcgggcg | tggcagaagc | 60 |

```
cgacggcgga gatgagctgc tggaagtacc tgcgcgcggt gtcctccttg aggcggccct    120
tggcgacgcg cgcgaagagc tccccgccgc ggacgaactc catgacgaag tagatcttgg    180
acctggtggc catgacctcg aagaggcgga cgatgttggg gtggcgcacg cggcggagga    240
tggcgatctc gcgcttgatg tgcgggacga ggccgttgcg cagggccttc tccttgtcga    300
gcaccttgat ggcgacggtc tcgccggtgt cgtcggcgtg gcgggcgtgg tacaccttgg    360
cgaaggtgcc gtggccgagc aggcggccca gctcgtagcg ccccagcagg aggccccgc     420 gcttggcggg ccccgaggag gaggccggcc gccggggctg cggtgacgcg tcccacgacg    480
gcggcggggt ggcggccatc aggtagagga ggaggtcagg cgcgcggaga acggagcgg     540 waggcagaat ggccgnttag gtggtggtgg tagcgaggg                           579
```

<210> SEQ ID NO 51
<211> LENGTH: 319
<212> TYPE: DNA
<213> ORGANISM: Zea mays
<220> FEATURE:
<221> NAME/KEY: misc_feature
<222> LOCATION: (21)..(279)
<223> OTHER INFORMATION: n is a, c, g, or t
<220> FEATURE:
<221> NAME/KEY: misc_feature
<222> LOCATION: (111)..(111)
<223> OTHER INFORMATION: s is c or g

<400> SEQUENCE: 51

```
cacctcggac accggaattc nccctgtag atcttacggt acatngccat gaggttctgg     60
tcatgaaaag gaaggtagcc agccatcagc acgaacagga tgacaccaca sgaccatatg   120
tccgcctngg cgccgtcata accgcggcgc gcgagcacct ccggggcgac gtagganggc   180
gtgccacana aggtgtggag gaggccgtcg gggtggaact gatcggccac cgccgagagg   240
ccaaaatcgg anaccttgag gtcgccgcgc tcgtcgacna gcagattctc gggcttgagg   300
tcgcggtgga agacgcccc                                                319
```

<210> SEQ ID NO 52
<211> LENGTH: 614
<212> TYPE: DNA
<213> ORGANISM: Zea mays
<220> FEATURE:
<221> NAME/KEY: misc_feature
<222> LOCATION: (44)..(568)
<223> OTHER INFORMATION: n is a, c, g, or t
<220> FEATURE:
<221> NAME/KEY: misc_feature
<222> LOCATION: (442)..(442)
<223> OTHER INFORMATION: s is c or g

<400> SEQUENCE: 52

```
gccaaacaag cactcttcta gttcttccgt ttctcacttt ctcnnnnnnn nnatctcccc     60
tttatatgaa taatataaat gtcannnnnn nncataagta aataaacaaa taaatcaatc    120
antattacta cgaagctgtc ctcaccgcct tctctctccc tccgaatcna aacgcggacg    180
caaatgttgc tccacgccgg tccctcgttc ctgctcgcac cacctccgcg cttngccgcc    240
gctccgtcgt cagcttcgcc gaggcgatcc aggacaccgc aatcctcgcc gncgangtcg    300
catttcgcgc gccccgctga tccgtggcc canagggngc gtcccgtcgc gcngaggccc    360
cccatggcga cggcgganga gggcgccagc tctgangtng gntcgccgt cgccgagtcc    420 gcacaggttc ggccgccact gscctcctc acatnncaga gtttacgcaa ttattatcac    480
ttgggncact cgtttgccaa ngattacgcg attacgccta acctgtcggt cgggtctaca    540
```

-continued

```
tngtagtcac actcacacga atgccccnaa ccgtttgtga gctcgtggtg atgatctgtg    600
ttccacctgc acca                                                      614
```

<210> SEQ ID NO 53
<211> LENGTH: 710
<212> TYPE: DNA
<213> ORGANISM: Zea mays
<220> FEATURE:
<221> NAME/KEY: misc_feature
<222> LOCATION: (1)..(710)
<223> OTHER INFORMATION: s is c or g
<220> FEATURE:
<221> NAME/KEY: misc_feature
<222> LOCATION: (1)..(710)
<223> OTHER INFORMATION: y is c or t
<220> FEATURE:
<221> NAME/KEY: misc_feature
<222> LOCATION: (1)..(710)
<223> OTHER INFORMATION: r is a or g
<220> FEATURE:
<221> NAME/KEY: misc_feature
<222> LOCATION: (1)..(710)
<223> OTHER INFORMATION: m is a or c
<220> FEATURE:
<221> NAME/KEY: misc_feature
<222> LOCATION: (1)..(710)
<223> OTHER INFORMATION: k is g or t
<220> FEATURE:
<221> NAME/KEY: misc_feature
<222> LOCATION: (1)..(710)
<223> OTHER INFORMATION: c is a or c or g
<220> FEATURE:
<221> NAME/KEY: misc_feature
<222> LOCATION: (593)..(617)
<223> OTHER INFORMATION: n is a, c, g, or t

<400> SEQUENCE: 53

```
agcatsacca gaagcagagc ctgatggaca aggcgaaggg gttcgtygyg gagaagatcg     60
cgcacatccc caagcccgag gcsacgctgg acggcgtgac gttcaagggc ctgagccggg    120
agtgcatcac gctgcacagc agcgtgaacg tgtccaaccc ctacgaccac cgcctcccca    180
tctgcgaggt gacctacacg ctccggtgcg ccggcaagga ggtggcgtcc ggcaccatgc    240
cggaccccgg ctggatcgcc gccagcggct ccaccgcgct ggagatcccc gccaaggtgc    300
cctacgactt cctcgtctcc ctcgtcaggg acgtcggccg ggactgggac atcgactacg    360
agctccaggt cggrctcacc gtcgacctcc ccatcgtcgg caacttcacc atcccgctct    420
ccacctcygg cgagttcaag ctccccaccc tcaaggactt gttctgatct agtagtagct    480
cgcttgcctt stgttctgtg cgggcgcgca ccagcgatct gtacgacgas cttttgcaaa    540
taaamgamgc agctcctctg ttctatatat ctmagkgrat gsmtrrkyta aknnnntnnn    600
tgrytnnryn nnnnnnnaaa taaagagctg gatttcrttc aggttcctgt ctcyaagctg    660
gattycatts gggcatccac crtgatstgg atgtgcctgc cgcgtccgtc               710
```

<210> SEQ ID NO 54
<211> LENGTH: 838
<212> TYPE: DNA
<213> ORGANISM: Zea mays
<220> FEATURE:
<221> NAME/KEY: misc_feature
<222> LOCATION: (8)..(825)
<223> OTHER INFORMATION: n is a, c, g, or t
<220> FEATURE:
<221> NAME/KEY: misc_feature
<222> LOCATION: (126)..(126)
<223> OTHER INFORMATION: r is a or g

<400> SEQUENCE: 54

```
acgacgangg cggcgtacnc cttggggatc tccgcgacgc cggagaagcc gaactnggcg    60
ccgatgaggc tgcccacgac gatctggcac gcgagcatct gggtgccgcc ctgcaggaac   120
agcttrcggc ggccgaggcg gtcgacggtg acgatggaca cgaaggtggc gaagacgttg   180
acgaggcccg tgatgacggc ggacatgagg gaggcgtcgt ccgcgaagcc cagcgtcttg   240
aagaggacng gggcgtagaa catgatgacg ttgatgcccg tgagctgctg aacatgggg    300
atgncgatng ccatgacnag ctgcgggcgg tagcgcggcn gcaggatgtt ncgccagggg   360
tgcgccacca gcttggactc gtcgctggcg gccaccaggt cnctgtactc ctcctccacg   420
tcgtcggtgc cccgnacgcg cttgagcatc cgcttggcgg cgtcggtgta gccgcggtcg   480
atgagggagt tgggngtgtc gggcaggaan agcgcgccca cggcgatgat ngccgccggc   540
acggccgcga gcgcgaggct gacgcgccag ccccagccgc ccntnatctt ggcggtgccg   600
tanttgatga ggttggcgca naggatgccg atggtgacca tgagctggaa gccgatgttg   660
agcatcccgc ggaggcgcgc cggcgccatc tccgagaggt agacgggcac ggactggttg   720
gcgaagccna cgccnacgcc gaggaggacg cggccgagga tgagcatgcc cacgtccttg   780
gcggcgccnt tgagcgcggc gccnacnagg aacgtgacgc cgccnccgaa catggacc    838
```

<210> SEQ ID NO 55
<211> LENGTH: 844
<212> TYPE: DNA
<213> ORGANISM: Zea mays
<220> FEATURE:
<221> NAME/KEY: misc_feature
<222> LOCATION: (69)..(824)
<223> OTHER INFORMATION: n is a, c, g, or t
<220> FEATURE:
<221> NAME/KEY: misc_feature
<222> LOCATION: (193)..(193)
<223> OTHER INFORMATION: r is a or g

<400> SEQUENCE: 55

```
ccagttcaag acagaggaga tgaccaacat catgaaggac ttcgacgagc ccgggttcct    60
ggccccgann ccggcctctt cctcggcccc accaagtaca tggntcatcc aaggcgagcc   120
cggcgctgtc atccgcggga agaaggtnnn nactgatccg tcgtcgtcta tgctcccct    180
ctcgatctcc cartataatg cacgtcgatc atctttctct tgtttcccta gggatctgga   240
ggcataactg tgaagaagac agggcaagcg atggtggtcg gcatctacga cgagcccatg   300
acccccggcc agtgcaacat ggtggtcgag aggctcggcg actacctcgt agagcaaggc   360
ctgtgaatgg attcatttaa cctcgctcgc tcgcttgtcc atggttcgag catccagcag   420
caacgatacc aacatcagca ttatttaatt ggtagcctcc tctagctacg cacgcatttt   480
nagtcccta cacgcccttg gattgtgcgt ggctctgtta atcatctctc atccttcgtc   540
tgccatttct cccctgcccg tcgccgatca ccagagattt tgttccttg ttggtaccat   600
gcattttggc aaataatttt gtaattccac ccccaaatta aagtttggtt gtcgtatggt   660
ttgtaaaccc agaacaatat atatannnnn ntgtgtgtga ttgaactgtt cctgtctatt   720
cttttttgtaa nacgggaata tatatgtatg cattttgtgt gatgcatgcc ttccagggcg   780
acgactaatt aatgtgcaac cagtcctcca tcnnnncatg nnnntatggt gaagggctaa   840
aggc                                                                844
```

<210> SEQ ID NO 56
<211> LENGTH: 652

```
<212> TYPE: DNA
<213> ORGANISM: Zea mays
<220> FEATURE:
<221> NAME/KEY: misc_feature
<222> LOCATION: (1)..(652)
<223> OTHER INFORMATION: k is g or t
<220> FEATURE:
<221> NAME/KEY: misc_feature
<222> LOCATION: (1)..(652)
<223> OTHER INFORMATION: s is c or g
<220> FEATURE:
<221> NAME/KEY: misc_feature
<222> LOCATION: (1)..(652)
<223> OTHER INFORMATION: y is c or t
<220> FEATURE:
<221> NAME/KEY: misc_feature
<222> LOCATION: (1)..(652)
<223> OTHER INFORMATION: v is a or c or g
<220> FEATURE:
<221> NAME/KEY: misc_feature
<222> LOCATION: (1)..(652)
<223> OTHER INFORMATION: m is a or c

<400> SEQUENCE: 56
gtggaagccg ccgcggcttt cttgaacaaa gccgtcaagc cagtgcttgt aggtgggcca      60
aagatgaggg tgtccaaagc atgcgaagcc ttkgcagagc tggcagatgc ctgcggctat     120
cccgtcgccg tgatgccttc tgcgaagggg ctagtgccag agcaccactc taggttcatt     180
ggcacgtact ggggtgcggt gagcactcca ttctgtgctg atcgtcga gtctgcvgat       240 gcctacctat ttgctggccc cgtattcaac gactacagct cggttgggta ctcgctgctc     300
ctcaagaagg agaaggccat cattgtccaa ccagagcggg tggtggtcgg scayggaccc     360
gcgtttgggt gtgttctgat gaaggatttc cttcatgccc ttgcaacccg tctgaagaag     420
aacactgcyg cgtatgagaa ctaccgtcga atttatgtgc ctyyaggcga accacttyca     480
tcygaacctg gcgagccgtt gagagtgaac gtgctmttca agcatattca ggcaatgctg     540
tcyggcgaca cggctgtcat cgcagagact ggggactcgt ggtttaactg ccagaagctg     600
aagctaccgg aaggctgtgg gtaagctcct ctttcgaatc atggttttgc tg             652

<210> SEQ ID NO 57
<211> LENGTH: 659
<212> TYPE: DNA
<213> ORGANISM: Zea mays
<220> FEATURE:
<221> NAME/KEY: misc_feature
<222> LOCATION: (23)..(647)
<223> OTHER INFORMATION: n is a, c, g, or t
<220> FEATURE:
<221> NAME/KEY: misc_feature
<222> LOCATION: (173)..(173)
<223> OTHER INFORMATION: k is g or t

<400> SEQUENCE: 57
ccaacagatg ctcaggtgaa ccnagtccag cagcataggc ttctaaacct actattaggg      60
gaaaangaaa taacttatgg cgtcgaccac aaacacactg atgcacgaga agtatttcta     120
gctgttgtta tctgtgaggt tgatcctgcg gcggcggcgg gctcgacacg atktgaccat     180
aaacgaactg gttccacgtg tccggcacgc cggggaggca ccagtggatg caatccgcga     240
acttcctcgg gttcgccttc tgctcgggcg tcaggagctt ccctgccgc agcgtgtgca      300 cggaggtgtg cgcgtccttg cggatctccg acagcgcggt cacgtcgacg aagcgcaccg     360
gcaccttctc catcgacctc gtcacgcgct gggcggccgc gaagaggtcc cagtccgtgc     420
ccacctccag tttcttcgtg tagttgatcg ccggctgcgt ctcggagaag cattttacgg     480
```

```
cgttggggct gccccagcct tcactcctgg accacaacaa gacagtgagt gannnnnnnn    540
nnnctgtgga ggggcagaaa ttctgcatat caagcaaggt acggatggat acttactgca    600
tatgtaccgg tgacacgctc atgaatagga ccgtgcttct cttgggnatc aatgtgcgc     659
```

<210> SEQ ID NO 58
<211> LENGTH: 600
<212> TYPE: DNA
<213> ORGANISM: Zea mays
<220> FEATURE:
<221> NAME/KEY: misc_feature
<222> LOCATION: (21)..(486)
<223> OTHER INFORMATION: m is a or c
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (173)..(173)
<223> OTHER INFORMATION: k is g or t

<400> SEQUENCE: 58

```
ggatctggac aatatttcac magccaaaaa gacnaaaaaa aaatcaagca cctgtcttcc     60
atccaagcaa cactgtacag gtcacccaag caagtgtcat actccggtgg agggctcggg    120
aactcgccag ggcagtatgt cccccagctg ctctcctctg catttgacgc ggkggtcgca    180
tacacattga tgtcattcgg caggaggccc tcaaagatgc tcccagattc gcatgcttca    240
aggtaaaaga cctacaaaag gtgaaagaat acacatatac ctcaagccct tgctttacat    300
atcacaacat ttcagagcag aactgaacaa acagctaacg gtaccaggct tttgtaggtc    360
ccggcagcat gcttcttctt caggacatct acgaggtcat caccatagag atatggatac    420
gtaggcattc ctgaattttt ttacagagta ataactgtg tctatttgg ttctacatgc     480 atgtamgaac tgatatttta tctaagaaac atctaatctg aatgaaatca gtagcaatta    540
gttgcgagta cagaccaagg acaccaggac ccccatggtc actgtagaaa acaaagatat    600
```

<210> SEQ ID NO 59
<211> LENGTH: 890
<212> TYPE: DNA
<213> ORGANISM: Zea mays
<220> FEATURE:
<221> NAME/KEY: misc_feature
<222> LOCATION: (1)..(890)
<223> OTHER INFORMATION: k is g or t
<220> FEATURE:
<221> NAME/KEY: misc_feature
<222> LOCATION: (1)..(890)
<223> OTHER INFORMATION: m is a or c
<220> FEATURE:
<221> NAME/KEY: misc_feature
<222> LOCATION: (1)..(890)
<223> OTHER INFORMATION: r is a or g
<220> FEATURE:
<221> NAME/KEY: misc_feature
<222> LOCATION: (1)..(890)
<223> OTHER INFORMATION: s is c or g
<220> FEATURE:
<221> NAME/KEY: misc_feature
<222> LOCATION: (1)..(890)
<223> OTHER INFORMATION: w is a or t
<220> FEATURE:
<221> NAME/KEY: misc_feature
<222> LOCATION: (1)..(890)
<223> OTHER INFORMATION: y is c or t

<400> SEQUENCE: 59

```
taactgctaa waactatagg cgggattatc atctgggttc aaatatttgg acttatgtgc     60
```

```
tcctttgagg cggcgaggca gccacaccca cacgcagtgg cctgtggcgc ctgggcggtg    120
agtccgccta tgactgcgaa ygttayratt ttattrggca tccttttag ttgattgrat     180 tggttgtagc ytgaaccta tctaccatty tatctcccct gcttgtsgtg ttytatgtcc     240
ctgttcrgca gctcatccca gcgctgcttg gcagccatac cayagtsctt ttatgctcac    300
agaggcagca gcagcagcag ccgagacaky agtggcttga agtgcagccr agaygrmyta    360
ttggcatttt atctrtctct yctgagakat gaaatgrgac attgtaggtt tatgcatatt    420
cagccrcctt tgctagttat tatgtgattt tgtaaayttc ctgagcctgc sactaaatta    480
tttcaacata tttagtaatg cgmtgggagt atatgcagaa sttaagtacc ttttctgttt    540
gttttgtcaa caaagtgagc aaaaaaacaa tgcttygttw tgtgtggcca tgttgcatga    600
gtgawgaagc acrtgtttct ttcttttcac ctgaaaagta aaatarttct gcaagyagaa    660
tctckagtta yggaatgtta tttctgaatm ygcagttcrc atcatgttca gtcaagtact    720
agcactgarg gttgcttcct ttttgatatg tgcagaaagc acttgcaggt ctgagaagaa    780
tcaatttaga tgggcttcga tggcgcgtat ttgatgctaa gggtcaggtt aggattgttt    840
ttctagyttg artagcatgg atgaacttat ctcaagaagg atagaggcta               890

<210> SEQ ID NO 60
<211> LENGTH: 505
<212> TYPE: DNA
<213> ORGANISM: Zea mays
<220> FEATURE:
<221> NAME/KEY: misc_feature
<222> LOCATION: (267)..(505)
<223> OTHER INFORMATION: r is a or g
<220> FEATURE:
<221> NAME/KEY: misc_feature
<222> LOCATION: (387)..(411)
<223> OTHER INFORMATION: n is a, c, g, or t
<220> FEATURE:
<221> NAME/KEY: misc_feature
<222> LOCATION: (481)..(505)
<223> OTHER INFORMATION: k is g or t
<220> FEATURE:
<221> NAME/KEY: misc_feature
<222> LOCATION: (481)..(505)
<223> OTHER INFORMATION: s is c or g
<220> FEATURE:
<221> NAME/KEY: misc_feature
<222> LOCATION: (481)..(505)
<223> OTHER INFORMATION: w is a or t
<220> FEATURE:
<221> NAME/KEY: misc_feature
<222> LOCATION: (481)..(505)
<223> OTHER INFORMATION: y is c or t

<400> SEQUENCE: 60
atcaacgtgc agaacaagaa ctcgtcctac ttcgtggagt ggatccccaa caacgtgaag     60
tccagcgtgt gtgacatccc gccgaggggc ctgtccatgg cgtccacctt cgtcggcaac    120
tcaacttcca tccaggagat gttccggagg gtgagcgagc agttcactgc catgttcagg    180
aggaaggctt tcttgcactg gtacacgggc gagggcatgg acgagatgga gttcaccgag    240
gccgagagca atatgaatga cctcgtrtcg gagtaccagc agtaccagga tgcgactgct    300
gatgacgatg aggaggccga gtatgaggac gaggaggagc cagctgatgg catgtgaggg    360
gaggctgtta aatgtgaagc ctggtgnnnn nnnnnnnnnn nnnnnnnnnn natgtcccct    420
ttcgtgttgt cgccatgtta tactagtaca ctagcatacc accctcgtgg cccattccgt    480
cgatsgtrsy tgttktrsct kgwgw                                          505
```

<210> SEQ ID NO 61
<211> LENGTH: 547
<212> TYPE: DNA
<213> ORGANISM: Zea mays

<400> SEQUENCE: 61

```
tagggtcctg ctacaagaga tcgccacatt ttattgctac ggaagtccag ttgtgtctgt      60
ctgtttggtg gtcatggata tggttcggtt tttactgctg taaaaaggga ctggggaaaa     120
aatgcaaact gacttggatt ttttgttctg ttctgcatga agatgaaatg gtagggtcgt     180
cggaggagga cgaagcatgc tcgggaggag acacggaggc gacggagccg ggcagcagg      240
agcacagctc ccgcctggcg gaccgtgagc tgaaggagat gctgctgaag aagtacagcg     300
ggtgcctgag ccggctgcgg tccgagttcc tgaagaagag gaagaaaggg aagctgccca     360
aggacgcgcg gtcggcgctc atggactggt ggaacacgca ctaccgctgg ccgtacccta     420
cggtaaccat gcatgcatcc tgcaaaacac gcagcagcag catcgctcgc tggaatggca     480
gatctgtgac cagcattagc cggcggtgca ggaggaggac aaggtgaggc tggcggcggc     540
gactggg                                                              547
```

<210> SEQ ID NO 62
<211> LENGTH: 490
<212> TYPE: DNA
<213> ORGANISM: Zea mays

<400> SEQUENCE: 62

```
tagccgtcct gcaaacctcc tggataaagt ttggacctta tttaggaaga gaagcaccct      60
ggacgagccg cgtggtatca attcttgccg ctctcctccg ctttcatctt cttctcccac     120
ctacgtttct ggtggaaaaa aagtttcaaa gcacgaacag agagatgagc cagttagatc     180
ttttttcaag ggatgccttc gttcaatcac tattacagct atcgttacat ttgatctgaa     240
aacacaaaca tggcatcttt gtgcaccaag gtcaatgcag gataaaaagc tggatcgctg     300
acaacagata tttgattgtc cgttggaaaa tatttttttca atggccacag ttttagaaaa     360
tattttccca aaattatgtc attactatta ctagactagc aaagtagata atggcgagca     420
accatcagga aatcttgcca tcagtgcagc agaactgcag accttatat agcgcacca      480
gcagaatcta                                                            490
```

<210> SEQ ID NO 63
<211> LENGTH: 420
<212> TYPE: DNA
<213> ORGANISM: Zea mays

<400> SEQUENCE: 63

```
cgagtggttt gaggttggca cacaagtatt gaatattgat aaatcacaca tacatctaca      60
gggcggacaa aggtgacacc attaaagtgt caggtgttta tcaccttgat gagaaacaga     120
aggcctcagc tgtggctgag ctaacccgga ggctctcaac aaatcagaac acactcacag     180
tcggtggact gtacacagtt gatccccaga cagctgtgaa ggcaagactc aataacactg     240
gaacgcttgc cgcgcttctt cagcatgagc ttaaacccaa gtcgctcttg acaatctctg     300
gtgaattcga cacaaaggcc ctggacagat ccccaaagtt tgggttggcg cttgcactga     360
agccctgatc agatcatccc atgttgattg gtggtgaatc ttgaattcat tttttttttt     420
```

<210> SEQ ID NO 64
<211> LENGTH: 1015

```
<212> TYPE: DNA
<213> ORGANISM: Zea mays

<400> SEQUENCE: 64
cttaatatgt gagttttcta agttagcaat cttatatatt taggcactgt atgcgactgt      60
tgtttgacaa cccttaagct tatttgatac ctgtaatatc tttattgatg gttaattgca     120
aatccctgct tgatgcatct caacttcaag ttgttttgta gctggtttag tgcataaaat     180
tagtcaaaat attaatatac cggtcaccgt catttcacct tttctcactg acatttctca     240
aatggagttt tgaaagaagg ttttacttca cttatatacg tttgcaacaa acatgagttt     300
ctaactcact cagattataa aaaaactcag ccggggaggg aatgaccgtc ttgctggtat     360
tatattaaga agagaccgaa acaatggtcc tgccgagaaa atcctcgaac cctggccccc     420
atcactaacg gaccggtgtc aaccgtcaac tctgcaacgg cccaaccgga gggtggcgca     480
taggacatcg taacccgaga ccgagagcgg atggggcaca acgagggaat ttttttaacc     540
aagccgaaaa attcgcccct gaggtgttac tcggaagcct ttaatcacta ggttagaggc     600
cctttcgcaa ctcactcaga ttattgcatg tacagaaatt ggtcaatgta actgactttg     660
ctagtgtttt tagtttcact gaaaaaagga tctcttgcag taagctggta gcagtatggc     720
taatattaag ctgtgcctcc agtaagggtt tggtgctcag cattttgttt ttctaattga     780
gtcaaaagtc ttatgtataa tcttatatta aatgaaattg atgtcatagt tcctcaacag     840
atataatccc atttttaagg acgtttaacg tcttattatt gcagttacat ccaaattttc     900
tgtaacttat ccaaccttct cttgcaggaa caacaaggga gacaacctta ctggagctta     960
ctaccacaag gtgagcgaat tgacaaacac agctgttggg gcagagctta cccac         1015

<210> SEQ ID NO 65
<211> LENGTH: 900
<212> TYPE: DNA
<213> ORGANISM: Zea mays

<400> SEQUENCE: 65
acaactacaa ggacctcgaa gccgaggctg ctgcggcgac ggaccaggtg ccgccgtcca      60
tcgtcaaccc cctgctcagg acggggtacc acttccagcc ccccaagaac tggatcaatg     120
gtaatgtaaa gctactaact aatccaccac ccaacgtcgt ttgaaggtga tgtgtgtgtt     180
aagcatctcc tgaaatatat aagagagcga ggctagtaat cggcttgttg ttcagggttt     240
tggtttacca cttgtagcct caactaataa agctatatat atgagagcga cgagagagaa     300
gagacaaaac attcatgagt atggtcagac agactagcta gctagacacg gcagagaaat     360
tacgagagtt aaaaaaaatg cgcttgaagg gtgaaccaaa acaaaacaac tttagtacta     420
tgcgtcaaca aagctgtgtt catgtgtcag ctagcactag agtcatagtg cgtggccagt     480
gagctgttgt ctagcaacca acgcgaactg aagtttgaga gcgtactcgt gttctcgatc     540
tcttgcagcg caaaggtctt cgtacgtgat caggaatatt gcaccattta ctgcttaatt     600
aattaagtac gtacgtactg tacgtttggc tctacctcat cttctaatct tttcggtgct     660
gtcttgtgct ctctcggctc tgattgcatc gatcggcggc ggcgtgaact ttgcaacggc     720
ggcagatccc aacggtaata agtcgttttc cccacccttt ttatttcctc taataatgca     780
tcaatattcc aactgggtgc atatgcatgc gcgcagcgcc catgtactac aagggtggt      840
accatttctt ctaccaatac aatcccaagg gcgccgtatg gggcaacatc gtgtgggcgc     900

<210> SEQ ID NO 66
```

```
<211> LENGTH: 344
<212> TYPE: DNA
<213> ORGANISM: Zea mays

<400> SEQUENCE: 66
gggcaggcgt gtacaagccg ccatacggag gattcgtgga cgtcgacgtt gaggagcacg      60
agaccatcaa tttgagaacc ctggtgagtt ttttttttctt tttactttttt tgctgctttg     120
tccttcagcg atctgctcag ttcgtttgtg atttgcacag attgatcact cggtggtgga     180
gagcttcgga gctgacgggc ggatgtgcat cacggctaga gtgtaccctg agcacgcgga     240
gacgagcaac aacccacatgt tcgtgttcaa caatggcaca ggcacggtgg aggtgtacaa     300
gctcgaggca tgggagctcg cggcggcgac cgtaaattcc gttg                       344

<210> SEQ ID NO 67
<211> LENGTH: 7375
<212> TYPE: DNA
<213> ORGANISM: Zea mays

<400> SEQUENCE: 67
aatgtcaagt atatccattt aaatatcatt aggtcccgtt tgtttccttt cattttaagg      60
aattggaatc ttactaataa aataagctat tttttttagaa tacgagattc caccactttc     120
caaagttatc agataagcct atctcaaatt catggggtga gagatggaaa ttgattctat     180
agatttacat gttattttcc cgatgtacaa cttatatcat actctcctaa ttgcttcgct     240
ataacataaa tgcactatat aactatctct cttatatgat ttaggataat atacaaatat     300
attacatata taaatatatt aacttaatta gttttgtcta aattataatt attaaaatgg     360
aattcaattc aacgaaaaca aacgggccct tacaaaattt ctagtatcat ttaaccatct     420
attcaacaca ccaaagataa ttggataaaa tagcaacact aggacaaata ctacatagca     480
cattacatgt tccattatat ggtcattaaa ttgtcgttaa gccttctata acattatggc     540
ctaaaaggtt gttaaatagt aaaaaaagat ggatgactaa agtccaagtt catgcttggg     600
ctaagtttat attgggtatt ttataccacg ggttaacggg tatgggtgaa ggcggaacgt     660
tctgattccc gttacttat tgggtgaaga ttttttgccta ataatagacc tacgggtgaa     720
tatttatccc acatatatat cctagtggag tcaatatcca tcggatatcg gtcgtgggta     780
cccattgcca tctctagatc gaagagtaga aattacttc ctaaacctct ctctgtctca     840
tgcagcacaa tagacgcttt gtttcgttgc aacagcttgt ttctcttttga cgtccaaatt     900
cgtctatcta cggacccacg gccgcccaga ttttgaaatt tcaaaacgga acacaccccg     960
gggttcggag tatctgctgc ccctgcggtc ctggaaagcc cggcccacct ctcacttgca    1020
ccaccagctc accggttccg gtcaacagtc tctcgcgggt gcctgtgccg gtggtcctcc    1080
gtcctggctc tggctgccac ccacctcccg attaccgttc tcgcctcgac ttcaaaacaa    1140
gagcccagat ctaaaccaag cacgcccatc tttgccacac cacaccccca gtattcgaat    1200
ctctcgtgcc cagatgcggc aaattaaaaa caacggacag acgcggaacc cctccggcca    1260
acggatctca ccctctgcgg catgggtccc actcacgctc gggtccactc gacagcgtgt    1320
agggcagaga ggcgagcggt accagtacca taggcctccc gacgcagtcc gggcagcggg    1380
ccccgcggat tggaccggtc aaaaggcgtg gcccaaccaa accccaaggg atccggcgct    1440
ttgtctgcac gtgaatggtg ccaagatcgc ctggttgaca ggtgggaccc gtgaggttgt    1500
agacccacat gtctgtggcg ttaaaggagg ggggagggat cggcgggcgg gtggtgcgcg    1560
cgggcaggcg ggcgtcgcgt ggtggtggtg gtggtgggtg ctttgactgc aggcctcggc    1620
```

```
agcaggcaga gaggactaga ggagtcgggg cctcggagga ggggagggag agggcgaaga    1680 gtaggggaa  ccaaatcttg aagggtaaac ggagagttct ttcgtggagg aggaaggggg    1740
ggacagcagg aggagggtag aggtatgtgc gcacccatct gttcttgctc ctgatttggc    1800
tgtttgtttt ttctgtctgt tcttcgctgt tggtagtttg tgaccgtgaa tgggcgttcc    1860
tggtccatgt tcgcgtgcgc tgctgccgat tctgggagct ctctggtcgt ccgtctcgct    1920
gggatctgcc ttttccccgg tgagagccgc ggaacgttcg ccgccttttc ttactcgcgg    1980
gccagttatg gtttctggag cgttttctct gttcttggcg aggtggtcat cgctctgaga    2040
acgatgcgct ctttctccga gtttgtgctc aagttttcgt cagcctagag gctatagcgt    2100
ttgctgcgga tctcacgact tctctcttcc tcttctctat tggtgcatac gttttcatcc    2160
gaaatccatt agttagtgcc cgagccgtca attcttgtg  gatttgcttg ttccccttcg    2220
ttacaggctc ggaaatgccc ctgaacagat tcacagggt  cctagattag gattattttc    2280
tatgactttc caagagtcag gagcacgatt gctttctctc ggctgtctgc ctggttcatg    2340
actcagccgg gtttgcaagc ctaggaagaa cttgctcacg tttcttacat ttatctagat    2400
tcgagggacg ggttgtactc gttaacaaag ttcacctcgt tagtcattaa agctccgctg    2460
ttgtgaatga tgctgccatt gcgatatctg gaatcatcgc tctgatcgat ttggttgtta    2520
atccacttac aggtagctca atagatctac tgctctcggg ggagttaatg caaagctgag    2580
ttgctgcacg ttggctttct tcagagatgg cttcagctgg tgtagcccca tctgggtaca    2640
aaaacagcag cagcactagc attggtgccg agaagttgca agatcagatg aacgagctaa    2700
agattagaga tgataaggtg aagatgcctt gatatcttgt ttcgggctta ctgtaatttc    2760
ctcaagatta tgtgaaaaat gggactgtga tgtaaccttt ggtgtgaatg ccaaatgcag    2820
gaagttgaag caaccataat taatgggaaa gggactgaaa ctgggcacat aattgtcacc    2880
actactggtg gcaagaatgg tcaaccaaaa caggtgagtg cttttactgca tttgatcatg    2940 atttatcaac tattctacat gttttagtg  catgtctgaa tctaataatt gagagtcaag    3000
accataattt aatgtccttc ttttgcatat tgccaatata tccatgttgc taacttataa    3060
gattgtggag ttgttctgat cagttttgtc agattctttt tgtataataa tgtgtattta    3120
ttggttgcat ttgcagacag tgagctacat ggctgagcgc attgtaggtc aaggttcttt    3180
tgggatcgtc ttccaggtta tttgcaataa cttgtgactg actttgatat gtactattat    3240
gtagccgcct gtggtgttgc tttccacggc gctgcacatg ttttagatct tcatatcttg    3300
cgtgctataa atcacctttc ttaatcagat gccatttcac ctgttcatag gctaagtgtt    3360
tggagacggg tgagactgtt gccataaaga aggttcttca ggataagcgt tacaagaacc    3420
gcgagttgca gaccatgcgc cttccttgacc accctaatgt tgttgctttg aagcattgct    3480
tcttttcaac taccgagaag gatgagcttt atctgaactt ggtccttgag tatgtgccgg    3540
agacagttca tcgagttgtg aagcatcaca acaagatgaa ccaacgcatg ccacttattt    3600
atgtgaagct gtatatgtac caggtaatgg tttgtcctgt tccttttttgc tgttgtttta    3660 attatacctt aaagcttatg ttttgggccc tgtttgatgt tgaaactaac aaacatattt    3720
catttcgcct aaatattgtc tgctccaatg aatgtgctag ttcttttttca atatttgata    3780 ttatattgga ttttggcaga tatgtagggc attggcttac attcatggca ctattggtgt    3840
ctgccacaga gatattaagc cacaaaacct tctggtatgc tggaaaatct gctattttgc    3900
tactgtatct tttttgtaaag aaatgatttg tactttgaaa ttgatgttca aacttcacta    3960
```

```
caggtgaacc cacacaccca ccagcttaaa ctatgtgact ttggcagtgc aaaagttctg    4020
gtcaaggggg aaccaaacat atcgtacatc tgctcccgat actataggc tccagagctc    4080 atatttggtg ccactgagta taccacagcg attgacattt ggtctgctgg atgtgttctt    4140
gctgagctta tgctagggca ggtaaggtgt ctcaaatttt tattgccatt ttaaaaaagg    4200
ttttcaagcc aacaaggtcc tttcagttca cactgtctta caagaactat ttggacagcc    4260
tttgtttccg ggtgaaagtg gtgtggacca acttgttgaa atcatcaagg taattgtcgg    4320
ttctacaagc ttgtgaattg tcttctatag aagcataaaa tctgatcacc cctaaaatga    4380
ttttgtatgg caggtcctcg gtacgccaac aagggaagaa attaaatgca tgaacccaaa    4440
ttacacagag tttaagttcc cacaaatcaa agcacaccca tggcacaagg tgctcaaatc    4500
tttctacatt ttgttacaat actctaagaa aactgttact gttgtgttac taatttactt    4560
tttgtacatt ttatctttca ggtattccac aaaaggatgc cgccagaagc tgttgatctg    4620
gtctctcggc tactccagta ctccccaaat ctgagatgca ctgctgtaag tgcatgccat    4680
tgtacattat acatgatgga aatacccctg ttgactttgg ttttctaaga tcttcatgaa    4740
tgttttgtcc agatggaggc acttgttcac ccattctttg atgagcttcg agatcctaat    4800
actcgccttc caaatggtcg cttttttgcca ccactattca atttcaagcc tcacggtatg    4860
tttcatgcct acataattca acatcgttat catagctgct acaaccaggt agcagtgtag    4920
tactaagttt gttctttgta tatcaccacc ttacatgctc gccacctctg ttctgcagaa    4980
cttaaaggag tcccatcaga cattgtcgcg aaattgattc cagaacatgc aaagaagcaa    5040
tgctcctatg ttggattgtg aaatgaccgc gccttgagac tggaacctgt ggttgcaatt    5100
gtgaatttcc cctgggatgt ttgacgatct gaggcatgcg agcctgttgt tgaagatgca    5160
aggttacgta cttgtacgac aatgtgacct gtgtagctga gtagtctatg tcgcagtgac    5220
atgtaacggc accccccttc ctactaactg acgcttactc gagattgcca tagttgatct    5280
tgtaatttgt tatagagcag tatgaatgta tttatggtag cttgaatcta tgtatggatt    5340
cacttcgttt ttccatgttt ccttgtctcc agacccagat tgctaccgta ttgtttcaga    5400
attcctagct acctgttgcc tattgagtat tgactaccag cttgcacttg tctgttattg    5460
cactggctgt ggaatcagct gttgattttt gccacaatat tttagttcag atgtactccc    5520
tattctaaaa agaatgtgaa atcttactaa tagaatagac tacttttttt agaatttctt    5580
tccattttga ggaattaaaa tcttactaat agaatagact actttttttt agaatgtgac    5640
attacaccac tttctaaagt tatcatataa gcctatctca tttatggggt gagagatgaa    5700
aattgattat atagatttac atactgttttt tccgatgtac aatttatagc acacccttct    5760
acttgcttcg ctataacata aatgtagtat ataactatct ctttcatgtg atttaagata    5820
atatataaat atattacata tataaatata tgaacttaat tagtttatc taaattataa    5880 ctattaaaat aaaattcaat ttcaacgaaa caaacggggc cttgattaat tataaaatgt    5940
atttttgtaa taagttgatt taaagctata atgtaaatac tatttactag aaacttggtt    6000
aaatatgaat tagtttaact aacgagttta attggcatac cacttatagt tatattcttt    6060
gagacggagg gacgagtacg ttgttcgatc ggtctggaag tatgctgact tgatcgttct    6120
taccagaaag ttgcattatt gcagcgtttg agacgactga cgaggaaatg tgacacgcag    6180
atgctactca gtgcttggca ggactgcatt ccaagtggtc cttctgggga gagaggaatc    6240
atagactgta gctccggttt cttgaaaaaa aacggttccc gtgaaatggc aggtatggtt    6300
ctccggttcc tttgaaaact actctttgta aaatgaagta tgcttggctc tatcgaagtt    6360
```

```
agctgttgtt aacagccata ccagacaggt tctttcagtg tccggttaga ttttgaggcg   6420
tcgagggttg tttggttgag aagtggagag ttcctttaga gtgtgtttag ttgagaagtg   6480
gaggaaaatg gatcgactat attcctattt tttttatgtt tagtttccaa gaaaagcgga   6540
gcagagcggc tcctgaagtt ttagaaattt accataaata gtttaaatgc tcccgctccg   6600
tcaaaacgaa catacacgag cgctctcctc cctctacttc cttctacaac cgtatgtctt   6660
tccaatcaag caaagaacgg agtagctctg ctctattcta ctcttaacca aacaaaaaaa   6720
tgaagtgact ctgttctgct tgtcaaatgc gaaatagaat gattctattc taaaaaattg   6780
gaatagagcc gctccaacca aactaacctc actcgaggga ctaaagttta gtctttactc   6840
tatttgattc caaggactaa aagtattcat aacatattaa atgacttgaa aactaaaatg   6900
ttcttaacat tcttccgcca ttagcataac taaaataaac tagggataag tgaaattaat   6960
atggactaaa acaatttggt cgctgtttta ttcccatatt tgacaattta gaaattaaat   7020
aaaactaaaa tagatggatt aatttttagt tcctcaaaca attttttcta acaatttcg    7080 atggactaag tttagtcatt tttcataaga aattaatatg gactaagggc ctgtttgttt   7140
acccctcaga ttatataatc tggattaaat aatcctaaga ggcaaacaaa cagtctagct   7200
tatttgtcga gattatataa tctaactcct ggattatgat aatccataag caagtgagga   7260
ggtgcttatt tcagattatt ttttccact tctccactac cctttcaagt ttcctagaaa    7320
ttacccacca ttgccattat aacccaccat tggcattctt gtcttcctca tacaa        7375

<210> SEQ ID NO 68
<211> LENGTH: 568
<212> TYPE: DNA
<213> ORGANISM: Zea mays

<400> SEQUENCE: 68
ggtgggaaaa ctgaaaaaga caatcatgaa ggtgtaaatt ctttactatc tgaggagttg     60
gaaaaactag ctaatgggaa tagcaaggta tgatataccc tccatgattc tgctttcatt    120
tattctttgt tcatatggta tggttattta acagtgctat gtattgccgt aaatgcagat    180
tcctggtaca ttagatgagt atagaaagct tgtcgttcca ataattgagg agtattttag    240
tacaggagat gtggaattgg cagcttctga gctgaagtgt cttggatctg atcagtttca    300
tcattacttt gtgaagaagc ttatatctat ggcaatggat cgccatgaca agaaaaaga     360 aatggcatcg attctgttat catctttgta tgctgatcta ctgagctcct acaggatcag    420
tgaaggtttt atgatgcttc tggagtctac agaagatcta actgttgata taccggatgc    480
tactgatgta ttggcagttt ttattgcacg ggctattgtt gatgaaattt gcctcctgt     540 tttcctcact cgagctaggg cactactt                                       568

<210> SEQ ID NO 69
<211> LENGTH: 477
<212> TYPE: DNA
<213> ORGANISM: Zea mays

<400> SEQUENCE: 69
catatcccac gtttgctggc tgaattgtct ggccttgaga agttacttgc tgcaactggc     60
ccagttccag acccatggca tcatttgcag accctgtcag catgttaggt ggtaagaacg    120
aaaatgtgtc atcatatggt gcctggacat tggcggatga actctgcagc tgagatggat    180
gtgttgcgct ttggtcgacg ccatacccctg cagaatcagt tccacctgaa aaaaaattat    240
```

| | | |
|---|---|---|
| agagagcact gcattcaaat ttcaaaggct cactatactg aagtagcata tttacatatc | 300 | |
| ttaaagcctt tgtatcaaac taaatatcca tatcaatgta cttacaacaa caattagggt | 360 | |
| ttccagttaa cataagctac aaactgaaac gatcaagata atagagctct gttaattgta | 420 | |
| tctgagcctc agatgctgct cacctgatgg tgatggccct ggcatgctca tcgaaga | 477 | |

<210> SEQ ID NO 70
<211> LENGTH: 1216
<212> TYPE: DNA
<213> ORGANISM: Zea mays

<400> SEQUENCE: 70

| | |
|---|---|
| ggcgaggcag ggtgtcgtcg cttccatgca tgcgctggca ttgcttctcg gagcattcgc | 60 |
| agccattcct acaggtagac tatacctata cgtgcatgcg catccaccca taatccgtgc | 120 |
| atgcatgcat gattattgac actaatgtcc ttattactaa acaggagtcc aatccatcgg | 180 |
| cgtgtgctac ggcgtgaacg cgacaacct gccccggcg agcgacgtgg tgcagctgta | 240 |
| ccagtccaac ggcatcaacc tgatgcgcat ctacttcccg gacgccaacg cgctgaacgc | 300 |
| gctgagcggc accagcatcg ggctcatcat ggacgtgccc aacacggacc tcgcctcgct | 360 |
| ggcctccgac ccgagcgcgg cggccgcctg gtgcagagc aacgtgcagg cgttcccgtc | 420 |
| ggtcagcttc cgctacatcg ccgtgggcaa cgaggcctcc ggcggggaca ccggcagcat | 480 |
| ccttcccgcc atgaagaacc tcaacgcggc gctggccaac gccggcctgg gcggcagcat | 540 |
| caaggtgtcc acggcggtgc agagcgacgt cacccagggc ttcccgccgt cgcagggcac | 600 |
| cttctcgcag ggctacatgg cgcccatcgc gcagtacctg cagagcaccg cgcccccgct | 660 |
| gctgtgcaac gtctaccccct acttctccta catcggcaac ccggcccaga tcgacctcag | 720 |
| ctacgcgctc ttcacctcgc cgggcaccgt cgtgcaggac ggcagcaacg cgtaccagaa | 780 |
| cctcttcgac gcgctcgtcg acaccttcgt ctccgcgctc cagaacgccg cgccggcaa | 840 |
| cgtcccagtc gtcgtgtccg agagcggctg ccgtccgcc ggggcgacg ccgccaccgc | 900 |
| ggccaacgcg cagacctaca accagaacct catcaaccac gtcggccagg gcacgcccaa | 960 |
| gcgccctggc ccatcgaga cctacatctt cgccatgttc aacgaggacc agaagacggg | 1020 |
| agccgagtcg gagaggcact tcggcctctt caacccggac aaatcgccgg cgtacccat | 1080 |
| caatttctcc taattcctaa acaagacgcc gaggtccatt ccaagacatt tataaggcaa | 1140 |
| tacacacaca tagatatata catacacata catacgggag aaagtagaat aaataaactg | 1200 |
| cctgcagtag aatgca | 1216 |

<210> SEQ ID NO 71
<211> LENGTH: 522
<212> TYPE: DNA
<213> ORGANISM: Zea mays

<400> SEQUENCE: 71

| | |
|---|---|
| aaggactttg gaggagatac tctatgctct ggttgttcag aagttcgttg aagctggtgt | 60 |
| ctctctggtt ccagcactct cacgctccac cgatccttct ggaagagttg atcagtgggc | 120 |
| agaaactgtg gaagaaaagc ttcaacgtct gcactcgcat gaggcctatg aaatgatcga | 180 |
| gaatcacctc accctcattc tggggcagcg tcaaggtgac gccactatcg cagccataag | 240 |
| taagctccgt gttggccagg tctatgctgc atctgtgatg tacggttatt tcctgaagag | 300 |
| agttgaccag aggttccagc tcgagaagac aatgaagggc ctcccttggg ggtcagaaga | 360 |
| ggaagacagc gctttgaatc aagttatgat gaccgacttg atgccttcag ctcagacttc | 420 |

| | |
|---|---|
| tagctctcat ccagagatgg gctcgtggac cgcgcctgcc ttcagcacag gagggcccag | 480 |
| ccaatctatc aagccttgcc gccttaggtc gtatgtcatg tc | 522 |

<210> SEQ ID NO 72
<211> LENGTH: 439
<212> TYPE: DNA
<213> ORGANISM: Zea mays

<400> SEQUENCE: 72

| | |
|---|---|
| gtagtccttg agcgaccaga agctgatcag cgcggtggcc gccatggcga cgcagaccat | 60 |
| gaagttgctc gtcacccaca ccaccctcgg cccgaccttc cggcacatgg gctcgatcag | 120 |
| gaacgagctg aatcctagaa cgatctgcac gtacggttca ccagcctcgt ggtcagctat | 180 |
| ctatctatct gtcactgaca tagtgcacgc cctggcaatg gacgaaacga ggctactgaa | 240 |
| tctcaccgag ttgagcagca gcccgaacga gccaactctg acgccttcgt cgaacgccga | 300 |
| gatctgagcg ttgctaccct tggggtcgcc gtggtagatc tcacggccca tccagtcggt | 360 |
| gtcgtagagg atgaacggga accaagagag ctgcatggac gacacagtgc atggcagcag | 420 |
| cgtcagccgt cagtaaaga | 439 |

<210> SEQ ID NO 73
<211> LENGTH: 369
<212> TYPE: DNA
<213> ORGANISM: Zea mays

<400> SEQUENCE: 73

| | |
|---|---|
| gggtgcacag attgggatat gacaaatgtt gtgattttca ggccaagacc accaagaaaa | 60 |
| tcgtattgaa gctgcagtgc cagagctgca agcactactc acagcacgca attaaggtgc | 120 |
| agtgtctcat tttcctgtgt taggcttgct gttgcacaaa gtattgtctc actttgattt | 180 |
| agctcactct ttcctgactg actcaccgtg tcacagagg tgcaagcatt ttgagattgg | 240 |
| tggagacaag aagggcaagg gaacatctct cttctaagtt tctcatcgcc catctcgatg | 300 |
| ttggatcgaa cctgtgggtc tactactgtt ctaaaaactc gtcaaatttc aatgttacta | 360 |
| gtagttctg | 369 |

<210> SEQ ID NO 74
<211> LENGTH: 836
<212> TYPE: DNA
<213> ORGANISM: Zea mays

<400> SEQUENCE: 74

| | |
|---|---|
| gagaagacct gctccttctt tgtcgggatg gtggtgttcc tggggatgag cacagtcatg | 60 |
| acgcctccgg ccgtctccag gccgagcgag agcggcgaga cgtcgagcag gagcagatcc | 120 |
| tgaaccttct cgttgccctc gccagtgagg atggcggcct ggacggccgc gccgtacgcg | 180 |
| acagcctcgt ctgggttgat gctcttgcac agctccttgc cgttgaagaa gtcctggagc | 240 |
| agctgctgca cgcggggat gcgagtggag ccgcccacga gaacgacgtc gtgcacgctg | 300 |
| ctcttgtcca tcttggcgtc gcggaggcac ttctccacgg gctccatgca cttgcggaag | 360 |
| aggtccatgt tgagctcctc gaaccgggca cgggtgatgg tcgtgtagaa gtcgatgccc | 420 |
| tcatagagcg agtcgatctc gatggtggtt gggcggtgg aggagagcgt cctcttagcc | 480 |
| ctctcgcagg cggtcctcag ccgccggagc gccctgggt tgccagtgat gtccttcttg | 540 |
| ttcttcctct tgaactcctg gacgaagtgg ttcacgagcg ggttgtcgaa gtcctcgcct | 600 |

```
cccaggtggg tatcgccggc ggtggccttg acctcaaaga tgccctcctc gatggtgagg    660
agcgagacgt caaaggtacc gccgccgagg tcgaagatga ggacgttctt ctcgccgtcg    720
ctgctcgact tcttgtcgag cccgtatgcg atggccgcgg cggtgggctc gttgatgatg    780
cgcatgacgt tgaggccgga gatgacgccg gcgtccttgg tggcctggcg ctggga        836

<210> SEQ ID NO 75
<211> LENGTH: 1019
<212> TYPE: DNA
<213> ORGANISM: Zea mays

<400> SEQUENCE: 75
tatagtacgt tttattcgac aagcagcctc tgcatgcaat aatagtacac cccccgattt     60
aattggacta atgcatgctg aggatggatc agatggagat gctgctgggg atgcccctcc    120
cggtgactcc cggcttggag aagggcttga gcagctcgta cggcacgatc ccggcgccgc    180
agcggttctt gaggtccagg ttgttgttgc actcgtcgat gaaccccctcg atctccttca   240 tcctgccgcc gaacttctcg aacgccgcct tcaccatggg ctccgccagc acgacggct    300 ccgcgaactc ccccatgtac tcctcgtcgg gcgagtgcga cgagaggatg tccagcgtcg    360
tcatgacctt gatggcctgc atctgcgtgg gcagcatgtc cagcagcgtc gtctccggct    420
gcttgaggaa cttctccatc tcctcgcccg gcccgccctc ctccaccggc atgttcttcc    480
ggatggtggt cggccggttg gggaagtagc cggcgaagtg gtactggccg aagttgacgg    540
ccgagtggtg gccggaggtg acccacatga tggtggtcag cgtctccacc aggctgtcgc    600
gggtgtccag cacgggccac cacgcgctcgt ccttcttgtc gccgtgcccc acgttgcgca   660
cctcgtccca gaacgccctc agctcggggt cggcggccac ggcctcgtcg gacttgtagt    720
agacgttgac gtactcggac gcccactgcc tgatggagtc ccagaccagg agcccgtcgt    780
gggcgtaggg gtagtccttg atggtgagct ccagctcccc gtcctccccg cgcacggcca    840
gcccgcgctt gatgaggtcg ttgggcagcg cctccgtgtc gaactgccac gtcgcgccgt    900
acgccacgga gctgagctcg acggcgtact gcccggcca aaggactcc tcgatgatgc     960 cgtcggcgtt gatgagcgcc tccctggcca gcgcgttgat ctccatggtg tagcggaag   1019

<210> SEQ ID NO 76
<211> LENGTH: 499
<212> TYPE: DNA
<213> ORGANISM: Zea mays

<400> SEQUENCE: 76
gacaagctcg ccatactggg tctcccgatc tggattactg agttggatgt cacagcagag     60
aacgagcaca tacgagctga tgatctagag gtgttcctcc gggaagcatt tgcacatcct    120
gctgtggggg gaatcatcct ctggggattc tgggagatgt ttatgtttcg agagcacgcc    180
catctggtcg atgctgatgg gacaatcaac gaggctggca ggaggtacct tgctctcaaa    240
caagagtggc tgacccgtat gaacggcagt gtcgatcacc aaggagagtt taagttcaga    300
ggataccatg gttcgtacac agtggaagtg aacacgcctt caggcaaggt agctagatcg    360
tttgttgttg acaaggatag cccggttcag gtgatcgctc tgaatgttta atgtgtggga    420
aatcatgcgc gtgtcctgta ttttagcgat gtactgaggt gttgaacaca gatagtttca    480
tagctgatgc cacgccttc                                                 499

<210> SEQ ID NO 77
<211> LENGTH: 886
```

<212> TYPE: DNA
<213> ORGANISM: Zea mays

<400> SEQUENCE: 77

```
gtcagtagtt catccatttg tcccattttt tcagctagga agtttggtta cactggcctt      60
ggtctaataa ctgagtagtc attttattac gttgtttcga caagtcagta gctcatccat     120
ctgtcccatt tttttcagct aggaagtttg gttacactgg acttggtcta ataactgagt     180
agtcatttta ttacgttgtt tcgacaagtc attagctcat ccatctgtcc cattttcag      240
ctaggaagtt cggttgcact gaatttgtga acccaaaaga ccacaacaag ccagtgcagg     300
aggtctgtct ctttacccaa gacaacaaaa ggttatcaca gcttatgctg aacttggcca     360
taacattcaa taattccttt atggtctagg tacttgctga gatgaccaac ggaggggtcg     420
accgcagtgt ggaatgcact ggcaacatta atgctatgat ccaagctttc gaatgtgttc     480
atgatgtaag tatatgtata cactctcagc tactttcctt ctccaggttc ccttcatcca     540
gacatgcatg ttctaactgc cgcgctcgtg atccagggct ggggtgttgc tgtgctggtg     600
ggtgtgccac ataaggacgc tgagttcaag acccacccga tgaacttcct gaacgaaagg     660
accctgaagg ggaccttctt tggcaactat aagccacgca ctgatctgcc aaatgtggtg     720
gagctgtaca tgaaaaaggt aaattgcaaa gtgccgttcc ttcagtttcc ttacctgccg     780
agcttttgct gaaaaactgt taagaatcgt tcctgcaatt ctgcttggct ctgcacagga     840
gctggaggtg gagaagttca tcacgcacag cgtcccgttc gccgag                    886
```

<210> SEQ ID NO 78
<211> LENGTH: 847
<212> TYPE: DNA
<213> ORGANISM: Zea mays

<400> SEQUENCE: 78

```
atgcgccctt gggtacatag caggagactg gaaaggtaac aaatggaata cggacacgta      60
gataaccatg gaggcccagc aatgttgagg tattgtttgg tcactgcata gccgatgatg     120
atcaccacgc ctcgtggatg cctcatgtct taacagcagc cagatgatct ctgagcccgg     180
ttgccaccta ccacatccac ggtatctggc ataccttc aagaacaaat cgataaggtc       240
aaaaaagggg acggctttta cacagataat aaaggaccag cacagggaaa caatgaagg      300
aaatcaaaag tgattgatga ttttacatag atataatact gaaaacgaga tcagcagaag     360
aagctagtct tattgcagca gctaatgatg ccaaccctgg tacaccccca gaaagaggat     420
caacagaaag tgccttattt tgctgatgac taataactgg agcaaaaaga ccaacagaag     480
gaccagttga tattaaaaat gtaattactt ttacagcagt gctccggttt tctagtactt     540
gcaacgatta atgtcacata aaacagtac tgtcaaatgc caatcaaaca aacaaagaaa      600
cgagaataag tgtgcttaca attcttcctc cggttcattc ttcagagcat tctttacaat     660
acactggaag gcatcttcca cgttcgttcc atccttagca gacgtctcaa agtacgggat     720
gttcccttta gaggcgcacc atgcctttgc cttttttctcc gacacctaaa accaaagcag     780
attatgtttc taagcagctc atgatccagt tcaagagaag aatttattca gagagcaaat     840
catgtag                                                               847
```

<210> SEQ ID NO 79
<211> LENGTH: 815
<212> TYPE: DNA
<213> ORGANISM: Zea mays

<400> SEQUENCE: 79

```
ggtttgtctg tttcatgaat aatgttctgt tgcgtcaaat taatagcaag tttctgatat      60
ttttttttct ccagcatgtt tttgaatact ttacagaaag aaccccaaga tcccatttcg     120
aacatcgtga acatcatttt gtgtggaact ataagtatgc tggtaagtgt ttatcttcca     180
aacattcttt ttaagcaagg tctgtgcagt aacattttat ttccaccttc tatctcaaag     240
atgttgagtt cggaaggcta caagcaagag atatgctgca gcacttgtgg acaggtccga     300
tctcaaatgc agctgttgat gttgttcaag ggagtcgatc agttgaagtt cggtctgttg     360
gagttaccaa ggtaagtggt gctgtatgat ggtccatgac agtagatggt ttgacctagt     420
tgaggtttta aacatcatttt gtctccttcc tatagggtgc tgcaattgat cgtatttttag     480
gggagatagt tcacagcgaa aacatgatta ctccaattga ctatgtcctg tgcatagggc     540
atttccttgg gaaggtaatt tccaattctt cacgttattg ttctgatctg gttttagttc     600
tgtggatagg atcaagaaac ttatgaatga agaaatgaaa gggtttagaa cattcaaaat     660
gcattgccaa ggaaaggaga aggatgtgga cttaattaga aaaatcacta tggtttactt     720
tatatgtttg gtctgtccct attctttttcg actttggtct gttttgtaac atctggttcc     780
tcgtgtttca ggatgaggac atctacgtct tcttt                                815
```

<210> SEQ ID NO 80
<211> LENGTH: 426
<212> TYPE: DNA
<213> ORGANISM: Zea mays

<400> SEQUENCE: 80

```
tcttcagtct ccaccctgat tcaacaacag actctgacag cttgcacggt agctgccccg      60
ccatcgaagg ccagaagtgg tccgcgacta atggatcca tgtgaggtca tttgacctca     120
ccgtcaagca gccgggtccc tctgatggat gtgaggacga caatgtcctc tgcccccagt     180
gggcggccgt gggcgagtgc gccaagaacc ctaactacat ggtggggacc aaggaagcac     240
ctggcttctg ccggaagagc tgcaaagtat gcgcagagta aggtatcggt cctctgcgtc     300
tgatgagtaa tcgtggcgta cgtgttacgt agttgctgtc accatttac cagggtttag     360
gtacgaccga gtacagcatg tataagacag tacaaacccg gaagaaggaa tcgtaagagt     420
taggg                                                                426
```

<210> SEQ ID NO 81
<211> LENGTH: 419
<212> TYPE: DNA
<213> ORGANISM: Zea mays

<400> SEQUENCE: 81

```
aagcgaacga ggaaaggaag aacaagttgg cttcgattga aggctcgaca actgccgagt      60
accatctgcc tgttctggca atgacagccg atgttatcca ggcaacttac gaagagtgca     120
taaaatcggg aatggatgga tacgtatcta aaccccttcga cgaggagcag ctataccaag     180
cagtctccag attggtagtg ggaacgacgg attcggctgt ttgatgttca aaatacgatg     240
gacctgactt ctcattcatc gaagtgaagc atcaccatct tgcctctgtc cagctgactc     300
tatatcccctt gacaatgggc ctctgacatg gcctctcaca agactagatg aaaaaagaag     360
atgaaagtgc cgtgagttag gtacgtgtca cacatgacat gaagttgctg cggcagccc     419
```

<210> SEQ ID NO 82
<211> LENGTH: 868

<212> TYPE: DNA
<213> ORGANISM: Zea mays

<400> SEQUENCE: 82

```
attttgatcc gtcattatct tgctcaaatt ctgtaacttt catcccaaag ttcgccagaa      60
ttcgtttctt ttttattttg ttaccagtag agcatctcct gatctacctc ttcgtcgtgt     120
ttggtaaaga ctattgagct caggtgtgtt gcgttgtgca gagcacaggt ggtgggatgg     180
ccaccagtct gcaactaccg caagaacacg atgactacca cccagctgga gggcagcaag     240
gaggatggtg atgccaagca gggtcagggg ttcctgtacg tcaaggtcag catggatggc     300
gcgccgtacc tcaggaagat cgacctcaag acttacaaga actacaagga cctgtcgacc     360
gcgcttgaga agatgttcag tggcttcagt actggtgaga tgtctcgggg ttactctctc     420
tctctctctc tttcggatgg cgcgtcagtg agtaattatg tttcgttttg atgtggatgg     480
tgttagaagt acatcaagaa gcctttaaaa agcagcatac tcctacttga ttcctaggat     540
aagcaatagc ttgaacttac cccgttatat tttgagtaat tgtaagatta caaacaatct     600
ggcaccccct tgttttgttaa ttttttgggtg aacttttat tcctcccaaa acaaataccc     660
tggtgattgt tcagttattg catccgtatc aagtctctct tagaaagatg ttgtttcctg     720
taaggcaaaa taagttttgg ctccatcttt atgattattc gatgatatct tcgagtcctg     780
ggtattattc catagaaagc tactaatcac tatgagagtg acatccccta tatatttctg     840
aaatttgtgg agatctgtgg tcctgtat                                         868
```

<210> SEQ ID NO 83
<211> LENGTH: 909
<212> TYPE: DNA
<213> ORGANISM: Zea mays

<400> SEQUENCE: 83

```
cgctgaatcc aacctaatgc tgtacagaat atcctttaca gccaagccgc caaccaagac      60
gctgagtcta atgccatgtc ctggtggatc caactatcca acaacagat caccccctttt     120
gagctgactg acgatcatga tgctgaaagt attggatgct ggtcgaaggc ttcaccctct     180
tgctggctgt gaagtggaag acagagtcat gtaatcagtt tgcttgcctt caaatcatac     240
acctggtgta aagtacagtt tggttttgaat ataaacaagt atcataaagt acttctttaa     300
aattgtccaa cgggggagtc agctgtcttt tgcacctcag ggtgcttcac acgtagctat     360
atgatggtca ctggttaact catttacata gacaatttca gaagggataa tctatgcaaa     420
atctaatgat attattatga cccctgatcc atttagaaca acatgagctg tactcctcct     480
agatatgatt acataagcat cttgatctat caggcctttg gtgagtactc aacactcaac     540
agaaacctac taactcctat cgttctctga ttaaacgagt gaacagttca ggacactgca     600
gaagattttt ttttctataa gccaccgcta ttcaacaatc aacggttttg ctaatcagat     660
gtcacaaatg ccaacatatt gtcatccgag gatattccgt aaggtggaca agatagaacc     720
agttatctca gaaaaaaagg ccattaaagg atatctggta ataactacat caccatcctt     780
ctgtattcaa gtattagcag aagagattga taatggaagg aaatcatccc tgaataagca     840
ccagtaatgg gatatggtca tgtatcaaat gtaatttatt aagcatcgca agttttagaa     900
ttagcaacc                                                              909
```

<210> SEQ ID NO 84
<211> LENGTH: 827
<212> TYPE: DNA

<213> ORGANISM: Zea mays

<400> SEQUENCE: 84

```
acaaaggaaa gggaagaaa atgacttcta ggttttcacg tctccttttg gttgaccaag      60
aagagatggt cggtagagtg aatggccttg tgccatctca attctttcgc gtggatcata     120
cattgtctca tctcttatag cctgaagaat cgaatcagca ggacggtccc tgtgcacata     180
tgtaaacaga ccaactcagt caaatatcag aaaaccttag ttcaatgaat tattccaaac    240
tattgaaaga taaagtagaa tagctggcac acatgcaggg gcagaaggaa ccatgccaat    300
caagttatcg gtatgtatgg gttagtaata taggttactg gcatataggt aatacgctga    360
aaatataact ggtgtagagt atgtgacgtt ggtcttaggt tctaacctcg tgatcagaat    420
cctatgtagt gcttttagga tcgggcacat ctcaaccggc gcaacagatc tgttggcttc    480
tggatgcatg acacttaagc tatcctgact aagaagctca taaaacgcat caactgcaga    540
gacaccctga atggaacgg caacaggata attcatcaca tgattcattt aggcatattc    600
atgcagttct ttgaagtttc gttgtcgacc aaaattaaaa gggcatacct gaatggtccc    660
ttttccttta atactgtcac ccatttctaa tgtcaattca cctttagcta acttctgccc    720
ataccatgca ttacgacctt tcaacaatgt gacataagtg tcagctaata agggtccagc    780
aagttttca ggttcttctt ccagaaggtg tgtgatgtag atcatct                    827
```

<210> SEQ ID NO 85
<211> LENGTH: 1867
<212> TYPE: DNA
<213> ORGANISM: Zea mays

<400> SEQUENCE: 85

```
taccttgttt ccccaccaga gatagataga acatctgggg agtacttggt gaagaatggc      60
atccgcacct tgcttgcag gcaagtacta tctatttctc agcctttctc ttgatacttt     120
tttatttact tcaatatcgt aaatcactt agttttctg agtcatctaa gtcagcatgc     180
tccatttatt ttgaatcaac attatcaagt gtacttcgta caatcttgta catacctgtg    240
aggagcactg accttctgga aagatatcat ttttcacttc acagaacatc aggaattcaa    300
gattcactca gttaattgat attttaaata attttgaaaa ttgaaataca ggaaaatatg    360
tgttttaag gcattacatt ttgcatataa atattcaatc tcactaaagg aaaatgtttt    420
aagaacattt ttctttagtg aaaaggaatc caaatgcttt cgaattctgt tgtgacttat    480
ctctattacc ttatactgca tccgtactag tatatttgac atctgtagag aagagttctt    540
ttttctaggg taatcttcta gctgcagtgc agtatgctga cattgtgcta acttaggctg    600
atatttggtt gcattgctct gcccatgatt tgtgccctaa tactgtatat tagggctgca    660
taatgttatt tttggattga ttcattgttg tatcatcctt gtgcttgcaa catgatctac    720
attttcccctt ctctctctct ctctctctac ttatgcagca acattgtttt gtgtgtgaca    780
gtgagacagt taaatttggc catgtcacat ttttctggaa cggtaaccgt tcgggatact    840
ttgatgcaac taaggaggag tatgtagaag tacctagtga cagtggtatt acattcaatg    900
ttgcacccaa tatgaaggcg cttgaaattg ctgagaaagc cagggatgct ctcctaagtg    960
gaaagtttga ccaggtaaat aatttgaagt ttctattaga gcactctttc ggtttccctg    1020
ttgcttagcc tagcgttgtt acaggtacgt gtcaacctgc caaatggtga catggttggt    1080
cacactggtg atattgaggc caccgtagtt gcttgcaagg cagctgatga agctgttaag    1140
gtgagagcac caatgaaagt tcgctgacat gtgtgttgtc ttattatctg cattggaagt    1200
```

```
tcgcttatac atcaataaag gttcttacag tagcacgctt cataggcctt tgcctatttt    1260
ttaaccaagt gttcttctga acagattatt ttggatgctg tcgagcaagt tggtggtatt    1320
taccttgtta ccgccgatca tggcaatgct gaggatatgg tgaaaggaa caagtctggc     1380 aagccgttgc tcgacaagaa tgaccgtatc cagattctta cctcgcatac ccttcagccg    1440
gtgagtgcaa tgccatttga ccccatgtct tttggttctc tcccagcaaa atcatacccg    1500
tgttgattgc ttgatgcta atgcctctgt aaaacttgca ggtcccggtt gccattggag     1560
gccctggcct tcaccctgga gtgaaattcc ggaacgacat ccaaacccct gggctcgcca    1620
acgtagccgc aaccgtgatg aacctccacg gatttgaggc tcctgctgac tacgagcaaa    1680
ccctcattga agtggctgac aactaaacac tggccacctg tgtccaattt tggttatatg    1740
tagttctgag aatggacatt caataattta tgtttgcaag cacgttgctc aaactcacca    1800
aaacatcgag ggatgccttt tgactttggc atttacagca ttttcgtttg gctttaatcc    1860
ttatcgg                                                               1867

<210> SEQ ID NO 86
<211> LENGTH: 560
<212> TYPE: DNA
<213> ORGANISM: Zea mays

<400> SEQUENCE: 86
cgtccgcggc agcggccgcg tccaggtggt cgggcccgac ggggtgcgcg tcctggagac      60
gcgcgtcgag ggcggcttcc tcttcatcgt gccccgcttc cacgtcgtct ccaagatcgc     120
cgacgcgtcc ggcatggagt ggttctccat catcaccacc cccaagtaat tgttgtctc     180 gatcgatcga tccatcgatc ttttttttatt gcgaattgca ctggagattt gattgcacgt    240
gaattaatgc ttgcattgca ttgcagcccg atcttcagcc acctggccgg aagacgtcg     300 gtgtggaagg ccatctcggc ggaggtgctg caggcgtcgt tcaacaccac gccggagatg    360
gagaagctgt tccggtccaa gaggctcgac tcggagatct tcttcgctcc cccatccaac    420
tgagaaaata ggccggaagc cccacggtgg agtcctctcg ttaggtcgtc gtgcttagat     480
taggttagct agcttgcctt taataaaaag agagtggtgg tcgtcggcgt cggcttcggc    540
ggtctgcttc ttcttcattc                                                  560

<210> SEQ ID NO 87
<211> LENGTH: 496
<212> TYPE: DNA
<213> ORGANISM: Zea mays

<400> SEQUENCE: 87
ccgtgttggt tggatctatg gctcggtgac ggaggatgtg gtcactgggt accggatgca      60
caaccggggt tggaagtcgg tgtactgtgt caccaagcgt gacgccttcc gcggcaccgc     120
gcccatcaac ctgaccgacc gtctccacca ggtgctccgg tgggctactg gatcagtgga    180
gatcttcttc tcccgcaaca acgcgctgct ggcgagccgc agaatgaagt tcttgcagag    240
gatcgcgtac ctgaacgtgg gtatctaccc gttcacgtcc atcttcctga tcgtctactg    300
cttcctgccg gcgctgtcgc tgttctcggg gcagttcatc gtgaagacgc tgaacgtgac    360
gttcctgacg tacctgctgg tgatcacgct gacgctgtgc ctgctggcgg tgctggagat    420
caagtggtcg gggatcagcc tggaggagtg gtggcggaac gagcagttct ggctgatcgg    480
cggcacgagc gcgcac                                                     496
```

<210> SEQ ID NO 88
<211> LENGTH: 924
<212> TYPE: DNA
<213> ORGANISM: Zea mays

<400> SEQUENCE: 88

| | | | | | |
|---|---|---|---|---|---|
| aatgtgatat | catgatactc | atgcacctgt | accttagcca | atgcaggagt | ctgttaaagt | 60 |
| ctcaatagca | ttttgtgatg | ctcaccaaca | gttccttttt | acaggattca | tctggtatat | 120 |
| tctgggataa | tgacagttta | gctggtcttt | tggctattga | acttaaagca | gatctccttg | 180 |
| ttctactaag | tgatgtagat | ggtctataca | gcggtccacc | aagcgaaccg | ggatcaaaga | 240 |
| tcattcatac | ctacattaaa | gataaacatt | acagtggaat | aacttttggg | ataagtcac | 300 |
| gtgtaggtag | aggaggaatg | acagctaaag | tgaaggctgc | ttttgtggct | tcgaacagtg | 360 |
| gcacacctgt | tgttattaca | aggtatgtat | tgcattttc | attctttatc | gagaataaaa | 420 |
| actgccttc | gttgctcatt | tatatgttcc | catgtgattg | tgatctatca | aactttccct | 480 |
| gtgacatgca | accaataata | aggaatttag | acaaaacagt | tgataggtgg | tgtgattaac | 540 |
| tacatatttg | gtgtagacta | catttgactc | aagtgtttat | ttttgggtgt | agactacatt | 600 |
| tgactcgagt | gtttcttaca | tctttaatga | tgtgaagaat | tggttttcag | aagtgaaata | 660 |
| tttccttaga | ctttttctc | tctcgaacgc | gcaggagagc | tgcacatcat | tatatttcct | 720 |
| tagactgtta | tgctgaatcc | tcgcttgtga | tgttcactta | tttttctatg | ttggatttta | 780 |
| tttacatata | ataaggtctg | ctgttcaaat | ccaaatacgc | catctgtttt | caatgtttgt | 840 |
| tcatggcctt | aggaaaatgt | gttgcacatt | gtttgtctat | tgaggatatc | aggagtgtag | 900 |
| ttattgctat | gtttccactc | tccc | | | | 924 |

<210> SEQ ID NO 89
<211> LENGTH: 1140
<212> TYPE: DNA
<213> ORGANISM: Zea mays

<400> SEQUENCE: 89

| | | | | | |
|---|---|---|---|---|---|
| gtgaaggaca | ggggactcct | ggacagcctt | ctcggcagga | acaagcacga | cgaccaggag | 60 |
| aagaagaacc | agcaggagga | ggaggagctc | gcgaccggca | tggagaaggt | cacggtggct | 120 |
| gagcccgacc | acaaggagga | gggacacgag | gccgccgaga | agaaggacag | ccttctcgcc | 180 |
| aagctgcacc | gcaccagctc | cagttccagc | tcggtgagtt | cgtcgtaaaa | catgatctgc | 240 |
| tgctagctag | tttaattgac | tccgccttcg | gatcagtaag | ctaataaacc | ggcttctcac | 300 |
| tgcgatcgtg | gtgcctgcgc | gcatgcagtc | gagcgacgac | gaggaagagg | aggtgatcga | 360 |
| tgagaacggc | gaaattgtca | agaggaagaa | gaagggcctt | aaggagaagg | tcaaggagaa | 420 |
| gctggcggcc | cacaaggccc | acgatgaggg | cgaccaccac | cagccgggcg | tacctgcccc | 480 |
| ggcgcccgca | ccgcccgtgg | cggtggacac | gcatgctcac | caccaggagg | gagagcacaa | 540 |
| gccgcacttc | ccggcgccgg | cgcctccccc | gcacgtggag | acgcaccacc | ccgtcgtcgt | 600 |
| ccacaagatc | gaggacgacg | acacgaagac | tcagacccca | ccacaggcac | cggaggagga | 660 |
| gaagaaaggc | ctgctggaca | agatcaagga | gaagctaccc | ggtggccaca | agaagccgga | 720 |
| agacgctgct | gccgccgccg | ccgcgccggc | cgtccacgcg | ccaccgccgc | ggcgccccca | 780 |
| cgccgaggtc | gacgtcagca | gcccggatgg | caagaagggc | ttgctgggca | agatcatgga | 840 |
| caagataccc | ggctaccaca | agagctcggg | tgaagaagac | cgcaaggacg | ccgccggcga | 900 |
| gcacaagacc | agctcctaag | gtcgcagcgt | gtgcgtgtcc | gtcgtacgtt | ctggccggcc | 960 |

```
gggccttggg cgcgcgatca gaagcgttgc gttggcgtgt gtgtgcttct ggtttgcttt    1020
aattttacca agtttgtttc aaggtggatc gcgtggtcaa ggtccgtgtg ctttaaagac    1080
ccaccggcac tggcagtgag tgttgctgct tgtgtaggct ttggtacgta tgggctttat    1140
```

<210> SEQ ID NO 90
<211> LENGTH: 477
<212> TYPE: DNA
<213> ORGANISM: Zea mays

<400> SEQUENCE: 90

```
gcaaaggtac agcgtaaaaa ctaagaggag agccagcaag ctagcatttt atttagtaaa      60
atcgttcact cgcaggtacc caatcttctc agctttacac actcgccatc ttgaggctgt     120
tgcccttctc ctgcaggctc acgagtaggc tgtcaaagct cttcttgaag gagtccacgc     180
cttccagctc aagctgcttt ccaacctctt cccagtcgat gccaagcttc tccaaggcac     240
tgtatacacc ttccgcctca gacacgttcg catcaactgt ccttgaaacg gtgccgtggt     300
ctatgaatgc ttgcaaagct tggtcgggca tcgtgttgac ctgaaagtgc accactacag     360
agttattttt ttgtgatgat aagaaacaat gccagttcaa gtgggaaact cgtcgtgaca     420
acataccgtg tcaggtccga tgagactgtc cacataaaga gtgtcaggat aagctgg       477
```

<210> SEQ ID NO 91
<211> LENGTH: 376
<212> TYPE: DNA
<213> ORGANISM: Zea mays

<400> SEQUENCE: 91

```
ccaggcgacc aagggggttca agaacaagat gctgctcggc accggcggct tcgggagggt     60
gtacaagggc gtgctctccg gtccaagct cgaggtcgcc gtgaagaggg tgtcgcacga     120
ctcgaagcag gggatgaagg agttcatcgc ggaggtggtg agcatcggcc acctccgcca     180
ccggaacctg gtgcagctgc tgggctattg ccggcggaag ggcgagctgc tgctggtgta     240
cgactacatg tccaacggca gcctggacaa gtacctctac gacgacagga ccgccaggcc     300
cgtcctggac tgggggcaga ggttccagat cgtcaggggc gtcgccgccg gcctgctgta     360
cctgcacgag gactgg                                                     376
```

<210> SEQ ID NO 92
<211> LENGTH: 820
<212> TYPE: DNA
<213> ORGANISM: Zea mays

<400> SEQUENCE: 92

```
aaacaacaac ttgtagttgt ccacaacagg ttaacagatc aaagaaggat aggtgagcgg      60
cactactcat ctcgtggctt ccggtgacag atgatcagcc cacgaaggaa aaagaaaaag     120
ggactcgctt gatttgcgtt gctttgcttt ccgcgcaagg ccgaaagctt aaggtcgggg     180
caacgacaca ccgagagcga cggagatata ccacgctctg ctgcttcatg atagctggaa     240
ggacatcagc atgacacgca tgccaataat gtagtagaag actagtttat ttgtcaccta     300
ctaggcagag agtgcggtgg ttccatgaac caaccattcg tgcgtgcgtg cccaccgcac     360
gaccacgagg gggcatgcaa catatacttt acaaaattca ttcggttgtt gacttggttt     420
caattcattg ggttgggaag acaaaactaa catggatgcg ttgcgtactc acaggaaggt     480
gatggctcag actggtgaga tccggtgcgc catggatcac atcctcgagg ccgagaggaa     540
```

```
gggcgagatc aaccacgaca acgtcctcta catcgtcgag aacatcaacg tcgcaggtat    600
cgataatcgt cactgctcag tgcaatgaaa cggaaacaga gtatgctatg tctgaagaac    660
caagtgagac ttatcattca actactgcag tccagcgcta ctacacaaac aaatagcact    720
gcaatatcgg aagatataat aatataaggc acgtcttaat caagtctccg tcagccaact    780
taattccgtc cttaattaac cggcaacata ctgagcctaa                          820
```

<210> SEQ ID NO 93
<211> LENGTH: 683
<212> TYPE: DNA
<213> ORGANISM: Zea mays

<400> SEQUENCE: 93

```
tgacctacaa ctcaaacagg ctcgtcttca atggccacga gatctacccg tcagcagtcg     60
tgtctaaacc aagagtagag gttcaagggg gtgacttgcg gtcgttcttc acattggtta    120
gcaccagtcc aacactactc cacacagtta gctctccaag ttgttctata tatatatgta    180
tcccggcgcc ccttcctttc cctaatggcc atagttcctg aatttccagg ttatgacaga    240
cccagacgtc ccaggaccaa gcgatccata tctaagggag caccttcact ggtaacatct    300
ggcatttcct accaacatct aggggaatgc tgtgtgactg gtatatgtcc tttacatttg    360
caggatcgtg actgatatac ctgggacaac tgatgcctca ttcggtagtt ttttctcccc    420
cctctgcttt gtggttaatt agtcgttcca gttgttcttg gagctagtta attagtagca    480
ggcatttttt ttcagggaga gaagtcgtaa gctatgagag cccgagacct ggcattggta    540
tccacaggtt catctttgtt ctcttcaagc agaagcgcag gcagcagcag actgtagcgg    600
cggtgccatc ctccagcagg gaccatttca tcacgcgtca gttcgctgcg gaaaacgatc    660
ttggccaccc tgtagccgct gtg                                            683
```

<210> SEQ ID NO 94
<211> LENGTH: 765
<212> TYPE: DNA
<213> ORGANISM: Zea mays

<400> SEQUENCE: 94

```
tatgcatgat ttatgcccgc caaacagaca gaaaacgcaa caaactacaa ccatttacag     60
accggagcca agtgaaccta acttgttaac atcatatgaa ggaacatcct aaacgagcaa    120
tgcttactca aatttactgc tatgctactt ctattgctgt taatgaggca gtcactcaca    180
ggctgctgct gactggaaag ccaggggaaa ttagcgttct ggcttcaggt cacgatcaat    240
gtactgcctc acagcctctt ggtttacatg gaaaataaac ctcatgtcct ttatctggaa    300
agggggggaa aaaggtagct aaattagtac agcatgaaga tacttaatta aatgcatcag    360
tgatatctca gtcaaataac aagggaagga ttgtcaggta tagcaaaggt taacttgtca    420
aaaagtaatt gtttcatgtc tgcttacata tcaccatagt atcattcgta ctgttttag     480 atactctata aaaccccaaa ataacataat ggcaagaagt aaaacttcaa gcaccctcta    540
ccagtagaac cataaactat gacaggatca caggaatagt tacaaaaact gtgcattgac    600
taaccaccag gttacagatt cattaaaaaa tgaaggtata ctagaacggg gaagtattgg    660
tacctcgatt aatgagtctg agcttaggtt gatgcgtttg cagcttggta tttccttgct    720
attaacaaag attggacatt ttccagtgtt cttaatatga aaata                    765
```

<210> SEQ ID NO 95
<211> LENGTH: 770

```
<212> TYPE: DNA
<213> ORGANISM: Zea mays

<400> SEQUENCE: 95
agcatcatgg agtacggtca gcaggggcag cgcggccacg gcgccacggg ccatgtcgac      60
cagtacggca acccagtcgg cggcgtcgag cacggcaccg gcggcatgag gcacggcacg     120
ggaaccaccg gcggcatggg ccagctgggt gagcacggcg cgctggcat gggtggcggg     180
cagttccagc ctgcgaggga ggagcacaag accggcggca tcctgcatcg ctccggcagc     240
tccagctcca gctcggtaat tacgactctg gatacttctt tcttttgtgt gcgcgctgct     300
tcgtcctata tataataata catgagttag gcttagtaat aatcaattaa tttaatccgt     360
gggtttcgtg tttaagtcgg aggacgacgg catgggcgga aggaggaaga agggaatcaa     420
ggagaagatc aaagagaagc tgcccggagg ccacaaggac gaccagcacg ccacggcgac     480
gaccggcggc gcctatgggc agcagggaca caccggcagc gcctacgggc agcagggaca     540
caccggcggc gcctacgcca ccggcaccga gggcaccggc gagaagaaag gcattatgga     600
caagatcaag gagaagctgc ccggacagca ctgagcggcg cctatacgtg gctgtgctgt     660
gctgtgctgg cgcgtcaaag ccgtactctt cagcgttcca tagataataa gataaaccca     720
tgaataagtg tccctacccct tgatcatgt gacagggaca gggacaggga                770

<210> SEQ ID NO 96
<211> LENGTH: 422
<212> TYPE: DNA
<213> ORGANISM: Zea mays

<400> SEQUENCE: 96
aaggcaacat tctgaagatg cagcgcaagc agaagccatg cactcccctc ccctccaaca      60
agcagagtcg gtactaccgg cctcgggtca aggtatgcgc cagaacccga ctccttgagg     120
cgatgttccc cgcaggggca agagtctctg aagctgcctg tctgtctgtc tgtgtgtgtt     180
ctcgctttct ttcgcagggg aggtttgtca gcaaggcttg tttcctccag cgacagcaag     240
cgttagagaa ggagagctag agaaagatgg atcctgctcc aaggcgcatt tctgggctc     300
tcttggagaa gcagcagagc ttctccgttt tcatctctgc ggcggtacag tgcggcagat     360
gtagagatgc ctgtagagtg gtgccttgtga acctcaattc tcagtttctt ctatccattc     420
ca                                                                   422

<210> SEQ ID NO 97
<211> LENGTH: 553
<212> TYPE: DNA
<213> ORGANISM: Zea mays

<400> SEQUENCE: 97
cacaaaagag aaggctctca aggtgaacta gaacagaatc tcccgacggc cggggctcaa      60
accagctcat cctcggcgat atctcgagga ttcctcacca gctcgagcat gctcacgacc     120
tcacccatgc caggccggtt cgacggcacc tgagaggtgc acacaaggcc cagcttgatg     180
accggcaggg cctcgtccat ggggaactcg ccgcgcagcc gagggtcgac gcagtcctct     240
ggcctgcctt cctccagcgc gcctctgacc aggtcacaca ggacaaccac gtcgtcttcc     300
aagtactcca cgggcctcct gcccgtcaag gcctccagca gaagcacccc gaagccatag     360
acgtcgcatt tctcggtgat cttcaccgtc ttgcacgcaa actctggcgc catgtacccg     420
agcgcgctct ggaccttact gctcaggacg taccggtcca gcatcggcag cagcttggcg     480
```

```
aggccgtagt cacccacctt tggctcgccg ttgctgtcca gcagcacgtt gcttgacttg    540
agattgtagt gga                                                       553
```

<210> SEQ ID NO 98
<211> LENGTH: 612
<212> TYPE: DNA
<213> ORGANISM: Zea mays

<400> SEQUENCE: 98

```
gcattcattg ctgatgtttt tgaatgactc ttaggacaag tgtggctaca ccggagcatg     60
tcgaagaggc attcagactg ttcaatgttt ccaccgttga tgctgcaaga tccggaatca    120
atgagcattt gaacctgtca ccggagatcg caaacgaaat caaggttagt atttgcatcc    180
cagggtatac aaaattcagc tattgaacct tgcattttcc tgaacggctt tcatcatttt    240 ttttcatct gacagcaagc ggaggcacaa ataaagagaa gaatgggcat cggcagccac     300
atatccgagc gacggctgat tgatgatcta aaccggatgg ggatgaatga atccatcgta    360
ggaaccctgt catcgaatct tagaactgaa actatggttt tcaagtaaga cccgttcgtt    420
tttctgacaa tatcttgcac actttgtttc aggtcagaag agcccttctg atcatgcatc    480
aaagggacga ggtggagtac aagagagagc gccacgtgat cgtccgaaag gcttgaggtg    540
gagaggccag tcagattcac ggcatacaac gtacactgga ggcggtcctt cctcttcgga    600
cgtgtgtata cc                                                        612
```

<210> SEQ ID NO 99
<211> LENGTH: 664
<212> TYPE: DNA
<213> ORGANISM: Zea mays

<400> SEQUENCE: 99

```
ttcctctata agtacccgcc ccacatctgc gccattttct catcgcagaa atcctccgca     60
acttcacagc gtatcatcgt tttccatcgc tcctactcct atcatccaga aaatctgagc    120
ggtattgatg gcgcccaagg cggagaagaa gccggcggcg aagaaggtgg cggaggagga    180
gccctcggag aaggcggctc cggcggagaa ggccccgcg gggaagaagc caaggcgga     240 gaagcggcta cctgcgggca gtccgccgg caaggagggc ggcgacaaga agggtaggaa    300
gaaggcgaag aagagcgtgg agacctacaa gatctacatc ttcaaggtcc tgaagcaggt    360
gcaccccgac atcggcatct cctccaaggc catgtccatc atgaactcct tcatcaacga    420
catcttcgag aagctcgccg cggaggccgc caagctcgcc cggtacaaca agaagcccac    480
catcacctcc cgcgagatcc agacctccgt ccgcctcgtc ctccccggcg agctcgccaa    540
gcacgccgtc tcgagggta ccaaggccgt caccaagttc acctcgtctt agccgccttg     600
ttgtaggcgt cgttgttgtc tgcttctcaa gcaagcactg tcatgtgccg cttctcatgg    660
cagt                                                                 664
```

<210> SEQ ID NO 100
<211> LENGTH: 680
<212> TYPE: DNA
<213> ORGANISM: Zea mays

<400> SEQUENCE: 100

```
aaacaacaca gtcatctgat cgtcataaaa tgatataatc tgtctatacc gcacccaagt     60
gtttcagtct ttcagagttc caaaacgttc gaatcttttc tttagccatc ttcttcctcc    120
cgacgccgcc gcggctatga ccgcgtatga gttccaacac tcgagtgagg tgtagagtgt    180
```

```
agacttaccg aaatgatatg tatacttgta gtaatacatg acaaaacgac ggttaattct      240
tgtgtaacaa tgcgatacga gcagggccga tgtactacaa cggcatgtac catctcttct      300
accagtacaa cccgcacggc gcgctctggg gcgttggcaa cctctcctgg ggccactccg      360
tttccggcga cctcgtgaac tgggccgccc tggacacggc gctggacccg acgtcgccct      420
tcgacgccaa cggctgctgg tcgggctccg ccaccatcct ccccggcggc accccggcca      480
tcctctacac gggcatcgac gccaacgggg agcaggtgca gaacgtggcg ttccccaggg      540
acccggcgga cccgctcctt cgccggtggg acaagcccgg ctacaacccc gtcatcccgc      600
tccccgccga cgtcccgggc gacaagttcc gggaccttc  gacggcgtgg ctcggccgcg      660
acgggctgtg gcgcgtcgcg                                                  680

<210> SEQ ID NO 101
<211> LENGTH: 935
<212> TYPE: DNA
<213> ORGANISM: Zea mays

<400> SEQUENCE: 101
ctgtcatcca tgtccaggag gtctgttgct gcacaccctt ggcatgatct ggagataggt       60
attgtacacg ctctagcttg acaaatggtc agccgttgat ctctgctatt gcaaccaga      120 gcttaagttc atcttggatt catgcaggtc ctggtgctcc aaccatattc aactgcgtaa      180
ggccaccctg tcatgcttga ctggtcctct tgtgatatgt tcatgttaat agcatgatgt      240
cttttgttct attggaaaat aaaaagtctc cctggactct aaaatcaatg cctgtgaaca      300
catgaactgt ttgtgtcacc catgttcctc tgctccttgg cactttctga tgcatgctca      360
aatgcttaag aaagactcat agaagcgact cctattccta tgccaggtca ttgagatacc      420
aaggggcagc aaggttaaat atgaacttga caagaaaact ggactgatca aggtaaagca      480
atgttgtttt cctcccgctg aagtcttatt gtgaagctat atttcttgcc agttctaata      540
tttactcctt tccgtttcaa tctgtgtgca tgtgcaggtg gaccgtgtgc tgtattcatc      600
agttgtttac cctcacaact atggattcat tcctcgcacg ctttgtgaag acagtgatcc      660
tttggatgta ctggttataa tgcaggtatg cttctttttt atatatatca ttgggattca      720
caaaatggta catcagtagt gatctgagta tccttgggca taagttgagc taattttcaa      780
atcttgtcat tttccatttc tgggaatggt cgagaacatg tctataaact gttacttcca      840
agcatgtagg agccagtcat tttccatttc tgtttatagt tgcctagtcg ggaacatgta      900
tgtaaactgt tacttccgtg catgcaggag cctgt                                 935

<210> SEQ ID NO 102
<211> LENGTH: 805
<212> TYPE: DNA
<213> ORGANISM: Zea mays

<400> SEQUENCE: 102
ggatccatac aaggtgcttt tttttcgatt tagaattctt tcttcatcga ttttgcccta       60
tgtgctagat cctcaaatca attccgcatc ttgtttccgc ccttgattga tgcattcgct      120
cgtctgactt gattgatgcg ctcgatctgg gggactcttg gttcttgcag caccgcccgt      180
ctagtgggag caactccagc ttctggacca ccaactccgg cgccccgtc  tggaacaaca      240 actctgccct caccgtcgga cagcgaggtc agaccacaac ccctctctct gtttatcctg      300
tagctgacat gctgctgcct tcatttgtct cgtctctcca tcccggtttc attttcccgt      360
```

```
gcacgatcct gtatgtactc actatgtatg tagcatatat gttcttgatt tgtgcgagac    420
ccatccgagg cataaatgat ctgttctagc tttgctttga ggcctattat tgcaccgtgg    480
aagccagagg atttcgcttc ccatccattc aaagcttgca tcttgatgtg cttttaatta    540
atttccagtg actaattttg cctgctctgt acatgcgggt tgtcgttgat tcacctgtcc    600
gaatatcgtc aatgaatttg agacttgccc aaaggactta ttccttgtat cagctgtaag    660
gtgaagcttt tgtcctgata ttttttgccag tcgctgtcga accattacgt tacttaaggg    720
aaagaaagca cattcccggt acgaaatgcc atcatggagt catagtgata atcctaggtg    780
agggacactt ggagagtagt aaagt                                           805

<210> SEQ ID NO 103
<211> LENGTH: 1582
<212> TYPE: DNA
<213> ORGANISM: Zea mays

<400> SEQUENCE: 103
gtacctccta ttcttagcca gctagcgaga gagaccaaat cctggcctca catgagatcg     60
actggttcct gggctccttc tctcctcccc ccgttaagtt gcccgtcgga ggaggatcct    120
gagcacatcg atcagtcgcg tgtctaggtt tcctctctca ccatagcgcc cgctctgtcg    180
cccttcgttc acctctcctt cctctcgtcc ctgcctgcca gggagagggg aagtcagagg    240
cacggagtgg cgcagagcag acgcccgtga accattgtag ctgtccctgt cgtcgtcgtc    300
gtcaacgaac ccacacaagg aaaggatgga gaagaagccg accatcctca tgaacaggta    360
cgagctcggg cgcacgctcg ggcagggcac cttcgccaag gtgtaccacg gccggaacct    420
cgcgtccggc gagagcgtgg ccatcaaggt catcgacaag gagaaggtga tgcgcgtcgg    480
catgatcgac cagatcaagc gcgagatctc cgtcatgcgc ctcgtccgcc accccaacgt    540
cgtgcagctg cacgaggtga tggccagcaa gagcaagata tacttcgcca tggagtacgt    600
ccggggcggc gagctcttcg cccgcgtcgc ccgcggccgg ctcaaggagg acgccgcgag    660
aaggtacttc caccagctcg tcggcgccgt cgacttctgc cacagccgcg gcgtctacca    720
ccgcgacctc aagcccgaga acctcctcgt cgacgagcac ggcaacctca aggtctccga    780
cttcggcctc agcgcgctca gggagtgcca gaagcaggac ggcctgctgc acaccacctg    840 cggcacccc gcgtacgtcg cgccggagat catcaacaag aagggctacg acggggccaa    900
ggccgacatc tggtcctgcg gcgtcatcct cttcgtgctc ctcgccggct acctcccgtt    960
ccacgacgcc aacctggtgg agatgtaccg caagatcagc agagccgacg tcaagtaccc   1020
gcagtggttc tcccctgagc tccggcggtt gatgcccaag ctcctcgaac cgaacccaaa   1080
caacaggatc acgatcgaga agctggtcga gcacccctgg ttcaagaagg ggtacaggcc   1140
ggccgtcatg ctggcacagc cgcacggctc cagcagcctc aaggatgtcc aggtcgcctt   1200
cagcaacgcc gaccacaagg acagcagcag caaggtggaa cagccggcgg acagctcctt   1260
gaagccggcg agcctgaacg cgttcgacat catctcccac tccagagggt cgacctgtc   1320 aagcctgttc gaggtggacc aagagcagaa ggccagcaac tcgcggttca tgacccagaa   1380
gccggcgtcg gcgatagtgt caaagctgga gcagatcgct gagacagagc gcttcatggt   1440
gaaaaaacag gacgggctgg tgaagctgca ggggtccaag caagggagga aggggcagct   1500
cgcgatcgac gccgagatct tcgaggtgac accggccttt cacgtcgtcg aggtgaagaa   1560
gtcggcaggc gacacgctgg ag                                            1582
```

```
<210> SEQ ID NO 104
<211> LENGTH: 741
<212> TYPE: DNA
<213> ORGANISM: Zea mays

<400> SEQUENCE: 104
gcaatgtgaa tgaatatatg acgcaccatt atgttatgtg tgacatattt tgatttctat      60
acttctaagt attctctgat catctgggac gtgtaaacat aaaaagataa taaactaact     120
gcattcgaga tcatgaccag taataacaaa caaatgtaat ctgcagtgag aacagataag     180
tggccacata accaaaacct tgagtctgca cagcatctta attgtcactt aacacaagaa     240
aacaatttag acagttataa gcaacatata acattgacca ttgatcattt aggttaacat     300
ggggacaaga cataattgat tgctaaatct atctgtaagc tttattaatc ttataattca     360
taattacaat gagttcattg caaccctcaa ggtgtaatgt tacagcaagt caaccacagc     420
agcacagaac aagaacatgt tgtagaccta aggttttagt ctcccttga actctattac      480 tcagatatag agtatatatc taacaaaaat ggtacggaaa agcataccta agaaaccaca     540
agccacagaa ttgatgtagc ttcgagcttc aattgaatcc agacctagga caattatgtg     600
gaactgactg tagaactcta tctctttatc ttcaatcctg caaaaatgag gaactatgtt     660
caccccatta actcgctcca taaccctctt cgctgctact tcagccttgg acttcccaac     720
atcttgaact ctgtacagca g                                              741

<210> SEQ ID NO 105
<211> LENGTH: 628
<212> TYPE: DNA
<213> ORGANISM: Zea mays

<400> SEQUENCE: 105
gagaagcaac atgacggcaa gctcagtggc tacattcgaa taaggagcaa gacccaggga      60
attgcactca gcttagggga caagatcact ctcaagcaga aggtggcag ttaactgtga      120 caagtaatcg cagttgtatc atcatttttc gcatttagga aatccacgtg ccagagagag     180
accagtgccg tggcattgaa ctgagtataa atgcttttt gtacaaaagg atcgatcaag      240
gagagagata agaggacagt tatgaggaag tcacgaagtt gtcggtcgaa gatatatgtt     300
gctgtagtaa cgaagctgtt ccaaacttcc ttgaaatagt tgtgaagttt atgttgattt     360
ctcgacaggt agttcaattg tgatcttgta ctactattat gaatccctct tgttttaatg     420
ttttatttgc ctttatttta gttgtctgga cttggaaaca aagcttgga ggcggtgttg      480 tcacgttatt tttgtagaga tgaattggag ctcatttcct gttgcatata gatttgccaa     540
ttgtgttagg gtacttttat ggtgtttatt taagaaatga ggtagtccat tatctttta      600 ctcagtttct ttggtttgtg gaataaat                                       628

<210> SEQ ID NO 106
<211> LENGTH: 1084
<212> TYPE: DNA
<213> ORGANISM: Zea mays

<400> SEQUENCE: 106
atagtgcaaa tctgagtgtt aaccataata acacaaatct gagtgttgca cagagaaaag      60
gataacgcat gtagcagatc aacatattta taatcatagt gcatcgcagc ccaatattga     120
aacagataaa aatacattaa ccagtagaga gttgtaccaa gagagaacag aacttacttc     180
ctgagcctga gctggggtgg cgactttgcc agttccaata gcccagactg gttcataggc     240
```

```
aagaacaacg ttgctccagt ccttgatctt ctctgtaaaa caaacagcca tttgatccat      300
tcagcctgat ttttcgtata gggtcaaaaa acttggtaac ttcaaagcaa ggcactaaat      360
gttcacatga acaaaacaaa gggcagaccc agctcccaca tgaatgtggg gtctttcccc      420
cacaaatgcg gaaggaaaa tccagcatgt aaattcatcc aagcaacaga aacaaaaact       480
cggccaggga aggaaagacc gccctcccgg tattctatta agaagagacc gaaacatggt      540
cccggccgaa aaatccccg aaccctagcc ccccatcact agttggccga catcgcgcac       600
tctgcaaatg cccagccgga gggtgggtg catgacataa cccgagggcg ggcggggcac       660
aacgaaggga ttttttaacc aagcccgaaa ttcgccccca aggggatcg aacccgggac       720 ctggaggtgc tacttggaag ctttaaccat tacgctaaag gcccttttcgc agcgacagaa      780 acacacataa gttgattcct aaactaaagc tgttacagaa aaacagtaat gtccgaactc      840
cggatatgta gattatctaa cagaactgat caccagaagc aaagggcctg ttcagtttgg      900
gtttcagctg ctgtggctag ctgcagctag cttatgacta cagtaactct actgtgacac      960
ctgagaggca gcagccaacg actgaataaa tgccagacga acaatctcaa ccaaaagatg     1020
tatagctaca tttatataat gaaccaacaa ggcagcaact cttcattacc attaaaaaac     1080
taac                                                                 1084

<210> SEQ ID NO 107
<211> LENGTH: 929
<212> TYPE: DNA
<213> ORGANISM: Zea mays

<400> SEQUENCE: 107
atcaagagca gcagctgctt tgctgagaaa caggctgacc ccgcatttgc acagttgcag       60
gcctactagc accacttgca gctggttgac ttgccatcct atccaacaag gagaatgaag      120
aatgattagg tgctcccgta tacagataaa caatagcaaa catagtgatc atgggattca      180
tggcttattt ttcactttga atcatatgca atattatgtt gcacagtgtt ctttgtttgt      240
actcagtccc tcaataaaag agggcctcca tatgttgaca tactatactt gatgactcca      300
aaaggaatga gaaaatgctg ccacaaaaaa gtctacaaca caaatgatct agttacctgt      360
tctttatctc ccctgccatg gtcatgaatg ccttctccac atttgttgca tccttggcac      420
tagtctcaag gaatggtatt ccgatgtcat cagcaagggc ctatgatgac aagcaacatg      480
cagccaattt aactatcatc ccggttgaaa gaagcatgtc cagtaaaagt aattaatgca      540
gagaaatatt accttgccag cctcgtaaga aactactctg ttctcagcca ggtcacactt      600
gttccccacc aaaagcttgt tcacattttc actggcatac ctatcaattt cattcagcca      660
ctgcttgaca ttgttaaagc tctcctggtc agttacatca tacacaacct atagaaatac      720
aaaagtttaa acaagactca gattaacaaa gatgagataa tagcagatag gaaaaaaacg      780
aaataagaaa aagaaagctc acaataatgc catgagctcc acggtagtag ctgcttgtga      840
tggtcctaaa gcgttcttgg ccagcagtat cccactaaat cagaagaatg tggagaaaca      900
taagtgtcaa agcttctaac tgttaggaa                                        929

<210> SEQ ID NO 108
<211> LENGTH: 850
<212> TYPE: DNA
<213> ORGANISM: Zea mays

<400> SEQUENCE: 108
ctcgggcacc ggaattcccc cctgtagatc ttacggtaca tcgccatgag gttctggtcg       60
```

```
tggaaaggga ggtagccagc catgagcacg aacaggatga caccgcacga ccatatgtcc    120
gccttggcgc cgtcgtagcc gcggcgcgcg agcacctccg gagcgacgta tgacggcgtg    180
ccacagaagg tgtggaggag gccgtcgggg tggaactggt cggcgaccgc cgagaggccg    240
aagtcggaga ccttgaggtc gccgcgctcg tcgacgagga gattctcggg cttgaggtcg    300
cggtggaaga cgccgcgggc gtggcagaag ccgacggcgg agatgagctg ctggaagtac    360
ctgcgcgcgg tgtcctcctt gaggcggccc ttggcgacgc gcgcgaagag ctccccgccg    420
cggacgaact ccatgacgaa gtagatcttg gacctggtgg ccatgacctc gaagaggcgg    480
acgatgttgg ggtggcgcac gcggcggagg atggcgatct cgcgcttgat gtgcgggacg    540
aggccgttgc gcagggcctt ctccttgtcg agcaccttga tggcgacggt ctcgccggtg    600
tcgtcggcgt ggcgggcgtg gtacaccttg gcgaaggtgc cgtggccgag caggcggccc    660
agctcgtagc gccccagcag gaggcccccg cgcttggcgg gccccgagga ggaggccggc    720
cgccggggct gcggtgacgc gtcccacgac ggcggcgggg tggcggccat caggtagagg    780
aggaggtcag gcgcgcggag aaacggagcg gaaggcagaa tggccgatta ggtggtggtg    840
gtagcgaggg                                                            850

<210> SEQ ID NO 109
<211> LENGTH: 606
<212> TYPE: DNA
<213> ORGANISM: Zea mays

<400> SEQUENCE: 109
gccaaacaag cactcttcta gttcttccgt ttctcacttt ctcttcctga gaatctcccc     60
tttatatgaa taatataaat gtcacataag taaataaaca aataaatcaa tcaatattac    120
tacgaagctg tcctcaccgc cttctctctc cctccgaatc caaacgcgga cgcaaatgtt    180
gctccacgcc ggtccctcgt tcctgctcgc accactccg cgctttgccg ccgctccgtc    240
gtcagcttcg ccgaggcgat ccaggacacc gcaatcctcg ccgccgacgt cgcatttcgc    300
gcgccccgct gatcccgtgg cccaaagggt gcgtcccgtc gcgccgaggc ccccatggc    360 gacggcggag gagggcgcca gctctgacgt cggcgtcgcc gtcgccgagt ccgcacaggt    420
tcggccgcca ctgcccctcc tcacattcca gagtttacgc aattattatc acttgggcca    480
ctcgtttgcc aatgattacg cgattacgcc taacctgtcg gtcgggtcta cattgtagtc    540
acactcacac gaatgccccc aaccgtttgt gagctcgtgg tgatgatctg tgttccacct    600
gcacca                                                                606

<210> SEQ ID NO 110
<211> LENGTH: 710
<212> TYPE: DNA
<213> ORGANISM: Zea mays

<400> SEQUENCE: 110
agcatgacca gaagcagagc ctgatggaca aggcgaaggg gttcgtcgcg gagaagatcg     60
cgcacatccc caagcccgag gcgacgctgg acggcgtgac gttcaagggc ctgagccggg    120
agtgcatcac gctgcacagc agcgtgaacg tgtccaaccc ctacgaccac cgcctccccca   180 tctgcgaggt gacctacacg ctccggtgcg ccggcaagga ggtggcgtcc ggcaccatgc    240
cggaccccgg ctggatcgcc gccagcggct ccaccgcgct ggagatcccc gccaaggtgc    300
cctacgactt cctcgtctcc ctcgtcaggg acgtcggccg ggactgggac atcgactacg    360
```

| agctccaggt cgggctcacc gtcgacctcc ccatcgtcgg caacttcacc atcccgctct | 420 |
| ccacctctgg cgagttcaag ctccccaccc tcaaggactt gttctgatct agtagtagct | 480 |
| cgcttgcctt gtgttctgtg cgggcgcgca ccagcgatct gtacgacgag cttttgcaaa | 540 |
| taaacgacgc agctcctctg ttctatatat ctcaatgaat gcctaagcta agggatgga | 600 |
| tggtttaatt tgactgcaaa taagagctg gatttcgttc aggttcctgt ctctaagctg | 660 |
| gatttcattc gggcatccac catgatgtgg atgtgcctgc cgcgtccgtc | 710 |

<210> SEQ ID NO 111
<211> LENGTH: 838
<212> TYPE: DNA
<213> ORGANISM: Zea mays

<400> SEQUENCE: 111

| acgacgatgg cggcgtaccc cttggggatc tccgcgacgc cggagaagcc gaacttggcg | 60 |
| ccgatgaggc tgcccacgac gatctggcac gcgagcatct gggtgccgcc ctgcaggaac | 120 |
| agcttgcggc ggccgaggcg gtcgacggtg acgatggaca cgaaggtggc gaagacgttg | 180 |
| acgaggcccg tgatgacggc ggacatgagg gaggcgtcgt ccgcgaagcc cagcgtcttg | 240 |
| aagaggaccg gggcgtagaa catgatgacg ttgatgcccg tgagctgctg gaacatgggg | 300 |
| atggcgatgg ccatgacgag ctgcgggcgg tagcgcggca gcaggatgtt gcgccagggg | 360 |
| tgcgccacca gcttggactc gtcgctggcg gccaccaggt cgctgtactc ctcctccacg | 420 |
| tcgtcggtgc cccggacgcg cttgagcatc cgcttggcgg cgtcggtgta gccgcggtcg | 480 |
| atgagggagt tgggtgtgtc gggcaggaag agcgcgccca cggcgatgat ggccgccggc | 540 |
| acggccgcga gcgcgaggct gacgcgccag ccccagccgc ccctgatctt ggcggtgccg | 600 |
| tagttgatga ggttggcgca gaggatgccg atggtgacca tgagctggaa gccgatgttg | 660 |
| agcatcccgc ggaggcgcgc cggcgccatc tccgagaggt agacgggcac ggactggttg | 720 |
| gcgaagccga cgccgacgcc gaggaggacg cggccgagga tgagcatgcc cacgtccttg | 780 |
| gcggcgccgt tgagcgcggc gccgaccagg aacgtgacgc cgccgccgaa catggacc | 838 |

<210> SEQ ID NO 112
<211> LENGTH: 821
<212> TYPE: DNA
<213> ORGANISM: Zea mays

<400> SEQUENCE: 112

| ccagttcaag acagaggaga tgaccaacat catgaaggac ttcgacgagc ccgggttcct | 60 |
| ggccccgacc ggcctcttcc tcggccccac caagtacatg gtcatccaag gcgagcccgg | 120 |
| cgctgtcatc cgcgggaaga aggtactgat ccgtcgtcgt ctatgctccc cctctcgatc | 180 |
| tcccaatata atgcacgtcg atcatctttc tcttgtttcc ctaggatct ggaggcataa | 240 |
| ctgtgaagaa gacagggcaa gcgatggtgg tcggcatcta cgacgagccc atgaccccg | 300 |
| gccagtgcaa catggtggtc gagaggctcg gcgactacct cgtagagcaa ggcctgtgaa | 360 |
| tggattcatt taacctcgct cgctcgcttg tccatggttc gagcatccag cagcaacgat | 420 |
| accaacatca gcattattta attggtagcc tcctctagct acgcacgcat tttagtcccc | 480 |
| tacacgccct tggattgtgc gtggctctgt taatcatctc tcatccttcg tctgccattt | 540 |
| ctcccctgcc cgtcgccgat caccagagat ttttgttcct tgttggtacc atgcattttg | 600 |
| gcaaataatt ttgtaattcc acccccaaat taaagtttgg ttgtcgtatg gtttgtaaac | 660 |
| ccagaacaat atatatatgt gtgtgattga actgttcctg tctattcttt ttgtaaacgg | 720 |

```
gaatatatat gtatgcattt tgtgtgatgc atgccttcca gggcgacgac taattaatgt    780
gcaaccagtc ctccatccat gtatggtgaa gggctaaagg c                        821

<210> SEQ ID NO 113
<211> LENGTH: 652
<212> TYPE: DNA
<213> ORGANISM: Zea mays

<400> SEQUENCE: 113
gtggaagccg ccgcggcttt cttgaacaaa gccgtcaagc cagtgcttgt aggtgggcca     60
aagatgaggg tgtccaaagc atgggaagcc ttggcagagc tggcagatgc ctgcggctat    120
cccgttgccg tgatgccttc tgcgaagggg ctagtgccag tgcaccactc taggttcatt    180
ggcacgtact ggggtgcggt gagcactcca ttctgtgctg agatcgtcga gtctgccgat    240
gcctacctat ttgctggccc cgtattcaac gactacagct cggttgggta ctcgctgctc    300
ctcaagaagg agaaggccat cattgtccaa ccagagcggg tggtggtcgg gcatggaccc    360
gcgtttgggt gtgttctgat gaaggatttc cttcatgccc ttgcaacccg tctgaagaag    420
aacactgtcg cgtatgagaa ctaccgtcga atttatgtgc ctccaggcga accactttca    480
tctgaacctg gcgagccgtt gagagtgaac gtgctcttca agcatattca ggcaatgctg    540
tccggcgaca tggctgtcat cgcagagact ggggactcgt ggtttaactg ccagaagctg    600
aagctaccgg aaggatgtgg gtaagctcct ctttcgaatc atgattttgc tg            652

<210> SEQ ID NO 114
<211> LENGTH: 646
<212> TYPE: DNA
<213> ORGANISM: Zea mays

<400> SEQUENCE: 114
ccaacagatg ctcaggtgaa ccagtccagc agcataggct tctaaaccta ctattagggg     60
aaaaagaaat aacttatggc gtcgaccaca aacacactga tgcacgagaa gtatttctag    120
ctgttgttat ctgtgaggtt gatcctgcgc ggcggcggg ctcgacacga tgtgaccata    180
aacgaactgg ttccacgtgt ccggcacgcc ggggaggcac cagtggatgc aatccgcgaa    240
cttcctcggg ttcgccttct gctcgggcgt caggagcttc ccctgccgca gcgtgtgcac    300
ggaggtgtgc gcgtccttgc ggatctccga cagcgcggtc acgtcgacga agcgcaccgg    360
caccttctcc atcgacctcg tcacgcgctg ggcggccgcg aagaggtccc agtccgtgcc    420
cacctccagt ttcttcgtgt agttgatcgc cggctgcgtc tcggagaagc attttacggc    480 gttgggctg ccccagcctt cactcctgga ccacaacaag acagtgagtg actgtggagg     540
ggcagaaatt ctgcatatca agcaaggtac ggatggatac ttactgcata tgtaccggtg    600
acacgctcat gaataggacc gtgcttctct tgggatcaat gtgcgc                   646

<210> SEQ ID NO 115
<211> LENGTH: 603
<212> TYPE: DNA
<213> ORGANISM: Zea mays

<400> SEQUENCE: 115
ggatctggac aatatttcac aagccaaaaa gacaaaaaaa aaaaaaatca agtacctgtc     60
ttccatccaa gcaacactgt acaggtctcc caaacaagtg tcatactccg gtggagggct    120
cgggaactcg ccagggcagt acgtccccca gctgctctcg tctgcatttg acgcggtggt    180
```

```
cgcatacaca ttgatgtcat tcggcaggag gccctcaaag atgctcccag attcgcatgc    240
ttcaaggtaa aagacctaca aaaggtgaaa gaatacgcat atacctcaag cccttgcttg    300
acatatcaca aaatttcaga gcagaactga acaaacagct aacggtacca ggcttttgta    360
ggtcccggca gcatgcttct tcttcaggac atctacgagg tcatcaccat agagatatgg    420
atacgtaggc attcctgaat tttttacaga gtaagtaact gtgtctattt tggttctaca    480
tgcatgtacg aactgatatt ttatctaaga aacatctaat ctgaatgaaa tcagtagcaa    540
ttagttgcga gtacagacca aggacaccag gacccccatg gtcactgtag aaaacaaaga    600
tat                                                                  603

<210> SEQ ID NO 116
<211> LENGTH: 841
<212> TYPE: DNA
<213> ORGANISM: Zea mays

<400> SEQUENCE: 116
taactgctaa taactatagg cgggattatc atctgggttc aaatatttgg acttatgtgc     60
tcctttgagg cggcgaggca gccacaccca cacgcagtgg cctgtggcgc ctgggcggtg    120
agtccgccta tgactgcgaa tgttataatt ttattgggca tccttttagt tgattgaatt    180
ggttgtagcc tgaaccttat ctaccatttt atctcccctg cttgtcgtgt tctatgtccc    240
tgttcagcag ctataccaca gtcttttatg ctcacagagg cagacattag tggcttgaag    300
tgcagccaaa cggcttaggt ttatctatct cttctgagat atgaaatggg acattgtagg    360
tttatgcata ttcagccacc tttgctagtt attatgtgat tttgtaaatt tcctgagcct    420
gcgactaaat tatttcaaca tatttagtaa tgcgctggga gtatatgcag aacttaagta    480
ccttttctgt ttgttttgtc aacaaagtga gcaaaaaaca atgctttgtt atgtgtggcc    540
atgttgcatg agtgaagaag cacgtgtttc tttcttttca cctgaaaagt aaaatagttc    600
tgcaagcaga atctctagtt atggaatgtt atttctgaat ccgcagttca catcatgttc    660
agtcaagtac tagcactgac ggttgcttcc tttttgatat gtgcagaaag cacttgcagg    720
tctgagaaga atcaatttag atgggcttcg atggcgcgta tttgatgcta agggtcaggt    780
taggattgtt tttctagctt gagtagcatg gatgaactta tctcaagaag gatagaggct    840
a                                                                    841

<210> SEQ ID NO 117
<211> LENGTH: 459
<212> TYPE: DNA
<213> ORGANISM: Zea mays

<400> SEQUENCE: 117
atcaacgtgc agaacaagaa ctcgtcctac ttcgtggagt ggatccccaa caacgtgaag     60
tccagcgtgt gtgacatccc gccgaggggc ctgtccatgg cgtccacctt cgtcggcaac    120
tcaacttcca tccaggagat gttccggagg gtgagcgagc agttcactgc catgttcagg    180
aggaaggctt tcttgcactg gtacacgggc gagggcatgg acgagatgga gttcaccgag    240
gccgagagca atatgaatga cctcgtgtcg gagtaccagc agtaccagga tgcgactgct    300
gatgacgatg aggaggccga gtatgaggac gaggaggagc cagctgatgg catgtgaggg    360
gaggctgtta aatgtgaagc ctggtgatgt cccctttcgt gttgtcgcca tgttatacta    420
gtacactagc ataccaccct cgtggcccat tccgtcgat                           459
```

```
<210> SEQ ID NO 118
<211> LENGTH: 24
<212> TYPE: DNA
<213> ORGANISM: Zea mays

<400> SEQUENCE: 118
ctagggtcct gctacaagag atcg                                          24

<210> SEQ ID NO 119
<211> LENGTH: 17
<212> TYPE: DNA
<213> ORGANISM: Zea mays

<400> SEQUENCE: 119
ggtccagccc agtcgcc                                                  17

<210> SEQ ID NO 120
<211> LENGTH: 20
<212> TYPE: DNA
<213> ORGANISM: Zea mays

<400> SEQUENCE: 120
gaagagaagc accctggacg                                               20

<210> SEQ ID NO 121
<211> LENGTH: 27
<212> TYPE: DNA
<213> ORGANISM: Zea mays
<220> FEATURE:
<221> NAME/KEY: misc_feature
<222> LOCATION: (18)..(18)
<223> OTHER INFORMATION: y is c or t

<400> SEQUENCE: 121
aacggacaat caaatatytg ttgtcag                                       27

<210> SEQ ID NO 122
<211> LENGTH: 26
<212> TYPE: DNA
<213> ORGANISM: Zea mays

<400> SEQUENCE: 122
tcaacaaatc agaacacact cacagt                                        26

<210> SEQ ID NO 123
<211> LENGTH: 25
<212> TYPE: DNA
<213> ORGANISM: Zea mays

<400> SEQUENCE: 123
caagcgttcc agtgttattg agtct                                         25

<210> SEQ ID NO 124
<211> LENGTH: 19
<212> TYPE: DNA
<213> ORGANISM: Zea mays

<400> SEQUENCE: 124
ggcgcatagg acatcgtaa                                                19

<210> SEQ ID NO 125
<211> LENGTH: 25
<212> TYPE: DNA
<213> ORGANISM: Zea mays
```

<400> SEQUENCE: 125
gtgattaaag gcttccgagt aacac          25

<210> SEQ ID NO 126
<211> LENGTH: 20
<212> TYPE: DNA
<213> ORGANISM: Zea mays

<400> SEQUENCE: 126
agtcgttttc cccacccttt          20

<210> SEQ ID NO 127
<211> LENGTH: 20
<212> TYPE: DNA
<213> ORGANISM: Zea mays

<400> SEQUENCE: 127
cacacgatgt tgccccatac          20

<210> SEQ ID NO 128
<211> LENGTH: 17
<212> TYPE: DNA
<213> ORGANISM: Zea mays

<400> SEQUENCE: 128
agctgacggg cggatgt          17

<210> SEQ ID NO 129
<211> LENGTH: 21
<212> TYPE: DNA
<213> ORGANISM: Zea mays

<400> SEQUENCE: 129
tgccattgtt gaacacgaac a          21

<210> SEQ ID NO 130
<211> LENGTH: 21
<212> TYPE: DNA
<213> ORGANISM: Zea mays

<400> SEQUENCE: 130
catgcctcag atcgtcaaac a          21

<210> SEQ ID NO 131
<211> LENGTH: 23
<212> TYPE: DNA
<213> ORGANISM: Zea mays

<400> SEQUENCE: 131
cgccaacaag ggaagaaatt aaa          23

<210> SEQ ID NO 132
<211> LENGTH: 21
<212> TYPE: DNA
<213> ORGANISM: Zea mays

<400> SEQUENCE: 132
aagaaagaca atgttggtgg g          21

<210> SEQ ID NO 133
<211> LENGTH: 21
<212> TYPE: DNA
<213> ORGANISM: Zea mays

```
<400> SEQUENCE: 133
ttcaacaacc tgcagaactt g                                              21

<210> SEQ ID NO 134
<211> LENGTH: 23
<212> TYPE: DNA
<213> ORGANISM: Zea mays

<400> SEQUENCE: 134 gccatacccct gcagaatcag ttc                                           23

<210> SEQ ID NO 135
<211> LENGTH: 21
<212> TYPE: DNA
<213> ORGANISM: Zea mays

<400> SEQUENCE: 135
ccatcaggtg agcagcatct g                                              21

<210> SEQ ID NO 136
<211> LENGTH: 21
<212> TYPE: DNA
<213> ORGANISM: Zea mays

<400> SEQUENCE: 136
cattcgcagc cattcctaca g                                              21

<210> SEQ ID NO 137
<211> LENGTH: 24
<212> TYPE: DNA
<213> ORGANISM: Zea mays

<400> SEQUENCE: 137
ccgatggatt ggactcctgt ttag                                           24

<210> SEQ ID NO 138
<211> LENGTH: 23
<212> TYPE: DNA
<213> ORGANISM: Zea mays

<400> SEQUENCE: 138
tgggcagaaa ctgtggaaga aaa                                            23

<210> SEQ ID NO 139
<211> LENGTH: 22
<212> TYPE: DNA
<213> ORGANISM: Zea mays

<400> SEQUENCE: 139
tgagggtgag gtgattctcg at                                             22

<210> SEQ ID NO 140
<211> LENGTH: 19
<212> TYPE: DNA
<213> ORGANISM: Zea mays

<400> SEQUENCE: 140
tcaccgagtt gagcagcag                                                 19

<210> SEQ ID NO 141
<211> LENGTH: 15
<212> TYPE: DNA
```

<213> ORGANISM: Zea mays

<400> SEQUENCE: 141
cggctgacgc tgctg                                              15

<210> SEQ ID NO 142
<211> LENGTH: 26
<212> TYPE: DNA
<213> ORGANISM: Zea mays

<400> SEQUENCE: 142
aaatgttgtg attttcaggc caagac                                  26

<210> SEQ ID NO 143
<211> LENGTH: 20
<212> TYPE: DNA
<213> ORGANISM: Zea mays

<400> SEQUENCE: 143
tgctgtgagt agtgcttgca                                         20

<210> SEQ ID NO 144
<211> LENGTH: 22
<212> TYPE: DNA
<213> ORGANISM: Zea mays

<400> SEQUENCE: 144
aggtcgaaga tgaggacgtt ct                                      22

<210> SEQ ID NO 145
<211> LENGTH: 20
<212> TYPE: DNA
<213> ORGANISM: Zea mays

<400> SEQUENCE: 145
gtcatgcgca tcatcaacga                                         20

<210> SEQ ID NO 146
<211> LENGTH: 24
<212> TYPE: DNA
<213> ORGANISM: Zea mays

<400> SEQUENCE: 146
ggacttgtag tagacgttga cgta                                    24

<210> SEQ ID NO 147
<211> LENGTH: 16
<212> TYPE: DNA
<213> ORGANISM: Zea mays

<400> SEQUENCE: 147
cgggctcctg gtctgg                                             16

<210> SEQ ID NO 148
<211> LENGTH: 26
<212> TYPE: DNA
<213> ORGANISM: Zea mays

<400> SEQUENCE: 148
gtgatcgctc tgaatgttta atgtgt                                  26

<210> SEQ ID NO 149
<211> LENGTH: 25

```
<212> TYPE: DNA
<213> ORGANISM: Zea mays

<400> SEQUENCE: 149
ttcaacacct cagtacatcg ctaaa                                         25

<210> SEQ ID NO 150
<211> LENGTH: 27
<212> TYPE: DNA
<213> ORGANISM: Zea mays

<400> SEQUENCE: 150
gctttcgaat gtgttcatga tgtaagt                                       27

<210> SEQ ID NO 151
<211> LENGTH: 17
<212> TYPE: DNA
<213> ORGANISM: Zea mays

<400> SEQUENCE: 151
ccccagccct ggatcac                                                  17

<210> SEQ ID NO 152
<211> LENGTH: 19
<212> TYPE: DNA
<213> ORGANISM: Zea mays

<400> SEQUENCE: 152
tgatggaact gcacaaatg                                                19

<210> SEQ ID NO 153
<211> LENGTH: 18
<212> TYPE: DNA
<213> ORGANISM: Zea mays

<400> SEQUENCE: 153
caccctgctc aaggtcat                                                 18

<210> SEQ ID NO 154
<211> LENGTH: 27
<212> TYPE: DNA
<213> ORGANISM: Zea mays

<400> SEQUENCE: 154
aggagaagga tgtggactta attagaa                                       27

<210> SEQ ID NO 155
<211> LENGTH: 24
<212> TYPE: DNA
<213> ORGANISM: Zea mays

<400> SEQUENCE: 155
tagatgtcct catcctgaaa cacg                                          24

<210> SEQ ID NO 156
<211> LENGTH: 22
<212> TYPE: DNA
<213> ORGANISM: Zea mays

<400> SEQUENCE: 156
ccctggtaac tcgtcccta ac                                             22

<210> SEQ ID NO 157
```

```
<210> SEQ ID NO 157
<211> LENGTH: 22
<212> TYPE: DNA
<213> ORGANISM: Zea mays

<400> SEQUENCE: 157
gatgccctgc tgttcttcag tc                                              22

<210> SEQ ID NO 158
<211> LENGTH: 24
<212> TYPE: DNA
<213> ORGANISM: Zea mays

<400> SEQUENCE: 158
caagcagtct ccagattggt agtg                                            24

<210> SEQ ID NO 159
<211> LENGTH: 25
<212> TYPE: DNA
<213> ORGANISM: Zea mays

<400> SEQUENCE: 159
catctagtct tgtgagaggc catgt                                           25

<210> SEQ ID NO 160
<211> LENGTH: 25
<212> TYPE: DNA
<213> ORGANISM: Zea mays

<400> SEQUENCE: 160
tgttaccagt agagcatctc ctgat                                           25

<210> SEQ ID NO 161
<211> LENGTH: 20
<212> TYPE: DNA
<213> ORGANISM: Zea mays

<400> SEQUENCE: 161
gcatcaccat cctccttgct                                                 20

<210> SEQ ID NO 162
<211> LENGTH: 30
<212> TYPE: DNA
<213> ORGANISM: Zea mays

<400> SEQUENCE: 162
gctaatactt gaatacagaa ggatggtgat                                      30

<210> SEQ ID NO 163
<211> LENGTH: 25
<212> TYPE: DNA
<213> ORGANISM: Zea mays

<400> SEQUENCE: 163
gccaacatat tgtcatccga ggata                                           25

<210> SEQ ID NO 164
<211> LENGTH: 20
<212> TYPE: DNA
<213> ORGANISM: Zea mays

<400> SEQUENCE: 164
acgcatcaac tgcagagaca                                                 20
```

```
<210> SEQ ID NO 165
<211> LENGTH: 23
<212> TYPE: DNA
<213> ORGANISM: Zea mays

<400> SEQUENCE: 165
gaaaagggac cattcaggta tgc                                              23

<210> SEQ ID NO 166
<211> LENGTH: 25
<212> TYPE: DNA
<213> ORGANISM: Zea mays

<400> SEQUENCE: 166
tctgcattgg aagttcgctt ataca                                            25

<210> SEQ ID NO 167
<211> LENGTH: 25
<212> TYPE: DNA
<213> ORGANISM: Zea mays

<400> SEQUENCE: 167
gctcgacagc atccaaaata atctg                                            25

<210> SEQ ID NO 168
<211> LENGTH: 25
<212> TYPE: DNA
<213> ORGANISM: Zea mays

<400> SEQUENCE: 168
gcgaattgca ctggagattt gattg                                            25

<210> SEQ ID NO 169
<211> LENGTH: 20
<212> TYPE: DNA
<213> ORGANISM: Zea mays

<400> SEQUENCE: 169
ctgaagatcg ggctgcaatg                                                  20

<210> SEQ ID NO 170
<211> LENGTH: 20
<212> TYPE: DNA
<213> ORGANISM: Zea mays

<400> SEQUENCE: 170
tgctggtacg aagacaagac                                                  20

<210> SEQ ID NO 171
<211> LENGTH: 24
<212> TYPE: DNA
<213> ORGANISM: Zea mays

<400> SEQUENCE: 171
aaaacaaaag aacaaaagaa ctac                                             24

<210> SEQ ID NO 172
<211> LENGTH: 21
<212> TYPE: DNA
<213> ORGANISM: Zea mays

<400> SEQUENCE: 172
aagcgaaccg ggatcaaaga t                                                21
```

```
<210> SEQ ID NO 173
<211> LENGTH: 25
<212> TYPE: DNA
<213> ORGANISM: Zea mays

<400> SEQUENCE: 173
cctacacgtg acttatcccc aaaag                                  25

<210> SEQ ID NO 174
<211> LENGTH: 19
<212> TYPE: DNA
<213> ORGANISM: Zea mays

<400> SEQUENCE: 174
gctggacaag atcaaggag                                         19

<210> SEQ ID NO 175
<211> LENGTH: 20
<212> TYPE: DNA
<213> ORGANISM: Zea mays

<400> SEQUENCE: 175
gctgaattac aatacgcaac                                        20

<210> SEQ ID NO 176
<211> LENGTH: 19
<212> TYPE: DNA
<213> ORGANISM: Zea mays

<400> SEQUENCE: 176
cctgcaggct cacgagtag                                         19

<210> SEQ ID NO 177
<211> LENGTH: 18
<212> TYPE: DNA
<213> ORGANISM: Zea mays

<400> SEQUENCE: 177
gtgtctgagg cggaaggt                                          18

<210> SEQ ID NO 178
<211> LENGTH: 15
<212> TYPE: DNA
<213> ORGANISM: Zea mays

<400> SEQUENCE: 178
ccgccaccgg aacct                                             15

<210> SEQ ID NO 179
<211> LENGTH: 16
<212> TYPE: DNA
<213> ORGANISM: Zea mays

<400> SEQUENCE: 179
agcagctcgc ccttcc                                            16

<210> SEQ ID NO 180
<211> LENGTH: 15
<212> TYPE: DNA
<213> ORGANISM: Zea mays

<400> SEQUENCE: 180
cccaccgcac gacca                                             15
```

```
<210> SEQ ID NO 181
<211> LENGTH: 21
<212> TYPE: DNA
<213> ORGANISM: Zea mays

<400> SEQUENCE: 181
agtctgagcc atcaccttcc t                                             21

<210> SEQ ID NO 182
<211> LENGTH: 24
<212> TYPE: DNA
<213> ORGANISM: Zea mays

<400> SEQUENCE: 182
ggtcgttctt cacattggtt agca                                          24

<210> SEQ ID NO 183
<211> LENGTH: 17
<212> TYPE: DNA
<213> ORGANISM: Zea mays

<400> SEQUENCE: 183
caccgccgct acagtct                                                  17

<210> SEQ ID NO 184
<211> LENGTH: 25
<212> TYPE: DNA
<213> ORGANISM: Zea mays

<400> SEQUENCE: 184
cagaaaacgc aacaaactac aacca                                         25

<210> SEQ ID NO 185
<211> LENGTH: 25
<212> TYPE: DNA
<213> ORGANISM: Zea mays

<400> SEQUENCE: 185
agtaagcatt gctcgtttag gatgt                                         25

<210> SEQ ID NO 186
<211> LENGTH: 19
<212> TYPE: DNA
<213> ORGANISM: Zea mays

<400> SEQUENCE: 186
acacgatcga gcacacaag                                                19

<210> SEQ ID NO 187
<211> LENGTH: 22
<212> TYPE: DNA
<213> ORGANISM: Zea mays

<400> SEQUENCE: 187
cgtagcataa acagtacacg ga                                            22

<210> SEQ ID NO 188
<211> LENGTH: 19
<212> TYPE: DNA
<213> ORGANISM: Zea mays

<400> SEQUENCE: 188
```

```
gctccaaggc gcatttctg                                                   19

<210> SEQ ID NO 189
<211> LENGTH: 25
<212> TYPE: DNA
<213> ORGANISM: Zea mays

<400> SEQUENCE: 189
cactctacag gcatctctac atctg                                            25

<210> SEQ ID NO 190
<211> LENGTH: 20
<212> TYPE: DNA
<213> ORGANISM: Zea mays

<400> SEQUENCE: 190
caggtcacac aggacaacca                                                  20

<210> SEQ ID NO 191
<211> LENGTH: 22
<212> TYPE: DNA
<213> ORGANISM: Zea mays

<400> SEQUENCE: 191
ccgagaaatg cgacgtctat gg                                               22

<210> SEQ ID NO 192
<211> LENGTH: 22
<212> TYPE: DNA
<213> ORGANISM: Zea mays

<400> SEQUENCE: 192
ccatcgtagg aaccctgtca tc                                               22

<210> SEQ ID NO 193
<211> LENGTH: 23
<212> TYPE: DNA
<213> ORGANISM: Zea mays

<400> SEQUENCE: 193
gatgcatgat cagaagggct ctt                                              23

<210> SEQ ID NO 194
<211> LENGTH: 19
<212> TYPE: DNA
<213> ORGANISM: Zea mays

<400> SEQUENCE: 194
aggccgtcac caagttcac                                                   19

<210> SEQ ID NO 195
<211> LENGTH: 18
<212> TYPE: DNA
<213> ORGANISM: Zea mays

<400> SEQUENCE: 195
gccatgagaa gcggcaca                                                    18

<210> SEQ ID NO 196
<211> LENGTH: 24
<212> TYPE: DNA
<213> ORGANISM: Zea mays

<400> SEQUENCE: 196
```
acccaagtgt ttcagtcttt caga　　　　　　　　　　　　　　　　　　　24

<210> SEQ ID NO 197
<211> LENGTH: 15
<212> TYPE: DNA
<213> ORGANISM: Zea mays

<400> SEQUENCE: 197
cccaccggcg aagga　　　　　　　　　　　　　　　　　　　　　　15

<210> SEQ ID NO 198
<211> LENGTH: 21
<212> TYPE: DNA
<213> ORGANISM: Zea mays

<400> SEQUENCE: 198
atctgcctct ccctgatcaa t　　　　　　　　　　　　　　　　　　21

<210> SEQ ID NO 199
<211> LENGTH: 21
<212> TYPE: DNA
<213> ORGANISM: Zea mays

<400> SEQUENCE: 199
ctgtagaagc cgtgaaggag a　　　　　　　　　　　　　　　　　　21

<210> SEQ ID NO 200
<211> LENGTH: 25
<212> TYPE: DNA
<213> ORGANISM: Zea mays

<400> SEQUENCE: 200
tgtaaggtga agcttttgtc ctgat　　　　　　　　　　　　　　　　25

<210> SEQ ID NO 201
<211> LENGTH: 22
<212> TYPE: DNA
<213> ORGANISM: Zea mays

<400> SEQUENCE: 201
tgactccatg atggcatttc gt　　　　　　　　　　　　　　　　　22

<210> SEQ ID NO 202
<211> LENGTH: 16
<212> TYPE: DNA
<213> ORGANISM: Zea mays

<400> SEQUENCE: 202
acggagtggc gcagag　　　　　　　　　　　　　　　　　　　　　16

<210> SEQ ID NO 203
<211> LENGTH: 22
<212> TYPE: DNA
<213> ORGANISM: Zea mays

<400> SEQUENCE: 203
tgctccagct ttgacactat cg　　　　　　　　　　　　　　　　　22

<210> SEQ ID NO 204
<211> LENGTH: 25
<212> TYPE: DNA
<213> ORGANISM: Zea mays

```
<400> SEQUENCE: 204
tctgcacagc atcttaattg tcact                                           25

<210> SEQ ID NO 205
<211> LENGTH: 27
<212> TYPE: DNA
<213> ORGANISM: Zea mays

<400> SEQUENCE: 205
gttcaaaggg agactaaaac cttaggt                                         27

<210> SEQ ID NO 206
<211> LENGTH: 23
<212> TYPE: DNA
<213> ORGANISM: Zea mays

<400> SEQUENCE: 206
ccagggaatt gcactcagct tag                                             23

<210> SEQ ID NO 207
<211> LENGTH: 23
<212> TYPE: DNA
<213> ORGANISM: Zea mays

<400> SEQUENCE: 207
ctctggcacg tggatttcct aaa                                             23

<210> SEQ ID NO 208
<211> LENGTH: 20
<212> TYPE: DNA
<213> ORGANISM: Zea mays

<400> SEQUENCE: 208
cccagctccc acatgaatgt                                                 20

<210> SEQ ID NO 209
<211> LENGTH: 25
<212> TYPE: DNA
<213> ORGANISM: Zea mays

<400> SEQUENCE: 209
ggaccatgtt tcggtctctt cttaa                                           25

<210> SEQ ID NO 210
<211> LENGTH: 20
<212> TYPE: DNA
<213> ORGANISM: Zea mays

<400> SEQUENCE: 210
cgtgggattt cccatctctc                                                 20

<210> SEQ ID NO 211
<211> LENGTH: 20
<212> TYPE: DNA
<213> ORGANISM: Zea mays

<400> SEQUENCE: 211
ccacatttgt tgcatccttg                                                 20

<210> SEQ ID NO 212
<211> LENGTH: 20
<212> TYPE: DNA
<213> ORGANISM: Zea mays
```

```
<400> SEQUENCE: 212
gccatcagca cgaacaggat                                                    20

<210> SEQ ID NO 213
<211> LENGTH: 20
<212> TYPE: DNA
<213> ORGANISM: Zea mays

<400> SEQUENCE: 213
tcgctaccac caccacctaa                                                    20

<210> SEQ ID NO 214
<211> LENGTH: 17
<212> TYPE: DNA
<213> ORGANISM: Zea mays

<400> SEQUENCE: 214
ccgagtccgc acaggtt                                                       17

<210> SEQ ID NO 215
<211> LENGTH: 21
<212> TYPE: DNA
<213> ORGANISM: Zea mays

<400> SEQUENCE: 215
ccgacaggtt aggcgtaatc g                                                  21

<210> SEQ ID NO 216
<211> LENGTH: 22
<212> TYPE: DNA
<213> ORGANISM: Zea mays

<400> SEQUENCE: 216
agcaaaagtt cagttctcta gc                                                 22

<210> SEQ ID NO 217
<211> LENGTH: 19
<212> TYPE: DNA
<213> ORGANISM: Zea mays

<400> SEQUENCE: 217
acgacgaagc tggagatac                                                     19

<210> SEQ ID NO 218
<211> LENGTH: 16
<212> TYPE: DNA
<213> ORGANISM: Zea mays

<400> SEQUENCE: 218
ggcacgcgag catctg                                                        16

<210> SEQ ID NO 219
<211> LENGTH: 19
<212> TYPE: DNA
<213> ORGANISM: Zea mays

<400> SEQUENCE: 219
ccaccttcgt gtccatcgt                                                     19

<210> SEQ ID NO 220
<211> LENGTH: 14
<212> TYPE: DNA
```

<213> ORGANISM: Zea mays

<400> SEQUENCE: 220
gcccggcgct gtca                                                     14

<210> SEQ ID NO 221
<211> LENGTH: 19
<212> TYPE: DNA
<213> ORGANISM: Zea mays

<400> SEQUENCE: 221
ccatcgcttg ccctgtctt                                                19

<210> SEQ ID NO 222
<211> LENGTH: 23
<212> TYPE: DNA
<213> ORGANISM: Zea mays

<400> SEQUENCE: 222
tctaggttca ttggcacgta ctg                                           23

<210> SEQ ID NO 223
<211> LENGTH: 19
<212> TYPE: DNA
<213> ORGANISM: Zea mays

<400> SEQUENCE: 223
cccagtctct gcgatgaca                                                19

<210> SEQ ID NO 224
<211> LENGTH: 26
<212> TYPE: DNA
<213> ORGANISM: Zea mays

<400> SEQUENCE: 224
ctgttgttat ctgtgaggtt gatcct                                        26

<210> SEQ ID NO 225
<211> LENGTH: 22
<212> TYPE: DNA
<213> ORGANISM: Zea mays

<400> SEQUENCE: 225
acacgtggaa ccagttcgtt ta                                            22

<210> SEQ ID NO 226
<211> LENGTH: 28
<212> TYPE: DNA
<213> ORGANISM: Zea mays

<400> SEQUENCE: 226
gatatggata cgtaggcatt cctgaatt                                      28

<210> SEQ ID NO 227
<211> LENGTH: 33
<212> TYPE: DNA
<213> ORGANISM: Zea mays

<400> SEQUENCE: 227
tgctactgat ttcattcaga ttagatgttt ctt                                33

<210> SEQ ID NO 228
<211> LENGTH: 20

```
<212> TYPE: DNA
<213> ORGANISM: Zea mays

<400> SEQUENCE: 228
tggccatgtt gcatgagtga                                             20

<210> SEQ ID NO 229
<211> LENGTH: 21
<212> TYPE: DNA
<213> ORGANISM: Zea mays

<400> SEQUENCE: 229
tcagacctgc aagtgctttc t                                           21

<210> SEQ ID NO 230
<211> LENGTH: 20
<212> TYPE: DNA
<213> ORGANISM: Zea mays

<400> SEQUENCE: 230
ccgaggccga gagcaatatg                                             20

<210> SEQ ID NO 231
<211> LENGTH: 19
<212> TYPE: DNA
<213> ORGANISM: Zea mays

<400> SEQUENCE: 231
gcagtcgcat cctggtact                                              19

<210> SEQ ID NO 232
<211> LENGTH: 15
<212> TYPE: DNA
<213> ORGANISM: Zea mays

<400> SEQUENCE: 232
ctggaatggc agatc                                                  15

<210> SEQ ID NO 233
<211> LENGTH: 16
<212> TYPE: DNA
<213> ORGANISM: Zea mays

<400> SEQUENCE: 233
ctggaatgac agatct                                                 16

<210> SEQ ID NO 234
<211> LENGTH: 15
<212> TYPE: DNA
<213> ORGANISM: Zea mays

<400> SEQUENCE: 234
acagctttga aggca                                                  15

<210> SEQ ID NO 235
<211> LENGTH: 14
<212> TYPE: DNA
<213> ORGANISM: Zea mays

<400> SEQUENCE: 235
acagctgtga aggc                                                   14

<210> SEQ ID NO 236
```

```
<210> SEQ ID NO 236
<211> LENGTH: 13
<212> TYPE: DNA
<213> ORGANISM: Zea mays

<400> SEQUENCE: 236
cgctctcggt ctc                                                        13

<210> SEQ ID NO 237
<211> LENGTH: 13
<212> TYPE: DNA
<213> ORGANISM: Zea mays

<400> SEQUENCE: 237
cgctctcagt ctc                                                        13

<210> SEQ ID NO 238
<211> LENGTH: 14
<212> TYPE: DNA
<213> ORGANISM: Zea mays

<400> SEQUENCE: 238
atgcatgcgc gcag                                                       14

<210> SEQ ID NO 239
<211> LENGTH: 16
<212> TYPE: DNA
<213> ORGANISM: Zea mays

<400> SEQUENCE: 239
catatgcatg cagcgc                                                     16

<210> SEQ ID NO 240
<211> LENGTH: 14
<212> TYPE: DNA
<213> ORGANISM: Zea mays

<400> SEQUENCE: 240
acgagcaaca acca                                                       14

<210> SEQ ID NO 241
<211> LENGTH: 14
<212> TYPE: DNA
<213> ORGANISM: Zea mays

<400> SEQUENCE: 241
acgagcaaca gcca                                                       14

<210> SEQ ID NO 242
<211> LENGTH: 23
<212> TYPE: DNA
<213> ORGANISM: Zea mays

<400> SEQUENCE: 242
caaagaacaa acttagtact aca                                             23

<210> SEQ ID NO 243
<211> LENGTH: 17
<212> TYPE: DNA
<213> ORGANISM: Zea mays

<400> SEQUENCE: 243
acaaacttgg aactaca                                                    17
```

```
<210> SEQ ID NO 244
<211> LENGTH: 20
<212> TYPE: DNA
<213> ORGANISM: Zea mays

<400> SEQUENCE: 244
tctttcaggt attccacaaa                                               20

<210> SEQ ID NO 245
<211> LENGTH: 20
<212> TYPE: DNA
<213> ORGANISM: Zea mays

<400> SEQUENCE: 245
atctttcagg tcttccacaa                                               20

<210> SEQ ID NO 246
<211> LENGTH: 16
<212> TYPE: DNA
<213> ORGANISM: Zea mays

<400> SEQUENCE: 246
atttgagcac cttgtg                                                   16

<210> SEQ ID NO 247
<211> LENGTH: 16
<212> TYPE: DNA
<213> ORGANISM: Zea mays

<400> SEQUENCE: 247
agatttgcac cttgtg                                                   16

<210> SEQ ID NO 248
<211> LENGTH: 19
<212> TYPE: DNA
<213> ORGANISM: Zea mays

<400> SEQUENCE: 248
aaaacattca taaagatct                                                19

<210> SEQ ID NO 249
<211> LENGTH: 19
<212> TYPE: DNA
<213> ORGANISM: Zea mays

<400> SEQUENCE: 249
aaaacattca tgaagatct                                                19

<210> SEQ ID NO 250
<211> LENGTH: 16
<212> TYPE: DNA
<213> ORGANISM: Zea mays

<400> SEQUENCE: 250
aagctcatca aagaat                                                   16

<210> SEQ ID NO 251
<211> LENGTH: 16
<212> TYPE: DNA
<213> ORGANISM: Zea mays

<400> SEQUENCE: 251
aagctcatcg aagaat                                                   16
```

```
<210> SEQ ID NO 252
<211> LENGTH: 17
<212> TYPE: DNA
<213> ORGANISM: Zea mays

<400> SEQUENCE: 252
agcttgtcgt tccaata                                                        17

<210> SEQ ID NO 253
<211> LENGTH: 18
<212> TYPE: DNA
<213> ORGANISM: Zea mays

<400> SEQUENCE: 253
agcttgtcat tccaataa                                                       18

<210> SEQ ID NO 254
<211> LENGTH: 17
<212> TYPE: DNA
<213> ORGANISM: Zea mays

<400> SEQUENCE: 254
aaaggctcaa tatactg                                                        17

<210> SEQ ID NO 255
<211> LENGTH: 18
<212> TYPE: DNA
<213> ORGANISM: Zea mays

<400> SEQUENCE: 255
caaaggctca ctatactg                                                       18

<210> SEQ ID NO 256
<211> LENGTH: 21
<212> TYPE: DNA
<213> ORGANISM: Zea mays

<400> SEQUENCE: 256
catgattatt gacactagtg t                                                   21

<210> SEQ ID NO 257
<211> LENGTH: 21
<212> TYPE: DNA
<213> ORGANISM: Zea mays

<400> SEQUENCE: 257
catgattatt gacactaatg t                                                   21

<210> SEQ ID NO 258
<211> LENGTH: 14
<212> TYPE: DNA
<213> ORGANISM: Zea mays

<400> SEQUENCE: 258
caacggctgc actc                                                           14

<210> SEQ ID NO 259
<211> LENGTH: 17
<212> TYPE: DNA
<213> ORGANISM: Zea mays

<400> SEQUENCE: 259
cttcaacgtc tgcactc                                                        17
```

<210> SEQ ID NO 260
<211> LENGTH: 14
<212> TYPE: DNA
<213> ORGANISM: Zea mays

<400> SEQUENCE: 260
ctcggcccca cctt                                                      14

<210> SEQ ID NO 261
<211> LENGTH: 13
<212> TYPE: DNA
<213> ORGANISM: Zea mays

<400> SEQUENCE: 261
tcggcccgac ctt                                                       13

<210> SEQ ID NO 262
<211> LENGTH: 16
<212> TYPE: DNA
<213> ORGANISM: Zea mays

<400> SEQUENCE: 262
aacgagccta ctctga                                                    16

<210> SEQ ID NO 263
<211> LENGTH: 16
<212> TYPE: DNA
<213> ORGANISM: Zea mays

<400> SEQUENCE: 263
aacgagccaa ctctga                                                    16

<210> SEQ ID NO 264
<211> LENGTH: 17
<212> TYPE: DNA
<213> ORGANISM: Zea mays

<400> SEQUENCE: 264
atgaacggga accacga                                                   17

<210> SEQ ID NO 265
<211> LENGTH: 17
<212> TYPE: DNA
<213> ORGANISM: Zea mays

<400> SEQUENCE: 265
atgaacggga accaaga                                                   17

<210> SEQ ID NO 266
<211> LENGTH: 13
<212> TYPE: DNA
<213> ORGANISM: Zea mays

<400> SEQUENCE: 266
ccatgcagct gtc                                                       13

<210> SEQ ID NO 267
<211> LENGTH: 13
<212> TYPE: DNA
<213> ORGANISM: Zea mays

<400> SEQUENCE: 267
ccatgcagct ctc                                                          13

<210> SEQ ID NO 268
<211> LENGTH: 19
<212> TYPE: DNA
<213> ORGANISM: Zea mays

<400> SEQUENCE: 268
caagaaaatc gtgttgaag                                                    19

<210> SEQ ID NO 269
<211> LENGTH: 20
<212> TYPE: DNA
<213> ORGANISM: Zea mays

<400> SEQUENCE: 269
ccaagaaaat cgtattgaag                                                   20

<210> SEQ ID NO 270
<211> LENGTH: 13
<212> TYPE: DNA
<213> ORGANISM: Zea mays

<400> SEQUENCE: 270
cgatggccgc ggc                                                          13

<210> SEQ ID NO 271
<211> LENGTH: 16
<212> TYPE: DNA
<213> ORGANISM: Zea mays

<400> SEQUENCE: 271
atgcgatagc cgcggc                                                       16

<210> SEQ ID NO 272
<211> LENGTH: 17
<212> TYPE: DNA
<213> ORGANISM: Zea mays

<400> SEQUENCE: 272
actccatcag gcagtgg                                                      17

<210> SEQ ID NO 273
<211> LENGTH: 17
<212> TYPE: DNA
<213> ORGANISM: Zea mays

<400> SEQUENCE: 273
actccatcaa gcagtgg                                                      17

<210> SEQ ID NO 274
<211> LENGTH: 14
<212> TYPE: DNA
<213> ORGANISM: Zea mays

<400> SEQUENCE: 274
catgcgcgtg tcct                                                         14

<210> SEQ ID NO 275
<211> LENGTH: 17
<212> TYPE: DNA
<213> ORGANISM: Zea mays

<400> SEQUENCE: 275

```
aatcatgcgc ctgtcct                                                        17

<210> SEQ ID NO 276
<211> LENGTH: 16
<212> TYPE: DNA
<213> ORGANISM: Zea mays

<400> SEQUENCE: 276
ctggagaagg aaagta                                                         16

<210> SEQ ID NO 277
<211> LENGTH: 17
<212> TYPE: DNA
<213> ORGANISM: Zea mays

<400> SEQUENCE: 277
cctggagaat gaaagta                                                        17

<210> SEQ ID NO 278
<211> LENGTH: 17
<212> TYPE: DNA
<213> ORGANISM: Zea mays

<400> SEQUENCE: 278
cagaaagtgc cttattt                                                        17

<210> SEQ ID NO 279
<211> LENGTH: 17
<212> TYPE: DNA
<213> ORGANISM: Zea mays

<400> SEQUENCE: 279
cagaaagtgg cttattt                                                        17

<210> SEQ ID NO 280
<211> LENGTH: 17
<212> TYPE: DNA
<213> ORGANISM: Zea mays

<400> SEQUENCE: 280
atgatctctg agcccgg                                                        17

<210> SEQ ID NO 281
<211> LENGTH: 17
<212> TYPE: DNA
<213> ORGANISM: Zea mays

<400> SEQUENCE: 281
atgatctctg ggcccgg                                                        17

<210> SEQ ID NO 282
<211> LENGTH: 21
<212> TYPE: DNA
<213> ORGANISM: Zea mays

<400> SEQUENCE: 282
cttttgattt cctttatttg t                                                   21

<210> SEQ ID NO 283
<211> LENGTH: 21
<212> TYPE: DNA
<213> ORGANISM: Zea mays
```

```
<400> SEQUENCE: 283
cttttgattt ccttcatttg t                                      21

<210> SEQ ID NO 284
<211> LENGTH: 18
<212> TYPE: DNA
<213> ORGANISM: Zea mays

<400> SEQUENCE: 284
ttgtaacatc tggttcct                                          18

<210> SEQ ID NO 285
<211> LENGTH: 16
<212> TYPE: DNA
<213> ORGANISM: Zea mays

<400> SEQUENCE: 285
tgtaacatgt gcttcc                                            16

<210> SEQ ID NO 286
<211> LENGTH: 19
<212> TYPE: DNA
<213> ORGANISM: Zea mays

<400> SEQUENCE: 286
ctgatgagta tcgtgttac                                         19

<210> SEQ ID NO 287
<211> LENGTH: 15
<212> TYPE: DNA
<213> ORGANISM: Zea mays

<400> SEQUENCE: 287
tggcgtacgt gttac                                             15

<210> SEQ ID NO 288
<211> LENGTH: 14
<212> TYPE: DNA
<213> ORGANISM: Zea mays

<400> SEQUENCE: 288
aacgacagat tcgg                                              14

<210> SEQ ID NO 289
<211> LENGTH: 14
<212> TYPE: DNA
<213> ORGANISM: Zea mays

<400> SEQUENCE: 289
aacgacggat tcgg                                              14

<210> SEQ ID NO 290
<211> LENGTH: 16
<212> TYPE: DNA
<213> ORGANISM: Zea mays

<400> SEQUENCE: 290
ctgttgccat tccatt                                            16

<210> SEQ ID NO 291
<211> LENGTH: 16
<212> TYPE: DNA
<213> ORGANISM: Zea mays
```

```
<400> SEQUENCE: 291
ctgttgccgt tccatt                                                         16

<210> SEQ ID NO 292
<211> LENGTH: 15
<212> TYPE: DNA
<213> ORGANISM: Zea mays

<400> SEQUENCE: 292
aatgcaagca ttaat                                                          15

<210> SEQ ID NO 293
<211> LENGTH: 16
<212> TYPE: DNA
<213> ORGANISM: Zea mays

<400> SEQUENCE: 293
caatgcaaac attaat                                                         16

<210> SEQ ID NO 294
<211> LENGTH: 15
<212> TYPE: DNA
<213> ORGANISM: Zea mays

<400> SEQUENCE: 294
cctccagact gatcc                                                          15

<210> SEQ ID NO 295
<211> LENGTH: 14
<212> TYPE: DNA
<213> ORGANISM: Zea mays

<400> SEQUENCE: 295
ctccaggctg atcc                                                           14

<210> SEQ ID NO 296
<211> LENGTH: 15
<212> TYPE: DNA
<213> ORGANISM: Zea mays

<400> SEQUENCE: 296
cggcgagatt gtcaa                                                          15

<210> SEQ ID NO 297
<211> LENGTH: 17
<212> TYPE: DNA
<213> ORGANISM: Zea mays

<400> SEQUENCE: 297
aacggcgaaa ttgtcaa                                                        17

<210> SEQ ID NO 298
<211> LENGTH: 16
<212> TYPE: DNA
<213> ORGANISM: Zea mays

<400> SEQUENCE: 298
tagcagcagg tcatgt                                                         16

<210> SEQ ID NO 299
<211> LENGTH: 17
<212> TYPE: DNA
```

```
<213> ORGANISM: Zea mays

<400> SEQUENCE: 299
ctagcagcag atcatgt                                                  17

<210> SEQ ID NO 300
<211> LENGTH: 15
<212> TYPE: DNA
<213> ORGANISM: Zea mays

<400> SEQUENCE: 300
tccaaggcgc tgtat                                                    15

<210> SEQ ID NO 301
<211> LENGTH: 17
<212> TYPE: DNA
<213> ORGANISM: Zea mays

<400> SEQUENCE: 301
tctccaaggc actgtat                                                  17

<210> SEQ ID NO 302
<211> LENGTH: 14
<212> TYPE: DNA
<213> ORGANISM: Zea mays

<400> SEQUENCE: 302
ccggcaatag ccca                                                     14

<210> SEQ ID NO 303
<211> LENGTH: 14
<212> TYPE: DNA
<213> ORGANISM: Zea mays

<400> SEQUENCE: 303
ccggcagtag ccca                                                     14

<210> SEQ ID NO 304
<211> LENGTH: 16
<212> TYPE: DNA
<213> ORGANISM: Zea mays

<400> SEQUENCE: 304
ctactccaca gttagc                                                   16

<210> SEQ ID NO 305
<211> LENGTH: 15
<212> TYPE: DNA
<213> ORGANISM: Zea mays

<400> SEQUENCE: 305
ctccacacag ttagc                                                    15

<210> SEQ ID NO 306
<211> LENGTH: 14
<212> TYPE: DNA
<213> ORGANISM: Zea mays

<400> SEQUENCE: 306
caatgccagg tctc                                                     14

<210> SEQ ID NO 307
<211> LENGTH: 15
```

```
<212> TYPE: DNA
<213> ORGANISM: Zea mays

<400> SEQUENCE: 307
ccaatgcctg gtctc                                                    15

<210> SEQ ID NO 308
<211> LENGTH: 17
<212> TYPE: DNA
<213> ORGANISM: Zea mays

<400> SEQUENCE: 308
caagttgttc taaatat                                                  17

<210> SEQ ID NO 309
<211> LENGTH: 20
<212> TYPE: DNA
<213> ORGANISM: Zea mays

<400> SEQUENCE: 309
ctccaagttg ttctatatat                                               20

<210> SEQ ID NO 310
<211> LENGTH: 15
<212> TYPE: DNA
<213> ORGANISM: Zea mays

<400> SEQUENCE: 310
ccaagtgagc ctaac                                                    15

<210> SEQ ID NO 311
<211> LENGTH: 15
<212> TYPE: DNA
<213> ORGANISM: Zea mays

<400> SEQUENCE: 311
ccaagtgaac ctaac                                                    15

<210> SEQ ID NO 312
<211> LENGTH: 18
<212> TYPE: DNA
<213> ORGANISM: Zea mays

<400> SEQUENCE: 312
cttattcatg gatttatc                                                 18

<210> SEQ ID NO 313
<211> LENGTH: 18
<212> TYPE: DNA
<213> ORGANISM: Zea mays

<400> SEQUENCE: 313
cttattcatg ggtttatc                                                 18

<210> SEQ ID NO 314
<211> LENGTH: 14
<212> TYPE: DNA
<213> ORGANISM: Zea mays

<400> SEQUENCE: 314
ccgcactgta ccgc                                                     14

<210> SEQ ID NO 315
```

```
<211> LENGTH: 14
<212> TYPE: DNA
<213> ORGANISM: Zea mays

<400> SEQUENCE: 315
ccgcactata ccgc                                                    14

<210> SEQ ID NO 316
<211> LENGTH: 13
<212> TYPE: DNA
<213> ORGANISM: Zea mays

<400> SEQUENCE: 316
ccgcaaagat gaa                                                     13

<210> SEQ ID NO 317
<211> LENGTH: 13
<212> TYPE: DNA
<213> ORGANISM: Zea mays

<400> SEQUENCE: 317
ccgcagagat gaa                                                     13

<210> SEQ ID NO 318
<211> LENGTH: 14
<212> TYPE: DNA
<213> ORGANISM: Zea mays

<400> SEQUENCE: 318
cccgtggagt actt                                                    14

<210> SEQ ID NO 319
<211> LENGTH: 14
<212> TYPE: DNA
<213> ORGANISM: Zea mays

<400> SEQUENCE: 319
cccgtcgagt actt                                                    14

<210> SEQ ID NO 320
<211> LENGTH: 13
<212> TYPE: DNA
<213> ORGANISM: Zea mays

<400> SEQUENCE: 320
cagcagaagc acc                                                     13

<210> SEQ ID NO 321
<211> LENGTH: 14
<212> TYPE: DNA
<213> ORGANISM: Zea mays

<400> SEQUENCE: 321
ccagcagcag cacc                                                    14

<210> SEQ ID NO 322
<211> LENGTH: 16
<212> TYPE: DNA
<213> ORGANISM: Zea mays

<400> SEQUENCE: 322
aaagtgtgca agatat                                                  16
```

```
<210> SEQ ID NO 323
<211> LENGTH: 18
<212> TYPE: DNA
<213> ORGANISM: Zea mays

<400> SEQUENCE: 323
acaaagtgtg aaagatat                                                18

<210> SEQ ID NO 324
<211> LENGTH: 14
<212> TYPE: DNA
<213> ORGANISM: Zea mays

<400> SEQUENCE: 324
cgcctacaac aagg                                                    14

<210> SEQ ID NO 325
<211> LENGTH: 17
<212> TYPE: DNA
<213> ORGANISM: Zea mays

<400> SEQUENCE: 325
cgacgcctac tacaagg                                                 17

<210> SEQ ID NO 326
<211> LENGTH: 17
<212> TYPE: DNA
<213> ORGANISM: Zea mays

<400> SEQUENCE: 326
cactcgagtg aggtgta                                                 17

<210> SEQ ID NO 327
<211> LENGTH: 17
<212> TYPE: DNA
<213> ORGANISM: Zea mays

<400> SEQUENCE: 327
cactcgagtg aggtata                                                 17

<210> SEQ ID NO 328
<211> LENGTH: 15
<212> TYPE: DNA
<213> ORGANISM: Zea mays

<400> SEQUENCE: 328
ttccccagcg acccg                                                   15

<210> SEQ ID NO 329
<211> LENGTH: 13
<212> TYPE: DNA
<213> ORGANISM: Zea mays

<400> SEQUENCE: 329
ccccagggac ccg                                                     13

<210> SEQ ID NO 330
<211> LENGTH: 15
<212> TYPE: DNA
<213> ORGANISM: Zea mays

<400> SEQUENCE: 330
cagggagact ttatt                                                   15
```

```
<210> SEQ ID NO 331
<211> LENGTH: 17
<212> TYPE: DNA
<213> ORGANISM: Zea mays

<400> SEQUENCE: 331
cagggagact ttttatt                                                   17

<210> SEQ ID NO 332
<211> LENGTH: 19
<212> TYPE: DNA
<213> ORGANISM: Zea mays

<400> SEQUENCE: 332
tcgaaccatt aagttactt                                                 19

<210> SEQ ID NO 333
<211> LENGTH: 18
<212> TYPE: DNA
<213> ORGANISM: Zea mays

<400> SEQUENCE: 333
cgaaccatta cgttactt                                                  18

<210> SEQ ID NO 334
<211> LENGTH: 16
<212> TYPE: DNA
<213> ORGANISM: Zea mays

<400> SEQUENCE: 334
catacctatc gatttc                                                    16

<210> SEQ ID NO 335
<211> LENGTH: 16
<212> TYPE: DNA
<213> ORGANISM: Zea mays

<400> SEQUENCE: 335
catacctatc aatttc                                                    16

<210> SEQ ID NO 336
<211> LENGTH: 14
<212> TYPE: DNA
<213> ORGANISM: Zea mays

<400> SEQUENCE: 336
ctgcctaccg ctcc                                                      14

<210> SEQ ID NO 337
<211> LENGTH: 17
<212> TYPE: DNA
<213> ORGANISM: Zea mays

<400> SEQUENCE: 337
attctgcctt ccgctcc                                                   17

<210> SEQ ID NO 338
<211> LENGTH: 14
<212> TYPE: DNA
<213> ORGANISM: Zea mays

<400> SEQUENCE: 338
ccactgcccc tcct                                                      14
```

<210> SEQ ID NO 339
<211> LENGTH: 14
<212> TYPE: DNA
<213> ORGANISM: Zea mays

<400> SEQUENCE: 339
ccactggccc tcct                                                        14

<210> SEQ ID NO 340
<211> LENGTH: 16
<212> TYPE: DNA
<213> ORGANISM: Zea mays

<400> SEQUENCE: 340
cttgccttgt gttctg                                                      16

<210> SEQ ID NO 341
<211> LENGTH: 16
<212> TYPE: DNA
<213> ORGANISM: Zea mays

<400> SEQUENCE: 341
cttgccttct gttctg                                                      16

<210> SEQ ID NO 342
<211> LENGTH: 14
<212> TYPE: DNA
<213> ORGANISM: Zea mays

<400> SEQUENCE: 342
actcgccaga ggtg                                                        14

<210> SEQ ID NO 343
<211> LENGTH: 14
<212> TYPE: DNA
<213> ORGANISM: Zea mays

<400> SEQUENCE: 343
actcgccgga ggtg                                                        14

<210> SEQ ID NO 344
<211> LENGTH: 15
<212> TYPE: DNA
<213> ORGANISM: Zea mays

<400> SEQUENCE: 344
acagcttacg gcggc                                                       15

<210> SEQ ID NO 345
<211> LENGTH: 13
<212> TYPE: DNA
<213> ORGANISM: Zea mays

<400> SEQUENCE: 345
agcttgcggc ggc                                                         13

<210> SEQ ID NO 346
<211> LENGTH: 17
<212> TYPE: DNA
<213> ORGANISM: Zea mays

<400> SEQUENCE: 346

-continued cttgtgtcaa tgcagga                                               17

<210> SEQ ID NO 347
<211> LENGTH: 14
<212> TYPE: DNA
<213> ORGANISM: Zea mays

<400> SEQUENCE: 347
ccaaggtcaa tgca                                                  14

<210> SEQ ID NO 348
<211> LENGTH: 14
<212> TYPE: DNA
<213> ORGANISM: Zea mays

<400> SEQUENCE: 348
tcctccgctt tcat                                                  14

<210> SEQ ID NO 349
<211> LENGTH: 14
<212> TYPE: DNA
<213> ORGANISM: Zea mays

<400> SEQUENCE: 349
ctcctccact ttca                                                  14

<210> SEQ ID NO 350
<211> LENGTH: 23
<212> TYPE: DNA
<213> ORGANISM: Zea mays

<400> SEQUENCE: 350
caaagaacaa acttagtact aca                                        23

<210> SEQ ID NO 351
<211> LENGTH: 17
<212> TYPE: DNA
<213> ORGANISM: Zea mays

<400> SEQUENCE: 351
acaaacttgg aactaca                                               17

<210> SEQ ID NO 352
<211> LENGTH: 20
<212> TYPE: DNA
<213> ORGANISM: Zea mays

<400> SEQUENCE: 352
tctttcaggt attccacaaa                                            20

<210> SEQ ID NO 353
<211> LENGTH: 20
<212> TYPE: DNA
<213> ORGANISM: Zea mays

<400> SEQUENCE: 353
atctttcagg tcttccacaa                                            20

<210> SEQ ID NO 354
<211> LENGTH: 17
<212> TYPE: DNA
<213> ORGANISM: Zea mays

<400> SEQUENCE: 354

-continued cagaaagtgc cttattt                              17

<210> SEQ ID NO 355
<211> LENGTH: 17
<212> TYPE: DNA
<213> ORGANISM: Zea mays

<400> SEQUENCE: 355
cagaaagtgg cttattt                              17

<210> SEQ ID NO 356
<211> LENGTH: 21
<212> TYPE: DNA
<213> ORGANISM: Zea mays

<400> SEQUENCE: 356
cttttgattt cctttatttg t                         21

<210> SEQ ID NO 357
<211> LENGTH: 21
<212> TYPE: DNA
<213> ORGANISM: Zea mays

<400> SEQUENCE: 357
cttttgattt ccttcatttg t                         21

<210> SEQ ID NO 358
<211> LENGTH: 17
<212> TYPE: DNA
<213> ORGANISM: Zea mays

<400> SEQUENCE: 358
acgatgactg ccaccca                              17

<210> SEQ ID NO 359
<211> LENGTH: 18
<212> TYPE: DNA
<213> ORGANISM: Zea mays

<400> SEQUENCE: 359
cacgatgact accaccca                             18

<210> SEQ ID NO 360
<211> LENGTH: 17
<212> TYPE: DNA
<213> ORGANISM: Zea mays

<400> SEQUENCE: 360
ccaaacacaa cgaagag                              17

<210> SEQ ID NO 361
<211> LENGTH: 17
<212> TYPE: DNA
<213> ORGANISM: Zea mays

<400> SEQUENCE: 361
ccaaacacga cgaagag                              17

<210> SEQ ID NO 362
<211> LENGTH: 17
<212> TYPE: DNA
<213> ORGANISM: Zea mays

<400> SEQUENCE: 362
cctttaatgg cctttt 17

<210> SEQ ID NO 363
<211> LENGTH: 18
<212> TYPE: DNA
<213> ORGANISM: Zea mays

<400> SEQUENCE: 363
tcctttaatg gactttt 18

<210> SEQ ID NO 364
<211> LENGTH: 16
<212> TYPE: DNA
<213> ORGANISM: Zea mays

<400> SEQUENCE: 364
ctgttgccat tccatt 16

<210> SEQ ID NO 365
<211> LENGTH: 16
<212> TYPE: DNA
<213> ORGANISM: Zea mays

<400> SEQUENCE: 365
ctgttgccgt tccatt 16

<210> SEQ ID NO 366
<211> LENGTH: 17
<212> TYPE: DNA
<213> ORGANISM: Zea mays

<400> SEQUENCE: 366
cagtagcacg attcata 17

<210> SEQ ID NO 367
<211> LENGTH: 17
<212> TYPE: DNA
<213> ORGANISM: Zea mays

<400> SEQUENCE: 367
cagtagcacg cttcata 17

<210> SEQ ID NO 368
<211> LENGTH: 15
<212> TYPE: DNA
<213> ORGANISM: Zea mays

<400> SEQUENCE: 368
aatgcaagca ttaat 15

<210> SEQ ID NO 369
<211> LENGTH: 16
<212> TYPE: DNA
<213> ORGANISM: Zea mays

<400> SEQUENCE: 369
caatgcaaac attaat 16

<210> SEQ ID NO 370
<211> LENGTH: 20
<212> TYPE: DNA
<213> ORGANISM: Zea mays

```
<400> SEQUENCE: 370
ttcataccta cattaaagat                                            20

<210> SEQ ID NO 371
<211> LENGTH: 18
<212> TYPE: DNA
<213> ORGANISM: Zea mays

<400> SEQUENCE: 371
catacctaca tcaaagat                                              18

<210> SEQ ID NO 372
<211> LENGTH: 16
<212> TYPE: DNA
<213> ORGANISM: Zea mays

<400> SEQUENCE: 372
atgcagcata tacttt                                                16

<210> SEQ ID NO 373
<211> LENGTH: 17
<212> TYPE: DNA
<213> ORGANISM: Zea mays

<400> SEQUENCE: 373
catgcaacat atacttt                                               17

<210> SEQ ID NO 374
<211> LENGTH: 15
<212> TYPE: DNA
<213> ORGANISM: Zea mays

<400> SEQUENCE: 374
cagacgcacg tgaac                                                 15

<210> SEQ ID NO 375
<211> LENGTH: 15
<212> TYPE: DNA
<213> ORGANISM: Zea mays

<400> SEQUENCE: 375
cagacgcccg tgaac                                                 15

<210> SEQ ID NO 376
<211> LENGTH: 13
<212> TYPE: DNA
<213> ORGANISM: Zea mays

<400> SEQUENCE: 376
ccgacgccgg ttt                                                   13

<210> SEQ ID NO 377
<211> LENGTH: 13
<212> TYPE: DNA
<213> ORGANISM: Zea mays

<400> SEQUENCE: 377
ccgacgccgg ctt                                                   13

<210> SEQ ID NO 378
<211> LENGTH: 16
<212> TYPE: DNA
```

<213> ORGANISM: Zea mays

<400> SEQUENCE: 378
attgcaaccg tcaagg                                        16

<210> SEQ ID NO 379
<211> LENGTH: 18
<212> TYPE: DNA
<213> ORGANISM: Zea mays

<400> SEQUENCE: 379
tcattgcaac cctcaagg                                      18

<210> SEQ ID NO 380
<211> LENGTH: 16
<212> TYPE: DNA
<213> ORGANISM: Zea mays

<400> SEQUENCE: 380
cttgagagta atcttg                                        16

<210> SEQ ID NO 381
<211> LENGTH: 16
<212> TYPE: DNA
<213> ORGANISM: Zea mays

<400> SEQUENCE: 381
cttgagagtg atcttg                                        16

<210> SEQ ID NO 382
<211> LENGTH: 15
<212> TYPE: DNA
<213> ORGANISM: Zea mays

<400> SEQUENCE: 382
aagcaacaga aacaa                                         15

<210> SEQ ID NO 383
<211> LENGTH: 16
<212> TYPE: DNA
<213> ORGANISM: Zea mays

<400> SEQUENCE: 383
caagcaacaa aaacaa                                        16

<210> SEQ ID NO 384
<211> LENGTH: 16
<212> TYPE: DNA
<213> ORGANISM: Zea mays

<400> SEQUENCE: 384
acaccacagg accata                                        16

<210> SEQ ID NO 385
<211> LENGTH: 16
<212> TYPE: DNA
<213> ORGANISM: Zea mays

<400> SEQUENCE: 385
acaccacacg accata                                        16

<210> SEQ ID NO 386
<211> LENGTH: 17

```
<212> TYPE: DNA
<213> ORGANISM: Zea mays

<400> SEQUENCE: 386
tcgatctccc agtataa                                                 17

<210> SEQ ID NO 387
<211> LENGTH: 17
<212> TYPE: DNA
<213> ORGANISM: Zea mays

<400> SEQUENCE: 387
tcgatctccc aatataa                                                 17

<210> SEQ ID NO 388
<211> LENGTH: 16
<212> TYPE: DNA
<213> ORGANISM: Zea mays

<400> SEQUENCE: 388
taggcatccg cagact                                                  16

<210> SEQ ID NO 389
<211> LENGTH: 16
<212> TYPE: DNA
<213> ORGANISM: Zea mays

<400> SEQUENCE: 389
taggcatcgg cagact                                                  16

<210> SEQ ID NO 390
<211> LENGTH: 15
<212> TYPE: DNA
<213> ORGANISM: Zea mays

<400> SEQUENCE: 390
acgtgctctt caagc                                                   15

<210> SEQ ID NO 391
<211> LENGTH: 16
<212> TYPE: DNA
<213> ORGANISM: Zea mays

<400> SEQUENCE: 391
aacgtgctat tcaagc                                                  16

<210> SEQ ID NO 392
<211> LENGTH: 17
<212> TYPE: DNA
<213> ORGANISM: Zea mays

<400> SEQUENCE: 392
tcgacacgat gtgacca                                                 17

<210> SEQ ID NO 393
<211> LENGTH: 18
<212> TYPE: DNA
<213> ORGANISM: Zea mays

<400> SEQUENCE: 393
ctcgacacga tttgacca                                                18

<210> SEQ ID NO 394
```

```
<211> LENGTH: 16
<212> TYPE: DNA
<213> ORGANISM: Zea mays

<400> SEQUENCE: 394
atgcatgtac gaactg                                                    16

<210> SEQ ID NO 395
<211> LENGTH: 17
<212> TYPE: DNA
<213> ORGANISM: Zea mays

<400> SEQUENCE: 395
catgcatgta agaactg                                                   17

<210> SEQ ID NO 396
<211> LENGTH: 16
<212> TYPE: DNA
<213> ORGANISM: Zea mays

<400> SEQUENCE: 396
aagcaaccat cagtgc                                                    16

<210> SEQ ID NO 397
<211> LENGTH: 16
<212> TYPE: DNA
<213> ORGANISM: Zea mays

<400> SEQUENCE: 397
aagcaaccgt cagtgc                                                    16

<210> SEQ ID NO 398
<211> LENGTH: 19
<212> TYPE: DNA
<213> ORGANISM: Zea mays

<400> SEQUENCE: 398
aatgacctcg tatcggagt                                                 19

<210> SEQ ID NO 399
<211> LENGTH: 18
<212> TYPE: DNA
<213> ORGANISM: Zea mays

<400> SEQUENCE: 399
atgacctcgt gtcggagt                                                  18

<210> SEQ ID NO 400
<211> LENGTH: 663
<212> TYPE: DNA
<213> ORGANISM: Zea mays
<220> FEATURE:
<221> NAME/KEY: misc_feature
<222> LOCATION: (24)..(641)
<223> OTHER INFORMATION: n is a, c, g, or t
<220> FEATURE:
<221> NAME/KEY: misc_feature
<222> LOCATION: (83)..(83)
<223> OTHER INFORMATION: y is c or t
<220> FEATURE:
<221> NAME/KEY: misc_feature
<222> LOCATION: (119)..(119)
<223> OTHER INFORMATION: m is a or c
<220> FEATURE:
<221> NAME/KEY: misc_feature
<222> LOCATION: (601)..(601)
<223> OTHER INFORMATION: w is a or t
```

<400> SEQUENCE: 400

```
ttcctctata agtacccgcc ccanatctgc gccattttct catcgcagaa atcctccgca      60
cttcacagcg tatcatcgtt ttycatcgct cctactccta ncatccagaa aatctgagmg     120
gtattgatgg cgcccaaggc ggagaagaag ccggcggcna agaaggtggc ggaggaggag     180
ccctcggaga aggcggctcc ggcggagaag gccccgcgg ggaagaagnc caaggcggag      240
aagcggctnc cngcgggcaa gtcngcnggc aaggagggcg cgacaagaa gggnaggaag      300
aaggcgaaga agagcgtgga gacctacaag atctacatct tcaaggtcct gaagcaggtg     360
cacccccgaca tcggcatctc ctccaaggcc atgtccatca tgaactcctt catcaacgac    420
atcttcgaga agctcgccnc ggaggccgcc aagctcgccc gntacaacaa gaagcccacc    480
atcacctccc gcgagatcca gacctccgtc cgcctcgtcc tccccggcga gctcgccaag   540
cacgccgtct cggagggtac caaggccgtc accaagttca cctcgtcnta gccnccttgt    600
wgtaggcgtc gttgtnnnct gcttctcaag caagcactgt natgtgccgc ttctcatggc    660
agt                                                                  663
```

<210> SEQ ID NO 401
<211> LENGTH: 664
<212> TYPE: DNA
<213> ORGANISM: Zea mays

<400> SEQUENCE: 401

```
ttcctctata agtacccgcc ccacatctgc gccattttct catcgcagaa atcctccgca      60
acttcacagc gtatcatcgt tttccatcgc tcctactcct atcatccaga aaatctgagc    120
ggtattgatg cgcccaagg cggagaagaa gccggcggcg aagaaggtgg cggaggagga     180
gccctcggag aaggcggctc cggcggagaa ggccccgcg gggaagaagc caaggcgga      240
gaagcggcta cctgcgggca gtccgccgg caaggagggc ggcgacaaga agggtaggaa    300
gaaggcgaag aagagcgtgg agacctacaa gatctacatc ttcaaggtcc tgaagcaggt    360
gcaccccgac atcggcatct cctccaaggc catgtccatc atgaactcct tcatcaacga    420
catcttcgag aagctcgccg cggaggccgc caagctcgcc cggtacaaca agaagcccac    480
catcacctcc cgcgagatcc agacctccgt ccgcctcgtc ctcccggcg agctcgccaa    540
gcacgccgtc tcggagggta ccaaggccgt caccaagttc acctcgtctt agccgccttg    600
ttgtaggcgt cgttgttgtc tgcttctcaa gcaagcactg tcatgtgccg cttctcatgg    660
cagt                                                                 664
```

<210> SEQ ID NO 402
<211> LENGTH: 22
<212> TYPE: DNA
<213> ORGANISM: Zea mays

<400> SEQUENCE: 402

```
agaaatcctc cgcaacttca ca                                              22
```

<210> SEQ ID NO 403
<211> LENGTH: 19
<212> TYPE: DNA
<213> ORGANISM: Zea mays

<400> SEQUENCE: 403

```
cttgggcgcc atcaatacc                                                  19
```

<210> SEQ ID NO 404
<211> LENGTH: 25
<212> TYPE: DNA
<213> ORGANISM: Zea mays

<400> SEQUENCE: 404
caacttcaca gcgtatcatc gtttt                                             25

<210> SEQ ID NO 405
<211> LENGTH: 16
<212> TYPE: DNA
<213> ORGANISM: Zea mays

<400> SEQUENCE: 405
gccgccggct tcttct                                                       16

<210> SEQ ID NO 406
<211> LENGTH: 19
<212> TYPE: DNA
<213> ORGANISM: Zea mays

<400> SEQUENCE: 406
aggccgtcac caagttcac                                                    19

<210> SEQ ID NO 407
<211> LENGTH: 18
<212> TYPE: DNA
<213> ORGANISM: Zea mays

<400> SEQUENCE: 407
gccatgagaa gcggcaca                                                     18

<210> SEQ ID NO 408
<211> LENGTH: 18
<212> TYPE: DNA
<213> ORGANISM: Zea mays

<400> SEQUENCE: 408
tcatcgtttt tcatcgct                                                     18

<210> SEQ ID NO 409
<211> LENGTH: 18
<212> TYPE: DNA
<213> ORGANISM: Zea mays

<400> SEQUENCE: 409
tcatcgtttt ccatcgct                                                     18

<210> SEQ ID NO 410
<211> LENGTH: 18
<212> TYPE: DNA
<213> ORGANISM: Zea mays

<400> SEQUENCE: 410
aaaatctgag aggtattg                                                     18

<210> SEQ ID NO 411
<211> LENGTH: 17
<212> TYPE: DNA
<213> ORGANISM: Zea mays

<400> SEQUENCE: 411
aaatctgagc ggtattg                                                      17

```
<210> SEQ ID NO 412
<211> LENGTH: 14
<212> TYPE: DNA
<213> ORGANISM: Zea mays

<400> SEQUENCE: 412
cgcctacaac aagg                                                        14

<210> SEQ ID NO 413
<211> LENGTH: 17
<212> TYPE: DNA
<213> ORGANISM: Zea mays

<400> SEQUENCE: 413
cgacgcctac tacaagg                                                     17
```

GENETIC MARKERS ASSOCIATED WITH DROUGHT TOLERANCE IN MAIZE

CROSS REFERENCES TO RELATED APPLICATIONS

The presently disclosed subject matter is a divisional of U.S. patent application Ser. No. 12/977,966 filed Dec. 23, 2010 and claims the benefit of U.S. Provisional Patent Application Ser. No. 61/289,718, filed Dec. 23, 2009; and U.S. Provisional Patent Application Ser. No. 61/369,999, filed Aug. 2, 2010; the disclosure of each of which is incorporated herein by reference in its entirety.

STATEMENT REGARDING ELECTRONIC SUBMISSION OF A SEQUENCE LISTING

A Sequence Listing in ASCII text format, submitted under 37 C.F.R. §1.821, entitled "72670-US-PX-D-NAT-1_Sequence_Listing_ST25", 195 kilobytes and was filed with U.S. patent application Ser. No. 12/977,966 filed Dec. 23, 2009 which claims the benefit of U.S. Provisional Patent Application Ser. No. 61/289,718, filed Dec. 23, 2009; and U.S. Provisional Patent Application Ser. No. 61/369,999, filed Aug. 2, 2010; for which this application claims the benefit thereof. The Sequence Listing is attached and filed herewith and is incorporated herein by reference.

TECHNICAL FIELD

The presently disclosed subject matter relates to maize, such as maize of the species Zea mays, and methods of breeding the same. More particularly, the presently disclosed subject matter relates to maize lines, such as Zea mays lines, with one or more improved water optimization genotypes, and methods for breeding the same, which methods involve in some embodiments genetic marker analysis and/or nucleic acid sequence analysis.

BACKGROUND

Drought is one of the major limitations to maize production worldwide—15% of the world's maize crop is lost every year to drought. Periods of drought stress can occur at any time during the growing season, but maize is particularly sensitive to drought stress in the period just before and during flowering. When drought stress occurs during this critical period, a significant decrease in grain yield can result.

Identifying genes that enhance the drought tolerance of maize could lead to more efficient crop production by allowing for the identification, selection and production of maize plants with enhanced drought tolerance.

As such, a goal of plant breeding is to combine, in a single plant, various desirable traits. For field crops such as corn, these traits can include greater yield and better agronomic quality. However, genetic loci that influence yield and agronomic quality are not always known, and even if known, their contributions to such traits are frequently unclear. Thus, new loci that can positively influence such desirable traits need to be identified and/or the abilities of known loci to do so need to be discovered.

Once discovered, these desirable loci can be selected for as part of a breeding program in order to generate plants that carry desirable traits. An exemplary embodiment of a method for generating such plants includes the transfer by introgression of nucleic acid sequences from plants that have desirable genetic information into plants that do not by crossing the plants using traditional breeding techniques.

Desirable loci can be introgressed into commercially available plant varieties using marker-assisted selection (MAS) or marker-assisted breeding (MAB). MAS and MAB involves the use of one or more of the molecular markers for the identification and selection of those progeny plants that contain one or more loci that encode the desired traits. Such identification and selection can be based on selection of informative markers that are associated with desired traits. MAB can also be used to develop near-isogenic lines (NIL) harboring loci of interest, allowing a more detailed study of the effect each locus can have on a desired trait, and is also an effective method for development of backcross inbred line (BIL) populations.

Maize drought is one of the major limitations to maize production worldwide. When drought stress occurs just before or during the flowering period, an increase in the length of the anthesis-silking interval and a decrease in grain yield can result. 15% of the world's maize crop, or in excess of 19 millions tons, is lost every year to drought. Identifying candidate genes that can enhance drought-stress tolerance in maize could lead to more efficient crop production in affected areas.

What are needed, then, are new methods and compositions for genetically analyzing Zea mays varieties with respect to drought tolerance and for employing the information obtained for producing new Zea mays plants that have improved water optimization traits.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

Compositions and methods for identifying, selecting and producing maize plants with enhanced drought tolerance are provided. A drought tolerant maize plant or germplasm is also provided.

In some embodiments, methods of identifying a drought tolerant maize plant or germplasm are provided. Such methods can comprise detecting, in the maize plant or germplasm, a marker associated with enhanced drought tolerance.

In some embodiments, methods of producing a drought tolerant maize plant are provided. Such methods can comprise detecting, in a maize germplasm, the presence of a marker associated with enhanced drought tolerance and producing a progeny plant from said maize germplasm.

In some embodiments, the presence of a marker associated with enhanced drought tolerance is detected using a marker probe. In some such embodiments, the presence of a marker associated with enhanced drought tolerance is detected in an amplification product from a nucleic acid sample isolated from a maize plant or germplasm. In some embodiments, the marker comprises a haplotype, and a plurality of probes is used to detect the alleles that make up the haplotype. In some such embodiments, the alleles that make up the haplotype are detected in a plurality of amplification products from a nucleic acid sample isolated from a maize plant or germplasm.

In some embodiments, methods of selecting a drought tolerant maize plant or germplasm are provided. Such methods can comprise crossing a first maize plant or germplasm with a second maize plant or germplasm, wherein the first maize plant or germplasm comprises a marker associated with enhanced drought tolerance, and selecting a progeny plant or germplasm that possesses the marker.

In some embodiments, methods of introgressing an allele associated with enhanced drought tolerance into a maize plant or germplasm are provided. Such methods can comprise crossing a first maize plant or germplasm comprising an allele associated with enhanced drought tolerance with a second maize plant or germplasm that lacks said allele and repeatedly backcrossing progeny plants comprising said allele with the second maize plant or germplasm to produce a drought tolerant maize plant or germplasm comprising the allele associated with enhanced drought tolerance. Progeny comprising the allele associated with enhanced drought tolerance can be identified by detecting, in their genomes, the presence of a marker associated with said allele.

Maize plants and/or germplasms identified, produced or selected by any of the methods of the invention are also provided, as are any progeny or seeds derived from a maize plant or germplasm identified, produced or selected by these methods.

Non-naturally occurring maize plants and/or germplasms comprising one or more markers associated with enhanced drought tolerance are also provided.

Isolated and/or purified markers associated with enhanced drought tolerance are also provided. Such markers can comprise a nucleotide sequence at least 85%, 90%, 95%, or 99% identical to any of SEQ ID NOs: 1-117, 400, and 401, the reverse complement thereof, or an informative or functional fragment thereof.

Compositions comprising a primer pair capable of amplifying a nucleic acid sample isolated from a maize plant or germplasm to generate a marker associated with enhanced drought tolerance are also provided. Such compositions can comprise, consist essentially of, or consist of one of the amplification primer pairs identified in Table 1.

TABLE 1

SEQ ID NOs. of Exemplary Oligonucleotide Primers that can be Employed for Analyzing Water Optimization Loci, Alleles, and Haplotypes

| Genomic Locus | Exemplary Amplification Primers | Exemplary Assay Primers |
|---|---|---|
| 1, 61 | 118, 119 | 232, 233 |
| 2, 63 | 120, 121 | 346, 347; 348, 349 |
| 3, 63 | 122, 123 | 234, 235 |
| 4, 64 | 124, 125 | 236, 237 |
| 5, 65 | 126, 127 | 238, 239 |
| 6, 66 | 128, 129 | 240, 241 |
| 7, 67 | 130, 131 | 242, 243; 244, 245; 246, 247; 248, 249; 250, 251; 350, 351; 352, 353 |
| 8, 68 | 132, 133 | 252, 253 |
| 9, 69 | 134, 135 | 254, 255 |
| 10, 70 | 136, 137 | 256, 257 |
| 11, 71 | 138, 139 | 258, 259 |
| 12, 13, 72 | 140, 141 | 260, 261; 262, 263; 264, 265; 266, 267 |
| 14, 73 | 142, 143 | 268, 269 |
| 15, 74 | 144, 145 | 270, 271 |
| 16, 75 | 146, 147 | 272, 273 |
| 17, 76 | 148, 149 | 274, 275 |
| 18, 77 | 150, 151 | 276, 277 |
| 19, 78 | 152, 153 | 278, 279; 280, 281; 282, 283; 354, 355; 356, 357 |
| 20, 79 | 154, 155 | 284, 285 |
| 21, 80 | 156, 157 | 286, 287 |
| 22, 81 | 158, 159 | 288, 289 |
| 23, 82 | 160, 161 | 358, 359; 360, 361 |
| 24, 83 | 162, 163 | 362, 363 |
| 25, 84 | 164, 165 | 290, 291; 364, 365 |
| 26, 85 | 166, 167 | 366, 367 |
| 27, 86 | 168, 169 | 292, 293; 368, 369 |
| 28, 87 | 170, 171 | 294, 295 |
| 29, 88 | 172, 173 | 370, 371 |
| 30, 89 | 174, 175 | 296, 297; 298, 299 |
| 31, 90 | 176, 177 | 300, 301 |
| 32, 91 | 178, 179 | 302, 303 |
| 33, 92 | 180, 181 | 372, 373 |
| 34, 93 | 182, 183 | 304, 305; 306, 307; 308, 309 |
| 35, 94 | 184, 185 | 310, 311 |
| 36, 95 | 186, 187 | 312, 313 |
| 37, 96 | 188, 189 | 314, 315; 316, 317 |
| 38, 97 | 190, 191 | 318, 319; 320, 321 |
| 39, 98 | 192, 193 | 322, 323 |
| 40, 99 | 194, 195 | 324, 325 |
| 41, 100 | 196, 197 | 326, 327; 328, 329 |
| 42, 101 | 198, 199 | 330, 331 |
| 43, 102 | 200, 201 | 332, 333 |
| 44, 45, 103 | 202, 203 | 374, 375; 376, 377 |
| 46, 104 | 204, 205 | 378, 379 |
| 47, 105 | 206, 207 | 380, 381 |
| 48, 106 | 208, 209 | 382, 383 |
| 49, 107 | 210, 211 | 334, 335 |
| 50, 51, 108 | 212, 213 | 336, 337; 384, 385 |
| 52, 109 | 214, 215 | 338, 339 |
| 53, 110 | 216, 217 | 340, 341 |
| 54, 111 | 218, 219 | 344, 345 |
| 55, 112 | 220, 221 | 386, 387 |
| 56, 113 | 222, 223 | 388, 389; 390, 391 |
| 57, 114 | 224, 225 | 392, 393 |
| 58, 115 | 226, 227 | 394, 395 |
| 59, 116 | 228, 229 | 396, 397 |
| 60, 117 | 230, 231 | 398, 399 |
| 400, 401 | 402, 407 | 408, 409; 410, 411; 412, 413 |

A marker associated with enhanced drought tolerance can comprise, consist essentially of, and/or consist of a single allele or a combination of alleles at one or more genetic loci.

Thus, in some embodiments the presently disclosed subject matter provides methods for producing a hybrid plant with enhanced water optimization. In some embodiments, the method comprise (a) providing a first plant comprising a first genotype comprising any one of haplotypes A-M: (b) providing a second plant comprising a second genotype comprising any one of haplotypes A-M, wherein the second plant comprises at least one of haplotypes A-M that is not present in the first plant; (c) crossing the first plant and the second maize plant to produce an F1 generation; identifying one or more members of the F1 generation that comprises a desired genotype comprising any combination of haplotypes A-M, wherein the desired genotype differs from both the first genotype of (a) and the second genotype of (b), whereby a hybrid plant with enhanced water optimization is produced. In some embodiments, haplotypes A-M are defined as follows:

i. Haplotype A comprises a G nucleotide at the position that corresponds to position 115 of SEQ ID NO: 1, an A nucleotide at the position that corresponds to position 270 of SEQ ID NO: 1, a T nucleotide at the position that corresponds to position 301 of SEQ ID NO: 1, and an A nucleotide at the position that corresponds to position 483 of SEQ ID NO: 1 on chromosome 8 in the first plant's genome;

ii. Haplotype B comprises a deletion at positions 4497-4498 of SEQ ID NO: 7, a G nucleotide at the position that corresponds to position 4505 of SEQ ID NO: 7, a T nucleotide at the position that corresponds to position 4609 of SEQ ID NO: 7, an A nucleotide at the position that corresponds to position 4641 of SEQ ID NO: 7, a T nucleotide at the position that corresponds to position 4792 of SEQ ID NO: 7, a T nucleotide at the position that corresponds to position 4836 of SEQ ID NO: 7, a C nucleotide at the position that corresponds to position 4844 of SEQ ID NO: 7, a G nucleotide at the position that corresponds to position 4969 of SEQ ID NO: 7, and a TCC trinucleotide at the position that corresponds to positions 4979-4981 of SEQ ID NO: 7 on chromosome 8 in the first plant's genome;

iii. Haplotype C comprises an A nucleotide at the position that corresponds to position 217 of SEQ ID NO: 8, a G nucleotide at the position that corresponds to position 390 of SEQ ID NO: 8, and an A nucleotide at the position that corresponds to position 477 of SEQ ID NO: 8 on chromosome 2 in the first plant's genome;

iv. Haplotype D comprises a G nucleotide at the position that corresponds to position 182 of SEQ ID NO: 19, an A nucleotide at the position that corresponds to position 309 of SEQ ID NO: 19, a G nucleotide at the position that corresponds to position 330 of SEQ ID NO: 19, and a G nucleotide at the position that corresponds to position 463 of SEQ ID NO: 19 on chromosome 8 in the first plant's genome;

v. Haplotype E comprises a C nucleotide at the position that corresponds to position 61 of SEQ ID NO: 21, a C nucleotide at the position that corresponds to position 200 of SEQ ID NO: 21, and a deletion of nine nucleotides at the positions that corresponds to positions 316-324 of SEQ ID NO: 21 on chromosome 5 in the first plant's genome;

vi. Haplotype F comprises a G nucleotide at the position that corresponds to position 64 of SEQ ID NO: 27 and a T nucleotide at the position that corresponds to position 254 of SEQ ID NO: 27 on chromosome 8 in the first plant's genome;

vii. Haplotype G comprises an C nucleotide at the position that corresponds to position 98 of SEQ ID NO: 28, a T nucleotide at the position that corresponds to position 147 of SEQ ID NO: 28, a C nucleotide at the position that corresponds to position 224 of SEQ ID NO: 28, and a T nucleotide at the position that corresponds to position 496 of SEQ ID NO: 28 on chromosome 9 in the first plant's genome;

viii. Haplotype H comprises a T nucleotide at the position that corresponds to position 259 of SEQ ID NO: 30, a T nucleotide at the position that corresponds to position 306 of SEQ ID NO: 30, an A nucleotide at the position that corresponds to position 398 of SEQ ID NO: 30, and a C nucleotide at the position that corresponds to position 1057 of SEQ ID NO: 30 on chromosome 4 in the first plant's genome;

ix. Haplotype I comprises a C nucleotide at the position that corresponds to position 500 of SEQ ID NO: 36, a G nucleotide at the position that corresponds to position 568 of SEQ ID NO: 36, and a T nucleotide at the position that corresponds to position 698 of SEQ ID NO: 36 on chromosome 6 in the first plant's genome;

x. Haplotype J comprises an A nucleotide at the position that corresponds to position 238 of SEQ ID NO: 42, a deletion of the nucleotides that correspond to positions 266-268 of SEQ ID NO: 42, and a C nucleotide at the position that corresponds to position 808 of SEQ ID NO: 42 in the first plant's genome;

xi. Haplotype K comprises a C nucleotide at the position that corresponds to position 166 of SEQ ID NO: 49, and A nucleotide at the position that corresponds to position 224 of SEQ ID NO: 49, a G nucleotide at the position that corresponds to position 650 of SEQ ID NO: 49, and a G nucleotide at the position that corresponds to position 892 of SEQ ID NO: 49 on chromosome 8 in the first plant's genome;

xii. Haplotype L comprises a C nucleotide at the positions that correspond to positions 83, 428, 491, and 548 of SEQ ID NO: 53 on chromosome 9 in the first plant's genome; and xiii. Haplotype M comprises a C nucleotide at the position that corresponds to position 83 in SEQ ID NO: 400, an A nucleotide at the position that corresponds to position 119 of SEQ ID NO: 400, and a T nucleotide at the position that corresponds to position 601 of SEQ ID NO: 400.

In some embodiments, the hybrid plant with enhanced water optimization comprises each of haplotypes A-M that are present in the first plant as well as at least one additional haplotype selected from haplotypes A-M that is present in the second plant. In some embodiments, the first plant is a recurrent parent comprising at least one of haplotypes A-M and the second plant is a donor that comprises at least one of haplotypes A-M that is not present in the first plant. In some embodiments, the first plant is homozygous for at least two, three, four, or five of haplotypes A-M. In some embodiments, the hybrid plant comprises at least three, four, five, six, seven, eight, or nine of haplotypes A-M.

In some embodiments, the identifying comprises genotyping one or more members of an F1 generation produced by crossing the first plant and the second plant with respect to each of the haplotypes A-M present in either the first plant or the second plant.

In some embodiments, the first plant and the second plant are *Zea mays* plants.

In some embodiments, enhanced water optimization confers increased or stabilized yield in a water stressed environment as compared to a control plant. In some embodiments, the hybrid with enhanced water optimization can be planted at a higher crop density. In some embodiments, the hybrid with enhanced water optimization confers no yield drag when under favorable moisture levels.

The presently disclosed subject matter also provides in some embodiments hybrid *Zea mays* plants produced by the presently disclosed methods, or a cell, tissue culture, seed, or part thereof.

The presently disclosed subject matter also provides in some embodiments inbred *Zea mays* plants produced by backcrossing and/or selfing and/or producing double haploids from the hybrid *Zea mays* plants disclosed herein, or a cell, tissue culture, seed, or part thereof.

The presently disclosed subject matter also provides in some embodiments inbred or hybrid *Zea mays* plants, the genome of which comprises at least three, four, five, six, seven, eight, or nine of haplotypes A-M, wherein haplotypes A-M are associated with water optimization and are defined herein. In some embodiments, the inbred or hybrid *Zea mays* plant comprises a genome comprising Haplotypes C, D, and G; Haplotypes C, D, and L; Haplotypes C, G, and H; Haplotypes C, G, and I; Haplotypes C, I, and L; Haplotypes E, G, and I; Haplotypes F, G, and H; Haplotypes A, C, F, and G; Haplotypes C, E, H, and I; Haplotypes C, G, H, and I; Haplotypes C, H, I, and K; Haplotypes C, H, I, and L; Haplotypes E, F, G, and H; Haplotypes A, C, G, H, and I; Haplotypes B, C, D, G, and L; Haplotypes C, E, G, H, and I; Haplotypes C, G, H, I, and L; Haplotypes A, C, G, H, I, and K; Haplotypes C, E, F, G, H, I, J, K, and L; Haplotypes C, D, G, and M; Haplotypes C, D, L, and M; Haplotypes C, G, H, and M; Haplotypes C, G, I, and M; Haplotypes C, I, L, and M; Haplotypes E, G, I, and M; Haplotypes F, G, H, and M; Haplotypes A, C, F, G, and M; Haplotypes C, E, H, I, and M; Haplotypes C, G, H, I, and M; Haplotypes C, H, I, K, and M; Haplotypes C, H, I, L, and M; Haplotypes E, F, G, H, and M; Haplotypes A, C, G, H, I, and M; Haplotypes B, C, D, G, L, and M; Haplotypes C, E, G, H, I, and M; Haplotypes C, G, H, I, L, and M; Haplotypes A, C, G, H, I, K, and M; and Haplotypes C, E, F, G, H, I, J, K, L, and M. In some embodiments, the inbred or hybrid *Zea mays* plant is a hybrid plant that is homozygous for at least one of Haplotypes A-M.

In some embodiments, the inbred or hybrid *Zea mays* plant comprises a genome comprising Haplotypes A, C, E, G, H, and I, optionally further comprising Haplotype M; Haplotypes B, C, D, E, F, G, H, I, and L, optionally further comprising Haplotype M; Haploypyes C, D, E, F, G, H, and L, optionally further comprising Haplotype M; Haplotypes B, C, D, G, I, and L, optionally further comprising Haplotype M; Haplotypes B, C, D, E, G, H, I, and L, optionally further comprising Haplotype M; Haplotypes C, D, E, F, G, H, I, J, K, and L, optionally further comprising Haplotype M; Haplotypes A, C, G, H, and I, optionally further comprising Haplotype M; Haplotypes C, E, F, G, H, and I, optionally further comprising Haplotype M; Haplotypes C, E, F, G, H, I, and L, optionally further comprising Haplotype M; Haplotypes C, D, E, F, G, and H, optionally further comprising Haplotype M; Haplotypes D, E, F, G, and H, optionally further comprising Haplotype M; Haplotypes A, C, G, H, and I, optionally further comprising Haplotype M; Haplotypes A, C, E, G, H, I, and K, optionally further comprising Haplotype M; Haplotype C, E, G, H, I, and L, optionally further comprising Haplotype M; Haplotypes C, D, E, G, H, I, and L, optionally further comprising Haplotype M; Haplotypes B, C, D, E, G, H, I, and L, optionally further comprising Haplotype M; Haplotypes A, C, G, H, and I, optionally further comprising Haplotype M; Haplotypes A, C, G, H, I, and K, optionally further comprising Haplotype M; Haplotypes C, G H, I, and L, optionally further comprising Haplotype M; Haplotypes C, D, G, H, I, and L, optionally further comprising Haplotype M; Haplotypes B, C, D, G, H, I, and L, optionally further comprising Haplotype M; Haplotypes A, C, E, F, G, H, and I, optionally further comprising Haplotype M; Haplotypes A, C, E, F, G, H, I, and K, optionally further comprising Haplotype M; Haplotypes C, E, F, G, H, I, and L, optionally further comprising Haplotype M; Haplotypes C, D, E, F, G, H, I, and L, optionally further comprising Haplotype M; Haplotypes A, C, E, F, G, H, I, J, K, and L, optionally further comprising Haplotype M; Haplotypes A, C, E, F, G, H, I, J, K, and L, optionally further comprising Haplotype M; Haplotypes C, E, F, G, H, I, J, K, and L, optionally further comprising Haplotype M; Haplotypes C, D, E, F, G, H, I, J, K, and L, optionally further comprising Haplotype M; Haplotypes B, C, D, E, F, G, H, I, J, K, and L, optionally further comprising Haplotype M; Haplotypes A, C, E, F, G, H, and I, optionally further comprising Haplotype M; Haplotypes A, C, E, F, G, H, I, and K, optionally further comprising Haplotype M; Haplotypes C, E, F, G, H, I, and L, optionally further comprising Haplotype M; Haplotypes B, C, D, E, F, G, H, and L, optionally further comprising Haplotype M; Haplotypes C, E, F, G, H, I, J, K, and L, optionally further comprising Haplotype M; Haplotypes C, D, G, H, and L, optionally further comprising Haplotype M; Haplotypes C, E, F, G, H, I, and L, optionally further comprising Haplotype M; and/or Haplotypes B, C, D, E, G, I, and L, optionally further comprising Haplotype M.

The presently disclosed subject matter also provides in some embodiments hybrid or inbred *Zea mays* plants that have been modified to include a transgene. In some embodiments, the transgene encodes a gene product that provides resistance to a herbicide selected from among glyphosate, Sulfonylurea, imidazolinione, dicamba, glufisinate, phenoxy proprionic acid, cycloshexome, traizine, benzonitrile, and broxynil.

The presently disclosed subject matter also provides in some embodiments methods for identifying *Zea mays* plants comprising at least one allele associated with water optimization as disclosed herein. In some embodiments, the methods comprise (a) genotyping at least one *Zea mays* plant with at least one nucleic acid marker selected from among SEQ ID NOs: 1-60 and 400; and (b) selecting at least one *Zea mays* plant comprising an allele of at least one of the at least one nucleic acid markers that is associated with water optimization.

The presently disclosed subject matter also provides in some embodiments *Zea mays* plants produced by introgressing an allele of interest of a locus associated with a water optimization trait into *Zea mays* germplasm. In some embodiments, the introgressing comprises (a) selecting a *Zea mays* plant that comprises an allele of interest of a locus associated with a water optimization trait, wherein the locus associated with a water optimization trait comprises a nucleotide sequence that is at least 90% identical to any of SEQ ID NOs: 1-117, 400, and 401; and (b) introgressing the allele of interest into *Zea mays* germplasm that lacks the allele.

The presently disclosed subject matter also provides in some embodiments methods for identifying and/or selecting drought tolerant maize plants or germplasm. In some embodiments, the presently disclosed methods comprise detecting, in a maize plant or germplasm, the presence of a marker associated with enhanced drought tolerance, wherein the marker is selected from the group consisting of:

a G nucleotide at the position that corresponds to position 100 of SEQ ID NO: 2, a TCC trinucleotide at the position that corresponds to positions 4979-4981 of SEQ ID NO: 7, a G nucleotide at the position that corresponds to position 116 of SEQ ID NO: 23, an A nucleotide at the position that corresponds to position 391 of SEQ ID NO: 33, an A nucleotide at the position that corresponds to position 472 of SEQ ID NO: 48, an A nucleotide at the position that corresponds to position 237 of SEQ ID NO: 56, a T nucleotide at the position that corresponds to position 173 of SEQ ID NO: 57, and a G nucleotide at the position that corresponds to position 267 of SEQ ID NO: 60;

a TCC trinucleotide at the position that corresponds to positions 4979-4981 of SEQ ID NO: 7, an A nucleotide at the position that corresponds to position 309 of SEQ ID NO: 19, a G nucleotide at the position that corresponds to position 562 of SEQ ID NO: 25, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;

a G nucleotide at the position that corresponds to position 100, an A nucleotide at the position that corresponds to position 4641 of SEQ ID NO: 7, an A nucleotide at the position that corresponds to position 217 of SEQ ID NO: 23, a C nucleotide at the position that corresponds to position 746 of SEQ ID NO: 24, a C nucleotide at the position that corresponds to position 258 of SEQ ID NO: 29, an A nucleotide at the position that corresponds to position 266 of SEQ ID NO: 44, a G nucleotide at the position that corresponds to position 472 of SEQ ID NO: 48, a G nucleotide at the position that corresponds to position 193 of SEQ ID NO: 55, and a C nucleotide at the position that corresponds to position 486 of SEQ ID NO: 58;

a deletion at nucleotide at the position that corresponds to positions 264-271 of SEQ ID NO: 2, an A nucleotide at the position that corresponds to position 4641 of SEQ ID NO: 7, an A nucleotide at the position that corresponds to position 309 of SEQ ID NO: 19, an A nucleotide at the position that corresponds to position 391 of SEQ ID NO: 33, a G nucleotide at the position that corresponds to position 237 of SEQ ID NO: 56, and a C nucleotide at the position that corresponds to position 486 of SEQ ID NO: 58;

a TCC trinucleotide at the position that corresponds to positions 4979-4981 of SEQ ID NO: 7, a G nucleotide at the position that corresponds to position 463 of SEQ ID NO: 19, a C nucleotide at the position that corresponds to position 254 of SEQ ID NO: 27, an A nucleotide at the position that corresponds to position 391 of SEQ ID NO: 33, a T nucleotide at the position that corresponds to position 475 of SEQ ID NO: 45, a G nucleotide at the position that corresponds to position 193 of SEQ ID NO: 55, a C nucleotide at the position that corresponds to position 516 of SEQ ID NO: 56, a G nucleotide at the position that corresponds to position 729 of SEQ ID NO: 59, and a G nucleotide at the position that corresponds to position 267 of SEQ ID NO: 60;

an A nucleotide at the position that corresponds to position 4641 of SEQ ID NO: 7, a G nucleotide at the position that corresponds to position 463 of SEQ ID NO: 19, a C nucleotide at the position that corresponds to position 258 of SEQ ID NO: 29, a G nucleotide at the position that corresponds to position 193 of SEQ ID NO: 55, and a G nucleotide at the position that corresponds to position 237 of SEQ ID NO: 56;

a TCC trinucleotide at the position that corresponds to positions 4979-4981 of SEQ ID NO: 7, an A nucleotide at the position that corresponds to position 472 of SEQ ID NO: 48, an A nucleotide at the position that corresponds to position 237 of SEQ ID NO: 56, and a T nucleotide at the position that corresponds to position 173 of SEQ ID NO: 57;

a TCC trinucleotide at the position that corresponds to positions 4979-4981 of SEQ ID NO: 7, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;

an A nucleotide at the position that corresponds to position 4641 of SEQ ID NO: 7, a C nucleotide at the position that corresponds to position 258 of SEQ ID NO: 29, a G nucleotide at the position that corresponds to position 87 of SEQ ID NO: 47, a G nucleotide at the position that corresponds to position 472 of SEQ ID NO: 48, and a G nucleotide at the position that corresponds to position 193 of SEQ ID NO: 55;

an A nucleotide at the position that corresponds to position 4641 of SEQ ID NO: 7, an A nucleotide at the position that corresponds to position 309 of SEQ ID NO: 19, and a G nucleotide at the position that corresponds to position 237 of SEQ ID NO: 56;

a TCC trinucleotide at the position that corresponds to positions 4979-4981 of SEQ ID NO: 7, a G nucleotide at the position that corresponds to position 463 of SEQ ID NO: 19, a T nucleotide at the position that corresponds to position 475 of SEQ ID NO: 45, and a G nucleotide at the position that corresponds to position 193 of SEQ ID NO: 55;

a TCC trinucleotide at the position that corresponds to positions 4979-4981 of SEQ ID NO: 7;

an A nucleotide at the position that corresponds to position 4641 of SEQ ID NO: 7;

a TCC trinucleotide at the position that corresponds to positions 4979-4981 of SEQ ID NO: 7 and a C nucleotide at the position that corresponds to position 386 of SEQ ID NO: 46;

an A nucleotide at the position that corresponds to position 4641 of SEQ ID NO: 7 and a G nucleotide at the position that corresponds to position 472 of SEQ ID NO: 48, and combinations thereof, thereby identifying and/or selecting a drought tolerant maize plant or germplasm.

Thus, it is an object of the presently disclosed subject matter to provide methods for conveying one or more water optimization traits into maize germplasm.

An object of the presently disclosed subject matter having been stated hereinabove, and which is achieved in whole or in part by the presently disclosed subject matter, other objects will become evident as the description proceeds as best described herein below.

BRIEF DESCRIPTION OF THE DRAWINGS

FIG. 1 is a graphical depiction of the alleles present at several loci in certain of the maize varieties used in the breeding protocols described herein.

FIG. 4 is a graphical depiction of the haplotypes of the homozygous plant lines derived from the crossing of NP2391 and Cateto SP VII ("Cateto homozygous −" and "Cateto homozygous +") and of the F1 hybrid lines derived from the crossing of each of the aforementioned homozygous lines with NP2460 ("Cateto–" and "Cateto+"). Lower case letters represent alleles inherited from the Cateto SP VII donor line. Upper case letters represent alleles inherited from NP2391 or NP2460.

Figure 1:
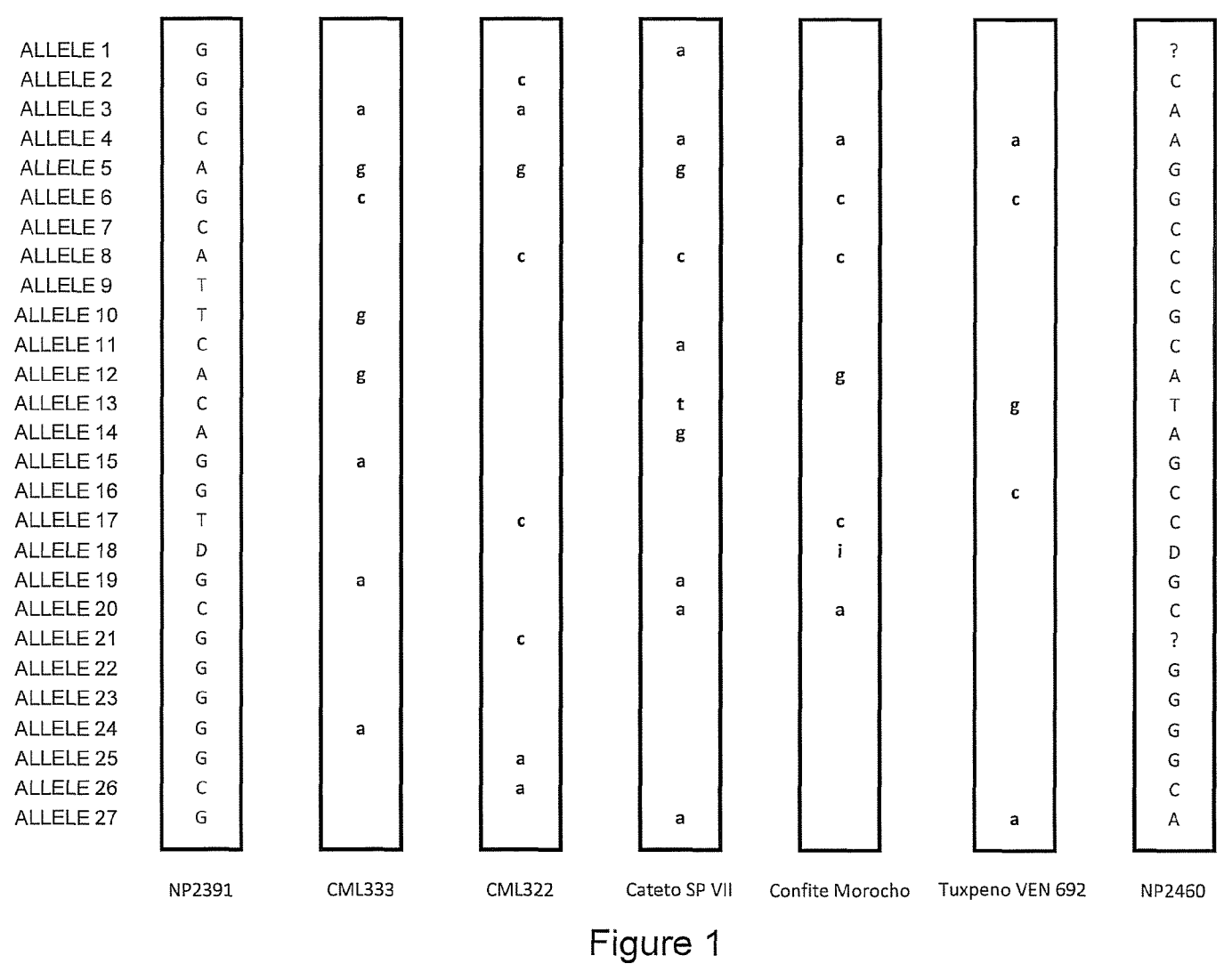
Figure 2:
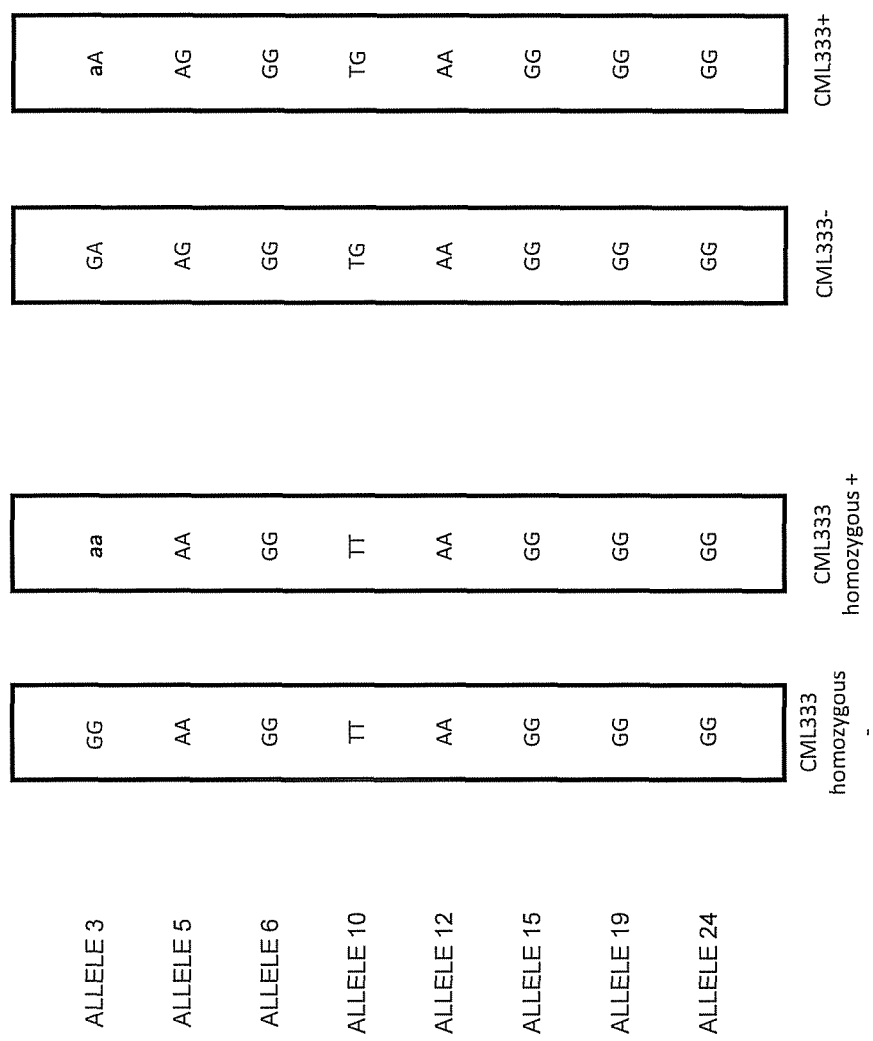
FIG. 2 is a graphical depiction of the haplotypes of the homozygous plant lines derived from the crossing of NP2391 and CML333 ("CML333 homozygous −" and "CML333 homozygous +") and of the F1 hybrid lines derived from the crossing of each of the aforementioned homozygous lines with NP2460 ("CML333−" and "CML333+"). Lower case letters represent alleles inherited from the CML333 donor line. Upper case letters represent alleles inherited from NP2391 or NP2460.
Figure 3:
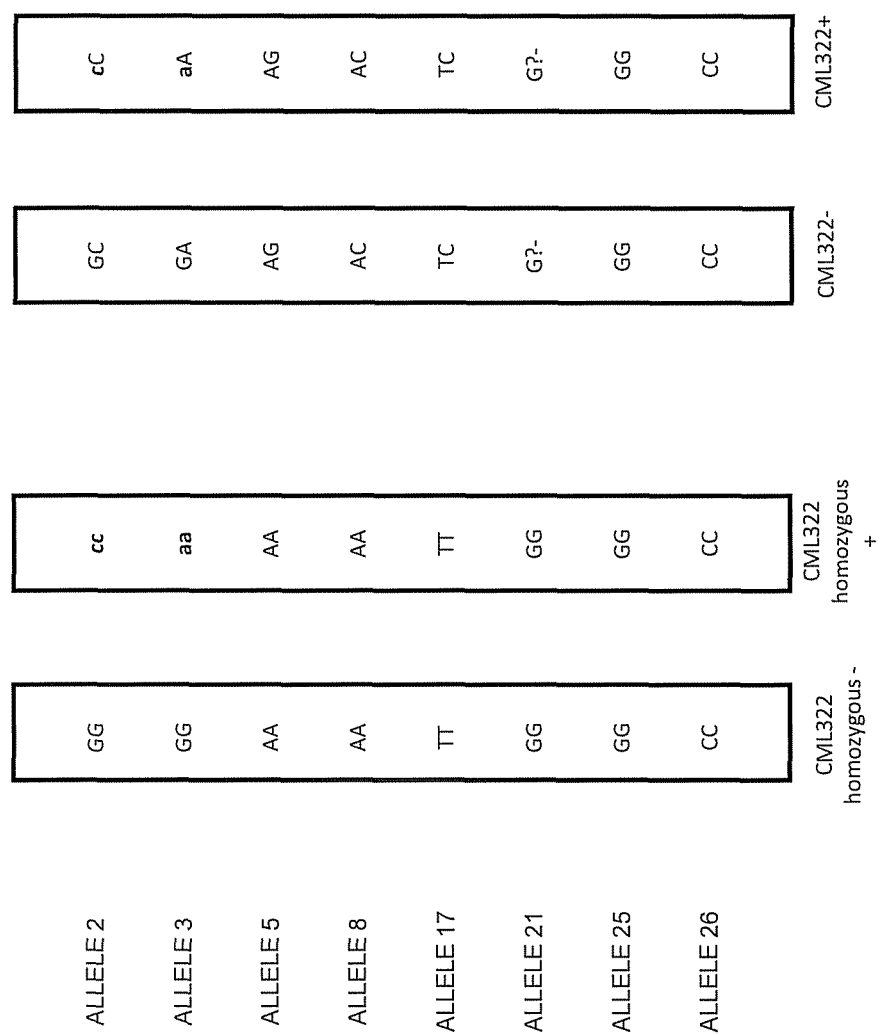
FIG. 3 is a graphical depiction of the haplotypes of the homozygous plant lines derived from the crossing of NP2391 and CML322 ("CML322 homozygous −" and "CML322 homozygous +") and of the F1 hybrid lines derived from the crossing of each of the aforementioned homozygous lines with NP2460 ("CML322−" and "CML322+"). Lower case letters represent alleles inherited from the CML322 donor line. Upper case letters represent alleles inherited from NP2391 or NP2460.
Figure 5:
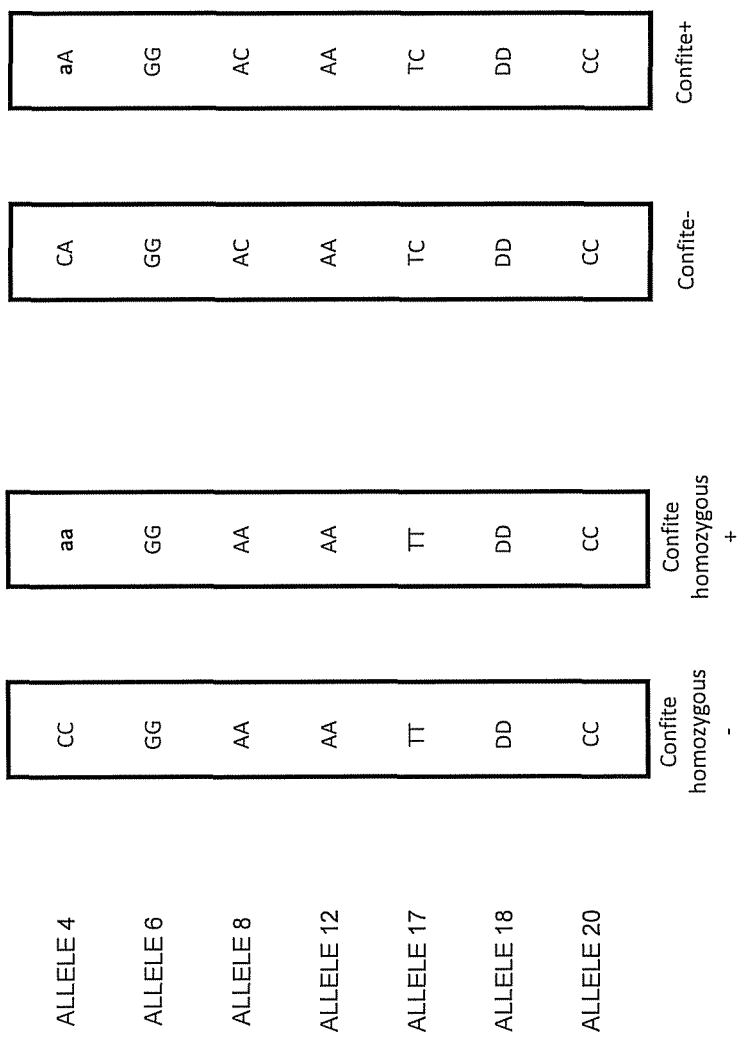
FIG. 5 is a graphical depiction of the haplotypes of the homozygous plant lines derived from the crossing of NP2391 and Confite Morocho AYA 38 ("Confite homozygous –" and "Confite homozygous +") and of the F1 hybrid lines derived from the crossing of each of the aforementioned homozygous lines with NP2460 ("Confite–" and "Confite+"). Lower case letters represent alleles inherited from the Confite Morocho AYA 38 donor line. Upper case letters represent alleles inherited from NP2391 or NP2460.
Figure 6:
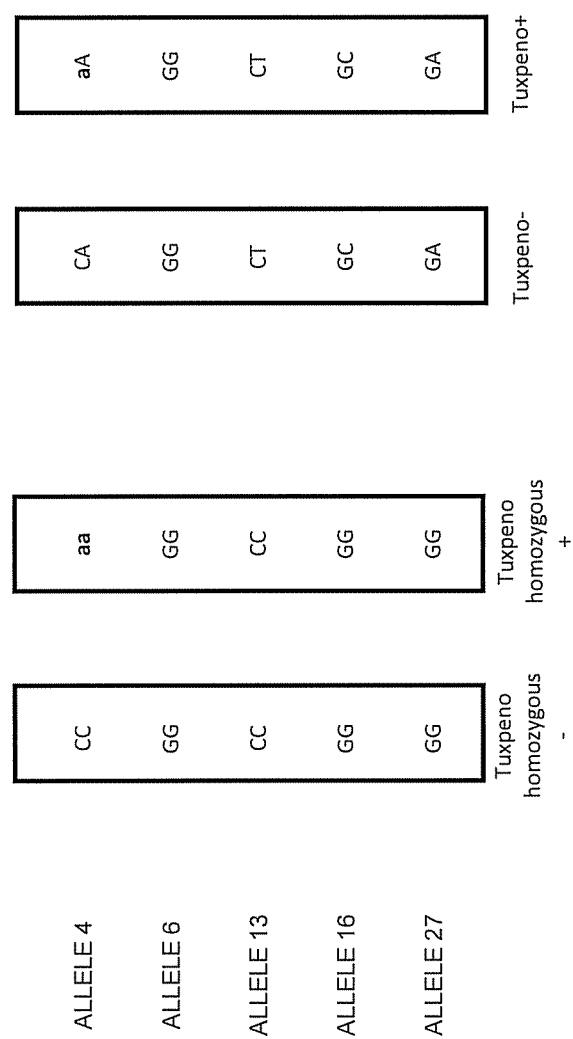
FIG. 6 is a graphical depiction of the haplotypes of the homozygous plant lines derived from the crossing of NP2391 and Tuxpeno VEN 692 ("Tuxpeno homozygous –" and "Tuxpeno homozygous +") and of the F1 hybrid lines derived from the crossing of each of the aforementioned homozygous lines with NP2460 ("Tuxpeno–" and "Tuxpeno+"). Lower case letters represent alleles inherited from the Tuxpeno VEN 692 donor line. Upper case letters represent alleles inherited from NP2391 or NP2460.

For each of FIGS. 1-6, the ALLELES are as follows:

| ALLELE | Nucleotide Position and SEQ ID NO: |
|---|---|
| 1 | position 87 of SEQ ID NO: 47 |
| 2 | position 386 of SEQ ID NO: 46 |
| 3 | positions 4979-4981 of SEQ ID NO: 7 |
| 4 | position 4641 of SEQ ID NO: 7 |
| 5 | position 472 of SEQ ID NO: 48 |
| 6 | position 237 of SEQ ID NO: 56 |
| 7 | position 516 of SEQ ID NO: 56 |
| 8 | position 266 of SEQ ID NO: 44 |
| 9 | position 475 of SEQ ID NO: 45 |
| 10 | position 173 of SEQ ID NO: 57 |
| 11 | position 746 of SEQ ID NO: 24 |
| 12 | position 391 of SEQ ID NO: 33 |
| 13 | position 258 of SEQ ID NO: 29 |
| 14 | position 217 of SEQ ID NO: 23 |
| 15 | position 116 of SEQ ID NO: 23 |
| 16 | position 463 of SEQ ID NO: 19 |
| 17 | position 309 of SEQ ID NO: 19 |
| 18 | positions 264-271 of SEQ ID NO: 2 |
| 19 | position 100 of SEQ ID NO: 2 |
| 20 | position 486 of SEQ ID NO: 58 |
| 21 | position 111 of SEQ ID NO: 51 |
| 22 | position 254 of SEQ ID NO: 27 |
| 23 | position 729 of SEQ ID NO: 59 |
| 24 | position 267 of SEQ ID NO: 60 |
| 25 | position 562 of SEQ ID NO: 25 |
| 26 | position 1271 of SEQ ID NO: 26 |
| 27 | position 193 of SEQ ID NO: 55 |

BRIEF DESCRIPTION OF THE SEQUENCE LISTING

The instant disclosure includes a plurality of nucleotide and/or amino acid sequences. Throughout the disclosure and the accompanying sequence listing, the WIPO Standard ST.25 (1998; hereinafter the "ST.25 Standard") is employed to identify nucleotides. This nucleotide identification standard is summarized below:

TABLE 2

Nucleotide Naming Conventions in WIPO Standard ST.25

| Symbol | Meaning | Symbol | Meaning |
|---|---|---|---|
| a | a | k | g or t/u |
| c | c | s | g or c |
| g | g | w | a or t/u |
| t | t | b | g or c or t/u |
| u | u | d | a or g or t/u |
| r | g or a | h | a or c or t/u |
| v | t/u or c | v | a or g or c |
| m | a or c | n | a or g or c or t/u, unknown, other, or absent |

In certain instances, the accompanying Sequence Listing includes one or more specifically identified definitions for certain nucleotide positions as set forth in lines <220> through <223> of the corresponding Sequence Listing entries. For example, whereas under the ST.25 Standard the nucleotide "n" generally substitutes for any of a, c, g, or t, in SEQ ID NO: 2 it is noted that the sequence "nnnnnnnn" at nucleotide positions 264-271 is defined to represent either the presence or the absence of the nucleotide sequence "CAC-CAAGG". Similarly, in SEQ ID NO: 5 it is noted that the sequence "nnnn" at nucleotide positions 818-821 is defined to represent either the presence or the absence of the nucleotide sequence "CGCG". As such, whereas the ST.25 Standard is to be followed throughout the instant specification, Statement s, and Sequence Listing, certain sequences disclosed herein represent specific departures from the ST.25 Standard, and are noted accordingly.

Additionally, whether specifically noted or not, for each recitation of "n" in the Sequence Listing, it is understood that any individual "n" (including some or all n's in a sequence of consecutive n's) can represent a, c, g, t/u, unknown, or other, or can be absent. Thus, unless specifically defined to the contrary in the Sequence Listing, an "n" can in some embodiments represent no nucleotide. For example, SEQ ID NO: 7 includes a string of 52 n's between nucleotides 4549 and 4600, inclusive. It is understood that one or more of these n's can be absent, including but not limited to all 52 or any subset thereof.

SEQ ID NO: 1 is a nucleotide sequence that is associated with the water optimization locus ZmIga4, subsequences of which can be amplified from chromosome 8 of the *Zea mays* genome using the polymerase chain reaction with amplification primers as set forth in Table 4 below.

SEQ ID NO: 2 is a nucleotide sequence that is associated with the a *Zea mays* water optimization locus, subsequences of which can be amplified from chromosome 8 of the *Zea mays* genome using the polymerase chain reaction with amplification primers as set forth in Table 4 below.

SEQ ID NO: 3 is a nucleotide sequence that is associated with the water optimization locus ZmDr1, subsequences of which can be amplified from the *Zea mays* genome using the polymerase chain reaction with amplification primers as set forth in Table 4 below.

SEQ ID NO: 4 is a nucleotide sequence that is associated with the water optimization locus ZmDrA encoding a voltage-dependent anion channel, subsequences of which can be amplified from chromosome 7 of the *Zea mays* genome using the polymerase chain reaction with amplification primers as set forth in Table 4 below.

SEQ ID NO: 5 is a nucleotide sequence that is associated with the water optimization locus ZmDr2, subsequences of which can be amplified from chromosome 2 of the *Zea mays* genome using the polymerase chain reaction with amplification primers as set forth in Table 4 below.

SEQ ID NO: 6 is a nucleotide sequence that is associated with the water optimization locus ZmDr3, subsequences of which can be amplified from chromosome 2 of the *Zea mays* genome using the polymerase chain reaction with amplification primers as set forth in Table 4 below.

SEQ ID NO: 7 is a nucleotide sequence that is associated with the water optimization locus ZmDr4, subsequences of which can be amplified from chromosome 8 of the *Zea mays* genome using the polymerase chain reaction with amplification primers as set forth in Table 4 below.

SEQ ID NO: 8 is a nucleotide sequence that is associated with a water optimization locus ZmMa3, subsequences of which can be amplified from chromosome 2 of the *Zea mays* genome using the polymerase chain reaction with amplification primers as set forth in Table 4 below.

SEQ ID NO: 9 is a nucleotide sequence that is associated with the water optimization locus ZmDr6, subsequences of which can be amplified from chromosome 4 of the *Zea mays* genome using the polymerase chain reaction with amplification primers as set forth in Table 4 below.

SEQ ID NO: 10 is a nucleotide sequence that is associated with the water optimization locus ZmBglcn, subsequences of which can be amplified from chromosome 3 of the *Zea mays* genome using the polymerase chain reaction with amplification primers as set forth in Table 4 below.

SEQ ID NO: 11 is a nucleotide sequence that is associated with the water optimization locus ZmLOC100276591, subsequences of which can be amplified from the *Zea mays* genome using the polymerase chain reaction with amplification primers as set forth in Table 4 below.

SEQ ID NOs: 12 and 13 are nucleotide sequences that are associated with the water optimization locus ZmDr7, subsequences of which can be amplified from chromosome 1 of the *Zea mays* genome using the polymerase chain reaction with amplification primers as set forth in Table 4 below.

SEQ ID NO: 14 is a nucleotide sequence that is associated with the water optimization locus ZmDr8, subsequences of which can be amplified from the *Zea mays* genome using the polymerase chain reaction with amplification primers as set forth in Table 4 below.

SEQ ID NO: 15 is a nucleotide sequence that is associated with the water optimization locus ZmHsp70, subsequences of which can be amplified from chromosome 1 of the *Zea mays* genome using the polymerase chain reaction with amplification primers as set forth in Table 4 below.

SEQ ID NO: 16 is a nucleotide sequence that is associated with the water optimization locus ZmDr9, subsequences of which can be amplified from chromosome 4 of the *Zea mays* genome using the polymerase chain reaction with amplification primers as set forth in Table 4 below.

SEQ ID NO: 17 is a nucleotide sequence that is associated with the water optimization locus ZmDrB, subsequences of which can be amplified from the *Zea mays* genome using the polymerase chain reaction with amplification primers as set forth in Table 4 below.

SEQ ID NO: 18 is a nucleotide sequence that is associated with the water optimization locus ZmAdh1-1s, subsequences of which can be amplified from chromosome 1 of the *Zea mays* genome using the polymerase chain reaction with amplification primers as set forth in Table 4 below.

SEQ ID NO: 19 is a nucleotide sequence that is associated with the water optimization locus ZmDr10, subsequences of which can be amplified from chromosome 8 of the *Zea mays* genome using the polymerase chain reaction with amplification primers as set forth in Table 4 below.

SEQ ID NO: 20 is a nucleotide sequence that is associated with the water optimization locus ZmDrC, subsequences of which can be amplified from the *Zea mays* genome using the polymerase chain reaction with amplification primers as set forth in Table 4 below.

SEQ ID NO: 21 is a nucleotide sequence that is associated with the water optimization locus ZmDr5, subsequences of which can be amplified from chromosome 5 of the *Zea mays* genome using the polymerase chain reaction with amplification primers as set forth in Table 4 below.

SEQ ID NO: 22 is a nucleotide sequence that is associated with the water optimization locus ZmDrD encoding a subtilisin-chymotrypsin inhibitor 2, subsequences of which can be amplified from chromosome 5 of the *Zea mays* genome using the polymerase chain reaction with amplification primers as set forth in Table 4 below.

SEQ ID NO: 23 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 24 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 25 is a nucleotide sequence that is associated with the water optimization locus ZmDr12, subsequences of which can be amplified from chromosome 8 of the *Zea mays* genome using the polymerase chain reaction with amplification primers as set forth in Table 4 below.

SEQ ID NO: 26 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 27 is a nucleotide sequence that is associated with the water optimization locus ZmDrE encoding a legumin-like protein (cl2-1), subsequences of which can be amplified from chromosome 8 of the *Zea mays* genome using the polymerase chain reaction with amplification primers as set forth in Table 4 below.

SEQ ID NO: 28 is a nucleotide sequence that is associated with the water optimization locus ZmDrF encoding a putative cellulose synthase, subsequences of which can be amplified from chromosome 9 of the *Zea mays* genome using the polymerase chain reaction with amplification primers as set forth in Table 4 below.

SEQ ID NO: 29 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 30 is a nucleotide sequence that is associated with the water optimization locus ZmDhn2, subsequences of which can be amplified from chromosome 4 of the *Zea mays* genome using the polymerase chain reaction with amplification primers as set forth in Table 4 below.

SEQ ID NO: 31 is a nucleotide sequence that is associated with the water optimization locus ZmDr16, subsequences of which can be amplified from chromosome 8 of the *Zea mays* genome using the polymerase chain reaction with amplification primers as set forth in Table 4 below.

SEQ ID NO: 32 is a nucleotide sequence that is associated with the water optimization locus ZmDr17, subsequences of which can be amplified from the *Zea mays* genome using the polymerase chain reaction with amplification primers as set forth in Table 4 below.

SEQ ID NO: 33 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 34 is a nucleotide sequences that is associated with the water optimization locus ZmZCN6, subsequences of which can be amplified from chromosome 4 of the *Zea mays* genome using the polymerase chain reaction with amplification primers as set forth in Table 4 below.

SEQ ID NO: 35 is a nucleotide sequence that is associated with the water optimization locus ZmDrG, subsequences of which can be amplified from chromosome 5 of the *Zea mays* genome using the polymerase chain reaction with amplification primers as set forth in Table 4 below.

SEQ ID NO: 36 is a nucleotide sequence that is associated with the water optimization locus ZmDhn1, subsequences of which can be amplified from chromosome 6 of the *Zea mays* genome using the polymerase chain reaction with amplification primers as set forth in Table 4 below.

SEQ ID NO: 37 is a nucleotide sequence that is associated with the water optimization locus ZmDrH, subsequences of which can be amplified from chromosome 5 of the *Zea mays* genome using the polymerase chain reaction with amplification primers as set forth in Table 4 below.

SEQ ID NO: 38 is a nucleotide sequence that is associated with the water optimization locus ZmDrI, subsequences of which can be amplified from chromosome 3 of the *Zea mays* genome using the polymerase chain reaction with amplification primers as set forth in Table 4 below.

SEQ ID NO: 39 is a nucleotide sequence that is associated with the water optimization locus ZmDrJ encoding a mcm5 DNA replication factor, subsequences of which can be amplified from chromosome 5 of the *Zea mays* genome using the polymerase chain reaction with amplification primers as set forth in Table 4 below.

SEQ ID NO: 40 is a nucleotide sequence that is associated with the water optimization locus ZmH2B1, subsequences of which can be amplified from chromosome 4 of the *Zea mays* genome using the polymerase chain reaction with amplification primers as set forth in Table 4 below.

SEQ ID NO: 41 is a nucleotide sequence that is associated with the water optimization locus ZmDr3, subsequences of which can be amplified from chromosome 2 of the *Zea mays* genome using the polymerase chain reaction with amplification primers as set forth in Table 4 below.

SEQ ID NO: 42 is a nucleotide sequence that is associated with a the water optimization locus ZmDrK encoding an inorganic phosphatase, subsequences of which can be amplified from the *Zea mays* genome using the polymerase chain reaction with amplification primers as set forth in Table 4 below.

SEQ ID NO: 43 is a nucleotide sequence that is associated with water optimization locus ZmCat1, subsequences of which can be amplified from chromosome 5 of the *Zea mays* genome using the polymerase chain reaction with amplification primers as set forth in Table 4 below.

SEQ ID NOs: 44 and 45 are nucleotide sequences that are associated with a *Zea mays* water optimization locus, subsequences of which can be amplified from chromosome 8 of the *Zea mays* genome using the polymerase chain reaction with amplification primers as set forth in Table 4 below.

SEQ ID NO: 46 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 47 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 48 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 49 is a nucleotide sequence that is associated with the water optimization locus ZmRIC1, subsequences of which can be amplified from chromosome 8 of the *Zea mays* genome using the polymerase chain reaction with amplification primers as set forth in Table 4 below.

SEQ ID NOs: 50 and 51 are nucleotide sequences that are associated with the water optimization locus ZmPK4, subsequences of which can be amplified from chromosome 8 of the *Zea mays* genome using the polymerase chain reaction with amplification primers as set forth in Table 4 below.

SEQ ID NO: 52 is a nucleotide sequence that is associated with the water optimization locus Zpu1, subsequences of which can be amplified from chromosome 2 of the *Zea mays* genome using the polymerase chain reaction with amplification primers as set forth in Table 4 below.

SEQ ID NO: 53 is a nucleotide sequence that is associated with the water optimization locus ZmDrL, subsequences of which can be amplified from chromosome 9 of the *Zea mays* genome using the polymerase chain reaction with amplification primers as set forth in Table 4 below.

SEQ ID NO: 54 is a nucleotide sequence that is associated with the water optimization locus ZmDrM encoding a hexose transporter, subsequences of which can be amplified from chromosome 7 of the *Zea mays* genome using the polymerase chain reaction with amplification primers as set forth in Table 4 below.

SEQ ID NO: 55 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NOs: 56 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 57 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 58 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 59 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 60 is a nucleotide sequence that is associated with a *Zea mays* water optimization locus, subsequences of which can be amplified from chromosome 8 of the *Zea mays* genome using the polymerase chain reaction with amplification primers as set forth in Table 4 below.

SEQ ID NO: 400 is a nucleotide sequence that is associated with a *Zea mays* water optimization locus, subsequences of which can be amplified from chromosome 4 of the *Zea mays* genome using the polymerase chain reaction with amplification primers as set forth in Table 4 below.

SEQ ID NOs: 61-117 and 401 are nucleotide sequences present in the GENBANK® database (available through the World Wide Web at the website for the National Center for Biotechnology Information (NCBI) of the United States National Institutes of Health) that correspond to (i.e., come from the same chromosomal loci in *Zea mays* as) SEQ ID NOs: 1-60 and 400. The relationships among SEQ ID NOs: 1-60 and 400 and 61-117 and 401 are set forth in Table 3.

TABLE 3

GENBANK ® Database Sequences that Correspond to SEQ ID NOs: 1-60 and 400

| SEQ ID NO. | GENBANK ® Accession No. | Corresponding Nucleotides* | SEQ ID NO. of Corresponding Nucleotides |
|---|---|---|---|
| 1 | AC214546.3 | 79631-80177 | 61 |
| 2 | AC206432.3 | 76561-76072 | 62 |
| 3 | AC218964.2 | 18179-18598 | 63 |
| 4 | AC198035.3 | 158268-157254 | 64 |
| 5 | AC204020.3 | 180680-179781 | 65 |
| 6 | AC206638.3 | 120959-121302 | 66 |
| 7 | AC206220.1 | 197895-190521 | 67 |
| 8 | AC213636.3 | 7053-6486 | 68 |
| 9 | AC184130.4 | 28529-28053 | 69 |
| 10 | AC186650.4 | 44576-75791 | 70 |
| 11 | AC214515.3 | 46309-46830 | 71 |
| 12, 13 | AC211214.4 | 215368-214930 | 72 |
| 14 | AC199476.4 | 103707-103339 | 73 |
| 15 | AC213668.4 | 30778-29943 | 74 |
| 16 | AC196196.4 | 76499-75481 | 75 |
| 17 | AC214144.3 | 162815-162317 | 76 |
| 18 | AC190915.3 | 6402-5517 | 77 |
| 19 | AC209819.3 | 153562-152716 | 78 |
| 20 | AC187243.3 | 135331-136145 | 79 |
| 21 | AC203390.3 | 86249-86674 | 80 |
| 22 | AC195458.3 | 170810-171228 | 81 |
| 23 | AC201782.4 | 26367-27234 | 82 |
| 24 | AC218166.3 | 71588-72496 | 83 |
| 25 | AC194405.3 | 40048-39222 | 84 |
| 26 | AC213631.3 | 77810-79676 | 85 |
| 27 | AC217937.3 | 111822-111263 | 86 |
| 28 | AC211740.4 | 24016-14511 | 87 |
| 29 | AC199040.3 | 88703-89626 | 88 |
| 30 | AC203943.3 | 104038-102899 | 89 |
| 31 | AC210725.4 | 219394-219870 | 90 |
| 32 | AC231410.4 | 60838-60463 | 91 |
| 33 | AC195798.3 | 48792-47973 | 92 |
| 34 | AC183820.4 | 23492-22810 | 93 |
| 35 | AC214256.3 | 19884-20648 | 94 |
| 36 | AC214345.3 | 27168-26399 | 95 |
| 37 | AC198140.3 | 149518-149097 | 96 |
| 38 | AC204009.3 | 60314-59762 | 97 |
| 39 | AC205343.3 | 136853-136242 | 98 |
| 40 | AC196429.3 | 5293-5956 | 99 |
| 41 | AC206638.3 | 118845-119524 | 100 |
| 42 | AC191554.3 | 29279-28345 | 101 |
| 43 | AC197489.3 | 40538-39734 | 102 |
| 44, 45 | AC212232.3 | 61043-62624 | 103 |
| 46 | AC187869.3 | 65344-64604 | 104 |
| 47 | AC212049.4 | 47472-46845 | 105 |
| 48 | AC194834.3 | 115968-117051 | 106 |
| 49 | AC187038.3 | 139008-139936 | 107 |
| 50, 51 | AC212049.4 | 54492-53643 | 108 |
| 52 | AC202148.4 | 92457-93062 | 109 |
| 53 | AC194911.4 | 42128-41419 | 110 |
| 54 | AC195167.2 | 55324-56161 | 111 |
| 55 | AC202530.4 | 20157-19337 | 112 |
| 56 | AC218457.2 | 26390-27041 | 113 |

TABLE 3-continued

GENBANK ® Database Sequences that Correspond to SEQ ID NOs: 1-60 and 400

| SEQ ID NO. | GENBANK ® Accession No. | Corresponding Nucleotides* | SEQ ID NO. of Corresponding Nucleotides |
|---|---|---|---|
| 57 | AC195989.4 | 114536-115181 | 114 |
| 58 | AC207558.3 | 122483-121881 | 115 |
| 59 | AC204398.3 | 137510-138350 | 116 |
| 60 | AC211925.4 | 71848-71390 | 117 |
| 400 | AC196429.3 | 5293-5956 | 401 |

*Numbers in this column that are listed from lower to higher indicate that the GENBANK ® database entry corresponds to the nucleotide sequence from the same strand as in the corresponding sequence disclosed in SEQ ID NOs: 1-60 and 400. For those entries in which the numbers in this column are listed from higher to lower, the nucleotide sequence disclosed in the GENBANK ® database entry is the reverse complement of the nucleotide sequence of the corresponding sequence in SEQ ID NOs: 1-60 and 400.

SEQ ID NOs: 61-117 and 401 have been added to the GENBANK® database by the Genome Sequencing Center, Washington University School of Medicine, St. Louis, Mo., United States of America. As set forth in the annotations to these database entries, the sequences were part of an effort by The Maize Sequencing Consortium to sequence the genome of *Zea mays*. Currently, the sequencing effort has not been completed, and various portions of the *Zea mays* genome remain unsequenced and/or the sequences have not been ordered (or potentially, have been misordered) in the GENBANK® database.

Table 4 lists SEQ ID NOs. for oligonucleotides that can be employed to amplify *Zea mays* nucleic acids derived from the loci that correspond to SEQ ID NOs: 1-117, 400, and 401 and exemplary amplicons produced thereby. Table 4 also lists the nucleotide position in each locus sequence of SEQ ID NOs 1-60 of a polymorphism (in some embodiments, an SNP) that is associated with a water optimization trait, as well as the corresponding nucleotide position for the polymorphism in each amplicon.

TABLE 4

SEQ ID NOs. for Oligonucleotides that can be Employed to Amplify and/or Assay *Zea mays* Loci Corresponding to SEQ ID NOs: 1-117, 400, and 401

| Locus (SEQ ID NOs.) | Exemplary Amplification Primers (SEQ ID NOs) | SNP Position(s) In SEQ ID NO: 1-60 | Exemplary Assay Primers (SEQ ID Nos) |
|---|---|---|---|
| 1, 61 | 118 and 119 | 115 | |
| | | 270 | 232, 233 |
| | | 301 | |
| | | 483 | |
| 2, 62 | 120 and 121 | 100 | 348, 349 |
| | | 264-271 | 346, 347 |
| 3, 63 | 122 and 123 | 216 | 234, 235 |
| 4, 64 | 124 and 125 | 503 | 236, 237 |
| 5, 65 | 126 and 127 | 818-821 | 238, 239 |
| 6, 66 | 128 and 129 | 254 | 240, 241 |
| 7, 67 | 130 and 131 | 4497-4498 | 246, 247 |
| | | 4505 | |
| | | 4609 | |
| | | 4641 | 244, 245 |
| | | | 352, 353 |
| | | 4792 | 248, 249 |
| | | 4836 | 250, 251 |
| | | 4844 | |
| | | 4969 | |
| | | 4979-4981 | 242, 243 |
| | | | 350, 351 |
| 8, 68 | 132 and 133 | 217 | 252, 253 |
| | | 390 | |
| | | 477 | |

TABLE 4-continued

SEQ ID NOs. for Oligonucleotides that can be Employed to Amplify and/or Assay *Zea mays* Loci Corresponding to SEQ ID NOs: 1-117, 400, and 401

| Locus (SEQ ID NOs.) | Exemplary Amplification Primers (SEQ ID NOs) | SNP Position(s) In SEQ ID NO: 1-60 | Exemplary Assay Primers (SEQ ID Nos) |
|---|---|---|---|
| 9, 69 | 134 and 135 | 292 | 254, 255 |
| 10, 70 | 136 and 137 | 166 | 256, 257 |
| 11, 71 | 138 and 139 | 148 | 258, 259 |
| 12, 13, 72 | 140 and 141 | 94 (12) | 260, 261 |
| | | 35 (13) | 262, 263 |
| | | 86 (13) | 264, 265 |
| | | 89 (13) | 266, 267 |
| 14, 73 | 142 and 143 | 432 | 268, 269 |
| 15, 74 | 144 and 145 | 753 | 270, 271 |
| 16, 75 | 146 and 147 | 755 | 272, 273 |
| 17, 76 | 148 and 149 | 431 | 274, 275 |
| 18, 77 | 150 and 151 | 518 | 276, 277 |
| 19, 78 | 152 and 153 | 182 | 280, 281 |
| | | 309 | 282, 283 |
| | | | 356, 357 |
| | | 330 | |
| | | 463 | 278, 279 |
| | | | 354, 355 |
| 20, 79 | 154 and 155 | 773-776 | 284, 285 |
| 21, 80 | 156 and 157 | 61 | |
| | | 200 | |
| | | 316-324 | 286, 287 |
| 22, 81 | 158 and 159 | 211 | 288, 289 |
| 23, 82 | 160 and 161 | 116 | 360, 361 |
| | | 217 | 358, 359 |
| 24, 83 | 162 and 163 | 746 | 362, 363 |
| 25, 84 | 164 and 165 | 562 | 290, 291 |
| | | | 364, 365 |
| 26, 85 | 166 and 167 | 1271 | 366, 367 |
| 27, 86 | 168 and 169 | 64 | |
| | | 254 | 292, 293 |
| | | | 368, 369 |
| 28, 87 | 170 and 171 | 98 | |
| | | 147 | |
| | | 224 | |
| | | 496 | 294, 295 |
| 29, 88 | 172 and 173 | 258 | 370, 371 |
| 30, 89 | 174 and 175 | 259 | 298, 299 |
| | | 296 | |
| | | 398 | 296, 297 |
| | | 1057 | |
| 31, 90 | 176 and 177 | 239 | 300, 301 |
| 32, 91 | 178 and 179 | 208 | 302, 303 |
| 33, 92 | 180 and 181 | 391 | 372, 373 |
| 34, 93 | 182 and 183 | 144-145 | 304, 305 |
| | | 169 | 308, 309 |
| | | 537 | 306, 307 |
| 35, 94 | 184 and 185 | 76 | 310, 311 |
| 36, 95 | 186 and 187 | 500 | |
| | | 568 | |
| | | 698 | 312, 313 |
| 37, 96 | 188 and 189 | 375 | 316, 317 |
| | | 386 | 314, 315 |
| 38, 97 | 190 and 191 | 309 | 318, 319 |
| | | 342 | 320, 321 |
| 39, 98 | 192 and 193 | 445 | 322, 323 |
| 40, 99 | 194 and 195 | 602 | 324, 325 |
| 41, 100 | 196 and 197 | 190 | 326, 327 |
| | | 580 | 328, 329 |
| 42, 101 | 198 and 199 | 238 | |
| | | 266-268 | 330, 331 |
| | | 808 | |
| 43, 102 | 200 and 201 | 708 | 332, 333 |
| 44, 45, 103 | 202 and 203 | 266 (44) | 374, 375 |
| | | 475 (45) | 376, 377 |
| 46, 104 | 204 and 205 | 386 | 378, 379 |
| 47, 105 | 206 and 207 | 87 | 380, 381 |
| 48, 106 | 208 and 209 | 472 | 382, 383 |
| 49, 107 | 210 and 211 | 166 | |
| | | 24 | |
| | | 650 | 334, 335 |
| | | 892 | |
| 50, 51, 108 | 212 and 213 | 111 (51) | 384, 385 |
| | | 541 (50) | 336, 337 |
| 52, 109 | 214 and 215 | 442 | 338, 339 |
| 53, 110 | 216 and 217 | 83 | |
| | | 428 | 342, 343 |
| | | 491 | 340, 341 |
| | | 548 | |
| 54, 111 | 218 and 219 | 126 | 344, 345 |
| 55, 112 | 220 and 221 | 193 | 386, 387 |
| 56, 113 | 222 and 223 | 237 | 388, 389 |
| | | 516 | 390, 391 |
| 57, 114 | 224 and 225 | 173 | 392, 393 |
| 58, 115 | 226 and 227 | 486 | 394, 395 |
| 59, 116 | 228 and 229 | 729 | 396, 397 |
| 60, 117 | 230 and 231 | 267 | 398, 399 |
| 400, 401 | 402, 403; | 83 | 408, 409; |
| | 404, 405; | 119 | 410, 411; |
| | 406, 407 | 601 | 412, 413 |

As can be seen in Tables 3 and 4, certain of the sequences of SEQ ID NOs: 1-399 are related to each other. By way of example, SEQ ID NO: 1 is a nucleotide sequence from *Zea mays* that has been mapped to the *Zea mays* ZmIga4 locus on chromosome 8. A subsequence of SEQ ID NO: 1 can be amplified in an amplification reaction (e.g., a PCR reaction) using oligonucleotides having the sequences set forth in SEQ ID NOs: 118 and 119 to yield an amplicon. At position 270 of SEQ ID NO: 1 there is an SNP, and the specific nucleotide that is present in any nucleic acid sample at this position can be determined using oligonucleotides that have the sequences set forth in SEQ ID NOs: 232 and 233.

Additionally, GENBANK® Accession No. AC214546.3 includes a subsequence (i.e., nucleotides 79,631-80, 177; SEQ ID NO: 61) that itself is highly similar to SEQ ID NO: 1 (i.e., 538/552 nucleotides identical; 98%) and thus is present at the same locus from which SEQ ID NO: 1 is derived. The differences between the two sequences (which can be identified using a BLAST algorithm, a ClustalX algorithm, or any other appropriate method of analysis) can be attributable to normal variation within *Zea mays* populations. A subsequence of SEQ ID NO: 61 can also be amplified in an amplification reaction (e.g., a PCR reaction) using oligonucleotides having the sequences set forth in SEQ ID NOs: 118 and 119 to yield an amplicon. Oligonucleotides with the sequences set forth in SEQ ID NOs: 232 and 233 can also be used to assay the base that is present at the position that corresponds to position 270 of SEQ ID NO: 1.

For SEQ ID NOs: 2-399, similar interrelationships exist with SEQ ID NOs: as are described hereinabove, and would be identifiable by one of ordinary skill in the art using routine sequence analysis techniques. It is noted that with respect to certain of SEQ ID NOs: 1-60 and 400, the complete nucleotide sequence of a genomic clone that includes the full length sequence that corresponds to these sequences might not been yet been added to the GENBANK® database by The Maize Sequencing Consortium. Nonetheless, with the sequence information disclosed herein, one of ordinary skill in the art can unambiguously identify the *Zea mays* loci that correspond to SEQ ID NOs: 1-117.

DETAILED DESCRIPTION

The presently disclosed subject matter provides compositions and methods for identifying, selecting, and/or producing maize plants with enhanced drought tolerance (also referred to herein as water optimization), as well as maize plants identified, selected and/or produced by a method of this invention. In addition, the presently disclosed subject matter provides maize plants and/or germplasms having within their genomes one or more markers associated with enhanced drought tolerance.

To assess the value of alleles and/or haplotypes under drought stress, diverse germplasm was screened in controlled field-experiments comprising a full irrigation control treatment and a limited irrigation treatment. A goal of the full irrigation treatment was to ensure that water did not limit the productivity of the crop. In contrast, a goal of the limited irrigation treatment was to ensure that water became the major limiting constraint to grain yield. Main effects (e.g., treatment and genotype) and interactions (e.g., genotype× treatment) could be determined when the two treatments were applied adjacent to one another in the field. Moreover, drought related phenotypes could be quantified for each genotype in the panel thereby allowing for marker:trait associations to be conducted.

In practice, the method for the limited irrigation treatment can vary widely depending upon the germplasm being screened, the soil type, climatic conditions at the site, pre-season water supply, and in-season water supply, to name just a few. Initially, a site is identified where in-season precipitation is low (to minimize the chance of unintended water application) and is suitable for cropping. In addition, determining the timing of the stress can be important, such that a target is defined to ensure that year-to-year, or location-to-location, screening consistency is in place. An understanding of the treatment intensity, or in some cases the yield loss desired from the limited irrigation treatment, can also be considered. Selection of a treatment intensity that is too light can fail to reveal genotypic variation. Selection of a treatment intensity that is too heavy can create large experimental error. Once the timing of stress is identified and treatment intensity is described, irrigation can be managed in a manner that is consistent with these targets.

I. DEFINITIONS

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods. Accordingly, unless indicated to the contrary, the numerical parameters set forth in this specification and attached claims are approximations that can vary depending upon the desired properties sought to be obtained by the presently disclosed subject matter.

As used herein, the term "and/or" refers to and encompasses any and all possible combinations of one or more of the associated listed items, as well as the lack of combinations when interpreted in the alternative ("or").

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "anthesis silk interval" (ASI) refers to the difference between when a plant starts shedding pollen (anthesis) and when it begins producing silk (female). Data are collected on a per plot basis. In some embodiments, this interval is expressed in days.

As used herein, the phrase "associated with" refers to a recognizable and/or assayable relationship between two entities. For example, the phrase "associated with a water optimization trait" refers to a trait, locus, gene, allele, marker, phenotype, etc., or the expression thereof, the presence or absence of which can influence an extent, degree, and/or rate at which a plant or a part of interest thereof that has the water optimization trait grows. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced drought tolerance" refers to a marker whose presence or absence can be used to predict whether and/or to what extent a plant will display a drought tolerant phenotype.

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., Marker-assisted Selection in Backcross Breeding, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on. In some embodiments, a backcross is performed repeatedly, with a progeny individual of each successive backcross generation being itself backcrossed to the same parental genotype.

A centimorgan ("cM") is a unit of measure of recombination frequency. One cM is equal to a 1% chance that a marker at one genetic locus will be separated from a marker at a second locus due to crossing over in a single generation.

As used herein, the term "chromosome" is used in its art-recognized meaning of the self-replicating genetic structure in the cellular nucleus containing the cellular DNA and bearing in its nucleotide sequence the linear array of genes. The *Zea mays* chromosome numbers disclosed herein refer to those as set forth in Perin et al., 2002, which relates to a reference nomenclature system adopted by L'institut National da la Recherché Agronomique (INRA; Paris, France).

As used herein, the phrase "consensus sequence" refers to a sequence of DNA built to identify nucleotide differences (e.g., SNP and Indel polymorphisms) in alleles at a locus. A consensus sequence can be either strand of DNA at the locus and states the nucleotide(s) at one or more positions (e.g., at one or more SNPs and/or at one or more Indels) in the locus. In some embodiments, a consensus sequence is used to design oligonucleotides and probes for detecting polymorphisms in the locus.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, the presently disclosed subject matter relates in some embodiments to introgressing favorable alleles and/or haplotypes into maize plants. One locus that comprises certain favorable alleles and/or haplotypes is represented by SEQ ID NO: 7, which includes nine (9) different polymorphisms as set forth herein, with nine different favorable alelles. For any given introgression effort with respect to the genetic locus corresponding to SEQ ID NO: 7, the method can "consist essentially of" introgressing a particular favorable allele selected from among these nine polymorphic locations, which means that the recited favorable allele is the only favorable allele introgressed into a progeny genome. It is noted, however, that additional polymorphic loci will also be introgressed into the genome, although the effects thereof might be unknown or not of interest.

With respect to the terms "comprising", "consisting essentially of", and "consisting of", where one of these three terms is used herein, the presently disclosed and claimed subject matter can include the use of either of the other two terms. For example, the presently disclosed subject matter relates in some embodiments to oligonucleotide primers comprise any of SEQ ID NOs: 118-399 and 402-413. It is understood that the presently disclosed subject matter thus also encompasses oligonucleotide primers that in some embodiments consist essentially of any of SEQ ID NOs: 118-399 and 402-113, as well as oligonucleotide primers that in some embodiments consist of any of SEQ ID NOs: 118-399 and 402-113. Similarly, it is also understood that in some embodiments the methods of the presently disclosed subject matter comprise the steps that are disclosed herein, in some embodiments the methods of the presently disclosed subject matter consist essentially of the steps that are disclosed, and in some embodiments the methods of the presently disclosed subject matter consist of the steps that are disclosed herein.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "desired allele" and "allele of interest" are used interchangeably to refer to an allele associated with a desired trait. In some embodiments, a "desired allele" and/or "allele of interest" can be associated with either an increase or a decrease of or in a given trait, depending on the nature of the desired phenotype. In some embodiments, a "desired allele" and/or "allele of interest" can be associated with a change in morphology, color, etc.

As used herein, the terms "drought tolerance" and "drought tolerant" refer to a plant's ability to endure and/or thrive under drought stress conditions. When used in reference to germplasm, the terms refer to the ability of a plant that arises from that germplasm to endure and/or thrive under drought conditions. In general, a plant or germplasm is labeled as "drought tolerant" if it displays "enhanced drought tolerance."

As used herein, the term "enhanced drought tolerance" refers to an improvement, enhancement, or increase in one or more water optimization phenotypes as compared to one or more control plants (e.g., one or both of the parents, or a plant lacking a marker associated with enhanced drought tolerance). Exemplary water optimization phenotypes include, but are not limited to, grain yield at standard moisture percentage (YGSMN), grain moisture at harvest (GMSTP), grain weight per plot (GWTPN), percent yield recovery (PYREC), yield reduction (YRED), anthesis silk interval (ASI) and percent barren (PB). Thus, a plant that demonstrates higher YGSMN than one or both of its parents when each is grown under drought stress conditions displays enhanced drought tolerance and can be labeled as "drought tolerant."

As used herein, the terms "elite" and "elite line" refer to any line that is substantially homozygous and has resulted from breeding and selection for desirable agronomic performance.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the phrase "genetic marker" refers to a nucleic acid sequence (e.g., a polymorphic nucleic acid sequence) that has been identified as associated with a locus or allele of interest and that is indicative of the presence or absence of the locus or allele of interest in a cell or organism. Examples of genetic markers include, but are not limited to genes, DNA or RNA-derived sequences, promoters, any untranslated regions of a gene, microRNAs, siRNAs, QTLs, transgenes, mRNAs, ds RNAs, transcriptional profiles, and methylation patterns.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) and/or haplotype(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants can be grown, as well as plant parts, such as leafs, stems, pollen, or cells that can be cultured into a whole plant.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

A "heterotic group" comprises a set of genotypes that perform well when crossed with genotypes from a different heterotic group. Hallauer et al., *Corn breeding*, in CORN AND CORN IMPROVEMENT p. 463-564 (1998). Inbred lines are classified into heterotic groups, and are further subdivided into families within a heterotic group, based on several criteria such as pedigree, molecular marker-based associations, and performance in hybrid combinations. Smith et al., *Theor. Appl. Gen.* 80:833 (1990).

As used herein, the term "heterozygous" refers to a genetic status wherein different alleles reside at corresponding loci on homologous chromosomes. As used herein, the term "homozygous" refers to a genetic status wherein identical alleles reside at corresponding loci on homologous chromosomes. It is noted that both of these terms can refer to single nucleotide positions, multiple nucleotide positions, whether contiguous or not, or entire loci on homologous chromosomes.

As used herein, the term "hybrid" refers to a seed and/or plant produced when at least two genetically dissimilar parents are crossed.

As used herein, the term "hybrid" when used in the context of nucleic acids, refers to a double-stranded nucleic acid molecule, or duplex, formed by hydrogen bonding between complementary nucleotide bases. The terms "hybridize" and "anneal" refer to the process by which single strands of nucleic acid sequences form double-helical segments through hydrogen bonding between complementary bases.

As used herein, the phrase "ILLUMINA® GOLDENGATE® Assay" refers to a high throughput genotyping assay sold by Illumina Inc. of San Diego, Calif., United States of America that can generate SNP-specific PCR products. This assay is described in detail at the website of Illumina Inc. and in Fan et al., 2006.

As used herein, the phrase "immediately adjacent", when used to describe a nucleic acid molecule that hybridizes to DNA containing a polymorphism, refers to a nucleic acid that hybridizes to a DNA sequence that directly abuts the polymorphic nucleotide base position. For example, a nucleic acid molecule that can be used in a single base extension assay is "immediately adjacent" to the polymorphism.

As used herein, the term "improved", and grammatical variants thereof, refers to a plant or a part, progeny, or tissue culture thereof, that as a consequence of having (or lacking) a particular water optimization associated allele (such as, but not limited to those water optimization associated alleles disclosed herein) is characterized by a higher or lower content of a water optimization associated trait, depending on whether the higher or lower content is desired for a particular purpose.

As used herein, the term "inbred" refers to a substantially homozygous plant or variety. The term can refer to a plant or variety that is substantially homozygous throughout the entire genome or that is substantially homozygous with respect to a portion of the genome that is of particular interest.

As used herein, the term "INDEL" (also spelled "indel") refers to an insertion or deletion in a pair of nucleotide sequences, wherein a first sequence can be referred to as having an insertion relative to a second sequence or the second sequence can be referred to as having a deletion relative to the first sequence.

As used herein, the term "informative fragment" refers to a nucleotide sequence comprising a fragment of a larger nucleotide sequence, wherein the fragment allows for the identification of one or more alleles within the larger nucleotide sequence. For example, an informative fragment of the nucleotide sequence of SEQ ID NO: 1 comprises a fragment of the nucleotide sequence of SEQ ID NO: 1 and allows for the identification of one or more alleles (e.g., a G nucleotide at position 115 of SEQ ID NO: 1, an A nucleotide at the position that corresponds to position 270 of SEQ ID NO: 1, a T nucleotide at the position that corresponds to position 301 of SEQ ID NO: 1, and/or an A nucleotide at the position that corresponds to position 483).

As used herein, the phrase "interrogation position" refers to a physical position on a solid support that can be queried to obtain genotyping data for one or more predetermined genomic polymorphisms.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced drought tolerance can be introgressed from a donor into a recurrent parent that is not drought tolerant or only partially drought tolerant. The resulting offspring could then be repeatedly backcrossed and selected until the progeny possess the drought tolerance allele in the recurrent parent background.

As used herein, the term "isolated" refers to a nucleotide sequence (e.g., a genetic marker) that is free of sequences that normally flank one or both sides of the nucleotide sequence in a plant genome. As such, the phrase "isolated and purified genetic marker associated with a water optimization trait in *Zea mays*" can be, for example, a recombinant DNA molecule, provided one of the nucleic acid sequences normally found flanking that recombinant DNA molecule in a naturally-occurring genome is removed or absent. Thus, isolated nucleic acids include, without limitation, a recombinant DNA that exists as a separate molecule (including, but not limited to genomic DNA fragments produced by PCR or restriction endonuclease treatment) with no flanking sequences present, as well as a recombinant DNA that is incorporated into a vector, an autonomously replicating plasmid, or into the genomic DNA of a plant as part of a hybrid or fusion nucleic acid molecule.

As used herein, the term "linkage" refers to a phenomenon wherein alleles on the same chromosome tend to be transmitted together more often than expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1 of the time.

As such, "linkage" typically implies and can also refer to physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a yield locus of the presently disclosed subject matter is linked to a marker (e.g., a genetic marker) if it is in some embodiments within 20, 15, 12, 10, 9, 8, 7, 6, 5, 4, 3, 2, or 1 cM of the marker.

Thus, the term "linkage" refers to the degree with which one marker locus is associated with another marker locus or some other locus (for example, a drought tolerance locus). The linkage relationship between a molecular marker and a phenotype can be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

In some embodiments of the presently disclosed subject matter, it is advantageous to define a bracketed range of linkage, for example, from about 10 cM and about 20 cM, from about 10 cM and about 30 cM, or from about 10 cM and about 40 cM. The more closely a marker is linked to a second locus, the better an indicator for the second locus that marker becomes. Thus, "closely linked loci" such as a marker locus and a second locus display an inter-locus recombination frequency of about 10%, 9%, 8%, 7%, 6%, 5%, 4%, 3%, or 2% or less. In some embodiments, the relevant loci display a recombination frequency of about 1% or less, e.g., about 0.75%, 0.5%, 0.25% or less. Two loci that are localized to the same chromosome, and at such a distance that recombination between the two loci occurs at a frequency of less than about 10% (e.g., about 9%, 8%, 7%, 6%, 5%, 4%, 3%, 2%, 1%, 0.75%, 0.5%, or 0.25%, or less) can also be said to be "proximal to" each other. Since one cM is the distance between two markers that show a 1% recombination frequency, any marker is closely linked (genetically and physically) to any other marker that is in close proximity, e.g., at or less than about 10 cM distant. Two closely linked markers on the same chromosome can be positioned about 9, 8, 7, 6, 5, 4, 3, 2, 1, 0.75, 0.5 or 0.25 cM or less from each other.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., drought tolerance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome). As such, the phrase "linkage disequilibrium" is defined as change from the expected relative frequency of gamete types in a population of many individuals in a single generation such that two or more loci act as genetically linked loci. If the frequency in a population of allele S is x, s is x', B is y, and b is y', then the expected frequency of genotype SB is xy, that of Sb is xy', that of sB is x'y, and that of sb is x'y', and any deviation from these frequencies is an example of disequilibrium.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region of (i.e., less than the entirety) of a given chromosome.

A "locus" is a position on a chromosome where a gene or marker or allele is located. In some embodiments, a locus can encompass one or more nucleotides.

As used herein, the term "maize" refers to a plant of the Zea mays L. ssp. mays and is also known as "corn."

As used herein, the term "maize plant" includes whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

As used herein, the terms "marker", "genetic marker", and "molecular marker" are used interchangeably to refer to an identifiable position on a chromosome the inheritance of which can be monitored and/or a reagent that is used in methods for visualizing differences in nucleic acid sequences present at such identifiable positions on chromosomes. Thus, in some embodiments a marker comprises a known or detectable nucleic acid sequence. Examples of markers include, but are not limited to genetic markers, protein composition, peptide levels, protein levels, oil composition, oil levels, carbohydrate composition, carbohydrate levels, fatty acid composition, fatty acid levels, amino acid composition, amino acid levels, biopolymers, starch composition, starch levels, fermentable starch, fermentation yield, fermentation efficiency (e.g., captured as digestibility at 24, 48, and/or 72 hours), energy yield, secondary compounds, metabolites, morphological characteristics, and agronomic characteristics. As such, a marker can comprise a nucleotide sequence that has been associated with an allele or alleles of interest and that is indicative of the presence or absence of the allele or alleles of interest in a cell or organism and/or to a reagent that is used to visualize differences in the nucleotide sequence at such an identifiable position or positions. A marker can be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234:177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)) or an RNA cleavage product (such as a Lynx tag). A marker can be present in genomic or expressed nucleic acids (e.g., ESTs). The term marker can also refer to nucleic acids used as probes or primers (e.g., primer pairs) for use in amplifying, hybridizing to and/or detecting nucleic acid molecules according to methods well known in the art. A large number of maize molecular markers are known in the art, and are published or available from various sources, such as the Maize GDB internet resource and the Arizona Genomics Institute internet resource run by the University of Arizona.

In some embodiments, a marker corresponds to an amplification product generated by amplifying a *Zea mays* nucleic acid with one or more oligonucleotides, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself and/or naturally occurring and/or artificial alleleic differences) as an amplification product that is generated by amplifying *Zea mays* genomic DNA with a particular set of oligonucleotides. In some embodiments, the amplifying is by PCR, and the oligonucleotides are PCR primers that are designed to hybridize to opposite strands of the *Zea mays* genomic DNA in order to amplify a *Zea mays* genomic DNA sequence present between the sequences to which the PCR primers hybridize in the *Zea mays* genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the *Zea mays* genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand of the genomic fragment—the reverse-complement of the reverse primer. Accordingly, a marker that "corresponds to" an amplified fragment is a marker that has the same sequence of one of the strands of the amplified fragment.

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele," also described as an "allele of a marker locus," can refer to one of a plurality of polymorphic nucleotide sequences found at a marker locus in a population that is polymorphic for the marker locus.

As used herein, the phrase "marker assay" refers to a method for detecting a polymorphism at a particular locus using a particular method such as but not limited to measurement of at least one phenotype (such as seed color, oil content, or a visually detectable trait); nucleic acid-based assays including, but not limited to restriction fragment length polymorphism (RFLP), single base extension, electrophoresis, sequence alignment, allelic specific oligonucleotide hybridization (ASO), random amplified polymorphic DNA (RAPD), microarray-based technologies, TAQMAN® Assays, ILLUMINA® GOLDENGATE® Assay analysis, nucleic acid sequencing technologies; peptide and/or polypeptide analyses; or any other technique that can be employed to detect a polymorphism in an organism at a locus of interest.

"Marker-assisted selection" (MAS) is a process by which phenotypes are selected based on marker genotypes.

"Marker-assisted counter-selection" is a process by which marker genotypes are used to identify plants that will not be selected, allowing them to be removed from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides can be used for nucleic acid hybridization. Alternatively, in some aspects, a marker probe refers to a probe of any type that is able to distinguish (i.e., genotype) the particular allele that is present at a marker locus.

As used herein, the term "molecular marker" can be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein are also referred to as hybridization markers when located on an indel region. This is because the insertion region is, by definition, a polymorphism vis-à-vis a plant without the insertion. Thus, the marker need only indicate whether the indel region is present or absent. Any suitable marker detection technology can be used to identify such a hybridization marker, e.g., SNP technology is used in the examples provided herein.

The presently disclosed subject matter provides in some embodiments markers for determining the presence of genetic polymorphisms in the maize loci disclosed herein. The loci that can be analyzed using the compositions and methods of the presently disclosed subject matter include, but are not limited to the loci referred to herein as "ZmAdh1-1s", "ZmBglcn", "ZmCat1", "ZmDhn1", "ZmDhn2", "ZmDr1", "ZmDr2", "ZmDr3", "ZmDr3", "ZmDr4", "ZmDr5", "ZmDr6", "ZmDr7", "ZmDr8", "ZmDr9", "ZmDr10", "ZmDr12", "ZmDr16", "ZmDr17" "ZmH2B1", "ZmHsp70", "ZmIga4", "ZmLOC100276591", "ZmMa3", "ZmPK4", "ZmRIC1", "ZmZCN6", "Zpu1", "ZmDrA", "ZmDrB", "ZmDrC", "ZmDrD", "ZmDrE", "ZmDrF", "ZmDrG", "ZmDrH", "ZmDrI", "ZmDrj", "ZmDrk", "ZmDrL", and "ZmDrM", which terms thus refer to genomic regions and/or genetic loci that are linked to water optimization associated traits present on Zea mays chromosomes and as described in more detail hereinbelow. Exemplary genomic nucleotide sequences that are derived from these loci are summarized herein above.

The term "ZmAdh1-1s" refers to a locus on Zea mays chromosome 1 that encodes a alcohol dehydrogenase 1 gene (Dennis et al., 1984). Exemplary gene products derived from the ZmAdh1-1s locus can be found in GENBANK® Accession Nos. X04049 and P00333.

The term "ZmBglcn" refers to a locus on Zea mays chromosome 3 that encodes a maize 1,3-β-glucanase polypeptide (Wu et al., 1994). Exemplary gene products derived from the ZmBglcn locus can be found in GENBANK® Accession Nos. M95407 and AAA74320.

The term "ZmCat1" refers to a locus on Zea mays chromosome 5 that encodes a maize catalyst 1 polypeptide (Guan & Scandalios, 1993). Exemplary gene products derived from the ZmCat1 locus can be found in GENBANK® Accession Nos. X60135 and CAA42720.

The term "ZmDhn1" refers to a locus on Zea mays chromosome 6 that encodes a maize dehydrin-1 (dhn1) polypeptide (Close et al., 1989). Exemplary gene products derived from the ZmDhn1 locus can be found in GENBANK® Accession Nos. X15290 and CAA33364.

The term "ZmDhn2" refers to a locus on Zea mays chromosome 4 that encodes a maize dehydrin-2 (dhn2) polypeptide. Exemplary gene products derived from the ZmDhn2 locus can be found in GENBANK® Accession Nos. L35913 and AA33480.

The term "ZmDr1" refers to a Zea mays locus that in some embodiments corresponds to GENBANK® Accession No. AY105200.

The term "ZmDr2" refers to a Zea mays locus that in some embodiments corresponds to GENBANK® Accession No. AF043347.

The term "ZmDr3" refers to a Zea mays locus that in some embodiments corresponds to nucleotides 120,959-121,302 of GENBANK® Accession No. AC206638.3 and in some embodiments corresponds to GENBANK® Accession No. AF043347.

The term "ZmDr4" refers to a Zea mays locus that in some embodiments corresponds to GENBANK® Accession No. AY103545.

The term "ZmDr5" refers to a *Zea mays* locus that in some embodiments corresponds to GENBANK® Accession No. AY109606.

The term "ZmDr6" refers to a *Zea mays* locus that encodes a maize calmodulin-binding protein. Exemplary gene products derived from the ZmDr6 locus can be found in GENBANK® Accession Nos. L01497, NM_001158968, AAA33447, and NP_001152440.

The term "ZmDr7" refers to a *Zea mays* locus that encodes a maize sucrose transporter protein. Exemplary gene products derived from the ZmDr7 locus can be found in GENBANK® Accession Nos. AB008464, NM_001111370, BAA83501, and NP_001104840.

The term "ZmDr8" refers to a *Zea mays* locus that in some embodiments corresponds to GENBANK® Accession No. EU976286.

The term "ZmDr9" refers to a *Zea mays* locus that in some embodiments corresponds to nucleotides 75,481-76,499 of GENBANK® Accession No. AC196196.4.

The term "ZmDr10" refers to a *Zea mays* locus that in some embodiments corresponds to GENBANK® Accession No. DQ245017.

The term "ZmDr12" refers to a *Zea mays* locus that in some embodiments corresponds to GENBANK® Accession No. AI770817.

The term "ZmDr16" refers to a *Zea mays* locus that in some embodiments corresponds to GENBANK® Accession No. NM_001156978.

The term "ZmDr17" refers to a *Zea mays* locus that in some embodiments corresponds to nucleotides 60,463-60,838 of GENBANK® Accession No. AC231410.4.

The term "ZmDrA" refers to a locus on *Zea mays* chromosome 7 that encodes a voltage-dependent anion channel protein. An exemplary gene product derived from the ZmDrA locus can be found in GENBANK® Accession No. BT018647.

The term "ZmDrB" refers to a *Zea mays* locus that encodes a xylan endohydrolase protein. An exemplary gene product derived from the ZmDrB locus can be found in GENBANK® Accession No. AI691894.

The term "ZmDrC" refers to a *Zea mays* locus that encodes a trehalose-P-synthase protein. An exemplary gene product derived from the ZmDrC locus can be found in GENBANK® Accession No. AY110270.

The term "ZmDrD" refers to a locus on *Zea mays* chromosome 5 that encodes a subtilisin-chymotrypsin inhibitor 2 protein. An exemplary gene product derived from the ZmDrD locus can be found in GENBANK® Accession No. BT066886.

The term "ZmDrE" refers to a locus on *Zea mays* chromosome 8 that encodes a legumin-like protein (cl2-1) protein. Exemplary gene products derived from the ZmDrE locus can be found in GENBANK® Accession Nos. NM_001111592 and NP_001105062.

The term "ZmDrF" refers to a locus on *Zea mays* chromosome 9 that encodes a putative cellulose synthase protein. Exemplary gene products derived from the ZmDrF locus can be found in GENBANK® Accession Nos. BT067558 and ACN34455.

The term "ZmDrG" refers to a locus on *Zea mays* chromosome 5 that in some embodiments corresponds to GENBANK® Accession No. AI691276.

The term "ZmDrH" refers to a locus on *Zea mays* chromosome 5 that in some embodiments corresponds to GENBANK® Accession No. AI665888.

The term "ZmDrI" refers to a locus on *Zea mays* chromosome 3 that in some embodiments corresponds to GENBANK® Accession No. AI737958.

The term "ZmDrJ" refers to a locus on *Zea mays* chromosome 5 that encodes a mcm5 DNA replication factor protein. An exemplary gene products derived from the ZmDrJ locus can be found in GENBANK® Accession No. AI666237.

The term "ZmDrK" refers to a *Zea mays* locus that encodes an inorganic phosphatase protein that in some embodiments corresponds to nucleotides 28,345-29,279 of GENBANK® Accession No. AC191554.3.

The term "ZmDrL" refers to a locus on *Zea mays* chromosome 9 that encodes a late embryonic abundant-like protein protein. An exemplary gene product derived from the ZmDrL locus can be found in GENBANK® Accession No. AY105938.

The term "ZmDrM" refers to a locus on *Zea mays* chromosome 7 that encodes a hexose transporter protein. Exemplary gene products derived from the ZmDrM locus can be found in GENBANK® Accession Nos. NM_001154535 and NP_001148007.

The term "ZmH2B1" refers to a locus on *Zea mays* chromosome 4 that encodes a *Zea mays* histone 2B1. An exemplary gene product derived from the ZmDr6 locus can be found in GENBANK® Accession No. AI737900.

The term "ZmHsp70" refers to a locus on *Zea mays* chromosome 1 that encodes a maize heat shock cognate 70 kDa protein 2 protein. Exemplary gene products derived from the ZmDr7 locus can be found in GENBANK® Accession Nos. EU971059, NM_001154726, and NP_001148198.

The term "ZmIga4" refers to a locus on *Zea mays* chromosome 8 that encodes a liguleless4 (lg4) protein. Exemplary gene products derived from the ZmIga4 locus can be found in GENBANK® Accession Nos. AF457121, NM_001111614, AAM27190, and NP_001105084.

The term "ZmLOC100276591" refers to a locus that in some embodiments corresponds to GENBANK® Accession Nos. NM_001150343 and NP_001143815.

The term "ZmMa3" refers to a locus on *Zea mays* chromosome 2 that encodes a maize topoisomerase-like apoptosis protein ma-3. Exemplary gene products derived from the ZmMa3 locus can be found in GENBANK® Accession Nos. NM_001154442 and NP_001147914.

The term "ZmPK4" refers to a locus on *Zea mays* chromosome 8 that encodes a maize protein kinase PK4 protein. Exemplary gene products derived from the ZmPK4 locus can be found in GENBANK® Accession Nos. AF141378, NM_001111470, AAF22219, and NP_001104940.

The term "ZmRIC1" refers to a locus on *Zea mays* chromosome 8 that encodes a maize ras-related protein RIC1. Exemplary gene products derived from the ZmRIC1 locus can be found in GENBANK® Accession Nos. EU952511, NM_001137272, ACG24629, and NP_001130744.

The term "ZmZCN6" refers to a locus on *Zea mays* chromosome 4 that encodes a maize ZCN6 protein. Exemplary gene products derived from the ZmZCN6 locus can be found in GENBANK® Accession Nos. EU241897, NM_001112774, ABX11008, and NP_001106245.

The term "Zpu1" refers to a locus on *Zea mays* chromosome 2 that encodes a pullulanase-type starch debranching enzyme (zpu1) protein. Exemplary gene products derived from the Zpu1 locus can be found in GENBANK® Accession Nos. AF080567, NM_001111450, AAD11599, and NP_001104920.

As used herein, the phrase "native trait" refers to any existing monogenic or oligogenic trait in a certain crop's germplasm. When identified through molecular marker(s), the information obtained can be used for the improvement of germplasm through marker assisted breeding of the water optimization associated traits disclosed herein.

A "non-naturally occurring variety of maize" is any variety of maize that does not naturally exist in nature. A "non-naturally occurring variety of maize" can be produced by any method known in the art, including, but not limited to, transforming a maize plant or germplasm, transfecting a maize plant or germplasm and crossing a naturally occurring variety of maize with a non-naturally occurring variety of maize. In some embodiments, a "non-naturally occurring variety of maize" can comprise one or more heterologous nucleotide sequences. In some embodiments, a "non-naturally occurring variety of maize" can comprise one or more non-naturally occurring copies of a naturally occurring nucleotide sequence (i.e., extraneous copies of a gene that naturally occurs in maize).

The "non-Stiff Stalk" heterotic group represents a major heterotic group in the northern U.S. and Canadian corn growing regions. It can also be referred to as the "Lancaster" or "Lancaster Sure Crop" heterotic group.

As used herein, the terms "nucleotide sequence," "polynucleotide," "nucleic acid sequence," "nucleic acid molecule" and "nucleic acid fragment" refer to a polymer of RNA or DNA that is single- or double-stranded, optionally containing synthetic, non-natural and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. The percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW programs, both available on the internet. Other suitable programs include, but are not limited to, GAP, BestFit, Plot Similarity, and FASTA, which are part of the Accelrys GCG Package available from Accelrys, Inc. of San Diego, Calif., United States of America. In some embodiments, a percentage of sequence identity refers to sequence identity over the full length of one of the sequences being compared. In some embodiments, a calculation to determine a percentage of sequence identity does not include in the calculation any nucleotide positions in which either of the compared nucleic acids includes an "N" (i.e., where any nucleotide could be present at that position).

As used herein, the term "percent barren" (PB) refers to the percentage of plants in a given area (e.g., plot) with no grain. It is typically expressed in terms of the percentage of plants per plot and can be calculated as:

$$\frac{\text{number of plants in the plot with no grain}}{\text{total numbers of plants in the plot}} \times 100$$

As used herein, the term "percent yield recovery" (PYREC) refers to the effect an allele and/or combination of alleles has on the yield of a plant grown under drought stress conditions as compared to that of a plant that is genetically identical except insofar as it lacks the allele and/or combination of alleles. PYREC is calculated as:

$$1 - \frac{\text{yield under full irrigation}(w/\text{allele}(s) \text{ of interest}) -}{\text{yield under drought conditions}(w/\text{allele}(s) \text{ of interest})} \times 100$$
$$\frac{}{\text{yield under full irrigation}(w/\text{out allele}(s) \text{ of interest}) -}$$
$$\text{yield under drought conditions}(w/\text{out allele}(s) \text{ of interest})$$

By way of example and not limitation, if a control plant yields 200 bushels under full irrigation conditions, but yields only 100 bushels under drought stress conditions, then its percentage yield loss would be calculated at 50%. If an otherwise genetically identical hybrid that contains the allele(s) of interest yields 125 bushels under drought stress conditions and 200 bushels under full irrigation conditions, then the percentage yield loss would be calculated as 37.5% and the PYREC would be calculated as 25% [1.00−(200−125)/(200−100)× 100)].

As used herein, the phrase "Grain Yield—Well Watered" refers to yield from an area that obtained enough irrigation to prevent plants from being water stressed during their growth cycle. In some embodiments, this trait is expressed in bushels per acre.

As used herein, the phrase "Yield Reduction—Hybrid" refers to a calculated trait obtained from a hybrid yield trial grown under stress and non-stress conditions. For a given hybrid, it equals:

$$\frac{\text{non-stress yield} - \text{yield under stress}}{\text{non-stressed yield}} \times 100.$$

In some embodiments, this trait is expressed as percent bushels per acre.

As used herein, the phrase "Yield Reduction—Inbred" refers to a calculated trait obtained from an inbred yield trial grown under stress and non-stress conditions. For a given inbred, it equals:

$$\frac{\text{non-stress yield} - \text{yield under stress}}{\text{non-stressed yield}} \times 100.$$

In some embodiments, this trait is expressed as percent bushels per acre.

As used herein, the phrase "Anthesis Silk Interval" (ASI) refers to the difference (in some embodiments, expressed in days) between when a plant starts shedding pollen (anthesis) and it starts producing silk (female). Data are collected on a per plot basis for anthesis and silking and the difference is calculated.

As used herein, the phrase "Percent Barren" refers to a percentage of plants in a given area (plot) with no grain. It is typically expressed in terms of plants per plot and can be calculated as:

$$\frac{\text{Number of plant with no grain in a plot}}{\text{Total number of plants in the plot}} \times 100.$$

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes. It is noted that, as used herein, the term "water optimization phenotype" takes into account environmental conditions that might affect water optimization such that the water optimization effect is real and reproducible.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "population" refers to a genetically heterogeneous collection of plants sharing a common genetic derivation.

As used herein, the term "primer" refers to an oligonucleotide which is capable of annealing to a nucleic acid target (in some embodiments, annealing specifically to a nucleic acid target) allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, a plurality of primers are employed to amplify Zea mays nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from a vegetative or sexual reproduction from one or more parent plants. A progeny plant can be obtained by cloning or selfing a single parent plant, or by crossing two parental plants. Thus, the phrase "progeny plant" refers to any plant resulting as progeny from a vegetative or sexual reproduction from one or more parent plants or descendants thereof. For instance, a progeny plant can be obtained by cloning or selfing of a parent plant or by crossing two parental plants and include selfings as well as the F1 or F2 or still further generations. An F1 is a first-generation progeny produced from parents at least one of which is used for the first time as donor of a trait, while progeny of second generation (F2) or subsequent generations (F3, F4, and the like) are specimens produced from selfings, intercrosses, backcrosses, or other crosses of F1 s, F2s, and the like. An F1 can thus be (and in some embodiments is) a hybrid resulting from a cross between two true breeding parents (i.e., parents that are true-breeding are each homozygous for a trait of interest or an allele thereof), while an F2 can be (and in some embodiments is) a progeny resulting from self-pollination of the F1 hybrids.

As used herein, the phrase "quantitative trait locus" (QTL; quantitative trait loci—QTLs) refers to a genetic locus (or loci) that control to some degree a numerically representable trait that, in some embodiments, is continuously distributed. In some embodiments, a QTL comprises a water optimization associated locus. As used herein, the phrase "water optimization associated locus" is used herein to refer to a chromosomal region containing alleles (e.g., in the form of genes or regulatory sequences) associated with the expression of a water optimization associated trait. Thus, a locus "associated with" a water optimization trait refers to one or more regions located on one or more chromosomes that includes at least one gene the expression of which influences water optimization and/or at least one regulatory region that controls the expression of one or more genes involved in one or more water optimization traits. The loci can be defined by indicating their genetic location in the genome of a given Zea mays plant using one or more molecular genomic markers. One or more markers, in turn, indicate a specific locus. Distances between loci are usually measured by the frequency of crossovers between loci on the same chromosome. The farther apart two loci are, the more likely that a crossover will occur between them. Conversely, if two loci are close together, a crossover is less likely to occur between them. Typically, one centiMorgan (cM) is equal to 1 recombination between loci. When a QTL can be indicated by multiple markers, the genetic distance between the end-point markers is indicative of the size of the QTL.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer to a meiotic crossover.

As used herein, the term "reference sequence" refers to a defined nucleotide sequence used as a basis for nucleotide sequence comparison. The reference sequence for a marker, for example, is obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence can not be a copy of an actual nucleic acid sequence from any particular organism; however, it is useful for designing primers and probes for actual polymorphisms in the locus or loci.

As used herein, the term "regenerate", and grammatical variants thereof, refers to the production of a plant from tissue culture.

As used herein, the phrases "selected allele", "desired allele", and "allele of interest" are used interchangeably to refer to a nucleic acid sequence that includes a polymorphic allele associated with a desired trait. It is noted that a "selected allele", "desired allele", and/or "allele of interest" can be associated with either an increase in a desired trait or a decrease in a desired trait, depending on the nature of the phenotype sought to be generated in an introgressed plant.

As used herein, the phrase "single nucleotide polymorphism", or "SNP", refers to a polymorphism that constitutes a single base pair difference between two nucleotide sequences. As used herein, the term "SNP" also refers to differences between two nucleotide sequences that result from simple alterations of one sequence in view of the other that occurs at a single site in the sequence. For example, the term "SNP" is intended to refer not just to sequences that differ in a single nucleotide as a result of a nucleic acid substitution in one versus the other, but is also intended to refer to sequences that differ in 1, 2, 3, or more nucleotides as a result of a deletion of 1, 2, 3, or more nucleotides at a single site in one of the sequences versus the other. It would be understood that in the case of two sequences that differ from each other only by virtue of a deletion of 1, 2, 3, or more nucleotides at a single site in one of the sequences versus the other, this same scenario can be considered an addition of 1, 2, 3, or more nucleotides at a single site in one of the sequences versus the other, depending on which of the two sequences is considered the reference sequence. Single site insertions and/or deletions are thus also considered to be encompassed by the term "SNP".

The "Stiff Stalk" heterotic group represents a major heterotic group in the northern U.S. and Canadian corn growing regions. It can also be referred to as the "Iowa Stiff Stalk Synthetic" or "BSSS" heterotic group.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Tijssen, 1993. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2× SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the phrase "TAQMAN® Assay" refers to real-time sequence detection using PCR based on the TAQMAN® Assay sold by Applied Biosystems, Inc. of Foster City, Calif., United States of America. For an identified marker, a TAQMAN® Assay can be developed for application in a breeding program.

As used herein, the term "tester" refers to a line used in a testcross with one or more other lines wherein the tester and the line(s) tested are genetically dissimilar. A tester can be an isogenic line to the crossed line.

As used herein, the term "trait" refers to a phenotype of interest, a gene that contributes to a phenotype of interest, as well as a nucleic acid sequence associated with a gene that contributes to a phenotype of interest. For example, a "water optimization trait" refers to a water optimization phenotype as well as a gene that contributes to a water optimization phenotype and a nucleic acid sequence (e.g., an SNP or other marker) that is associated with a water optimization phenotype.

As used herein, the term "transgene" refers to a nucleic acid molecule introduced into an organism or its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

An "unfavorable allele" of a marker is a marker allele that segregates with the unfavorable plant phenotype, therefore providing the benefit of identifying plants that can be removed from a breeding program or planting.

As used herein, the term "water optimization" refers to any measure of a plant, its parts, or its structure that can be measured and/or quantitated in order to assess an extent of or a rate of plant growth and development under conditions of sufficient water availability as compared to conditions of suboptimal water availability (e.g., drought). As such, a "water optimization trait" is any trait that can be shown to influence yield in a plant under different sets of growth conditions related to water availability.

Similarly, "water optimization" can be considered a "phenotype", which as used herein refers to a detectable, observable, and/or measurable characteristic of a cell or organism. In some embodiments, a phenotype is based at least in part on the genetic make up of the cell or the organism (referred to herein as the cell or the organism's "genotype"). Exemplary water optimization phenotypes are grain yield at standard moisture percentage (YGSMN), grain moisture at harvest (GMSTP), grain weight per plot (GWTPN), and percent yield recovery (PYREC). It is noted that as used herein, the term "phenotype" takes into account how the environment (e.g., environmental conditions) might affect water optimization such that the water optimization effect is real and reproducible. As used herein, the term "yield reduction" (YD) refers to the degree to which yield is reduced in plants grown under stress conditions. YD is calculated as:

$$\frac{\text{yield under non-stress conditions} - \text{yield under stress conditions}}{\text{yield under non-stress conditions}} \times 100$$

II. MOLECULAR MARKERS, WATER OPTIMIZATION ASSOCIATED LOCI, AND COMPOSITIONS FOR ASSAYING NUCLEIC ACID SEQUENCES

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., STS, SSR/microsatellites, AFLP, and the like.). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson, 1993; Zietkiewicz et al., 1994. The recombination frequencies of molecular markers on different chromosomes are generally 50%. Between molecular markers located on the same chromosome, the recombination frequency generally depends on the distance between the markers. A low recombination frequency typically corresponds to a small genetic distance between markers on a chromosome. Comparing all recombination frequencies results in the most logical order of the molecular markers on the chromosomes. This most logical order can be depicted in a linkage map (Paterson, 1996). A group of adjacent or contiguous markers on the linkage map that is associated with increased water optimization can provide the position of an MTL associated with increased water optimization. Genetic loci correlating with particular phenotypes, such as drought tolerance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers can also be used by breeders to design genotypes in silico and to practice whole genome selection.

The presently disclosed subject matter provides in some embodiments markers associated with enhanced drought tolerance/water optimization. Detection of these markers and/or other linked markers can be used to identify, select and/or produce drought tolerant plants and/or to eliminate plants that are not drought tolerant from breeding programs or planting.

The presently disclosed subject matter provides markers associated with improved water optimization traits. A marker of the presently disclosed subject matter can comprise a single allele or a combination of alleles at one or more genetic loci. In some embodiments, the one or more alleles are characterized by one or more loci selected from, but not limited to, the loci represented by SEQ ID NOs: 1-117, 400, and 401, which are located in the Zea mays genome as follows:

(i) SEQ ID NO: 1 is derived from the Zea mays ZmIga4 locus, and is defined by a first oligonucleotide and a second oligonucleotide, wherein said oligonucleotides can be employed to amplify a subsequence of SEQ ID NO: 1 generated by amplifying a Zea mays nucleic acid with a first oligonucleotide comprising a nucleotide sequence as set forth in SEQ ID NO: 118 and a second oligonucleotide comprising a nucleotide sequence as set forth in SEQ ID NO: 119; and further wherein this locus comprises alleles of a water optimization-associated trait wherein the alleles are characterized by a single nucleic polymorphism at nucleotide positions 115, 270, 301, and 483 and comprises any part of a DNA sequence within 1, 2, 3, 4, 5, 6, 7, 8, 9, 10, 15, 20, or 25 cM of SEQ ID NO: 1 on Zea mays chromosome 8 that confers an improved water optimization-associated trait;

(ii) SEQ ID NO: 2 is derived from a water optimization locus, and is defined by a first oligonucleotide and a second oligonucleotide, wherein said oligonucleotides can be employed to amplify a subsequence of SEQ ID NO: 2 generated by amplifying a Zea mays nucleic acid with a first oligonucleotide comprising a nucleotide sequence as set forth in SEQ ID NO: 120 and a second oligonucleotide comprising a nucleotide sequence as set forth in SEQ ID NO: 121; and further wherein this locus comprises alleles of a water optimization-associated trait wherein the alleles are characterized by a single nucleic polymorphism at nucleotide positions 100 and 264-271 and comprises any part of a DNA sequence within 1, 2, 3, 4, 5, 6, 7, 8, 9, 10, 15, 20, or 25 cM of SEQ ID NO: 2 on Zea mays chromosome 8 that confers an improved water optimization-associated trait;

(iii) SEQ ID NO: 3 is derived from the Zea mays ZmDr1 locus, and is defined by a first oligonucleotide and a second oligonucleotide, wherein said oligonucleotides can be employed to amplify a subsequence of SEQ ID NO: 2 generated by amplifying a Zea mays nucleic acid with a first oligonucleotide comprising a nucleotide sequence as set forth in SEQ ID NO: 122 and a second oligonucleotide comprising a nucleotide sequence as set forth in SEQ ID NO: 123; and further wherein this locus comprises alleles of a water optimization-associated trait wherein the alleles are characterized by a single nucleic polymorphism at nucleotide position 216 of SEQ ID NO: 3 and comprises any part of a DNA sequence within 1, 2, 3, 4, 5, 6, 7, 8, 9, 10, 15, 20, or 25 cM of SEQ ID NO: 3 in a Zea mays genome that confers an improved water optimization-associated trait;

(iv) SEQ ID NO: 4 is derived from the Zea mays ZmDrA locus, and is defined by a first oligonucleotide and a second oligonucleotide, wherein said oligonucleotides can be employed to amplify a subsequence of SEQ ID NO: 4 generated by amplifying a Zea mays nucleic acid with a first oligonucleotide comprising a nucleotide sequence as set forth in SEQ ID NO: 124 and a second oligonucleotide comprising a nucleotide sequence as set forth in SEQ ID NO: 125; and further wherein this locus comprises alleles of a water optimization-associated trait wherein the alleles are characterized by a single nucleic polymorphism at nucleotide position 503 of SEQ ID NO: 4 and comprises any part of a DNA sequence within 1, 2, 3, 4, 5, 6, 7, 8, 9, 10, 15, 20, or 25 cM of SEQ ID NO: 4 on *Zea mays* chromosome 7 that confers an improved water optimization-associated trait;

(v) SEQ ID NO: 5 is derived from the *Zea mays* ZmDr2 locus, and is defined by a first oligonucleotide and a second oligonucleotide, wherein said oligonucleotides can be employed to amplify a subsequence of SEQ ID NO: 4 generated by amplifying a *Zea mays* nucleic acid with a first oligonucleotide comprising a nucleotide sequence as set forth in SEQ ID NO: 126 and a second oligonucleotide comprising a nucleotide sequence as set forth in SEQ ID NO: 127; and further wherein this locus comprises alleles of a water optimization-associated trait wherein the alleles are characterized by a polymorphism at nucleotide positions 818-821 of SEQ ID NO: 5 and comprises any part of a DNA sequence within 1, 2, 3, 4, 5, 6, 7, 8, 9, 10, 15, 20, or 25 cM of SEQ ID NO: 5 on *Zea mays* chromosome 2 that confers an improved water optimization-associated trait;

(vi) SEQ ID NO: 6 is derived from the *Zea mays* ZmDr3 locus, and is defined by a first oligonucleotide and a second oligonucleotide, wherein said oligonucleotides can be employed to amplify a subsequence of SEQ ID NO: 6 generated by amplifying a *Zea mays* nucleic acid with a first oligonucleotide comprising a nucleotide sequence as set forth in SEQ ID NO: 128 and a second oligonucleotide comprising a nucleotide sequence as set forth in SEQ ID NO: 129; and further wherein this locus comprises alleles of a water optimization-associated trait wherein the alleles are characterized by a polymorphism at nucleotide position 254 of SEQ ID NO: 6 and comprises any part of a DNA sequence within 1, 2, 3, 4, 5, 6, 7, 8, 9, 10, 15, 20, or 25 cM of SEQ ID NO: 6 on *Zea mays* chromosome 2 that confers an improved water optimization-associated trait;

(vii) SEQ ID NO: 7 is derived from the *Zea mays* ZmDr4 locus, and is defined by a first oligonucleotide and a second oligonucleotide, wherein said oligonucleotides can be employed to amplify a subsequence of SEQ ID NO: 7 generated by amplifying a *Zea mays* nucleic acid with a first oligonucleotide comprising a nucleotide sequence as set forth in SEQ ID NO: 130 and a second oligonucleotide comprising a nucleotide sequence as set forth in SEQ ID NO: 131; and further wherein this locus comprises alleles of a water optimization-associated trait wherein the alleles are characterized by a polymorphism at nucleotide positions 4497-4498, 4505, 4609, 4641, 4792, 4836, 4844, 4969, and 4979-4981 of SEQ ID NO: 7 and comprises any part of a DNA sequence within 1, 2, 3, 4, 5, 6, 7, 8, 9, 10, 15, 20, or 25 cM of SEQ ID NO: 7 on *Zea mays* chromosome 8 that confers an improved water optimization-associated trait;

(viii) SEQ ID NO: 8 is derived from the *Zea mays* ZmMa3 locus, and is defined by a first oligonucleotide and a second oligonucleotide, wherein said oligonucleotides can be employed to amplify a subsequence of SEQ ID NO: 8 generated by amplifying a *Zea mays* nucleic acid with a first oligonucleotide comprising a nucleotide sequence as set forth in SEQ ID NO: 132 and a second oligonucleotide comprising a nucleotide sequence as set forth in SEQ ID NO: 133; and further wherein this locus comprises alleles of a water optimization-associated trait wherein the alleles are characterized by polymorphisms at nucleotide positions 217, 390, and 477 of SEQ ID NO: 8 and comprises any part of a DNA sequence within 1, 2, 3, 4, 5, 6, 7, 8, 9, 10, 15, 20, or 25 cM of SEQ ID NO: 8 on *Zea mays* chromosome 2 that confers an improved water optimization-associated trait;

(ix) SEQ ID NO: 9 is derived from the *Zea mays* genome, and is defined by a first oligonucleotide and a second oligonucleotide, wherein said oligonucleotides can be employed to amplify a subsequence of SEQ ID NO: 9 generated by amplifying a *Zea mays* nucleic acid with a first oligonucleotide comprising a nucleotide sequence as set forth in SEQ ID NO: 134 and a second oligonucleotide comprising a nucleotide sequence as set forth in SEQ ID NO: 135; and further wherein this locus comprises alleles of a water optimization-associated trait wherein the alleles are characterized by a polymorphism at nucleotide position 292 of SEQ ID NO: 9 and comprises any part of a DNA sequence within 1, 2, 3, 4, 5, 6, 7, 8, 9, 10, 15, 20, or 25 cM of SEQ ID NO: 9 on *Zea mays* chromosome 4 that confers an improved water optimization-associated trait;

(x) SEQ ID NO: 10 is derived from the *Zea mays* ZmBglcn locus, and is defined by a first oligonucleotide and a second oligonucleotide, wherein said oligonucleotides can be employed to amplify a subsequence of SEQ ID NO: 10 generated by amplifying a *Zea mays* nucleic acid with a first oligonucleotide comprising a nucleotide sequence as set forth in SEQ ID NO: 136 and a second oligonucleotide comprising a nucleotide sequence as set forth in SEQ ID NO: 137; and further wherein this locus comprises alleles of a water optimization-associated trait wherein the alleles are characterized by a polymorphism at nucleotide position 166 of SEQ ID NO: 10 and comprises any part of a DNA sequence within 1, 2, 3, 4, 5, 6, 7, 8, 9, 10, 15, 20, or 25 cM of SEQ ID NO: 10 on *Zea mays* chromosome 3 that confers an improved water optimization-associated trait;

(xi) SEQ ID NO: 11 is derived from the *Zea mays* ZmLOC100276591 locus, and is defined by a first oligonucleotide and a second oligonucleotide, wherein said oligonucleotides can be employed to amplify a subsequence of SEQ ID NO: 11 generated by amplifying a *Zea mays* nucleic acid with a first oligonucleotide comprising a nucleotide sequence as set forth in SEQ ID NO: 138 and a second oligonucleotide comprising a nucleotide sequence as set forth in SEQ ID NO: 139; and further wherein this locus comprises alleles of a water optimization-associated trait wherein the alleles are characterized by a polymorphism at nucleotide position 148 of SEQ ID NO: 11 and comprises any part of a DNA sequence within 1, 2, 3, 4, 5, 6, 7, 8, 9, 10, 15, 20, or 25 cM of SEQ ID NO: 11 in the *Zea mays* genome that confers an improved water optimization-associated trait;

(xii) SEQ ID NO: 12 is derived from the *Zea mays* ZmDr7 locus, and is defined by a first oligonucleotide and a second oligonucleotide, wherein said oligonucleotides can be employed to amplify a subsequence of SEQ ID NO: 12 generated by amplifying a *Zea mays* nucleic acid with a first oligonucleotide comprising a nucleotide sequence as set forth in SEQ ID NO: 140 and a second oligonucleotide comprising a nucleotide sequence as set forth in SEQ ID NO: 141; and further wherein this locus comprises alleles of a water optimization-associated trait wherein the alleles are characterized by a polymorphism at nucleotide position 94 of SEQ ID NO: 12 and comprises any part of a DNA sequence within 1, 2, 3, 4, 5, 6, 7, 8, 9, 10, 15, 20, or 25 cM of SEQ ID NO: 12 on *Zea mays* chromosome 1 that confers an improved water optimization-associated trait;

(xiii) SEQ ID NO: 13 is derived from the *Zea mays* ZmDr7 locus, and is defined by a first oligonucleotide and a second oligonucleotide, wherein said oligonucleotides can be employed to amplify a subsequence of SEQ ID NO: 13 generated by amplifying a *Zea mays* nucleic acid with a first oligonucleotide comprising a nucleotide sequence as set forth in SEQ ID NO: 140 and a second oligonucleotide comprising a nucleotide sequence as set forth in SEQ ID NO: 141; and further wherein this locus comprises alleles of a water optimization-associated trait wherein the alleles are characterized by one or more polymorphisms at nucleotide positions 35, 86, and/or 89 of SEQ ID NO: 13 and comprises any part of a DNA sequence within 1, 2, 3, 4, 5, 6, 7, 8, 9, 10, 15, 20, or 25 cM of SEQ ID NO: 13 on *Zea mays* chromosome 1 that confers an improved water optimization-associated trait;

(xiv) SEQ ID NO: 14 is derived from the *Zea mays* ZmDr8 locus, and is defined by a first oligonucleotide and a second oligonucleotide, wherein said oligonucleotides can be employed to amplify a subsequence of SEQ ID NO: 14 generated by amplifying a *Zea mays* nucleic acid with a first oligonucleotide comprising a nucleotide sequence as set forth in SEQ ID NO: 142 and a second oligonucleotide comprising a nucleotide sequence as set forth in SEQ ID NO: 143; and further wherein this locus comprises alleles of a water optimization-associated trait wherein the alleles are characterized by a polymorphism at nucleotide position 432 of SEQ ID NO: 14 and comprises any part of a DNA sequence within 1, 2, 3, 4, 5, 6, 7, 8, 9, 10, 15, 20, or 25 cM of SEQ ID NO: 14 in the *Zea mays* genome that confers an improved water optimization-associated trait;

(xv) SEQ ID NO: 15 is derived from the *Zea mays* ZmHsp70 locus, and is defined by a first oligonucleotide and a second oligonucleotide, wherein said oligonucleotides can be employed to amplify a subsequence of SEQ ID NO: 15 generated by amplifying a *Zea mays* nucleic acid with a first oligonucleotide comprising a nucleotide sequence as set forth in SEQ ID NO: 144 and a second oligonucleotide comprising a nucleotide sequence as set forth in SEQ ID NO: 145; and further wherein this locus comprises alleles of a water optimization-associated trait wherein the alleles are characterized by a polymorphism at nucleotide position 753 of SEQ ID NO: 15 and comprises any part of a DNA sequence within 1, 2, 3, 4, 5, 6, 7, 8, 9, 10, 15, 20, or 25 cM of SEQ ID NO: 15 on *Zea mays* chromosome 1 that confers an improved water optimization-associated trait;

(xvi) SEQ ID NO: 16 is derived from the *Zea mays* ZmDr9 locus, and is defined by a first oligonucleotide and a second oligonucleotide, wherein said oligonucleotides can be employed to amplify a subsequence of SEQ ID NO: 16 generated by amplifying a *Zea mays* nucleic acid with a first oligonucleotide comprising a nucleotide sequence as set forth in SEQ ID NO: 146 and a second oligonucleotide comprising a nucleotide sequence as set forth in SEQ ID NO: 147; and further wherein this locus comprises alleles of a water optimization-associated trait wherein the alleles are characterized by a polymorphism at nucleotide position 755 of SEQ ID NO: 16 and comprises any part of a DNA sequence within 1, 2, 3, 4, 5, 6, 7, 8, 9, 10, 15, 20, or 25 cM of SEQ ID NO: 16 on *Zea mays* chromosome 4 that confers an improved water optimization-associated trait;

(xvii) SEQ ID NO: 17 is derived from the *Zea mays* ZmDrB locus, and is defined by a first oligonucleotide and a second oligonucleotide, wherein said oligonucleotides can be employed to amplify a subsequence of SEQ ID NO: 17 generated by amplifying a *Zea mays* nucleic acid with a first oligonucleotide comprising a nucleotide sequence as set forth in SEQ ID NO: 148 and a second oligonucleotide comprising a nucleotide sequence as set forth in SEQ ID NO: 149; and further wherein this locus comprises alleles of a water optimization-associated trait wherein the alleles are characterized by a polymorphism at nucleotide position 431 of SEQ ID NO: 17 and comprises any part of a DNA sequence within 1, 2, 3, 4, 5, 6, 7, 8, 9, 10, 15, 20, or 25 cM of SEQ ID NO: 17 in the *Zea mays* genome that confers an improved water optimization-associated trait;

(xviii) SEQ ID NO: 18 is derived from the *Zea mays* ZmAdh1-1s locus, and is defined by a first oligonucleotide and a second oligonucleotide, wherein said oligonucleotides can be employed to amplify a subsequence of SEQ ID NO: 18 generated by amplifying a *Zea mays* nucleic acid with a first oligonucleotide comprising a nucleotide sequence as set forth in SEQ ID NO: 150 and a second oligonucleotide comprising a nucleotide sequence as set forth in SEQ ID NO: 151; and further wherein this locus comprises alleles of a water optimization-associated trait wherein the alleles are characterized by a polymorphism at nucleotide position 518 of SEQ ID NO: 18 and comprises any part of a DNA sequence within 1, 2, 3, 4, 5, 6, 7, 8, 9, 10, 15, 20, or 25 cM of SEQ ID NO: 18 on *Zea mays* chromosome 1 that confers an improved water optimization-associated trait;

(xix) SEQ ID NO: 19 is derived from the *Zea mays* ZmDr10 locus, and is defined by a first oligonucleotide and a second oligonucleotide, wherein said oligonucleotides can be employed to amplify a subsequence of SEQ ID NO: 19 generated by amplifying a *Zea mays* nucleic acid with a first oligonucleotide comprising a nucleotide sequence as set forth in SEQ ID NO: 152 and a second oligonucleotide comprising a nucleotide sequence as set forth in SEQ ID NO: 153; and further wherein this locus comprises alleles of a water optimization-associated trait wherein the alleles are characterized by one or more polymorphisms at nucleotide positions 182, 309, 330, and 463 of SEQ ID NO: 19 and comprises any part of a DNA sequence within 1, 2, 3, 4, 5, 6, 7, 8, 9, 10, 15, 20, or 25 cM of SEQ ID NO: 19 on *Zea mays* chromosome 8 that confers an improved water optimization-associated trait;

(xx) SEQ ID NO: 20 is derived from the *Zea mays* ZmDrC locus, and is defined by a first oligonucleotide and a second oligonucleotide, wherein said oligonucleotides can be employed to amplify a subsequence of SEQ ID NO: 20 generated by amplifying a *Zea mays* nucleic acid with a first oligonucleotide comprising a nucleotide sequence as set forth in SEQ ID NO: 154 and a second oligonucleotide comprising a nucleotide sequence as set forth in SEQ ID NO: 155; and further wherein this locus comprises one or more alleles of a water optimization-associated trait wherein the one or more alleles are characterized by a polymorphism at nucleotide positions 773-776 of SEQ ID NO: 20 and comprises any part of a DNA sequence within 1, 2, 3, 4, 5, 6, 7, 8, 9, 10, 15, 20, or 25 cM of SEQ ID NO: 20 in the *Zea mays* genome that confers an improved water optimization-associated trait;

(xxi) SEQ ID NO: 21 is derived from the *Zea mays* ZmDr5 locus, and is defined by a first oligonucleotide and a second oligonucleotide, wherein said oligonucleotides can be employed to amplify a subsequence of SEQ ID NO: 21 generated by amplifying a *Zea mays* nucleic acid with a first oligonucleotide comprising a nucleotide sequence as set forth in SEQ ID NO: 156 and a second oligonucleotide comprising a nucleotide sequence as set forth in SEQ ID NO: 157; and further wherein this locus comprises alleles of a water optimization-associated trait wherein the alleles are characterized by one or more polymorphisms at nucleotide positions 61, 200, and 316-324 of SEQ ID NO: 21 and comprises any part of a DNA sequence within 1, 2, 3, 4, 5, 6, 7, 8, 9, 10, 15, 20, or 25 cM of SEQ ID NO: 21 on *Zea mays* chromosome 5 that confers an improved water optimization-associated trait;

(xxii) SEQ ID NO: 22 is derived from the *Zea mays* ZmDrD locus, and is defined by a first oligonucleotide and a second oligonucleotide, wherein said oligonucleotides can be employed to amplify a subsequence of SEQ ID NO: 22 generated by amplifying a *Zea mays* nucleic acid with a first oligonucleotide comprising a nucleotide sequence as set forth in SEQ ID NO: 158 and a second oligonucleotide comprising a nucleotide sequence as set forth in SEQ ID NO: 159; and further wherein this locus comprises alleles of a water optimization-associated trait wherein the alleles are characterized by a polymorphism at nucleotide position 211 of SEQ ID NO: 22 and comprises any part of a DNA sequence within 1, 2, 3, 4, 5, 6, 7, 8, 9, 10, 15, 20, or 25 cM of SEQ ID NO: 22 on *Zea mays* chromosome 5 that confers an improved water optimization-associated trait;

(xxiii) SEQ ID NO: 23 is derived from a *Zea mays* water optimization locus, and is defined by a first oligonucleotide and a second oligonucleotide, wherein said oligonucleotides can be employed to amplify a subsequence of SEQ ID NO: 23 generated by amplifying a *Zea mays* nucleic acid with a first oligonucleotide comprising a nucleotide sequence as set forth in SEQ ID NO: 160 and a second oligonucleotide comprising a nucleotide sequence as set forth in SEQ ID NO: 161; and further wherein this locus comprises alleles of a water optimization-associated trait wherein the alleles are characterized by one or more polymorphisms at nucleotide positions 116 and 217 of SEQ ID NO: 21 and comprises any part of a DNA sequence within 1, 2, 3, 4, 5, 6, 7, 8, 9, 10, 15, 20, or 25 cM of SEQ ID NO: 23 on *Zea mays* chromosome 8 that confers an improved water optimization-associated trait;

(xxiv) SEQ ID NO: 24 is derived from a *Zea mays* water optimization locus, and is defined by a first oligonucleotide and a second oligonucleotide, wherein said oligonucleotides can be employed to amplify a subsequence of SEQ ID NO: 24 generated by amplifying a *Zea mays* nucleic acid with a first oligonucleotide comprising a nucleotide sequence as set forth in SEQ ID NO: 162 and a second oligonucleotide comprising a nucleotide sequence as set forth in SEQ ID NO: 163; and further wherein this locus comprises alleles of a water optimization-associated trait wherein the alleles are characterized by a polymorphism at nucleotide position 746 of SEQ ID NO: 24 and comprises any part of a DNA sequence within 1, 2, 3, 4, 5, 6, 7, 8, 9, 10, 15, 20, or 25 cM of SEQ ID NO: 24 on *Zea mays* chromosome 8 that confers an improved water optimization-associated trait;

(xxv) SEQ ID NO: 25 is derived from the *Zea mays* ZmDr12 locus, and is defined by a first oligonucleotide and a second oligonucleotide, wherein said oligonucleotides can be employed to amplify a subsequence of SEQ ID NO: 25 generated by amplifying a *Zea mays* nucleic acid with a first oligonucleotide comprising a nucleotide sequence as set forth in SEQ ID NO: 164 and a second oligonucleotide comprising a nucleotide sequence as set forth in SEQ ID NO: 165; and further wherein this locus comprises alleles of a water optimization-associated trait wherein the alleles are characterized by a polymorphism at nucleotide position 562 of SEQ ID NO: 25 and comprises any part of a DNA sequence within 1, 2, 3, 4, 5, 6, 7, 8, 9, 10, 15, 20, or 25 cM of SEQ ID NO: 25 on *Zea mays* chromosome 8 that confers an improved water optimization-associated trait;

(xxvi) SEQ ID NO: 26 is derived from a *Zea mays* water optimization locus, and is defined by a first oligonucleotide and a second oligonucleotide, wherein said oligonucleotides can be employed to amplify a subsequence of SEQ ID NO: 26 generated by amplifying a *Zea mays* nucleic acid with a first oligonucleotide comprising a nucleotide sequence as set forth in SEQ ID NO: 166 and a second oligonucleotide comprising a nucleotide sequence as set forth in SEQ ID NO: 167; and further wherein this locus comprises alleles of a water optimization-associated trait wherein the alleles are characterized by a polymorphism at nucleotide position 1271 of SEQ ID NO: 26 and comprises any part of a DNA sequence within 1, 2, 3, 4, 5, 6, 7, 8, 9, 10, 15, 20, or 25 cM of SEQ ID NO: 26 on *Zea mays* chromosome 8 that confers an improved water optimization-associated trait;

(xxvii) SEQ ID NO: 27 is derived from the *Zea mays* ZmDrE locus, and is defined by a first oligonucleotide and a second oligonucleotide, wherein said oligonucleotides can be employed to amplify a subsequence of SEQ ID NO: 27 generated by amplifying a *Zea mays* nucleic acid with a first oligonucleotide comprising a nucleotide sequence as set forth in SEQ ID NO: 168 and a second oligonucleotide comprising a nucleotide sequence as set forth in SEQ ID NO: 169; and further wherein this locus comprises alleles of a water optimization-associated trait wherein the alleles are characterized by one or more polymorphisms at nucleotide positions 64 and/or 254 of SEQ ID NO: 27 and comprises any part of a DNA sequence within 1, 2, 3, 4, 5, 6, 7, 8, 9, 10, 15, 20, or 25 cM of SEQ ID NO: 27 on *Zea mays* chromosome 8 that confers an improved water optimization-associated trait;

(xxviii) SEQ ID NO: 28 is derived from the *Zea mays* ZmDrF locus, and is defined by a first oligonucleotide and a second oligonucleotide, wherein said oligonucleotides can be employed to amplify a subsequence of SEQ ID NO: 28 generated by amplifying a *Zea mays* nucleic acid with a first oligonucleotide comprising a nucleotide sequence as set forth in SEQ ID NO: 170 and a second oligonucleotide comprising a nucleotide sequence as set forth in SEQ ID NO: 171; and further wherein this locus comprises alleles of a water optimization-associated trait wherein the alleles are characterized by one or more polymorphisms at nucleotide positions 98, 147, 224, and/or 496 of SEQ ID NO: 28 and comprises any part of a DNA sequence within 1, 2, 3, 4, 5, 6, 7, 8, 9, 10, 15, 20, or 25 cM of SEQ ID NO: 28 on *Zea mays* chromosome 9 that confers an improved water optimization-associated trait;

(xxix) SEQ ID NO: 29 is derived from a *Zea mays* water optimization locus, and is defined by a first oligonucleotide and a second oligonucleotide, wherein said oligonucleotides can be employed to amplify a subsequence of SEQ ID NO: 29 generated by amplifying a *Zea mays* nucleic acid with a first oligonucleotide comprising a nucleotide sequence as set forth in SEQ ID NO: 172 and a second oligonucleotide comprising a nucleotide sequence as set forth in SEQ ID NO: 173; and further wherein this locus comprises alleles of a water optimization-associated trait wherein the alleles are characterized by a polymorphism at nucleotide position 258 of SEQ ID NO: 29 and comprises any part of a DNA sequence within 1, 2, 3, 4, 5, 6, 7, 8, 9, 10, 15, 20, or 25 cM of SEQ ID NO: 29 on *Zea mays* chromosome 8 that confers an improved water optimization-associated trait;

(xxx) SEQ ID NO: 30 is derived from the *Zea mays* ZmDhn2 locus, and is defined by a first oligonucleotide and a second oligonucleotide, wherein said oligonucleotides can be employed to amplify a subsequence of SEQ ID NO: 30 generated by amplifying a *Zea mays* nucleic acid with a first oligonucleotide comprising a nucleotide sequence as set forth in SEQ ID NO: 174 and a second oligonucleotide comprising a nucleotide sequence as set forth in SEQ ID NO: 175; and further wherein this locus comprises alleles of a water optimization-associated trait wherein the alleles are characterized by one or more polymorphisms at nucleotide positions 259, 296, 398, and/or 1057 of SEQ ID NO: 30 and comprises any part of a DNA sequence within 1, 2, 3, 4, 5, 6, 7, 8, 9, 10, 15, 20, or 25 cM of SEQ ID NO: 30 on *Zea mays* chromosome 4 that confers an improved water optimization-associated trait;

(xxxi) SEQ ID NO: 31 is derived from the *Zea mays* ZmDr16 locus, and is defined by a first oligonucleotide and a second oligonucleotide, wherein said oligonucleotides can be employed to amplify a subsequence of SEQ ID NO: 31 generated by amplifying a Zea mays nucleic acid with a first oligonucleotide comprising a nucleotide sequence as set forth in SEQ ID NO: 176 and a second oligonucleotide comprising a nucleotide sequence as set forth in SEQ ID NO: 177; and further wherein this locus comprises alleles of a water optimization-associated trait wherein the alleles are characterized by a polymorphism at nucleotide position 239 of SEQ ID NO: 31 and comprises any part of a DNA sequence within 1, 2, 3, 4, 5, 6, 7, 8, 9, 10, 15, 20, or 25 cM of SEQ ID NO: 31 on *Zea mays* chromosome 8 that confers an improved water optimization-associated trait;

(xxxii) SEQ ID NO: 32 is derived from the *Zea mays* ZmDr17 locus, and is defined by a first oligonucleotide and a second oligonucleotide, wherein said oligonucleotides can be employed to amplify a subsequence of SEQ ID NO: 32 generated by amplifying a *Zea mays* nucleic acid with a first oligonucleotide comprising a nucleotide sequence as set forth in SEQ ID NO: 178 and a second oligonucleotide comprising a nucleotide sequence as set forth in SEQ ID NO: 179; and further wherein this locus comprises alleles of a water optimization-associated trait wherein the alleles are characterized by a polymorphism at nucleotide position 208 of SEQ ID NO: 32 and comprises any part of a DNA sequence within 1, 2, 3, 4, 5, 6, 7, 8, 9, 10, 15, 20, or 25 cM of SEQ ID NO: 32 in the *Zea mays* genome that confers an improved water optimization-associated trait;

(xxxiii) SEQ ID NO: 33 is derived from a *Zea mays* water optimization locus, and is defined by a first oligonucleotide and a second oligonucleotide, wherein said oligonucleotides can be employed to amplify a subsequence of SEQ ID NO: 33 generated by amplifying a *Zea mays* nucleic acid with a first oligonucleotide comprising a nucleotide sequence as set forth in SEQ ID NO: 180 and a second oligonucleotide comprising a nucleotide sequence as set forth in SEQ ID NO: 181; and further wherein this locus comprises alleles of a water optimization-associated trait wherein the alleles are characterized by a polymorphism at nucleotide position 391 of SEQ ID NO: 33 and comprises any part of a DNA sequence within 1, 2, 3, 4, 5, 6, 7, 8, 9, 10, 15, 20, or 25 cM of SEQ ID NO: 33 on *Zea mays* chromosome 8 that confers an improved water optimization-associated trait;

(xxxiv) SEQ ID NO: 34 is derived from the *Zea mays* ZmZCN6 locus, and is defined by a first oligonucleotide and a second oligonucleotide, wherein said oligonucleotides can be employed to amplify a subsequence of SEQ ID NO: 34 generated by amplifying a *Zea mays* nucleic acid with a first oligonucleotide comprising a nucleotide sequence as set forth in SEQ ID NO: 182 and a second oligonucleotide comprising a nucleotide sequence as set forth in SEQ ID NO: 183; and further wherein this locus comprises alleles of a water optimization-associated trait wherein the alleles are characterized by a polymorphism at nucleotide positions 144-145, 169, and/or 537 of SEQ ID NO: 34 and comprises any part of a DNA sequence within 1, 2, 3, 4, 5, 6, 7, 8, 9, 10, 15, 20, or 25 cM of SEQ ID NO: 34 on *Zea mays* chromosome 4 that confers an improved water optimization-associated trait;

(xxxv) SEQ ID NO: 35 is derived from the *Zea mays* ZmDrG locus, and is defined by a first oligonucleotide and a second oligonucleotide, wherein said oligonucleotides can be employed to amplify a subsequence of SEQ ID NO: 35 generated by amplifying a *Zea mays* nucleic acid with a first oligonucleotide comprising a nucleotide sequence as set forth in SEQ ID NO: 184 and a second oligonucleotide comprising a nucleotide sequence as set forth in SEQ ID NO: 185; and further wherein this locus comprises alleles of a water optimization-associated trait wherein the alleles are characterized by a polymorphism at nucleotide position 76 of SEQ ID NO: 35 and comprises any part of a DNA sequence within 1, 2, 3, 4, 5, 6, 7, 8, 9, 10, 15, 20, or 25 cM of SEQ ID NO: 35 on *Zea mays* chromosome 5 that confers an improved water optimization-associated trait;

(xxxvi) SEQ ID NO: 36 is derived from the *Zea mays* ZmDhn1 locus, and is defined by a first oligonucleotide and a second oligonucleotide, wherein said oligonucleotides can be employed to amplify a subsequence of SEQ ID NO: 36 generated by amplifying a *Zea mays* nucleic acid with a first oligonucleotide comprising a nucleotide sequence as set forth in SEQ ID NO: 186 and a second oligonucleotide comprising a nucleotide sequence as set forth in SEQ ID NO: 187; and further wherein this locus comprises alleles of a water optimization-associated trait wherein the alleles are characterized by one or more polymorphisms at nucleotide positions 500, 568, and/or 698 of SEQ ID NO: 36 and comprises any part of a DNA sequence within 1, 2, 3, 4, 5, 6, 7, 8, 9, 10, 15, 20, or 25 cM of SEQ ID NO: 36 on *Zea mays* chromosome 6 that confers an improved water optimization-associated trait;

(xxxvii) SEQ ID NO: 37 is derived from the *Zea mays* ZmDrH locus, and is defined by a first oligonucleotide and a second oligonucleotide, wherein said oligonucleotides can be employed to amplify a subsequence of SEQ ID NO: 37 generated by amplifying a *Zea mays* nucleic acid with a first oligonucleotide comprising a nucleotide sequence as set forth in SEQ ID NO: 188 and a second oligonucleotide comprising a nucleotide sequence as set forth in SEQ ID NO: 189; and further wherein this locus comprises alleles of a water optimization-associated trait wherein the alleles are characterized by one or more polymorphisms at nucleotide positions 375 and/or 386 of SEQ ID NO: 37 and comprises any part of a DNA sequence within 1, 2, 3, 4, 5, 6, 7, 8, 9, 10, 15, 20, or 25 cM of SEQ ID NO: 37 on *Zea mays* chromosome 5 that confers an improved water optimization-associated trait;

(xxxviii) SEQ ID NO: 38 is derived from the *Zea mays* ZmDrI locus, and is defined by a first oligonucleotide and a second oligonucleotide, wherein said oligonucleotides can be employed to amplify a subsequence of SEQ ID NO: 38 generated by amplifying a *Zea mays* nucleic acid with a first oligonucleotide comprising a nucleotide sequence as set forth in SEQ ID NO: 190 and a second oligonucleotide comprising a nucleotide sequence as set forth in SEQ ID NO: 191; and further wherein this locus comprises alleles of a water optimization-associated trait wherein the alleles are characterized by a polymorphism at nucleotide position 309 and/or 342 of SEQ ID NO: 38 and comprises any part of a DNA sequence within 1, 2, 3, 4, 5, 6, 7, 8, 9, 10, 15, 20, or 25 cM of SEQ ID NO: 38 on *Zea mays* chromosome 3 that confers an improved water optimization-associated trait;

(xxxix) SEQ ID NO: 39 is derived from the *Zea mays* ZmDrJ locus, and is defined by a first oligonucleotide and a second oligonucleotide, wherein said oligonucleotides can be employed to amplify a subsequence of SEQ ID NO: 39 generated by amplifying a *Zea mays* nucleic acid with a first oligonucleotide comprising a nucleotide sequence as set forth in SEQ ID NO: 192 and a second oligonucleotide comprising a nucleotide sequence as set forth in SEQ ID NO: 193; and further wherein this locus comprises alleles of a water optimization-associated trait wherein the alleles are characterized by a polymorphism at nucleotide position 445 of SEQ ID NO: 39 and comprises any part of a DNA sequence within 1, 2, 3, 4, 5, 6, 7, 8, 9, 10, 15, 20, or 25 cM of SEQ ID NO: 39 on *Zea mays* chromosome 5 that confers an improved water optimization-associated trait;

(xl) SEQ ID NO: 40 is derived from the *Zea mays* ZmH2B1 locus, and is defined by a first oligonucleotide and a second oligonucleotide, wherein said oligonucleotides can be employed to amplify a subsequence of SEQ ID NO: 40 generated by amplifying a Zea mays nucleic acid with a first oligonucleotide comprising a nucleotide sequence as set forth in SEQ ID NO: 194 and a second oligonucleotide comprising a nucleotide sequence as set forth in SEQ ID NO: 195; and further wherein this locus comprises alleles of a water optimization-associated trait wherein the alleles are characterized by a polymorphism at nucleotide position 602 of SEQ ID NO: 40 and comprises any part of a DNA sequence within 1, 2, 3, 4, 5, 6, 7, 8, 9, 10, 15, 20, or 25 cM of SEQ ID NO: 40 on Zea mays chromosome 4 that confers an improved water optimization-associated trait;

(xli) SEQ ID NO: 41 is derived from the Zea mays ZmDr3 locus, and is defined by a first oligonucleotide and a second oligonucleotide, wherein said oligonucleotides can be employed to amplify a subsequence of SEQ ID NO: 41 generated by amplifying a Zea mays nucleic acid with a first oligonucleotide comprising a nucleotide sequence as set forth in SEQ ID NO: 196 and a second oligonucleotide comprising a nucleotide sequence as set forth in SEQ ID NO: 198; and further wherein this locus comprises alleles of a water optimization-associated trait wherein the alleles are characterized by a polymorphism at nucleotide position 190 and/or 580 of SEQ ID NO: 41 and comprises any part of a DNA sequence within 1, 2, 3, 4, 5, 6, 7, 8, 9, 10, 15, 20, or 25 cM of SEQ ID NO: 41 on Zea mays chromosome 2 that confers an improved water optimization-associated trait;

(xlii) SEQ ID NO: 42 is derived from the Zea mays ZmDrK locus, and is defined by a first oligonucleotide and a second oligonucleotide, wherein said oligonucleotides can be employed to amplify a subsequence of SEQ ID NO: 42 generated by amplifying a Zea mays nucleic acid with a first oligonucleotide comprising a nucleotide sequence as set forth in SEQ ID NO: 198 and a second oligonucleotide comprising a nucleotide sequence as set forth in SEQ ID NO: 199; and further wherein this locus comprises alleles of a water optimization-associated trait wherein the alleles are characterized by a polymorphism at nucleotide positions 238, 266-267, and 808 of SEQ ID NO: 42 and comprises any part of a DNA sequence within 1, 2, 3, 4, 5, 6, 7, 8, 9, 10, 15, 20, or 25 cM of SEQ ID NO: 42 in the Zea mays genome that confers an improved water optimization-associated trait;

(xliii) SEQ ID NO: 43 is derived from the Zea mays ZmCat1 locus, and is defined by a first oligonucleotide and a second oligonucleotide, wherein said oligonucleotides can be employed to amplify a subsequence of SEQ ID NO: 43 generated by amplifying a Zea mays nucleic acid with a first oligonucleotide comprising a nucleotide sequence as set forth in SEQ ID NO: 200 and a second oligonucleotide comprising a nucleotide sequence as set forth in SEQ ID NO: 201; and further wherein this locus comprises alleles of a water optimization-associated trait wherein the alleles are characterized by a polymorphism at nucleotide position 708 of SEQ ID NO: 43 and comprises any part of a DNA sequence within 1, 2, 3, 4, 5, 6, 7, 8, 9, 10, 15, 20, or 25 cM of SEQ ID NO: 43 on Zea mays chromosome 5 that confers an improved water optimization-associated trait;

(xliv) SEQ ID NO: 44 is derived from a Zea mays water optimization locus, and is defined by a first oligonucleotide and a second oligonucleotide, wherein said oligonucleotides can be employed to amplify a subsequence of SEQ ID NO: 44 generated by amplifying a Zea mays nucleic acid with a first oligonucleotide comprising a nucleotide sequence as set forth in SEQ ID NO: 202 and a second oligonucleotide comprising a nucleotide sequence as set forth in SEQ ID NO: 203; and further wherein this locus comprises alleles of a water optimization-associated trait wherein the alleles are characterized by a polymorphism at nucleotide position 266 of SEQ ID NO: 44 and comprises any part of a DNA sequence within 1, 2, 3, 4, 5, 6, 7, 8, 9, 10, 15, 20, or 25 cM of SEQ ID NO: 44 on Zea mays chromosome 8 that confers an improved water optimization-associated trait;

(xlv) SEQ ID NO: 45 is derived from a Zea mays water optimization locus, and is defined by a first oligonucleotide and a second oligonucleotide, wherein said oligonucleotides can be employed to amplify a subsequence of SEQ ID NO: 45 generated by amplifying a Zea mays nucleic acid with a first oligonucleotide comprising a nucleotide sequence as set forth in SEQ ID NO: 202 and a second oligonucleotide comprising a nucleotide sequence as set forth in SEQ ID NO: 203; and further wherein this locus comprises alleles of a water optimization-associated trait wherein the alleles are characterized by a polymorphism at nucleotide position 475 of SEQ ID NO: 45 and comprises any part of a DNA sequence within 1, 2, 3, 4, 5, 6, 7, 8, 9, 10, 15, 20, or 25 cM of SEQ ID NO: 45 on Zea mays chromosome 8 that confers an improved water optimization-associated trait;

(xlvi) SEQ ID NO: 46 is derived from a Zea mays water optimization locus, and is defined by a first oligonucleotide and a second oligonucleotide, wherein said oligonucleotides can be employed to amplify a subsequence of SEQ ID NO: 46 generated by amplifying a Zea mays nucleic acid with a first oligonucleotide comprising a nucleotide sequence as set forth in SEQ ID NO: 204 and a second oligonucleotide comprising a nucleotide sequence as set forth in SEQ ID NO: 205; and further wherein this locus comprises alleles of a water optimization-associated trait wherein the alleles are characterized by a polymorphism at nucleotide position 386 of SEQ ID NO: 46 and comprises any part of a DNA sequence within 1, 2, 3, 4, 5, 6, 7, 8, 9, 10, 15, 20, or 25 cM of SEQ ID NO: 46 on Zea mays chromosome 8 that confers an improved water optimization-associated trait;

(xlvii) SEQ ID NO: 47 is derived from a Zea mays water optimization locus, and is defined by a first oligonucleotide and a second oligonucleotide, wherein said oligonucleotides can be employed to amplify a subsequence of SEQ ID NO: 47 generated by amplifying a Zea mays nucleic acid with a first oligonucleotide comprising a nucleotide sequence as set forth in SEQ ID NO: 206 and a second oligonucleotide comprising a nucleotide sequence as set forth in SEQ ID NO: 207; and further wherein this locus comprises alleles of a water optimization-associated trait wherein the alleles are characterized by a polymorphism at nucleotide position 87 of SEQ ID NO: 47 and comprises any part of a DNA sequence within 1, 2, 3, 4, 5, 6, 7, 8, 9, 10, 15, 20, or 25 cM of SEQ ID NO: 47 on Zea mays chromosome 8 that confers an improved water optimization-associated trait;

(xlviii) SEQ ID NO: 48 is derived from a Zea mays water optimization locus, and is defined by a first oligonucleotide and a second oligonucleotide, wherein said oligonucleotides can be employed to amplify a subsequence of SEQ ID NO: 48 generated by amplifying a Zea mays nucleic acid with a first oligonucleotide comprising a nucleotide sequence as set forth in SEQ ID NO: 208 and a second oligonucleotide comprising a nucleotide sequence as set forth in SEQ ID NO: 209; and further wherein this locus comprises alleles of a water optimization-associated trait wherein the alleles are characterized by a polymorphism at nucleotide position 472 of SEQ ID NO: 48 and comprises any part of a DNA sequence within 1, 2, 3, 4, 5, 6, 7, 8, 9, 10, 15, 20, or 25 cM of SEQ ID NO: 48 on Zea mays chromosome 8 that confers an improved water optimization-associated trait;

(xlix) SEQ ID NO: 49 is derived from the *Zea mays* ZmRIC1 locus, and is defined by a first oligonucleotide and a second oligonucleotide, wherein said oligonucleotides can be employed to amplify a subsequence of SEQ ID NO: 49 generated by amplifying a *Zea mays* nucleic acid with a first oligonucleotide comprising a nucleotide sequence as set forth in SEQ ID NO: 210 and a second oligonucleotide comprising a nucleotide sequence as set forth in SEQ ID NO: 211; and further wherein this locus comprises alleles of a water optimization-associated trait wherein the alleles are characterized by one or more polymorphisms at nucleotide positions 166, 224, 650, and/or 892 of SEQ ID NO: 49 and comprises any part of a DNA sequence within 1, 2, 3, 4, 5, 6, 7, 8, 9, 10, 15, 20, or 25 cM of SEQ ID NO: 49 on *Zea mays* chromosome 8 that confers an improved water optimization-associated trait;

(l) SEQ ID NO: 50 is derived from the *Zea mays* ZmPK4 locus, and is defined by a first oligonucleotide and a second oligonucleotide, wherein said oligonucleotides can be employed to amplify a subsequence of SEQ ID NO: 50 generated by amplifying a *Zea mays* nucleic acid with a first oligonucleotide comprising a nucleotide sequence as set forth in SEQ ID NO: 212 and a second oligonucleotide comprising a nucleotide sequence as set forth in SEQ ID NO: 213; and further wherein this locus comprises alleles of a water optimization-associated trait wherein the alleles are characterized by a polymorphism at nucleotide position 541 of SEQ ID NO: 50 and comprises any part of a DNA sequence within 1, 2, 3, 4, 5, 6, 7, 8, 9, 10, 15, 20, or 25 cM of SEQ ID NO: 50 on *Zea mays* chromosome 8 that confers an improved water optimization-associated trait;

(li) SEQ ID NO: 51 is derived from the *Zea mays* ZmPK4 locus, and is defined by a first oligonucleotide and a second oligonucleotide, wherein said oligonucleotides can be employed to amplify a subsequence of SEQ ID NO: 51 generated by amplifying a *Zea mays* nucleic acid with a first oligonucleotide comprising a nucleotide sequence as set forth in SEQ ID NO: 212 and a second oligonucleotide comprising a nucleotide sequence as set forth in SEQ ID NO: 213; and further wherein this locus comprises alleles of a water optimization-associated trait wherein the alleles are characterized by a polymorphism at nucleotide position 111 of SEQ ID NO: 51 and comprises any part of a DNA sequence within 1, 2, 3, 4, 5, 6, 7, 8, 9, 10, 15, 20, or 25 cM of SEQ ID NO: 51 on *Zea mays* chromosome 8 that confers an improved water optimization-associated trait;

(lii) SEQ ID NO: 52 is derived from the *Zea mays* Zpu1 locus, and is defined by a first oligonucleotide and a second oligonucleotide, wherein said oligonucleotides can be employed to amplify a subsequence of SEQ ID NO: 52 generated by amplifying a *Zea mays* nucleic acid with a first oligonucleotide comprising a nucleotide sequence as set forth in SEQ ID NO: 214 and a second oligonucleotide comprising a nucleotide sequence as set forth in SEQ ID NO: 215; and further wherein this locus comprises alleles of a water optimization-associated trait wherein the alleles are characterized by a polymorphism at nucleotide position 442 of SEQ ID NO: 52 and comprises any part of a DNA sequence within 1, 2, 3, 4, 5, 6, 7, 8, 9, 10, 15, 20, or 25 cM of SEQ ID NO: 52 on *Zea mays* chromosome 2 that confers an improved water optimization-associated trait;

(liii) SEQ ID NO: 53 is derived from the *Zea mays* ZmDrL locus, and is defined by a first oligonucleotide and a second oligonucleotide, wherein said oligonucleotides can be employed to amplify a subsequence of SEQ ID NO: 53 generated by amplifying a *Zea mays* nucleic acid with a first oligonucleotide comprising a nucleotide sequence as set forth in SEQ ID NO: 216 and a second oligonucleotide comprising a nucleotide sequence as set forth in SEQ ID NO: 217; and further wherein this locus comprises alleles of a water optimization-associated trait wherein the alleles are characterized by one or more polymorphisms at nucleotide positions 83, 428, 491 and/or 548 of SEQ ID NO: 53 and comprises any part of a DNA sequence within 1, 2, 3, 4, 5, 6, 7, 8, 9, 10, 15, 20, or 25 cM of SEQ ID NO: 53 on *Zea mays* chromosome 9 that confers an improved water optimization-associated trait;

(liv) SEQ ID NO: 54 is derived from the *Zea mays* ZmDrM locus, and is defined by a first oligonucleotide and a second oligonucleotide, wherein said oligonucleotides can be employed to amplify a subsequence of SEQ ID NO: 54 generated by amplifying a *Zea mays* nucleic acid with a first oligonucleotide comprising a nucleotide sequence as set forth in SEQ ID NO: 218 and a second oligonucleotide comprising a nucleotide sequence as set forth in SEQ ID NO: 219; and further wherein this locus comprises alleles of a water optimization-associated trait wherein the alleles are characterized by a polymorphism at nucleotide position 126 of SEQ ID NO: 54 and comprises any part of a DNA sequence within 1, 2, 3, 4, 5, 6, 7, 8, 9, 10, 15, 20, or 25 cM of SEQ ID NO: 54 on *Zea mays* chromosome 7 that confers an improved water optimization-associated trait;

(lv) SEQ ID NO: 55 is derived from a *Zea mays* water optimization locus, and is defined by a first oligonucleotide and a second oligonucleotide, wherein said oligonucleotides can be employed to amplify a subsequence of SEQ ID NO: 55 generated by amplifying a *Zea mays* nucleic acid with a first oligonucleotide comprising a nucleotide sequence as set forth in SEQ ID NO: 220 and a second oligonucleotide comprising a nucleotide sequence as set forth in SEQ ID NO: 221; and further wherein this locus comprises alleles of a water optimization-associated trait wherein the alleles are characterized by a polymorphism at nucleotide position 193 of SEQ ID NO: 55 and comprises any part of a DNA sequence within 1, 2, 3, 4, 5, 6, 7, 8, 9, 10, 15, 20, or 25 cM of SEQ ID NO: 55 on *Zea mays* chromosome 8 that confers an improved water optimization-associated trait;

(lvi) SEQ ID NO: 56 is derived from a *Zea mays* water optimization locus, and is defined by a first oligonucleotide and a second oligonucleotide, wherein said oligonucleotides can be employed to amplify a subsequence of SEQ ID NO: 56 generated by amplifying a *Zea mays* nucleic acid with a first oligonucleotide comprising a nucleotide sequence as set forth in SEQ ID NO: 222 and a second oligonucleotide comprising a nucleotide sequence as set forth in SEQ ID NO: 223; and further wherein this locus comprises alleles of a water optimization-associated trait wherein the alleles are characterized by one or more polymorphisms at nucleotide positions 237 and/or 516 of SEQ ID NO: 56 and comprises any part of a DNA sequence within 1, 2, 3, 4, 5, 6, 7, 8, 9, 10, 15, 20, or 25 cM of SEQ ID NO: 56 on *Zea mays* chromosome 8 that confers an improved water optimization-associated trait;

(lvii) SEQ ID NO: 57 is derived from a *Zea mays* water optimization locus, and is defined by a first oligonucleotide and a second oligonucleotide, wherein said oligonucleotides can be employed to amplify a subsequence of SEQ ID NO: 57 generated by amplifying a *Zea mays* nucleic acid with a first oligonucleotide comprising a nucleotide sequence as set forth in SEQ ID NO: 224 and a second oligonucleotide comprising a nucleotide sequence as set forth in SEQ ID NO: 225; and further wherein this locus comprises alleles of a water optimization-associated trait wherein the alleles are characterized by a polymorphism at nucleotide position 173 of SEQ ID NO: 57 and comprises any part of a DNA sequence within 1, 2, 3, 4, 5, 6, 7, 8, 9, 10, 15, 20, or 25 cM of SEQ ID NO: 57 on *Zea mays* chromosome 8 that confers an improved water optimization-associated trait;

(lviii) SEQ ID NO: 58 is derived from a *Zea mays* water optimization locus, and is defined by a first oligonucleotide and a second oligonucleotide, wherein said oligonucleotides can be employed to amplify a subsequence of SEQ ID NO: 58 generated by amplifying a *Zea mays* nucleic acid with a first oligonucleotide comprising a nucleotide sequence as set forth in SEQ ID NO: 226 and a second oligonucleotide comprising a nucleotide sequence as set forth in SEQ ID NO: 227; and further wherein this locus comprises alleles of a water optimization-associated trait wherein the alleles are characterized by a polymorphism at nucleotide position 486 of SEQ ID NO: 58 and comprises any part of a DNA sequence within 1, 2, 3, 4, 5, 6, 7, 8, 9, 10, 15, 20, or 25 cM of SEQ ID NO: 58 on *Zea mays* chromosome 8 that confers an improved water optimization-associated trait;

(lix) SEQ ID NO: 59 is derived from a *Zea mays* water optimization locus, and is defined by a first oligonucleotide and a second oligonucleotide, wherein said oligonucleotides can be employed to amplify a subsequence of SEQ ID NO: 59 generated by amplifying a *Zea mays* nucleic acid with a first oligonucleotide comprising a nucleotide sequence as set forth in SEQ ID NO: 228 and a second oligonucleotide comprising a nucleotide sequence as set forth in SEQ ID NO: 229; and further wherein this locus comprises alleles of a water optimization-associated trait wherein the alleles are characterized by a polymorphism at nucleotide position 729 of SEQ ID NO: 59 and comprises any part of a DNA sequence within 1, 2, 3, 4, 5, 6, 7, 8, 9, 10, 15, 20, or 25 cM of SEQ ID NO: 59 on *Zea mays* chromosome 8 that confers an improved water optimization-associated trait; and (lx) SEQ ID NO: 60 is derived from a *Zea mays* water optimization locus, and is defined by a first oligonucleotide and a second oligonucleotide, wherein said oligonucleotides can be employed to amplify a subsequence of SEQ ID NO: 60 generated by amplifying a *Zea mays* nucleic acid with a first oligonucleotide comprising a nucleotide sequence as set forth in SEQ ID NO: 230 and a second oligonucleotide comprising a nucleotide sequence as set forth in SEQ ID NO: 231; and further wherein this locus comprises alleles of a water optimization-associated trait wherein the alleles are characterized by a polymorphism at nucleotide position 267 of SEQ ID NO: 60 and comprises any part of a DNA sequence within 1, 2, 3, 4, 5, 6, 7, 8, 9, 10, 15, 20, or 25 cM of SEQ ID NO: 60 on *Zea mays* chromosome 8 that confers an improved water optimization-associated trait; and In some embodiments, a DNA sequence within 1, 2, 3, 4, 5, 6, 7, 8, 9, 10, 15, 20, or 25 cM of a marker of the presently disclosed subject matter displays a genetic recombination frequency of less than about 25%, 20%, 15%, 10%, 9%, 8%, 7%, 6%, 5%, 4%, 3%, 2%, or 1% with the marker of the presently disclosed subject matter. In some embodiments, the germplasm is a *Zea mays* line or variety.

DNA fragments associated with the presence of a water optimization associated trait, alleles, and/or haplotypes including, but not limited to SEQ ID NOs: 1-117, 400, and 401, are also provided. In some embodiments, the DNA fragments associated with the presence of a water optimization associated trait have a predicted length and/or nucleic acid sequence, and detecting a DNA fragment having the predicted length and/or the predicted nucleic acid sequence is performed such that the amplified DNA fragment has a length that corresponds (plus or minus a few bases; e.g., a length of one, two or three bases more or less) to the predicted length. In some embodiments, a DNA fragment is an amplified fragment and the amplified fragment has a predicted length and/or nucleic acid sequence as does an amplified fragment produced by a similar reaction with the same primers with the DNA from the plant in which the marker was first detected or the nucleic acid sequence that corresponds (i.e., as a nucleotide sequence identity of more than 80%, 81%, 82%, 83%, 84%, 85%, 86%, 87%, 88%, 89%, 90%, 91%, 92%, 93%, 94%, 95%, 96%, 97%, 98%, or 99%) to the expected sequence as based on the sequence of the marker associated with that water optimization associated trait in the plant in which the marker was first detected. Upon a review of the instant disclosure, one of ordinary skill in the art would appreciate that markers that are absent in plants while they were present in at least one parent plant (so-called trans-markers), can also be useful in assays for detecting a desired trait in an progeny plant, although testing for the absence of a marker to detect the presence of a specific trait is not optimal. The detecting of an amplified DNA fragment having the predicted length or the predicted nucleic acid sequence can be performed by any of a number of techniques, including but not limited to standard gel electrophoresis techniques and/or by using automated DNA sequencers. The methods are not described here in detail as they are well known to the skilled person.

The primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including but not limited to temperature and composition (A/T vs. G/C content) of the primer.

In the context of an amplification primer, these are typically provided as one or more sets of bidirectional primers that include one or more forward and one or more reverse primers as commonly used in the art of DNA amplification such as in PCR amplification, As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing. Primers can be prepared by any suitable method. Methods for preparing oligonucleotides of specific sequence are known in the art, and include, for example, cloning, and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,068.

Primers can be labeled, if desired, by incorporating detectable moieties by for instance spectroscopic, fluorescence, photochemical, biochemical, immunochemical, or chemical moieties.

Template-dependent extension of an oligonucleotide primer is catalyzed by a polymerizing agent in the presence of adequate amounts of the four deoxyribonucleotides triphosphates (dATP, dGTP, dCTP and dTTP; i.e., dNTPs) or analogues, in a reaction medium that comprises appropriate salts, metal cations, and a pH buffering system. Suitable polymerizing agents are enzymes known to catalyze primer- and template-dependent DNA synthesis. Known DNA polymerases include, for example, *E. coli* DNA polymerase or its Klenow fragment, T4 DNA polymerase, and Taq DNA polymerase, as well as various modified versions thereof. The reaction conditions for catalyzing DNA synthesis with these DNA polymerases are known in the art. The products of the synthesis are duplex molecules consisting of the template strands and the primer extension strands, which include the target sequence. These products, in turn, can serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension can result in the exponential accumulation of the target region defined by the primers. Sufficient cycles are run to achieve the desired amount of polynucleotide containing the target region of nucleic acid. The desired amount can vary, and is determined by the function which the product polynucleotide is to serve.

The PCR method is well described in handbooks and known to the skilled person. After amplification by PCR, the target polynucleotides can be detected by hybridization with a probe polynucleotide which forms a stable hybrid with that of the target sequence under stringent to moderately stringent hybridization and wash conditions. If it is expected that the probes will be essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell, 2001. Generally, lower salt concentration and higher temperature increase the stringency of hybridization conditions.

In order to detect the presence of two water optimization associated alleles on a single chromosome in a plant, chromosome painting methods can also be used. In such methods at least a first water optimization associated allele and at least a second water optimization associated allele can be detected in the same chromosome by in situ hybridization or in situ PCR techniques. More conveniently, the fact that two water optimization associated alleles are present on a single chromosome can be confirmed by determining that they are in coupling phase: i.e., that the traits show reduced segregation when compared to genes residing on separate chromosomes.

The water optimization associated alleles identified herein are located on a number of different chromosomes or linkage groups and their locations can be characterized by a number of otherwise arbitrary markers. In the present investigations, single nucleotide polymorphisms (SNPs), were used, although restriction fragment length polymorphism (RFLP) markers, amplified fragment length polymorphism (AFLP) markers, microsatellite markers (e.g., SSRs), insertion mutation markers, sequence-characterized amplified region (SCAR) markers, cleaved amplified polymorphic sequence (CAPS) markers, isozyme markers, microarray-based technologies, TAQMAN® Assays, ILLUMINA® GOLDEN-GATE® Assay analysis, nucleic acid sequencing technologies, or combinations of these markers might also have been used, and indeed can be used.

In general, providing complete sequence information for a water optimization associated allele and/or haplotype is unnecessary, as the way in which the water optimization associated allele and/or haplotype is first detected—through an observed correlation between the presence of one or more single nucleotide polymorphisms and the presence of a particular phenotypic trait—allows one to trace among a population of progeny plants those plants that have the genetic potential for exhibiting a particular phenotypic trait. By providing a non-limiting list of markers, the presently disclosed subject matter thus provides for the effective use of the presently disclosed water optimization associated alleles and/or haplotypes in breeding programs. In some embodiments, a marker is specific for a particular line of descent. Thus, a specific trait can be associated with a particular marker.

The markers as disclosed herein not only indicate the location of the water optimization associated allele, they also correlate with the presence of the specific phenotypic trait in a plant. It is noted that single nucleotide polymorphisms that indicate where a water optimization associated allele is present in the genome is non-limiting. In general, the location of a water optimization associated allele is indicated by a set of single nucleotide polymorphisms that exhibit statistical correlation to the phenotypic trait. Once a marker is found outside a single nucleotide polymorphism (i.e., one that has a LOD-score below a certain threshold, indicating that the marker is so remote that recombination in the region between that marker and the water optimization associated allele occurs so frequently that the presence of the marker does not correlate in a statistically significant manner to the presence of the phenotype), the boundaries of the water optimization associated allele can be considered set. Thus, it is also possible to indicate the location of the water optimization associated allele by other markers located within that specified region. It is further noted that a single nucleotide polymorphism can also be used to indicate the presence of the water optimization associated allele (and thus of the phenotype) in an individual plant, which in some embodiments means that it can be used in marker-assisted selection (MAS) procedures.

In principle, the number of potentially useful markers can be very large. Any marker that is linked to a water optimization associated allele (e.g., falling within the physically boundaries of the genomic region spanned by the markers having established LOD scores above a certain threshold thereby indicating that no or very little recombination between the marker and the water optimization associated allele occurs in crosses, as well as any marker in linkage disequilibrium to the water optimization associated allele, as well as markers that represent the actual causal mutations within the water optimization associated allele) can be used in the presently disclosed methods and compositions, and are within the scope of the presently disclosed subject matter. This means that the markers identified in the application as associated with the water optimization associated allele (e.g., markers that are present in or comprise any of SEQ ID NOs: 1-24) are non-limiting examples of markers suitable for use in the presently disclosed methods and compositions. Moreover, when a water optimization associated allele, or the specific trait-conferring part thereof, is introgressed into another genetic background (i.e., into the genome of another maize or another plant species), then some markers might no longer be found in the progeny although the trait is present therein, indicating that such markers are outside the genomic region that represents the specific trait-conferring part of the water optimization associated allele in the original parent line only and that the new genetic background has a different genomic organization. Such markers of which the absence indicates the successful introduction of the genetic element in the progeny are called "trans markers" and can be equally suitable with respect to the presently disclosed subject matter.

Upon the identification of a water optimization associated allele and/or haplotype, the water optimization associated allele and/or haplotype effect (e.g., the trait) can for instance be confirmed by assessing trait in progeny segregating for the water optimization associated alleles and/or haplotypes under investigation. The assessment of the trait can suitably be performed by using phenotypic assessment as known in the art for water optimization traits. For example, (field) trials under natural and/or irrigated conditions can be conducted to assess the traits of hybrid and/or inbred maize.

The markers provided by the presently disclosed subject matter can be used for detecting the presence of one or more water optimization trait alleles and/or haplotypes at loci of the presently disclosed subject matter in a suspected water optimization trait introgressed maize plant, and can therefore be used in methods involving marker-assisted breeding and selection of such water optimization trait bearing maize plants. In some embodiments, detecting the presence of a water optimization associated allele and/or haplotype of the presently disclosed subject matter is performed with at least one of the markers for a water optimization associated allele and/or haplotype as defined herein. The presently disclosed subject matter therefore relates in another aspect to a method for detecting the presence of a water optimization associated allele and/or haplotype for at least one of the presently disclosed water optimization traits, comprising detecting the presence of a nucleic acid sequence of the water optimization associated allele and/or haplotype in a trait bearing maize plant, which presence can be detected by the use of the disclosed markers.

In some embodiments, the detecting comprises determining the nucleotide sequence of a Zea mays nucleic acid associated with a water optimization associated trait, allele and/or haplotype. The nucleotide sequence of a water optimization associated allele and/or haplotype of the presently disclosed subject matter can for instance be resolved by determining the nucleotide sequence of one or more markers associated with the water optimization associated allele and/or haplotype and designing internal primers for the marker sequences that can then be used to further determine the sequence of the water optimization associated allele and/or haplotype outside of the marker sequences.

For example, the nucleotide sequence of the SNP markers disclosed herein can be obtained by isolating the markers from the electrophoresis gel used in the determination of the presence of the markers in the genome of a subject plant, and determining the nucleotide sequence of the markers by, for example, dideoxy chain termination sequencing methods, which are well known in the art. In some embodiments of such methods for detecting the presence of a water optimization associated allele and/or haplotype in a trait bearing maize plant, the method can also comprise providing a oligonucleotide or polynucleotide capable of hybridizing under stringent hybridization conditions to a nucleic acid sequence of a marker linked to the water optimization associated allele and/or haplotype, in some embodiments selected from the markers disclosed herein, contacting the oligonucleotide or polynucleotide with digested genomic nucleic acid of a trait bearing maize plant, and determining the presence of specific hybridization of the oligonucleotide or polynucleotide to the digested genomic nucleic acid. In some embodiments, the method is performed on a nucleic acid sample obtained from the trait-bearing maize plant, although in situ hybridization methods can also be employed. Alternatively, one of ordinary skill in the art can, once the nucleotide sequence of the water optimization associated allele and/or haplotype has been determined, design specific hybridization probes or oligonucleotides capable of hybridizing under stringent hybridization conditions to the nucleic acid sequence of the water optimization associated allele and/or haplotype and can use such hybridization probes in methods for detecting the presence of a water optimization associated allele and/or haplotype disclosed herein in a trait bearing maize plant.

In some embodiments, the markers can comprise, consist essentially of, or consist of:
1) a haplotype comprising an A allele at positions 4979-4981 of SEQ ID NO: 7, an A allele at position 472 of SEQ ID NO: 48, a G allele at position 237 of SEQ ID NO: 56, a T allele at position 173 of SEQ ID NO: 57, an A allele at position 391 of SEQ ID NO: 33, a G allele at position 116 of SEQ ID NO: 23, a G allele at position 100 of SEQ ID NO: 2 and a G allele at position 267 of SEQ ID NO: 60;
2) a haplotype comprising a C allele at position 386 of SEQ ID NO: 46, an A allele at positions 4979-4981 of SEQ ID NO: 7, an A allele at position 472 of SEQ ID NO: 48, an A allele at position 266 of SEQ ID NO: 44, a T allele at position 309 of SEQ ID NO: 19, a G allele at position 111 of SEQ ID NO: 51, a G allele at position 562 of SEQ ID NO: 25 and a C allele at position 1271 of SEQ ID NO: 26;
3) a haplotype comprising a G allele at position 87 of SEQ ID NO: 47, an A allele at position 4641 of SEQ ID NO: 7, a G allele at position 472 of SEQ ID NO: 48, an A allele at position 266 of SEQ ID NO: 44, a C allele at position 746 of SEQ ID NO: 24, a C allele at position 258 of SEQ ID NO: 29, an A allele at position 217 of SEQ ID NO: 23, a G allele at position 100 of SEQ ID NO: 2, a C allele at position 486 of SEQ ID NO: 58 and a G allele at position 193 of SEQ ID NO: 55;
4) a haplotype comprising an A allele at position 4641 of SEQ ID NO: 7, a G allele and position 237 of SEQ ID NO: 56, an A allele at position 391 of SEQ ID NO: 33, a T allele at position 309 of SEQ ID NO: 19, a deletion at positions 264-271 of SEQ ID NO: 2 and a C allele at position 486 of SEQ ID NO: 58;
5) a haplotype comprising an A allele at positions 4979-4981 of SEQ ID NO: 7, a C allele at position 516 of SEQ ID NO: 56, a T allele at position 475 of SEQ ID NO: 45, an A allele at position 391 of SEQ ID NO: 33, a G allele at position 463 of SEQ ID NO: 19, a G allele at position 254 of SEQ ID NO: 27, a G allele at position 729 of SEQ ID NO: 59, a G allele at position 267 of SEQ ID NO: 60 and a G allele at position 193 of SEQ ID NO: 55; or
6) a haplotype comprising an A allele at position 4641 of SEQ ID NO: 7, a G allele at position 237 of SEQ ID NO: 56, a C allele at position 258 of SEQ ID NO: 29, a G allele at position 463 of SEQ ID NO: 19 and a G allele at position 193 of SEQ ID NO: 55.

In some embodiments, the marker can comprise, consist essentially of, or consist of:
1) a haplotype comprising an A allele at positions 4979-4981 of SEQ ID NO: 7, an A allele at position 472 of SEQ ID NO: 48 and a T allele at position 173 of SEQ ID NO: 57;
2) a haplotype comprising a C allele at position 386 of SEQ ID NO: 46, an A allele at positions 4979-4981 of SEQ ID NO: 7, an A allele at position 472 of SEQ ID NO: 48, an A allele at position 266 of SEQ ID NO: 44, a T allele at position 309 of SEQ ID NO: 19 and a G allele at;
3) a haplotype comprising a G allele at position 87 of SEQ ID NO: 47, an A allele at position 4641 of SEQ ID NO: 7, a G allele at position 472 of SEQ ID NO: 48, an A allele at position 266 of SEQ ID NO: 44, a C allele at position 258 of SEQ ID NO: 29 and a G allele at position 193 of SEQ ID NO: 55;

4) a haplotype comprising an A allele at position 4641 of SEQ ID NO: 7, and a T allele at position 309 of SEQ ID NO: 19;
5) a haplotype comprising an A allele at positions 4979-4981 of SEQ ID NO: 7, a T allele at position 475 of SEQ ID NO: 45, a G allele at position 463 of SEQ ID NO: 19, and a G allele at position 193 of SEQ ID NO: 55; or
6) a haplotype comprising an A allele at position 4641 of SEQ ID NO: 7, a C allele at position 258 of SEQ ID NO: 29, a G allele at position 463 of SEQ ID NO: 19 and a G allele at position 193 of SEQ ID NO: 55.

In some embodiments, the marker can comprise, consist essentially of, or consist of:
1) an A allele at positions 4979-4981 of SEQ ID NO: 7;
2) an A allele at position 4641 of SEQ ID NO: 7;
3) a haplotype comprising a C allele at position 386 of SEQ ID NO: 46 and an A allele at positions 4979-4981 of SEQ ID NO: 7; or
4) a haplotype comprising an A allele at position 4641 of SEQ ID NO: 7 and a G allele at position 472 of SEQ ID NO: 48.

In some embodiments, the marker can comprise, consist essentially of, or consist of:
1) a haplotype comprising SEQ ID NO:3, SEQ ID NO:5, SEQ ID NO:7, SEQ ID NO:11, SEQ ID NO:13, SEQ ID NO:16, SEQ ID NO:20 and SEQ ID NO:25;
2) a haplotype comprising SEQ ID NO:2, SEQ ID NO:3, SEQ ID NO:5, SEQ ID NO:9, SEQ ID NO:18, SEQ ID NO:22, SEQ ID NO:26 and SEQ ID NO:27;
3) a haplotype comprising SEQ ID NO:1, SEQ ID NO:4, SEQ ID NO:6, SEQ ID NO:9, SEQ ID NO:12, SEQ ID NO:14, SEQ ID NO:15, SEQ ID NO:20, SEQ ID NO:21 and SEQ ID NO:28;
4) a haplotype comprising SEQ ID NO:4, SEQ ID NO:7, SEQ ID NO:9, SEQ ID NO:13, SEQ ID NO:18, SEQ ID NO:19 and SEQ ID NO:21;
5) a haplotype comprising SEQ ID NO:3, SEQ ID NO:8, SEQ ID NO:10, SEQ ID NO:13, SEQ ID NO:17, SEQ ID NO:23, SEQ ID NO:24, SEQ ID NO:25 and SEQ ID NO:28; or
6) a haplotype comprising SEQ ID NO:4, SEQ ID NO:7, SEQ ID NO:14, SEQ ID NO:17 and SEQ ID NO:28.

In some embodiments, the marker can comprise, consist essentially of, or consist of:
1) a haplotype comprising SEQ ID NO:3, SEQ ID NO:5 and SEQ ID NO:11
2) a haplotype comprising SEQ ID NO:2, SEQ ID NO:3, SEQ ID NO:5, SEQ ID NO:9, SEQ ID NO:18 and SEQ ID NO:22;
3) a haplotype comprising SEQ ID NO:1, SEQ ID NO:4, SEQ ID NO:6, SEQ ID NO:9, SEQ ID NO:14 and SEQ ID NO:28;
4) a haplotype comprising SEQ ID NO:4, SEQ ID NO:9 and SEQ ID NO:18;
5) a haplotype comprising SEQ ID NO:3, SEQ ID NO:10, SEQ ID NO:17 and SEQ ID NO:28; or
6) a haplotype comprising SEQ ID NO:4, SEQ ID NO:14, SEQ ID NO:17 and SEQ ID NO:28.

In some embodiments, the marker can comprise, consist essentially of, or consist of:
1) SEQ ID NO:3;
2) SEQ ID NO:4;
3) a haplotype comprising SEQ ID NO:2 and SEQ ID NO:3; or
4) a haplotype comprising SEQ ID NO:4 and SEQ ID NO:6.

In some embodiments, the marker can comprise, consist essentially of, or consist of:
1) a haplotype comprising SEQ ID NO:87, SEQ ID NO:89, SEQ ID NO:91, SEQ ID NO:95, SEQ ID NO:97, SEQ ID NO:100, SEQ ID NO:104 and SEQ ID NO:109;
2) a haplotype comprising SEQ ID NO:86, SEQ ID NO:87, SEQ ID NO:89, SEQ ID NO:93, SEQ ID NO:102, SEQ ID NO:106, SEQ ID NO:110 and SEQ ID NO:111;
3) a haplotype comprising SEQ ID NO:85, SEQ ID NO:88, SEQ ID NO:90, SEQ ID NO:93, SEQ ID NO:96, SEQ ID NO:98, SEQ ID NO:99, SEQ ID NO:104, SEQ ID NO:105 and SEQ ID NO:112;
4) a haplotype comprising SEQ ID NO:88, SEQ ID NO:91, SEQ ID NO:93, SEQ ID NO:97, SEQ ID NO:102, SEQ ID NO:103 and SEQ ID NO:105;
5) a haplotype comprising SEQ ID NO:87, SEQ ID NO:92, SEQ ID NO:94, SEQ ID NO:97, SEQ ID NO:101, SEQ ID NO:107, SEQ ID NO:108, SEQ ID NO:109 and SEQ ID NO:112; or
6) a haplotype comprising SEQ ID NO:88, SEQ ID NO:91, SEQ ID NO:98, SEQ ID NO:101 and SEQ ID NO:112.

In some embodiments, the marker can comprise, consist essentially of, or consist of:
1) a haplotype comprising SEQ ID NO:87, SEQ ID NO:89 and SEQ ID NO:95;
2) a haplotype comprising SEQ ID NO:86, SEQ ID NO:87, SEQ ID NO:89, SEQ ID NO:93, SEQ ID NO:102 and SEQ ID NO:106;
3) a haplotype comprising SEQ ID NO:85, SEQ ID NO:88, SEQ ID NO:90, SEQ ID NO:93, SEQ ID NO:98 and SEQ ID NO:112;
4) a haplotype comprising SEQ ID NO:88, SEQ ID NO:93 and SEQ ID NO:102;
5) a haplotype comprising SEQ ID NO:87, SEQ ID NO:94, SEQ ID NO:101 and SEQ ID NO:112; or
6) a haplotype comprising SEQ ID NO:88, SEQ ID NO:98, SEQ ID NO:101 and SEQ ID NO:112.

In some embodiments, the marker can comprise, consist essentially of, or consist of:
1) SEQ ID NO:87;
2) SEQ ID NO:88;
3) a haplotype comprising SEQ ID NO:86 and SEQ ID NO:87; or
4) a haplotype comprising SEQ ID NO:88 and SEQ ID NO:90.

Particular nucleotides that are present at particular locations in the markers and nucleic acids disclosed herein can be determined using standard molecular biology techniques including, but not limited to amplification of genomic DNA from plants and subsequent sequencing. Additionally, oligonucleotide primers can be designed that would be expected to specifically hybridize to particular sequences that include the polymorphisms disclosed herein. For example, oligonucleotides can be designed to distinguish between the "A" allele and the "G" allele at a nucleotide position that corresponds to position 270 of SEQ ID NO: 1 using oligonucleotides comprising, consisting essentially of, or consisting of SEQ ID NOs: 232 and 233. The relevant difference between SEQ ID NOs: 232 and 233 is that the former has a G nucleotide at position 19 and the latter has an A nucleotide at position 19. Thus, SEQ ID NO: 232 hybridization conditions can be designed that would permit SEQ ID NO: 232 to specifically hybridize to the "G" allele, if present, but not hybridize to the "A" allele, if present. Thus, hybridization using these two primers that differ in only one nucleotide can be employed to assay for the presence of one or the other allele at a nucleotide position that corresponds to position 270 of SEQ ID NO: 1.

In some embodiments, the alleles comprising the marker associated with enhanced drought tolerance are detected using a plurality of probes selected from the group consisting of:

(i) SEQ ID NOs: 348 and 349; SEQ ID NOs: 350 and 351; SEQ ID NOs: 360 and 361; SEQ ID NOs: 372 and 373; SEQ ID NOs: 382 and 383; SEQ ID NOs: 388 and 389; SEQ ID NOs: 382 and 383; and SEQ ID NOs: 398 and 399;

(ii) SEQ ID NOs: 350 and 251; SEQ ID NOs: 356 and 357; SEQ ID NOs: 364 and 365; SEQ ID NOs: 366 and 367; SEQ ID NOs: 374 and 375; SEQ ID NOs: 378 and 379; SEQ ID NOs: 382 and 383; and SEQ ID NOs: 384 and 385;

(iii) SEQ ID NOs: 348 and 349; SEQ ID NOs: 352 and 353; SEQ ID NOs: 358 and 359; SEQ ID NOs: 362 and 363; SEQ ID NOs: 370 and 371; SEQ ID NOs: 374 and 375; SEQ ID NOs: 382 and 383; SEQ ID NOs: 386 and 387; and SEQ ID NOs: 394 and 395;

(iv) SEQ ID NOs: 346 and 347; SEQ ID NOs: 352 and 353; SEQ ID NOs: 356 and 357; SEQ ID NOs: 372 and 373; SEQ ID NOs: 388 and 389; and SEQ ID NOs: 394 and 395;

(v) SEQ ID NOs: 351 and 351; SEQ ID NOs: 354 and 355; SEQ ID NOs: 368 and 369; SEQ ID NOs: 372 and 373; SEQ ID NOs: 376 and 377; SEQ ID NOs: 386 and 387; SEQ ID NOs: 390 and 391; SEQ ID NOs: 396 and 397; and SEQ ID NOs: 398 and 399;

(vi) SEQ ID NOs: 352 and 353; SEQ ID NOs: 354 and 355; SEQ ID NOs: 370 and 371; SEQ ID NOs: 386 and 387; SEQ ID NOs: 388 and 389;

(vii) SEQ ID NOs: 350 and 351; SEQ ID NOs: 382 and 383; SEQ ID NOs: 388 and 389; and SEQ ID NOs: 392 and 393;

(viii) SEQ ID NOs: 350 and 351; SEQ ID NOs: 366 and 367; SEQ ID NOs: 374 and 375; SEQ ID NOs: 378 and 379; SEQ ID NOs: 382 and 383; and SEQ ID NOs: 384 and 385;

(ix) SEQ ID NOs: 352 and 353; SEQ ID NOs: 370 and 371; SEQ ID NOs: 380 and 381; SEQ ID NOs: 382 and 383; and SEQ ID NOs: 386 and 387;

(x) SEQ ID NOs: 352 and 353; SEQ ID NOs: 356 and 357; and SEQ ID NOs: 388 and 389;

(xi) SEQ ID NOs: 350 and 351; SEQ ID NOs: 354 and 355; SEQ ID NOs: 376 and 377; and SEQ ID NOs: 386 and 387;

(xii) SEQ ID NOs: 350 and 351;

(xiii) SEQ ID NOs: 352 and 353;

(xiv) SEQ ID NOs: 350 and 351 and SEQ ID NOs: 378 and 379; and (xv) SEQ ID NOs: 352 and 353 and SEQ ID NOs: 382 and 383, In some embodiments, the marker can comprise, consist essentially of, or consist of the reverse complement of any of the aforementioned markers. In some embodiments, one or more of the alleles that make up a marker haplotype is present as described above, whilst one or more of the other alleles that make up the marker haplotype is present as the reverse complement of the allele(s) described above. In some embodiments, each of the alleles that make up a marker haplotype is present as the reverse complement of the allele(s) described above.

In some embodiments, the marker can comprise, consist essentially of, or consist of an informative fragment of any of the aforementioned markers, the reverse complement of any of the aforementioned markers, or an informative fragment of the reverse complement of any of the aforementioned markers. In some embodiments, one or more of the alleles/sequences that make up a marker haplotype is present as described above, whilst one or more of the other alleles/sequences that make up the marker haplotype is present as the reverse complement of the alleles/sequences described above. In some embodiments, one or more of the alleles/sequences that make up a marker haplotype is present as described above, whilst one or more of the other alleles/sequences that make up the marker haplotype is present as an informative fragment of the alleles/sequences described above. In some embodiments, one or more of the alleles/sequences that make up a marker haplotype is present as described above, whilst one or more of the other alleles/sequences that make up the marker haplotype is present as an informative fragment of the reverse complement of the alleles/sequences described above. In some embodiments, each of the alleles/sequences that make up a marker haplotype is present as an informative fragment of the alleles/sequences described above, the reverse complement of the alleles/sequences described above, or an informative fragment of the reverse complement of the alleles/sequences described above.

In some embodiments, the marker can comprise, consist essentially of, or consist of any marker linked to the aforementioned markers. That is, any allele and/or haplotype that is in linkage disequilibrium with any of the aforementioned markers can also be used to identify, select and/or produce a maize plant with enhanced drought tolerance. Linked markers can be determined, for example, by using resources available on the MaizeGDB website.

Isolated and purified markers associated with enhanced drought tolerance are also provided. Such markers can comprise, consist essentially of, or consist of a nucleotide sequence as set forth in any of SEQ ID NOs: 1-117, 400, AND 401, the reverse complement thereof, or an informative fragment thereof. In some embodiments, the marker comprises a detectable moiety. In some embodiments, the marker permits the detection of one or more of the marker alleles identified herein.

Compositions comprising a primer pair capable of amplifying a nucleic acid sample isolated from a maize plant or germplasm to generate a marker associated with enhanced drought tolerance are also provided. In some embodiments, the marker comprises a nucleotide sequence as set forth herein, the reverse complement thereof, or an informative fragment thereof. In some embodiments, the marker comprises a nucleotide sequence that is at least about 50%, 55%, 60%, 65%, 70%, 75%, 80%, 85%, 90%, 95%, 97%, 99% or 100%, identical to a nucleotide sequence set forth herein, the reverse complement thereof, or an informative fragment thereof. In some embodiments, the primer pair is one of the amplification primer pairs identified in Table 1 above. One of ordinary skill in the art will understand how to select alternative primer pairs according to methods well known in the art.

Table 5 provides a summary of favorable alleles and single-locus haplotypes that are associated with water optimization.

TABLE 5

Summary of Exemplary Alleles and Single-Locus Haplotypes

| SEQ ID NO: | Position | Favorable* | HAPL** | HAPL CODE |
|---|---|---|---|---|
| 1 | 115 |  | G | A |
|  | 270 | A (Y) | A |  |
|  | 301 |  | T |  |
|  | 483 |  | A |  |
| 2 | 100 | G |  |  |
|  | 264-271 | DEL |  |  |
| 3 | 216 | G (Y) |  |  |
| 4 | 503 | A (Y) |  |  |
| 5 | 818-821 | INS (Y) |  |  |
| 6 | 254 | G (Y); A (P) |  |  |

TABLE 5-continued

Summary of Exemplary Alleles and Single-Locus Haplotypes

| SEQ ID NO: | Position | Favorable* | HAPL** | HAPL CODE |
|---|---|---|---|---|
| 7 | 4497-4498 | GA (Y) | DEL | B |
|  | 4505 |  | G |  |
|  | 4609 |  | T |  |
|  | 4641 | A (Y); A | A |  |
|  | 4792 | C (Y); T (Y) | T |  |
|  | 4836 | T (Y) | T |  |
|  | 4844 |  | C |  |
|  | 4969 |  | G |  |
|  | 4979-4981 | A (Y); G (Y) | TCC |  |
| 8 | 217 | A (P) | A | C |
|  | 390 |  | G |  |
|  | 477 |  | A |  |
| 9 | 292 | C (Y); C (P) |  |  |
| 10 | 166 | A (Y); A (P) |  |  |
| 11 | 148 | G (P) |  |  |
| 12 | 94 | C (Y); C |  |  |
| 13 | 35 | A (P) |  |  |
|  | 86 | C (Y); C |  |  |
|  | 89 | G (Y) |  |  |
| 14 | 432 | G (P) |  |  |
| 15 | 753 | A (Y) |  |  |
| 16 | 755 | G (Y) |  |  |
| 17 | 431 | G (Y) |  |  |
| 18 | 518 | G (P); T (W) |  |  |
| 19 | 182 | A (P) | G | D |
|  | 309 | A (Y); A | A |  |
|  | 330 |  | G |  |
|  | 463 | G; C (P) | G |  |
| 20 | 773-776 | C (Y); C (P) |  |  |
| 21 | 61 |  | C | E |
|  | 200 |  | C |  |
|  | 316-324 | T (Y) | DEL |  |
| 22 | 211 | G (P) |  |  |
| 23 | 116 | G |  |  |
|  | 217 | A |  |  |
| 24 | 746 | C |  |  |
| 25 | 562 | G (Y); G (P); G |  |  |
| 26 | 1271 | C |  |  |
| 27 | 64 |  | G | F |
|  | 254 | C; T (Y); C (P) | T |  |
| 28 | 98 |  | C | G |
|  | 147 |  | T |  |
|  | 224 |  | C |  |
|  | 496 | T (Y) | T |  |
| 29 | 258 | C |  |  |
| 30 | 259 | T (R) | T | H |
|  | 296 |  | T |  |
|  | 398 | G (Y) | A |  |
|  | 1057 |  | C |  |
| 31 | 239 | G (Y); G (P) |  |  |
| 32 | 208 | G (Y) |  |  |
| 33 | 391 | A |  |  |
| 34 | 144-145 | C (Y); C(P) |  |  |
|  | 169 | T (Y) |  |  |
|  | 537 | A (P) |  |  |
| 35 | 76 | G (Y) |  |  |
| 36 | 500 |  | C | I |
|  | 568 |  | G |  |
|  | 698 | T (Y) | T |  |
| 37 | 375 | A |  |  |
|  | 386 | A (P); G (Y); A (Y) |  |  |
| 38 | 309 | C (P) |  |  |
|  | 342 | A (P) |  |  |
| 39 | 445 | G (Y); C (P) |  |  |
| 40 | 602 | A (Y) |  |  |
| 41 | 190 | G (Y); A (P) |  |  |
|  | 580 | C (Y) |  |  |
| 42 | 238 |  | A | J |
|  | 266-268 | INS (Y) | DEL |  |
|  | 808 |  | C |  |
| 43 | 708 | C (P); A (Y) |  |  |
| 44 | 266 | A |  |  |
| 45 | 475 | T |  |  |
| 46 | 386 | C |  |  |
| 47 | 87 | G |  |  |
| 48 | 472 | A; G |  |  |
| 49 | 166 |  | C | K |
|  | 224 |  | A |  |
|  | 650 | G (Y); G (P) | G |  |
|  | 892 |  | G |  |
| 50 | 541 | T (Y); A (Y) |  |  |
| 51 | 111 | G |  |  |
| 52 | 442 | C; G |  |  |
| 53 | 83 |  | C | L |
|  | 428 | C (P); T (Y) | C |  |
|  | 491 | C (Y); C (P) | C |  |
|  | 548 |  | C |  |
| 54 | 126 | A (Y) |  |  |
| 55 | 193 | G |  |  |
| 56 | 237 | G |  |  |
|  | 516 | C |  |  |
| 57 | 173 | T |  |  |
| 58 | 486 | C |  |  |
| 59 | 729 | G |  |  |
| 60 | 267 | G |  |  |
| 400 | 83 | C | C | M |
|  | 119 | A | A |  |
|  | 601 | T | T |  |

*(Y): YGSMN; (P): GMSTP; (W): GWTPN

**HAPL refers to single-locus haplotypes (i.e., haplotypes that comprise a particular grouping of favorable alleles present together).

As used herein, the phrase "haplotype code" refers to a collection of SNPs present in a plant, wherein each favorable allele listed in the single locus haplotype column of Table 5 is present in the plant. For example, a plant is said to have "haplotype A" when at least one locus corresponding to SEQ ID NO: 1 in the plant has a G at nucleotide position 115, an A at position 270 of SEQ ID NO: 1, a T at nucleotide position 301, and an A at position 483. Haplotype A can be alternatively referred to as "GATA" with respect to these particular nucleotide positions. Similarly, a plant is said to have "haplotype C" when at least one locus correspond to SEQ ID NO: 8 in the plant has an A at nucleotide position 217, a G at nucleotide position 290, and an A at position 477 of SEQ ID NO: 8. Haplotype C can thus be alternatively referred to as "AGA" with respect to these particular nucleotide positions.

The identification of plants with different alleles and/or haplotypes of interest can provide starting materials for combining alleles and/or haplotypes in progeny plants via breeding strategies designed to "stack" the alleles and/or haplotypes. As used herein, the term "stacking", and grammatical variants thereof, refers to the intentional accumulation by breeding (including but not limited to crossing two plants, selfing a single plant, and/or creating a double haploid from a single plant) of favorable water optimization haplotypes in plants such that a plant's genome has at least one additional favorable water optimization haplotype than its immediate progenitor(s). Stacking includes in some embodiments conveying one or more water optimization traits, alleles, and/or haplotypes into a progeny maize plant such that the progeny maize plant includes higher number of water optimization traits, alleles, and/or haplotypes than does either parent from which it was derived. By way of example and not limitation, if Parent 1 has haplotypes A, B, and C, and Parent 2 has haplotypes D, E, and F, "stacking" refers to the production of a plant that has any of A, B, and C, with any combination of D, E, and F. Particularly, "stacking" refers in some embodiments to producing a plant that has A, B, and C as well as one or more of D, E, and F, or producing a plant that has D, E, and F as well as one or more of A, B, and C. In some embodiments, "stacking" refers to the production of a plant from a biparental cross that contains all water optimization associated haplotypes possessed by either parent.

In some embodiments, the water optimization trait is Grain Yield—Drought, and the favorable haplotype comprises a nucleotide sequence comprising a T at nucleotide position 301, a G at nucleotide position 115, an A at nucleotide position 483, and an A at nucleotide position 270 of SEQ ID NO: 1; a TCC trinucleotide at nucleotide positions 4979-4981, a G at nucleotide position 4969, an A at nucleotide position 4641, a T at nucleotide position 4609, a deletion of nucleotide positions 4497-4498, a T at nucleotide position 4792, a T at nucleotide position 4836, a G at nucleotide position 4505, and a C at nucleotide position 4844 of SEQ ID NO: 7; an A at nucleotide position 217, a G at nucleotide position 390, and an A at nucleotide position 477 of SEQ ID NO: 8; a G at nucleotide position 463, a G at nucleotide position 330, a G at nucleotide position 182, and an A at nucleotide position 309 of SEQ ID NO: 19; a G at nucleotide position 64 and an A at nucleotide position 254 of SEQ ID NO: 27; a C at nucleotide position 98, a T at nucleotide position 147, a C at nucleotide position 224, and a T at nucleotide position 496 of SEQ ID NO: 28; a C at nucleotide position 500, a G at nucleotide position 568, and a T at nucleotide position 698 of SEQ ID NO: 36; a deletion of nucleotide positions 266-267, a C at nucleotide position 808, and an A at nucleotide position 238 of SEQ ID NO: 42; and/or a C at nucleotide position 166, an A at nucleotide position 224, a G at nucleotide position 650, and a G at nucleotide position 892 of SEQ ID NO: 49.

In some embodiments, the water optimization trait is Grain Yield—Well Watered, and the favorable haplotype comprises a nucleotide sequence comprising an A at nucleotide position 217, a G at nucleotide position 390, and an A at nucleotide position 477 of SEQ ID NO: 8; a C at nucleotide position 500, a G at nucleotide position 568, and a T at nucleotide position 698 of SEQ ID NO: 36; and/or a C at nucleotide position 83, a C at nucleotide position 548, a C at nucleotide position 491, and a C at nucleotide position 428 of SEQ ID NO: 53.

In some embodiments, the water optimization trait is Yield Reduction—Hybrid, and the favorable haplotype comprises a nucleotide sequence comprising a C at nucleotide position 98, a T at nucleotide position 147, a C at nucleotide position 224, and a T at nucleotide position 496 of SEQ ID NO: 28.

In some embodiments, the water optimization trait is Yield Reduction—Inbred, and the favorable haplotype comprises a nucleotide sequence comprising a TCC trinucleotide at nucleotide positions 4979-4981, a G at nucleotide position 4969, an A at nucleotide position 4641, a T at nucleotide position 4609, a deletion of nucleotide positions 4497-4498, a T at nucleotide position 4792, a T at nucleotide position 4836, a G at nucleotide position 4505, and a C at nucleotide position 4844 of SEQ ID NO: 7; an A at nucleotide position 217, a G at nucleotide position 390, and an A at nucleotide position 477 of SEQ ID NO: 8; a G at nucleotide position 64 and an A at nucleotide position 254 of SEQ ID NO: 27; and/or a C at nucleotide position 83, a C at nucleotide position 548, a C at nucleotide position 491, and a C at nucleotide position 428 of SEQ ID NO: 53.

In some embodiments, the water optimization trait is ASI, and the favorable haplotype comprises a nucleotide sequence comprising a TCC trinucleotide at nucleotide positions 4979-4981, a G at nucleotide position 4969, an A at nucleotide position 4641, a T at nucleotide position 4609, a deletion of nucleotide positions 4497-4498, a T at nucleotide position 4792, a T at nucleotide position 4836, a G at nucleotide position 4505, and a C at nucleotide position 4844 of SEQ ID NO: 7.

In some embodiments, the water optimization trait is Percent Barren, and the favorable haplotype comprises a nucleotide sequence comprising a TCC trinucleotide at nucleotide positions 4979-4981, a G at nucleotide position 4969, an A at nucleotide position 4641, a T at nucleotide position 4609, a deletion of nucleotide positions 4497-4498, a T at nucleotide position 4792, a T at nucleotide position 4836, a G at nucleotide position 4505, and a C at nucleotide position 4844 of SEQ ID NO: 7; a G at nucleotide position 463, a G at nucleotide position 330, a G at nucleotide position 182, and an A at nucleotide position 309 of SEQ ID NO: 19; a C at nucleotide position 61, a C at nucleotide position 200, and a deletion of nucleotide positions 316-324 of SEQ ID NO: 21; and/or an A at nucleotide position 398, a T at nucleotide position 296, a T at nucleotide position 259, and a C at nucleotide position 1057 of SEQ ID NO: 30.

In some embodiments of the presently disclosed subject matter, the genomes of inbred or hybrid Zea mays plants comprise at least three, four, five, six, seven, eight, or nine of haplotypes A-M, wherein haplotypes A-M are associated with water optimization and are defined herein. In some embodiments, the inbred or hybrid Zea mays plant comprises a genome comprising Haplotypes C, D, and G; Haplotypes C, D, and L; Haplotypes C, G, and H; Haplotypes C, G, and I; Haplotypes C, I, and L; Haplotypes E, G, and I; Haplotypes F, G, and H; Haplotypes A, C, F, and G; Haplotypes C, E, H, and I; Haplotypes C, G, H, and I; Haplotypes C, H, I, and K; Haplotypes C, H, I, and L; Haplotypes E, F, G, and H; Haplotypes A, C, G, H, and I; Haplotypes B, C, D, G, and L; Haplotypes C, E, G, H, and I; Haplotypes C, G, H, I, and L; Haplotypes A, C, G, H, I, and K; Haplotypes C, E, F, G, H, I, J, K, and L; Haplotypes C, D, G, and M; Haplotypes C, D, L, and M; Haplotypes C, G, H, and M; Haplotypes C, G, I, and M; Haplotypes C, I, L, and M; Haplotypes E, G, I, and M; Haplotypes F, G, H, and M; Haplotypes A, C, F, G, and M; Haplotypes C, E, H, I, and M; Haplotypes C, G, H, I, and M; Haplotypes C, H, I, K, and M; Haplotypes C, H, I, L, and M; Haplotypes E, F, G, H, and M; Haplotypes A, C, G, H, I, and M; Haplotypes B, C, D, G, L, and M; Haplotypes C, E, G, H, I, and M; Haplotypes C, G, H, I, L, and M; Haplotypes A, C, G, H, I, K, and M; and Haplotypes C, E, F, G, H, I, J, K, L, and M. In some embodiments, the inbred or hybrid Zea mays plant is a hybrid plant that is homozygous for at least one of Haplotypes A-M.

In some embodiments, the inbred or hybrid Zea mays plant comprises a genome comprising Haplotypes A, C, E, G, H, and I, optionally further comprising Haplotype M; Haplotypes B, C, D, E, F, G, H, I, and L, optionally further comprising Haplotype M; Haploypyes C, D, E, F, G, H, and L, optionally further comprising Haplotype M; Haplotypes B, C, D, G, I, and L, optionally further comprising Haplotype M; Haplotypes B, C, D, E, G, H, I, and L, optionally further comprising Haplotype M; Haplotypes C, D, E, F, G, H, I, J, K, and L, optionally further comprising Haplotype M; Haplotypes A, C, G, H, and I, optionally further comprising Haplotype M; Haplotypes C, E, F, G, H, and I, optionally further comprising Haplotype M; Haplotypes C, E, F, G, H, I, and L, optionally further comprising Haplotype M; Haplotypes C, D, E, F, G, and H, optionally further comprising Haplotype M; Haplotypes D, E, F, G, and H, optionally further comprising Haplotype M; Haplotypes A, C, G, H, and I, optionally further comprising Haplotype M; Haplotypes A, C, E, G, H, I, and K, optionally further comprising Haplotype M; Haplotype C, E, G, H, I, and L, optionally further comprising Haplotype M; Haplotypes C, D, E, G, H, I, and L, optionally further comprising Haplotype M; Haplotypes B, C, D, E, G, H, I, and L, optionally further comprising Haplotype M; Haplotypes A, C, G, H, and I, optionally further comprising Haplotype M; Haplotypes A, C, G, H, I, and K, optionally further comprising Haplotype M; Haplotypes C, G H, I, and L, optionally further comprising Haplotype M; Haplotypes C, D, G, H, I, and L, optionally further comprising Haplotype M; Haplotypes B, C, D, G, H, I, and L, optionally further comprising Haplotype M; Haplotypes A, C, E, F, G, H, and I, optionally further comprising Haplotype M; Haplotypes A, C, E, F, G, H, I, and K, optionally further comprising Haplotype M; Haplotypes C, E, F, G, H, I, and L, optionally further comprising Haplotype M; Haplotypes C, D, E, F, G, H, I, and L, optionally further comprising Haplotype M; Haplotypes A, C, E, F, G, H, I, J, K, and L, optionally further comprising Haplotype M; Haplotypes A, C, E, F, G, H, I, J, K, and L, optionally further comprising Haplotype M; Haplotypes C, E, F, G, H, I, J, K, and L, optionally further comprising Haplotype M; Haplotypes C, D, E, F, G, H, I, J, K, and L, optionally further comprising Haplotype M; Haplotypes B, C, D, E, F, G, H, I, J, K, and L, optionally further comprising Haplotype M; Haplotypes A, C, E, F, G, H, and I, optionally further comprising Haplotype M; Haplotypes A, C, E, F, G, H, I, and K, optionally further comprising Haplotype M; Haplotypes C, E, F, G, H, I, and L, optionally further comprising Haplotype M; Haplotypes B, C, D, E, F, G, H, and L, optionally further comprising Haplotype M; Haplotypes C, E, F, G, H, I, J, K, and L, optionally further comprising Haplotype M; Haplotypes C, D, G, H, and L, optionally further comprising Haplotype M; Haplotypes C, E, F, G, H, I, and L, optionally further comprising Haplotype M; and/or Haplotypes B, C, D, E, G, I, and L, optionally further comprising Haplotype M.

As used herein, a plant that comprises multiple haplotypes can also be referred to by a code designating the haplotypes its possesses. Thus, for example, a plant that comprises at least one copy of Haplotyes C, D, E, F, G, H, I, J, K, and L in its genome can be referred to as "CDEFGHIJKL"; a plant that comprises at least one copy of Haplotypes B, C, D, E, F, G, H, I, J, K, and L in its genome can be referred to as "BCDEFGHIJKL", etc. In some embodiments, uppercase and lowercase letters are employed to further delinate those haplotypes for which a plant (or a cell thereof) is either homozygous (e.g., uppercase) or heterozygous (e.g., lowercase). By way of example and not limitation, a plant or a cell that is referred to as CDEFGHIJKL has at least one of Haplotypes C, D, E, F, G, H, I, J, K, and L. In some embodiments, this designation would indicate that the plant or cell is homozygous for each of these haplotypes. Similarly, the designation cdefghijkl indicates that the plant or cell is heterozygous for Haplotypes C, D, E, F, G, H, I, J, K, and L. And finally, the designation CdeFGhijKL indicates that the plant or cell is homozygous for Haplotypes C, F, G, K, and L, is homozygous for Haplotypes D, E, H, I, and J. In some embodiments, this designation further indicates that plant or cell lacks Haplotypes A and B, although in some embodiments it indicates that the status of the plant or cell with respect to these Haplotypes is unknown or untested.

III. METHODS FOR INTROGRESSING ALLELES OF INTEREST AND FOR IDENTIFYING PLANTS COMPRISING THE SAME

III.A. Marker-Assisted Selection Generally

Markers can be used in a variety of plant breeding applications. See e.g., Staub et al., *Hortscience* 31: 729 (1996); Tanksley, *Plant Molecular Biology Reporter* 1: 3 (1983). One of the main areas of interest is to increase the efficiency of backcrossing and introgressing genes using marker-assisted selection (MAS). In general, MAS takes advantage of genetic markers that have been identified as having a significant likelihood of co-segregation with a desired trait. Such markers are presumed to be in/near the gene(s) that give rise to the desired phenotype, and their presence indicates that the plant will possess the desired trait. Plants which possess the marker are expected to transfer the desired phenotype to their progeny.

A marker that demonstrates linkage with a locus affecting a desired phenotypic trait provides a useful tool for the selection of the trait in a plant population. This is particularly true where the phenotype is hard to assay or occurs at a late stage in plant development. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing or imparting the trait. Having flanking markers decreases the chances that false positive selection will occur. The ideal situation is to have a marker in the gene itself, so that recombination cannot occur between the marker and the gene. Such a marker is called a "perfect marker."

When a gene is introgressed by MAS, it is not only the gene that is introduced but also the flanking regions. Gepts, *Crop Sci* 42:1780 (2002). This is referred to as "linkage drag." In the case where the donor plant is highly unrelated to the recipient plant, these flanking regions carry additional genes that can code for agronomically undesirable traits. This "linkage drag" can also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints. Young et al., *Genetics* 120:579 (1998). In classical breeding, it is usually only by chance that recombinations which contribute to a reduction in the size of the donor segment are selected. Tanksley et al., *Biotechnology* 7: 257 (1989). Even after 20 backcrosses, one can expect to find a sizeable piece of the donor chromosome still linked to the gene being selected. With markers, however, it is possible to select those rare individuals that have experienced recombination near the gene of interest. In 150 backcross plants, there is a 95% chance that at least one plant will have experienced a crossover within 1 cM of the gene, based on a single meiosis map distance. Markers allow for unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers. See Tanksley et al., supra. When the exact location of a gene is known, flanking markers surrounding the gene can be utilized to select for recombinations in different population sizes. For example, in smaller population sizes, recombinations can be expected further away from the gene, so more distal flanking markers would be required to detect the recombination.

The availability of integrated linkage maps of the maize genome containing increasing densities of public maize markers has facilitated maize genetic mapping and MAS.

See, e.g. the IBM2 Neighbors maps, which are available online on the MaizeGDB website.

Of all the molecular marker types, SNPs are the most abundant and have the potential to provide the highest genetic map resolution. Bhattramakki et al., *Plant Molec. Biol.* 48:539 (2002). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, *Hum. Mutat.* 17:475 (2001); Shi, *Clin. Chem.* 47:164 (2001); Kwok, *Pharmacogenomics* 1:95 (2000); Bhattramakki and Rafalski, *Discovery and application of single nucleotide polymorphism markers in plants, in* PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, Md.), Invader® (Hologic, Madison, Wis.), SnapShot® (Applied Biosystems, Foster City, Calif.), Taqman® (Applied Biosystems, Foster City, Calif.) and Beadarrays™ (Illumina, San Diego, Calif.).

A number of SNPs together within a sequence, or across linked sequences, can be used to describe a haplotype for any particular genotype. Ching et al., *BMC Genet.* 3:19 (2002); Gupta et al., (2001), Rafalski, *Plant Sci.* 162:329 (2002b). Haplotypes can be more informative than single SNPs and can be more descriptive of any particular genotype. For example, a single SNP can be allele "T" for a specific drought tolerant line or variety, but the allele "T" might also occur in the maize breeding population being utilized for recurrent parents. In this case, a combination of alleles at linked SNPs can be more informative. Once a unique haplotype has been assigned to a donor chromosomal region, that haplotype can be used in that population or any subset thereof to determine whether an individual has a particular gene. The use of automated high throughput marker detection platforms known to those of ordinary skill in the art makes this process highly efficient and effective.

The markers of the presently disclosed subject matter can be used in marker-assisted selection protocols to identify and/or select progeny with enhanced drought tolerance. Such methods can comprise, consist essentially of, or consist of crossing a first maize plant or germplasm with a second maize plant or germplasm, wherein the first maize plant or germplasm comprises a marker associated with enhanced drought tolerance, and selecting a progeny plant that possesses the marker. Either of the first and second maize plants, or both, can be of a non-naturally occurring variety of maize. In some embodiments, the first maize plant or germplasm is CML333, CML322, Cateto SP VII, Confite Morocho AYA 38, or Tuxpeno VEN 692. In some embodiments, the genome of the first maize plant or germplasm is at least about 50%, 55%, 60%, 65%, 70%, 75%, 80%, 85%, 90%, 95%, 97%, 99% or 100% identical to that of CML333, CML322, Cateto SP VII, Confite Morocho AYA 38, or Tuxpeno VEN 692. In some embodiments, the second maize plant or germplasm is of an elite variety of maize. In some embodiments, the genome of the second maize plant or germplasm is at least about 50%, 55%, 60%, 65%, 70%, 75%, 80%, 85%, 90%, 95%, 97%, 99% or 100% identical to that of an elite variety of maize. In some embodiments, the second maize plant is of the NP2391 variety. In some embodiments, the genome of the second maize plant is at least about 50%, 55%, 60%, 65%, 70%, 75%, 80%, 85%, 90%, 95%, 97%, 99% or 100% identical to that of NP2391.

III.B. Methods of Introgressing Alleles and/or Haplotypes of Interest

Thus, in some embodiments the presently disclosed subject matter provides methods for introgressing an allele associated with enhanced drought tolerance into a genetic background lacking said allele. In some embodiments, the methods comprise crossing a donor comprising said allele with a recurrent parent that lacks said allele; and repeatedly backcrossing progeny comprising said allele with the recurrent parent, wherein said progeny are identified by detecting, in their genomes, the presence of a haplotype associated with enhanced drought tolerance, wherein said haplotype is selected from the group consisting of:

a G nucleotide at the position that corresponds to position 100 of SEQ ID NO: 2, an ACT trinucleotide at the position that corresponds to positions 4979-4981 of SEQ ID NO: 7, a G nucleotide at the position that corresponds to position 116 of SEQ ID NO: 23, an A nucleotide at the position that corresponds to position 391 of SEQ ID NO: 33, an A nucleotide at the position that corresponds to position 472 of SEQ ID NO: 48, an A nucleotide at the position that corresponds to position 237 of SEQ ID NO: 56, a T nucleotide at the position that corresponds to position 173 of SEQ ID NO: 57, and a G nucleotide at the position that corresponds to position 267 of SEQ ID NO: 60;

an ACT trinucleotide at the position that corresponds to positions 4979-4981 of SEQ ID NO: 7, an A nucleotide at the position that corresponds to position 309 of SEQ ID NO: 19, a G nucleotide at the position that corresponds to position 562 of SEQ ID NO: 25, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;

a G nucleotide at the position that corresponds to position 100, an A nucleotide at the position that corresponds to position 4641 of SEQ ID NO: 7, an A nucleotide at the position that corresponds to position 217 of SEQ ID NO: 23, a C nucleotide at the position that corresponds to position 746 of SEQ ID NO: 24, a C nucleotide at the position that corresponds to position 258 of SEQ ID NO: 29, an A nucleotide at the position that corresponds to position 266 of SEQ ID NO: 44, a G nucleotide at the position that corresponds to position 472 of SEQ ID NO: 48, a G nucleotide at the position that corresponds to position 193 of SEQ ID NO: 55, and a C nucleotide at the position that corresponds to position 486 of SEQ ID NO: 58;

a deletion at nucleotide at the position that corresponds to positions 264-271 of SEQ ID NO: 2, an A nucleotide at the position that corresponds to position 4641 of SEQ ID NO: 7, an A nucleotide at the position that corresponds to position 309 of SEQ ID NO: 19, an A nucleotide at the position that corresponds to position 391 of SEQ ID NO: 33, a G nucleotide at the position that corresponds to position 237 of SEQ ID NO: 56, and a C nucleotide at the position that corresponds to position 486 of SEQ ID NO: 58;

an ACT trinucleotide at the position that corresponds to positions 4979-4981 of SEQ ID NO: 7, a G nucleotide at the position that corresponds to position 463 of SEQ ID NO: 19, a C nucleotide at the position that corresponds to position 254 of SEQ ID NO: 27, an A nucleotide at the position that corresponds to position 391 of SEQ ID NO: 33, a T nucleotide at the position that corresponds to position 475 of SEQ ID NO: 45, a G nucleotide at the position that corresponds to position 193 of SEQ ID NO: 55, a C nucleotide at the position that corresponds to position 516 of SEQ ID NO: 56, a G nucleotide at the position that corresponds to position 729 of SEQ ID NO: 59, and a G nucleotide at the position that corresponds to position 267 of SEQ ID NO: 60;

an A nucleotide at the position that corresponds to position 4641 of SEQ ID NO: 7, a G nucleotide at the position that corresponds to position 463 of SEQ ID NO: 19, a C nucleotide at the position that corresponds to position 258 of SEQ ID NO: 29, a G nucleotide at the position that corresponds to position 193 of SEQ ID NO: 55, and a G nucleotide at the position that corresponds to position 237 of SEQ ID NO: 56;

an ACT trinucleotide at the position that corresponds to positions 4979-4981 of SEQ ID NO: 7, an A nucleotide at the position that corresponds to position 472 of SEQ ID NO: 48, an A nucleotide at the position that corresponds to position 237 of SEQ ID NO: 56, and a T nucleotide at the position that corresponds to position 173 of SEQ ID NO: 57;

an ACT trinucleotide at the position that corresponds to positions 4979-4981 of SEQ ID NO: 7, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;

an A nucleotide at the position that corresponds to position 4641 of SEQ ID NO: 7, a C nucleotide at the position that corresponds to position 258 of SEQ ID NO: 29, a G nucleotide at the position that corresponds to position 87 of SEQ ID NO: 47, a G nucleotide at the position that corresponds to position 472 of SEQ ID NO: 48, and a G nucleotide at the position that corresponds to position 193 of SEQ ID NO: 55;

an A nucleotide at the position that corresponds to position 4641 of SEQ ID NO: 7, an A nucleotide at the position that corresponds to position 309 of SEQ ID NO: 19, and a G nucleotide at the position that corresponds to position 237 of SEQ ID NO: 56;

an ACT trinucleotide at the position that corresponds to positions 4979-4981 of SEQ ID NO: 7, a G nucleotide at the position that corresponds to position 463 of SEQ ID NO: 19, a T nucleotide at the position that corresponds to position 475 of SEQ ID NO: 45, and a G nucleotide at the position that corresponds to position 193 of SEQ ID NO: 55;

an ACT trinucleotide at the position that corresponds to positions 4979-4981 of SEQ ID NO: 7;

an A nucleotide at the position that corresponds to position 4641 of SEQ ID NO: 7;

an ACT trinucleotide at the position that corresponds to positions 4979-4981 of SEQ ID NO: 7 and a C nucleotide at the position that corresponds to position 386 of SEQ ID NO: 46; and an A nucleotide at the position that corresponds to position 4641 of SEQ ID NO: 7 and a G nucleotide at the position that corresponds to position 472 of SEQ ID NO: 48, and combinations thereof, thereby producing a drought tolerant maize plant or germplasm comprising said allele associated with enhanced drought tolerance in the genetic background of the recurrent parent, thereby introgressing the allele associated with enhanced drought tolerance into a genetic background lacking said allele. In some embodiments, the genome of said drought tolerant maize plant or germplasm comprising said allele associated with enhanced drought tolerance is at least about 95% identical to that of the recurrent parent. In some embodiments, either the donor or the recurrent parent, or both, is of a non-naturally occurring variety of maize.

In some embodiments of the presently disclosed methods, the genome of said donor is at least 95% identical to that of CML333, CML322, Cateto SP VII, Confite Morocho AYA 38, or Tuxpeno VEN 692. In some embodiments, said donor is selected from the group consisting of CML333, CML322, Cateto SP VII, Confite Morocho AYA 38, and Tuxpeno VEN 692. In some embodiments, the genome of said recurrent parent plant or germplasm is at least 95% identical to that of an elite variety of maize. In some embodiments, said recurrent parent is of an elite variety of maize. In some embodiments, 23.

III.D. Methods of Stacking Alleles and/or Haplotypes of Interest

The presently disclosed subject matter relates in some embodiments to "stacking" of haplotypes associated with water optimization in order to produce plants (and parts thereof) that have multiple favorable water optimization haplotypes. By way of example and not limitation, the presently disclosed subject matter relates in some embodiments to the identification and characterization of *Zea mays* loci that are each associated with one or more water optimization traits. These loci correspond to SEQ ID NOs: 1-413.

For each of these loci, favorable haplotypes have been identified that are associated with water optimization traits. These favorable haplotypes are summarized herein. The presently disclosed subject matter provides exemplary haplotypes that are associated with increases and decreases of various water optimization traits as defined herein. The phrase "favorable haplotype" refers to a haplotype that when present results in a quantitatively higher water optimization versus the case when an "unfavorable haplotype" is present. It is noted, however, then in the case where a lower water optimization is desirable, the haplotypes disclosed herein as "favorable" could be unfavorable haplotypes. As such, as used herein, "favorable" is employed in the context of increased water optimization, and would be reversed in the context of decreased water optimization.

III.E. Methods of Identifying Plants Comprising Alleles and/or Haplotypes of Interest Methods for identifying a drought tolerant maize plant or germplasm can comprise detecting the presence of a marker associated with enhanced drought tolerance. The marker can be detected in any sample taken from the plant or germplasm, including, but not limited to, the whole plant or germplasm, a portion of said plant or germplasm (e.g., a cell from said plant or germplasm) or a nucleotide sequence from said plant or germplasm. The maize plant can be of a non-naturally occurring variety of maize. In some embodiments, the genome of the maize plant or germplasm is at least about 50%, 55%, 60%, 65%, 70%, 75%, 80%, 85%, 90%, 95%, 97%, 99% or 100% identical to that of an elite variety of maize. In some embodiments, the genome of the maize plant is at least about 50%, 55%, 60%, 65%, 70%, 75%, 80%, 85%, 90%, 95%, 97%, 99% or 100%, identical to that of NP2391.

In some embodiments, the presently disclosed subject matter provides methods for introgressing an allele of interest of a locus associated with a water optimization trait into *Zea mays* germplasm. In some embodiments, the methods comprise:

(a) selecting a *Zea mays* plant that comprises an allele of interest of a locus associated with a water optimization trait, which allele is defined by at least one marker allele comprising a polymorphic site identifiable by PCR amplification of a *Zea mays* nucleic acid with a pair of oligonucleotides primers selected from among primer pair 1 represented by a primer comprising SEQ ID NO: 118 and a primer comprising SEQ ID NO: 119; primer pair 2 represented by a primer comprising SEQ ID NO: 120 and a primer comprising SEQ ID NO: 121; primer pair 3 represented by a primer comprising SEQ ID NO: 122 and a primer comprising SEQ ID NO: 123; primer pair 4 represented by a primer comprising SEQ ID NO: 124 and a primer comprising SEQ ID NO: 125; primer pair 5 represented by a primer comprising SEQ ID NO: 126 and a primer comprising SEQ ID NO: 127; primer pair 6 represented by a primer comprising SEQ ID NO: 128 and a primer comprising SEQ ID NO: 129; primer pair 7 represented by a primer comprising SEQ ID NO: 130 and a primer comprising SEQ ID NO: 131; primer pair 8 represented by a primer comprising SEQ ID NO: 132 and a primer comprising SEQ ID NO: 133; primer pair 9 represented by a primer comprising SEQ ID NO: 134 and a primer comprising SEQ ID NO: 135; primer pair 10 represented by a primer comprising SEQ ID NO: 136 and a primer comprising SEQ ID NO: 137; primer pair 11 represented by a primer comprising SEQ ID NO: 138 and a primer comprising SEQ ID NO: 139; primer pair 12 represented by a primer comprising SEQ ID NO: 140 and a primer comprising SEQ ID NO: 141; primer pair 13 represented by a primer comprising SEQ ID NO: 142 and a primer comprising SEQ ID NO: 143; primer pair 14 represented by a primer comprising SEQ ID NO: 144 and a primer comprising SEQ ID NO: 145; primer pair 15 represented by a primer comprising SEQ ID NO: 146 and a primer comprising SEQ ID NO: 147; primer pair 16 represented by a primer comprising SEQ ID NO: 148 and a primer comprising SEQ ID NO: 149; primer pair 17 represented by a primer comprising SEQ ID NO: 150 and a primer comprising SEQ ID NO: 151; primer pair 18 represented by a primer comprising SEQ ID NO: 152 and a primer comprising SEQ ID NO: 153; primer pair 19 represented by a primer comprising SEQ ID NO: 154 and a primer comprising SEQ ID NO: 155; primer pair 20 represented by a primer comprising SEQ ID NO: 156 and a primer comprising SEQ ID NO: 157; primer pair 21 represented by a primer comprising SEQ ID NO: 158 and a primer comprising SEQ ID NO: 159; primer pair 22 represented by a primer comprising SEQ ID NO: 160 and a primer comprising SEQ ID NO: 161; primer pair 23 represented by a primer comprising SEQ ID NO: 162 and a primer comprising SEQ ID NO: 163; primer pair 24 represented by a primer comprising SEQ ID NO: 164 and a primer comprising SEQ ID NO: 165; primer pair 25 represented by a primer comprising SEQ ID NO: 166 and a primer comprising SEQ ID NO: 167; primer pair 26 represented by a primer comprising SEQ ID NO: 168 and a primer comprising SEQ ID NO: 169; primer pair 27 represented by a primer comprising SEQ ID NO: 170 and a primer comprising SEQ ID NO: 171; primer pair 28 represented by a primer comprising SEQ ID NO: 172 and a primer comprising SEQ ID NO: 173; primer pair 29 represented by a primer comprising SEQ ID NO: 174 and a primer comprising SEQ ID NO: 175; primer pair 30 represented by a primer comprising SEQ ID NO: 176 and a primer comprising SEQ ID NO: 177; primer pair 31 represented by a primer comprising SEQ ID NO: 178 and a primer comprising SEQ ID NO: 179; primer pair 32 represented by a primer comprising SEQ ID NO: 180 and a primer comprising SEQ ID NO: 181; primer pair 33 represented by a primer comprising SEQ ID NO: 182 and a primer comprising SEQ ID NO: 183; primer pair 34 represented by a primer comprising SEQ ID NO: 184 and a primer comprising SEQ ID NO: 185; primer pair 35 represented by a primer comprising SEQ ID NO: 186 and a primer comprising SEQ ID NO: 187; primer pair 36 represented by a primer comprising SEQ ID NO: 188 and a primer comprising SEQ ID NO: 189; primer pair 37 represented by a primer comprising SEQ ID NO: 190 and a primer comprising SEQ ID NO: 191; primer pair 38 represented by a primer comprising SEQ ID NO: 192 and a primer comprising SEQ ID NO: 193; primer pair 39 represented by a primer comprising SEQ ID NO: 194 and a primer comprising SEQ ID NO: 195; primer pair 40 represented by a primer comprising SEQ ID NO: 196 and a primer comprising SEQ ID NO: 197; primer pair 41 represented by a primer comprising SEQ ID NO: 198 and a primer comprising SEQ ID NO: 199; primer pair 42 represented by a primer comprising SEQ ID NO: 200 and a primer comprising SEQ ID NO: 201; primer pair 43 represented by a primer comprising SEQ ID NO: 202 and a primer comprising SEQ ID NO: 203; primer pair 44 represented by a primer comprising SEQ ID NO: 204 and a primer comprising SEQ ID NO: 205; primer pair 45 represented by a primer comprising SEQ ID NO: 206 and a primer comprising SEQ ID NO: 207; primer pair 46 represented by a primer comprising SEQ ID NO: 208 and a primer comprising SEQ ID NO: 209; primer pair 47 represented by a primer comprising SEQ ID NO: 210 and a primer comprising SEQ ID NO: 211; primer pair 48 represented by a primer comprising SEQ ID NO: 212 and a primer comprising SEQ ID NO: 213; primer pair 49 represented by a primer comprising SEQ ID NO: 214 and a primer comprising SEQ ID NO: 215; primer pair 50 represented by a primer comprising SEQ ID NO: 216 and a primer comprising SEQ ID NO: 217; primer pair 51 represented by a primer comprising SEQ ID NO: 218 and a primer comprising SEQ ID NO: 219; primer pair 52 represented by a primer comprising SEQ ID NO: 220 and a primer comprising SEQ ID NO: 221; primer pair 53 represented by a primer comprising SEQ ID NO: 222 and a primer comprising SEQ ID NO: 223; primer pair 54 represented by a primer comprising SEQ ID NO: 224 and a primer comprising SEQ ID NO: 225; primer pair 55 represented by a primer comprising SEQ ID NO: 226 and a primer comprising SEQ ID NO: 227; primer pair 56 represented by a primer comprising SEQ ID NO: 228 and a primer comprising SEQ ID NO: 229; and primer pair 57 represented by a primer comprising SEQ ID NO: 230 and a primer comprising SEQ ID NO: 231; and (b) introgressing the allele of interest into *Zea mays* germplasm that lacks the allele. In some embodiments, the allele of interest comprises one of SEQ ID NOs: 1-117, 400, and 401 or a nucleotide sequence that is at least 85%, 90%, or 95% identical thereto over the full length of the one of SEQ ID NOs: 1-117, 400, and 401. In some embodiments, the allele of interest is a favorable allele and/or a favorable haplotype that positively correlates with a water optimization trait.

In some embodiments, the favorable allele comprises a nucleotide sequence at least 90% identical to one or more of SEQ ID NOs: 1-117, 400, and 401, and further comprises one or more of the particular nucleotide and position combinations disclosed herein. By way of example and not limitation, in some embodiments the favorable allele comprises a nucleotide sequence at least 90% identical to:

SEQ ID NO: 1, and further comprises a G nucleotide at the position that corresponds to position 115 of SEQ ID NO: 1, an A nucleotide at the position that corresponds to position 270 of SEQ ID NO: 1, a T nucleotide at the position that corresponds to position 301 of SEQ ID NO: 1, an A nucleotide at the position that corresponds to position 483 of SEQ ID NO: 1, or any combination thereof;

SEQ ID NO: 2, and further comprises a G nucleotide at the position that corresponds to position 100 and a deletion at the position that corresponds to positions 264-271 of SEQ ID NO: 2, or a combination thereof;

SEQ ID NO: 3, and further comprises a G nucleotide at the position that corresponds to position 216 of SEQ ID NO: 3;

SEQ ID NO: 4, and further comprises an A nucleotide at the position that corresponds to position 503 of SEQ ID NO: 4;

SEQ ID NO: 5, and further comprises a CGCG tetranucleotide at the position that corresponds to positions 818-821 of SEQ ID NO: 5;

SEQ ID NO: 6, and further comprises a G or an A nucleotide at the position that corresponds to position 254 of SEQ ID NO: 6;

SEQ ID NO: 7, and further comprises a GA dinucleotide at the position that corresponds to positions 4497-4498 of SEQ ID NO: 7, an A nucleotide at the position that corresponds to position 4641 of SEQ ID NO: 7, a C or a T nucleotide at the position that corresponds to position 4792 of SEQ ID NO: 7, a T nucleotide at the position that corresponds to position 4836 of SEQ ID NO: 7, an ACT or a TCC trinucleotide at the position that corresponds to positions 4979-4981 of SEQ ID NO: 7, or any combination thereof; or further comprises a deletion at positions 4497-4498 of SEQ ID NO: 7, a G nucleotide at the position that corresponds to position 4505 of SEQ ID NO: 7, a T nucleotide at the position that corresponds to position 4609 of SEQ ID NO: 7, an A nucleotide at the position that corresponds to position 4641 of SEQ ID NO: 7, a T nucleotide at the position that corresponds to position 4792 of SEQ ID NO: 7, a T nucleotide at the position that corresponds to position 4836 of SEQ ID NO: 7, a C nucleotide at the position that corresponds to position 4844 of SEQ ID NO: 7, a G nucleotide at the position that corresponds to position 4969 of SEQ ID NO: 7, and a TCC trinucleotide at the position that corresponds to positions 4979-4981 of SEQ ID NO: 7;

SEQ ID NO: 8, and further comprises an A nucleotide at the position that corresponds to position 217 of SEQ ID NO: 8, and optionally further comprises a G nucleotide at the position that corresponds to position 390 of SEQ ID NO: 8 and an A nucleotide at the position that corresponds to position 477 of SEQ ID NO: 8, or any combination thereof;

SEQ ID NO: 9, and further comprises a C nucleotide at the position that corresponds to position 292 of SEQ ID NO: 9;

SEQ ID NO: 10, and further comprises an A nucleotide at the position that corresponds to position 166 of SEQ ID NO: 10;

SEQ ID NO: 11, and further comprises a G nucleotide at the position that corresponds to position 148 of SEQ ID NO: 11;

SEQ ID NO: 12, and further comprises a C nucleotide at the position that corresponds to position 94 of SEQ ID NO: 12;

SEQ ID NO: 13, and further comprises an A nucleotide at the position that corresponds to position 35 of SEQ ID NO: 13, a C nucleotide at the position that corresponds to position 148 of SEQ ID NO: 13, or a G nucleotide at the position that corresponds to position 89 of SEQ ID NO: 13, or any combination thereof;

SEQ ID NO: 14, and further comprises a G nucleotide at the position that corresponds to position 432 of SEQ ID NO: 14;

SEQ ID NO: 15, and further comprises an A nucleotide at the position that corresponds to position 753 of SEQ ID NO: 15;

SEQ ID NO: 16, and further comprises a G nucleotide at the position that corresponds to position 755 of SEQ ID NO: 16;

SEQ ID NO: 17, and further comprises a G nucleotide at the position that corresponds to position 431 of SEQ ID NO: 17;

SEQ ID NO: 18, and further comprises a G or a T nucleotide at the position that corresponds to position 518 of SEQ ID NO: 18;

SEQ ID NO: 19, and further comprises an A nucleotide at the position that corresponds to position 182 of SEQ ID NO: 19, an A nucleotide at the position that corresponds to position 309 of SEQ ID NO: 19, or a G or a C nucleotide at the position that corresponds to position 463 of SEQ ID NO: 19, or any combination thereof; or that further comprises a G nucleotide at the position that corresponds to position 182 of SEQ ID NO: 19, an A nucleotide at the position that corresponds to position 309 of SEQ ID NO: 19, a G nucleotide at the position that corresponds to position 330 of SEQ ID NO: 19, and a G nucleotide at the position that corresponds to position 463 of SEQ ID NO: 19;

SEQ ID NO: 20, and further comprises a CTGG tetranucleotide at the position that corresponds to positions 773-776 of SEQ ID NO: 20;

SEQ ID NO: 21, and further comprises a deletion of nucleotide at the positions that correspond to positions 316-324 of SEQ ID NO: 21; or that further comprises a C nucleotide at the position that corresponds to position 61 of SEQ ID NO: 21, a C nucleotide at the position that corresponds to position 200 of SEQ ID NO: 21, and a deletion at the positions that correspond to positions 316-324 of SEQ ID NO: 21;

SEQ ID NO: 22, and further comprises a G nucleotide at the position that corresponds to position 211 of SEQ ID NO: 22;

SEQ ID NO: 23, and further comprises a G nucleotide at the position that corresponds to position 116 of SEQ ID NO: 23, an A nucleotide at the position that corresponds to position 217 of SEQ ID NO: 23, or a combination thereof;

SEQ ID NO: 24, and further comprises a C nucleotide at the position that corresponds to position 746 of SEQ ID NO: 24;

SEQ ID NO: 25, and further comprises a G nucleotide at the position that corresponds to position 562 of SEQ ID NO: 25;

SEQ ID NO: 26, and further comprises a C nucleotide at the position that corresponds to position 1271 of SEQ ID NO: 26;

SEQ ID NO: 27, and further comprises a C or a T nucleotide at the position that corresponds to position 254 of SEQ ID NO: 27; or that optionally further comprises a G nucleotide at the position that corresponds to position 64 of SEQ ID NO: 27 and a T nucleotide at the position that corresponds to position 254 of SEQ ID NO: 27;

SEQ ID NO: 28, and further comprises a T nucleotide at the position that corresponds to position 496 of SEQ ID NO: 28;

or further comprises a C nucleotide at the position that corresponds to position 98 of SEQ ID NO: 28, a T nucleotide at the position that corresponds to position 147 of SEQ ID NO: 28, a C nucleotide at the position that corresponds to position 224 of SEQ ID NO: 28, and a T nucleotide at the position that corresponds to position 496 of SEQ ID NO: 28;

SEQ ID NO: 29, and further comprises a C nucleotide at the position that corresponds to position 258 of SEQ ID NO: 29;

SEQ ID NO: 30, and further comprises a T nucleotide at the position that corresponds to position 259 of SEQ ID NO: 30, a G nucleotide at the position that corresponds to position 398 of SEQ ID NO: 30, or a combination thereof; or that further comprises a T nucleotide at the position that corresponds to position 259 of SEQ ID NO: 30, a T nucleotide at the position that corresponds to position 296 of SEQ ID NO: 30, an A nucleotide at the position that corresponds to position 398 of SEQ ID NO: 30, and a C nucleotide at the position that corresponds to position 1057 of SEQ ID NO: 30;

SEQ ID NO: 31, and further comprises a G nucleotide at the position that corresponds to position 239 of SEQ ID NO: 31;

SEQ ID NO: 32, and further comprises a G nucleotide at the position that corresponds to position 208 of SEQ ID NO: 32;

SEQ ID NO: 33, and further comprises an A nucleotide at the position that corresponds to position 391 of SEQ ID NO: 33;

SEQ ID NO: 34, and further comprises a CA dinucleotide at the position that corresponds to positions 144-145 of SEQ ID NO: 34, a T nucleotide at the position that corresponds to position 169 of SEQ ID NO: 34, an A nucleotide at the position that corresponds to position 537 of SEQ ID NO: 34, or any combination thereof;

SEQ ID NO: 35, and further comprises a G nucleotide at the position that corresponds to position 76 of SEQ ID NO: 35;

SEQ ID NO: 36, and further comprises a T nucleotide at the position that corresponds to position 698 of SEQ ID NO: 36; or that further comprises a C nucleotide at the position that corresponds to position 500 of SEQ ID NO: 36, a G nucleotide at the position that corresponds to position 568 of SEQ ID NO: 36, and a T nucleotide at the position that corresponds to position 698 of SEQ ID NO: 36;

SEQ ID NO: 37, and further comprises an A nucleotide at the position that corresponds to position 375 of SEQ ID NO: 37, an A or a G nucleotide at the position that corresponds to position 386 of SEQ ID NO: 37, or a combination thereof;

SEQ ID NO: 38, and further comprises a C nucleotide at the position that corresponds to position 309 of SEQ ID NO: 38, an A nucleotide at the position that corresponds to position 342 of SEQ ID NO: 38, or a combination thereof;

SEQ ID NO: 39, and further comprises a G or a C nucleotide at the position that corresponds to position 445 of SEQ ID NO: 39;

SEQ ID NO: 40, and further comprises an A nucleotide at the position that corresponds to position 602 of SEQ ID NO: 40;

SEQ ID NO: 41, and further comprises a G or an A nucleotide at the position that corresponds to position 190 of SEQ ID NO: 41, a C nucleotide at the position that corresponds to position 580 of SEQ ID NO: 41, or a combination thereof;

SEQ ID NO: 42, and further comprises a TTG trinucleotide at the position that corresponds to positions 266-268 of SEQ ID NO: 42; or that further comprises an A nucleotide at the position that corresponds to position 238 of SEQ ID NO: 42, a deletion of the nucleotides that corresponds to positions 266-268 of SEQ ID NO: 42, and a C nucleotide at the position that corresponds to position 808 of SEQ ID NO: 42;

SEQ ID NO: 43, and further comprises a C or an A nucleotide at the position that corresponds to position 708 of SEQ ID NO: 43;

SEQ ID NO: 44, and further comprises an A nucleotide at the position that corresponds to position 266 of SEQ ID NO: 44;

SEQ ID NO: 45, and further comprises a T nucleotide at the position that corresponds to position 475 of SEQ ID NO: 45;

SEQ ID NO: 46, and further comprises a C nucleotide at the position that corresponds to position 386 of SEQ ID NO: 46;

SEQ ID NO: 47, and further comprises a G nucleotide at the position that corresponds to position 87 of SEQ ID NO: 47;

SEQ ID NO: 48, and further comprises an A or a G nucleotide at the position that corresponds to position 472 of SEQ ID NO: 48;

SEQ ID NO: 49, and further comprises a G nucleotide at the position that corresponds to position 650 of SEQ ID NO: 49, and optionally also further comprises a C nucleotide at the position that corresponds to position 166 of SEQ ID NO: 49, and A nucleotide at the position that corresponds to position 224 of SEQ ID NO: 49, and a G nucleotide at the position that corresponds to position 892 of SEQ ID NO: 49;

SEQ ID NO: 50, and further comprises a T or an A nucleotide at the position that corresponds to position 541 of SEQ ID NO: 50;

SEQ ID NO: 51, and further comprises a G nucleotide at the position that corresponds to position 111 of SEQ ID NO: 51;

SEQ ID NO: 52, and further comprises a C or a G nucleotide at the position that corresponds to position 442 of SEQ ID NO: 52;

SEQ ID NO: 53, and further comprises a C or a T nucleotide at the position that corresponds to position 428 of SEQ ID NO: 53, a C nucleotide at the position that corresponds to position 491 of SEQ ID NO: 53, or a combination thereof; or that further comprises a C nucleotide at the positions that correspond to at positions 83, 428, 491, and 548 of SEQ ID NO: 53;

SEQ ID NO: 54, and further comprises an A nucleotide at the position that corresponds to position 126 of SEQ ID NO: 54;

SEQ ID NO: 55, and further comprises a G nucleotide at the position that corresponds to position 193 of SEQ ID NO: 55;

SEQ ID NO: 56, and further comprises and A or a G nucleotide at the position that corresponds to position 237 of SEQ ID NO: 56, a C nucleotide at the position that corresponds to position 516 of SEQ ID NO: 56, or a combination thereof;

SEQ ID NO: 57, and further comprises a T nucleotide at the position that corresponds to position 173 of SEQ ID NO: 57;

SEQ ID NO: 58, and further comprises a C nucleotide at the position that corresponds to position 486 of SEQ ID NO: 58;

SEQ ID NO: 59, and further comprises a G nucleotide at the position that corresponds to position 729 of SEQ ID NO: 59; and/or SEQ ID NO: 60, and further comprises a G nucleotide at the position that corresponds to position 267 of SEQ ID NO: 60.

Methods for producing a drought tolerant maize plant can comprise detecting, in a germplasm, a marker associated with enhanced drought tolerance and producing a maize plant from said germplasm. The germplasm can be of a non-naturally occurring variety of maize. In some embodiments, the genome of the germplasm is at least about 50%, 55%, 60%, 65%, 70%, 75%, 80%, 85%, 90%, 95%, 97%, 99% or 100% identical to that of an elite variety of maize. In some embodiments, the genome of the germplasm is at least about 50%, 55%, 60%, 65%, 70%, 75%, 80%, 85%, 90%, 95%, 97%, 99% or 100% identical to that of NP2391.

In some embodiments, the alleles comprising the marker associated with enhanced drought tolerance are detected using a plurality of probes selected from the group consisting of:
1) a haplotype comprising SEQ ID NO:87, SEQ ID NO:89, SEQ ID NO:91, SEQ ID NO:95, SEQ ID NO:97, SEQ ID NO:100, SEQ ID NO:104 and SEQ ID NO:109;
2) a haplotype comprising SEQ ID NO:86, SEQ ID NO:87, SEQ ID NO:89, SEQ ID NO:93, SEQ ID NO:102, SEQ ID NO:106, SEQ ID NO:110 and SEQ ID NO:111;
3) a haplotype comprising SEQ ID NO:85, SEQ ID NO:88, SEQ ID NO:90, SEQ ID NO:93, SEQ ID NO:96, SEQ ID NO:98, SEQ ID NO:99, SEQ ID NO:104, SEQ ID NO:105 and SEQ ID NO:112;
4) a haplotype comprising SEQ ID NO:88, SEQ ID NO:91, SEQ ID NO:93, SEQ ID NO:97, SEQ ID NO:102, SEQ ID NO:103 and SEQ ID NO:105;
5) a haplotype comprising SEQ ID NO:87, SEQ ID NO:92, SEQ ID NO:94, SEQ ID NO:97, SEQ ID NO:101, SEQ ID NO:107, SEQ ID NO:108, SEQ ID NO:109 and SEQ ID NO:112; and
6) a haplotype comprising SEQ ID NO:88, SEQ ID NO:91, SEQ ID NO:98, SEQ ID NO:101 and SEQ ID NO:112.

In some embodiments, the alleles comprising the marker associated with enhanced drought tolerance are detected using a plurality of probes selected from the group consisting of:
1) a haplotype comprising SEQ ID NO:87, SEQ ID NO:89 and SEQ ID NO:95;
2) a haplotype comprising SEQ ID NO:86, SEQ ID NO:87, SEQ ID NO:89, SEQ ID NO:93, SEQ ID NO:102 and SEQ ID NO:106;
3) a haplotype comprising SEQ ID NO:85, SEQ ID NO:88, SEQ ID NO:90, SEQ ID NO:93, SEQ ID NO:98 and SEQ ID NO:112;
4) a haplotype comprising SEQ ID NO:88, SEQ ID NO:93 and SEQ ID NO:102;
5) a haplotype comprising SEQ ID NO:87, SEQ ID NO:94, SEQ ID NO:101 and SEQ ID NO:112; and
6) a haplotype comprising SEQ ID NO:88, SEQ ID NO:98, SEQ ID NO:101 and SEQ ID NO:112.

In some embodiments, the allele(s) comprising the marker associated with enhanced drought tolerance is/are detected using a probe or probes selected from the group consisting of:
1) SEQ ID NO:87;
2) SEQ ID NO:88;
3) a haplotype comprising SEQ ID NO:86 and SEQ ID NO:87; and
4) a haplotype comprising SEQ ID NO:88 and SEQ ID NO:90.

In some embodiments, the alleles comprising the marker associated with enhanced drought tolerance are detected in amplification products from a nucleic acid sample isolated from a maize plant or germplasm, wherein the amplification products are produced using pairs of amplification primers selected from the group consisting of:
1) SEQ ID NO:31 and SEQ ID NO:59, SEQ ID NO:33 and SEQ ID NO:61, SEQ ID NO:35 and SEQ ID NO:63, SEQ ID NO:39 and SEQ ID NO:67, SEQ ID NO:41 and SEQ ID NO:69, SEQ ID NO:44 and SEQ ID NO:72, SEQ ID NO:48 and SEQ ID NO:76, and SEQ ID NO:53 and SEQ ID NO:81;
2) SEQ ID NO:30 and SEQ ID NO:58, SEQ ID NO:31 and SEQ ID NO:59, SEQ ID NO:33 and SEQ ID NO:61, SEQ ID NO:37 and SEQ ID NO:65, SEQ ID NO:46 and SEQ ID NO:74, SEQ ID NO:50 and SEQ ID NO:78, SEQ ID NO:54 and SEQ ID NO:82, and SEQ ID NO:55 and SEQ ID NO:83;
3) SEQ ID NO:29 and SEQ ID NO:57, SEQ ID NO:32 and SEQ ID NO:60, SEQ ID NO:34 and SEQ ID NO:62, SEQ ID NO:37 and SEQ ID NO:65, SEQ ID NO:40 and SEQ ID NO:68, SEQ ID NO:42 and SEQ ID NO:70, SEQ ID NO:43 and SEQ ID NO:71, SEQ ID NO:48 and SEQ ID NO:76, SEQ ID NO:49 and SEQ ID NO:77, and SEQ ID NO:56 and SEQ ID NO:84;
4) SEQ ID NO:32 and SEQ ID NO:60, SEQ ID NO:35 and SEQ ID NO:63, SEQ ID NO:37 and SEQ ID NO:65, SEQ ID NO:41 and SEQ ID NO:69, SEQ ID NO:46 and SEQ ID NO:74, SEQ ID NO:47 and SEQ ID NO:75, and SEQ ID NO:49 and SEQ ID NO:77;
5) SEQ ID NO:31 and SEQ ID NO:59, SEQ ID NO:36 and SEQ ID NO:64, SEQ ID NO:38 and SEQ ID NO:66, SEQ ID NO:41 and SEQ ID NO:69, SEQ ID NO:45 and SEQ ID NO:73, SEQ ID NO:51 and SEQ ID NO:79, SEQ ID NO:52 and SEQ ID NO:80, SEQ ID NO:53 and SEQ ID NO:81, and SEQ ID NO:56 and SEQ ID NO:84; and
6) SEQ ID NO:32 and SEQ ID NO:60, SEQ ID NO:35 and SEQ ID NO:63, SEQ ID NO:42 and SEQ ID NO:70, SEQ ID NO:45 and SEQ ID NO:73, and SEQ ID NO:56 and SEQ ID NO:84.

In some embodiments, the alleles comprising the marker associated with enhanced drought tolerance are detected in amplification products from a nucleic acid sample isolated from a maize plant or germplasm, wherein the amplification products are produced using pairs of amplification primers selected from the group consisting of:
1) SEQ ID NO:31 and SEQ ID NO:59, SEQ ID NO:33 and SEQ ID NO:61 and SEQ ID NO:39 and SEQ ID NO:67;
2) SEQ ID NO:30 and SEQ ID NO:58, SEQ ID NO:31 and SEQ ID NO:59, SEQ ID NO:33 and SEQ ID NO:61, SEQ ID NO:37 and SEQ ID NO:65, SEQ ID NO:46 and SEQ ID NO:74, and SEQ ID NO:50 and SEQ ID NO:78;
3) SEQ ID NO:29 and SEQ ID NO:57, SEQ ID NO:32 and SEQ ID NO:60, SEQ ID NO:34 and SEQ ID NO:62, SEQ ID NO:37 and SEQ ID NO:65, SEQ ID NO:42 and SEQ ID NO:70, and SEQ ID NO:56 and SEQ ID NO:84;
4) SEQ ID NO:32 and SEQ ID NO:60, SEQ ID NO:37 and SEQ ID NO:65, and SEQ ID NO:46 and SEQ ID NO:74;
5) SEQ ID NO:31 and SEQ ID NO:59, SEQ ID NO:38 and SEQ ID NO:66, SEQ ID NO:45 and SEQ ID NO:73, and SEQ ID NO:56 and SEQ ID NO:84; and
6) SEQ ID NO:32 and SEQ ID NO:60, SEQ ID NO:42 and SEQ ID NO:70, SEQ ID NO:45 and SEQ ID NO:73, and SEQ ID NO:56 and SEQ ID NO:84.

In some embodiments, the allele(s) comprising the marker associated with enhanced drought tolerance is/are detected in an amplification product or products from a nucleic acid sample isolated from a maize plant or germplasm, wherein the amplification product(s) is/are produced using a pair (or pairs) of amplification primers selected from the group consisting of:
1) SEQ ID NO:31 and SEQ ID NO:59;
2) SEQ ID NO:32 and SEQ ID NO:60;
3) SEQ ID NO:30 and SEQ ID NO:58, and SEQ ID NO:31 and SEQ ID NO:59; and 4) SEQ ID NO:32 and SEQ ID NO:60, and SEQ ID NO:34 and SEQ ID NO:62.

Methods for introgressing an allele associated with enhanced drought tolerance into a maize plant or germplasm can comprise crossing a first maize plant or germplasm comprising said allele (the donor) with a second maize plant or germplasm that lacks said allele (the recurrent parent) and repeatedly backcrossing progeny comprising said allele with the recurrent parent. Progeny comprising said allele can be identified by detecting, in their genomes, the presence of a marker associated with enhanced drought tolerance. Either the donor or the recurrent parent, or both, can be of a non-naturally occurring variety of maize. In some embodiments, the donor is CML333, CML322, Cateto SP VII, Confite Morocho AYA 38, or Tuxpeno VEN 692. In some embodiments, the genome of the donor is at least about 50%, 55%, 60%, 65%, 70%, 75%, 80%, 85%, 90%, 95%, 97%, 99% or 100% identical to that of CML333, CML322, Cateto SP VII, Confite Morocho AYA 38, or Tuxpeno VEN 692. In some embodiments, the recurrent parent is of an elite variety of maize. In some embodiments, the genome of the recurrent parent is at least about 50%, 55%, 60%, 65%, 70%, 75%, 80%, 85%, 90%, 95%, 97%, 99% or 100% identical to that of an elite variety of maize. In some embodiments, the recurrent parent is of the NP2391 variety. In some embodiments, the genome of the recurrent parent is at least about 50%, 55%, 60%, 65%, 70%, 75%, 80%, 85%, 90%, 95%, 97%, 99% or 100% identical to that of NP2391.

In some embodiments, the presently disclosed subject matter also provides methods of producing a drought tolerant maize plant. In some embodiments, the presently disclosed methods comprise detecting, in a maize germplasm, the presence of a marker associated with enhanced drought tolerance, wherein said marker is selected from the group consisting of:

a G nucleotide at the position that corresponds to position 100 of SEQ ID NO: 2, an ACT trinucleotide at the position that corresponds to positions 4979-4981 of SEQ ID NO: 7, a G nucleotide at the position that corresponds to position 116 of SEQ ID NO: 23, an A nucleotide at the position that corresponds to position 391 of SEQ ID NO: 33, an A nucleotide at the position that corresponds to position 472 of SEQ ID NO: 48, an A nucleotide at the position that corresponds to position 237 of SEQ ID NO: 56, a T nucleotide at the position that corresponds to position 173 of SEQ ID NO: 57, and a G nucleotide at the position that corresponds to position 267 of SEQ ID NO: 60;

an ACT trinucleotide at the position that corresponds to positions 4979-4981 of SEQ ID NO: 7, an A nucleotide at the position that corresponds to position 309 of SEQ ID NO: 19, a G nucleotide at the position that corresponds to position 562 of SEQ ID NO: 25, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;

a G nucleotide at the position that corresponds to position 100, an A nucleotide at the position that corresponds to position 4641 of SEQ ID NO: 7, an A nucleotide at the position that corresponds to position 217 of SEQ ID NO: 23, a C nucleotide at the position that corresponds to position 746 of SEQ ID NO: 24, a C nucleotide at the position that corresponds to position 258 of SEQ ID NO: 29, an A nucleotide at the position that corresponds to position 266 of SEQ ID NO: 44, a G nucleotide at the position that corresponds to position 472 of SEQ ID NO: 48, a G nucleotide at the position that corresponds to position 193 of SEQ ID NO: 55, and a C nucleotide at the position that corresponds to position 486 of SEQ ID NO: 58;

a deletion at nucleotide at the position that corresponds to positions 264-271 of SEQ ID NO: 2, an A nucleotide at the position that corresponds to position 4641 of SEQ ID NO: 7, an A nucleotide at the position that corresponds to position 309 of SEQ ID NO: 19, an A nucleotide at the position that corresponds to position 391 of SEQ ID NO: 33, a G nucleotide at the position that corresponds to position 237 of SEQ ID NO: 56, and a C nucleotide at the position that corresponds to position 486 of SEQ ID NO: 58;

an ACT trinucleotide at the position that corresponds to positions 4979-4981 of SEQ ID NO: 7, a G nucleotide at the position that corresponds to position 463 of SEQ ID NO: 19, a C nucleotide at the position that corresponds to position 254 of SEQ ID NO: 27, an A nucleotide at the position that corresponds to position 391 of SEQ ID NO: 33, a T nucleotide at the position that corresponds to position 475 of SEQ ID NO: 45, a G nucleotide at the position that corresponds to position 193 of SEQ ID NO: 55, a C nucleotide at the position that corresponds to position 516 of SEQ ID NO: 56, a G nucleotide at the position that corresponds to position 729 of SEQ ID NO: 59, and a G nucleotide at the position that corresponds to position 267 of SEQ ID NO: 60;

an A nucleotide at the position that corresponds to position 4641 of SEQ ID NO: 7, a G nucleotide at the position that corresponds to position 463 of SEQ ID NO: 19, a C nucleotide at the position that corresponds to position 258 of SEQ ID NO: 29, a G nucleotide at the position that corresponds to position 193 of SEQ ID NO: 55, and a G nucleotide at the position that corresponds to position 237 of SEQ ID NO: 56;

an ACT trinucleotide at the position that corresponds to positions 4979-4981 of SEQ ID NO: 7, an A nucleotide at the position that corresponds to position 472 of SEQ ID NO: 48, an A nucleotide at the position that corresponds to position 237 of SEQ ID NO: 56, and a T nucleotide at the position that corresponds to position 173 of SEQ ID NO: 57;

an ACT trinucleotide at the position that corresponds to positions 4979-4981 of SEQ ID NO: 7, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;

an A nucleotide at the position that corresponds to position 4641 of SEQ ID NO: 7, a C nucleotide at the position that corresponds to position 258 of SEQ ID NO: 29, a G nucleotide at the position that corresponds to position 87 of SEQ ID NO: 47, a G nucleotide at the position that corresponds to position 472 of SEQ ID NO: 48, and a G nucleotide at the position that corresponds to position 193 of SEQ ID NO: 55;

an A nucleotide at the position that corresponds to position 4641 of SEQ ID NO: 7, an A nucleotide at the position that corresponds to position 309 of SEQ ID NO: 19, and a G nucleotide at the position that corresponds to position 237 of SEQ ID NO: 56;

an ACT trinucleotide at the position that corresponds to positions 4979-4981 of SEQ ID NO: 7, a G nucleotide at the position that corresponds to position 463 of SEQ ID NO: 19, a T nucleotide at the position that corresponds to position 475 of SEQ ID NO: 45, and a G nucleotide at the position that corresponds to position 193 of SEQ ID NO: 55;

an ACT trinucleotide at the position that corresponds to positions 4979-4981 of SEQ ID NO: 7;

an A nucleotide at the position that corresponds to position 4641 of SEQ ID NO: 7;

an ACT trinucleotide at the position that corresponds to positions 4979-4981 of SEQ ID NO: 7 and a C nucleotide at the position that corresponds to position 386 of SEQ ID NO: 46; and an A nucleotide at the position that corresponds to position 4641 of SEQ ID NO: 7 and a G nucleotide at the position that corresponds to position 472 of SEQ ID NO: 48, and combinations thereof; and producing a plant from said maize germplasm, thereby producing a drought tolerant maize plant.

The presently disclosed subject matter also provides methods for identifying and/or selecting a drought tolerant maize plant or germplasm. Methods for selecting a drought tolerant maize plant or germplasm can comprise crossing a first maize plant or germplasm with a second maize plant or germplasm, wherein said first maize plant or germplasm comprises a marker associated with enhanced drought tolerance, and selecting a progeny plant or germplasm comprising said marker associated with enhanced drought tolerance. Either the first or second maize plant or germplasm, or both, can be of a non-naturally occurring variety of maize. In some embodiments, the first maize plant or germplasm is CML333, CML322, Cateto SP VII, Confite Morocho AYA 38, or Tuxpeno VEN 692. In some embodiments, the genome of the first maize plant or germplasm is at least about 50%, 55%, 60%, 65%, 70%, 75%, 80%, 85%, 90%, 95%, 97%, 99% or 100% identical to that of CML333, CML322, Cateto SP VII, Confite Morocho AYA 38, or Tuxpeno VEN 692. In some embodiments, the second maize plant or germplasm is of an elite variety of maize. In some embodiments, the genome of the second maize plant or germplasm is at least about 50%, 55%, 60%, 65%, 70%, 75%, 80%, 85%, 90%, 95%, 97%, 99% or 100% identical to that of an elite variety of maize. In some embodiments, the second maize plant or germplasm is of the NP2391 variety. In some embodiments, the genome of the second maize plant or germplasm is at least about 50%, 55%, 60%, 65%, 70%, 75%, 80%, 85%, 90%, 95%, 97%, 99% or 100% identical to that of NP2391.

Thus, in some embodiments the methods comprise detecting, in said maize plant or germplasm, the presence of a marker associated with enhanced drought tolerance, wherein said marker comprises a plurality of alleles, which are detected in amplification products from a nucleic acid sample isolated from said maize plant or germplasm, said amplification products having been produced using pairs of amplification primers selected from the group consisting of:

(i) SEQ ID NOs: 120 and 121; SEQ ID NOs: 130 and 131; SEQ ID NOs: 160 and 161; SEQ ID NOs: 180 and 181; SEQ ID NOs: 208 and 209; SEQ ID NOs: 222 and 223; SEQ ID NOs: 224 and 225; and SEQ ID NOs: 230 and 231;

(ii) SEQ ID NOs: 130 and 131; SEQ ID NOs: 152 and 153; SEQ ID NOs: 164 and 165; SEQ ID NOs: 166 and 167; SEQ ID NOs: 202 and 203; SEQ ID NOs: 204 and 205; SEQ ID NOs: 208 and 209; and SEQ ID NOs: 212 and 213;

(iii) SEQ ID NOs: 120 and 121; SEQ ID NOs: 130 and 131; SEQ ID NOs: 160 and 161; SEQ ID NOs: 162 and 163; SEQ ID NOs: 172 and 173; SEQ ID NOs: 202 and 203; SEQ ID NOs: 206 and 207; SEQ ID NOs: 208 and 209; SEQ ID NOs: 220 and 221; and SEQ ID NOs: 226 and 227;

(iv) SEQ ID NOs: 120 and 121; SEQ ID NOs: 130 and 131; SEQ ID NOs: 152 and 153; SEQ ID NOs: 180 and 181; SEQ ID NOs: 202 and 203; SEQ ID NOs: 222 and 223; and SEQ ID NOs: 226 and 227;

(v) SEQ ID NOs: 130 and 131; SEQ ID NOs: 152 and 153; SEQ ID NOs: 168 and 169; SEQ ID NOs: 180 and 181; SEQ ID NOs: 202 and 203; SEQ ID NOs: 220 and 221; SEQ ID NOs: 222 and 223; SEQ ID NOs: 228 and 229; and SEQ ID NOs: 230 and 231;

(vi) SEQ ID NOs: 130 and 131; SEQ ID NOs: 152 and 153; SEQ ID NOs: 172 and 173; SEQ ID NOs: 220 and 221; and SEQ ID NOs: 222 and 223;

(vii) SEQ ID NOs: 130 and 131; SEQ ID NOs: 208 and 209; SEQ ID NOs: 222 and 223; and SEQ ID NOs: 224 and 225;

(viii) SEQ ID NOs: 130 and 131; SEQ ID NOs: 152 and 153; SEQ ID NOs: 166 and 167; SEQ ID NOs: 202 and 203; SEQ ID NOs: 204 and 205; SEQ ID NOs: 208 and 209; and SEQ ID NOs: 212 and 213, (ix) SEQ ID NOs: 130 and 131; SEQ ID NOs: 172 and 173; SEQ ID NOs: 202 and 203; SEQ ID NOs: 206 and 207; SEQ ID NOs: 208 and 209; and SEQ ID NOs: 220 and 221;

(x) SEQ ID NOs: 130 and 131; SEQ ID NOs: 152 and 153; SEQ ID NOs: 202 and 203; and SEQ ID NOs: 222 and 223;

(xi) SEQ ID NOs: 130 and 131; SEQ ID NOs: 152 and 153; SEQ ID NOs: 202 and 203; and SEQ ID NOs: 220 and 221;

(xii) SEQ ID NOs: 130 and 131;

(xiii) SEQ ID NOs: 130 and 131; and SEQ ID NOs: 204 and 205; and (xiv) SEQ ID NOs: 130 and 131; and SEQ ID NOs: 208 and 209, thereby identifying and/or selecting a drought tolerant maize plant or germplasm.

The presently disclosed subject matter also provides methods for producing a drought tolerant maize plant comprising detecting, in a maize germplasm, the presence of a marker associated with enhanced drought tolerance, wherein said marker comprises a plurality of alleles, which are detected in amplification products from a nucleic acid sample isolated from said maize plant or germplasm, said amplification product having been produced using pairs of amplification primers selected from the group consisting of:

(i) SEQ ID NOs: 120 and 121; SEQ ID NOs: 130 and 131; SEQ ID NOs: 160 and 161; SEQ ID NOs: 180 and 181; SEQ ID NOs: 208 and 209; SEQ ID NOs: 222 and 223; SEQ ID NOs: 224 and 225; and SEQ ID NOs: 230 and 231;

(ii) SEQ ID NOs: 130 and 131; SEQ ID NOs: 152 and 153; SEQ ID NOs: 164 and 165; SEQ ID NOs: 166 and 167; SEQ ID NOs: 202 and 203; SEQ ID NOs: 204 and 205; SEQ ID NOs: 208 and 209; and SEQ ID NOs: 212 and 213;

(iii) SEQ ID NOs: 120 and 121; SEQ ID NOs: 130 and 131; SEQ ID NOs: 160 and 161; SEQ ID NOs: 162 and 163; SEQ ID NOs: 172 and 173; SEQ ID NOs: 202 and 203;

SEQ ID NOs: 206 and 207; SEQ ID NOs: 208 and 209; SEQ ID NOs: 220 and 221; and SEQ ID NOs: 226 and 227;
(iv) SEQ ID NOs: 120 and 121; SEQ ID NOs: 130 and 131; SEQ ID NOs: 152 and 153; SEQ ID NOs: 180 and 181; SEQ ID NOs: 202 and 203; SEQ ID NOs: 222 and 223; and SEQ ID NOs: 226 and 227;
(v) SEQ ID NOs: 130 and 131; SEQ ID NOs: 152 and 153; SEQ ID NOs: 168 and 169; SEQ ID NOs: 180 and 181; SEQ ID NOs: 202 and 203; SEQ ID NOs: 220 and 221; SEQ ID NOs: 222 and 223; SEQ ID NOs: 228 and 229; and SEQ ID NOs: 230 and 231;
(vi) SEQ ID NOs: 130 and 131; SEQ ID NOs: 152 and 153; SEQ ID NOs: 172 and 173; SEQ ID NOs: 220 and 221; and SEQ ID NOs: 222 and 223;
(vii) SEQ ID NOs: 130 and 131; SEQ ID NOs: 208 and 209; SEQ ID NOs: 222 and 223; and SEQ ID NOs: 224 and 225;
(viii) SEQ ID NOs: 130 and 131; SEQ ID NOs: 152 and 153; SEQ ID NOs: 166 and 167; SEQ ID NOs: 202 and 203; SEQ ID NOs: 204 and 205; SEQ ID NOs: 208 and 209; and SEQ ID NOs: 212 and 213,
(ix) SEQ ID NOs: 130 and 131; SEQ ID NOs: 172 and 173; SEQ ID NOs: 202 and 203; SEQ ID NOs: 206 and 207; SEQ ID NOs: 208 and 209; and SEQ ID NOs: 220 and 221;
(x) SEQ ID NOs: 130 and 131; SEQ ID NOs: 152 and 153; SEQ ID NOs: 202 and 203; and SEQ ID NOs: 222 and 223;
(xi) SEQ ID NOs: 130 and 131; SEQ ID NOs: 152 and 153; SEQ ID NOs: 202 and 203; and SEQ ID NOs: 220 and 221;
(xii) SEQ ID NOs: 130 and 131;
(xiii) SEQ ID NOs: 130 and 131; and SEQ ID NOs: 204 and 205; and
(xiv) SEQ ID NOs: 130 and 131; and SEQ ID NOs: 208 and 209, and
producing a plant from said maize germplasm, thereby producing a drought tolerant maize plant.

The presently disclosed subject matter also provides methods for identifying and/or selecting a drought tolerant maize plant or germplasm, comprising detecting, in said maize plant or germplasm, the presence of a marker associated with enhanced drought tolerance, wherein said marker comprises a plurality of alleles, which are detected using a plurality of probes selected from the group consisting of:
(i) SEQ ID NOs: 348 and 349; SEQ ID NOs: 350 and 351; SEQ ID NOs: 360 and 361; SEQ ID NOs: 372 and 373; SEQ ID NOs: 382 and 383; SEQ ID NOs: 388 and 389; SEQ ID NOs: 382 and 383; and SEQ ID NOs: 398 and 399;
(ii) SEQ ID NOs: 350 and 251; SEQ ID NOs: 356 and 357; SEQ ID NOs: 364 and 365; SEQ ID NOs: 366 and 367; SEQ ID NOs: 374 and 375; SEQ ID NOs: 378 and 379; SEQ ID NOs: 382 and 383; and SEQ ID NOs: 384 and 385;
(iii) SEQ ID NOs: 348 and 349; SEQ ID NOs: 352 and 353; SEQ ID NOs: 358 and 359; SEQ ID NOs: 362 and 363; SEQ ID NOs: 370 and 371; SEQ ID NOs: 374 and 375; SEQ ID NOs: 382 and 383; SEQ ID NOs: 386 and 387; and SEQ ID NOs: 394 and 395;
(iv) SEQ ID NOs: 346 and 347; SEQ ID NOs: 352 and 353; SEQ ID NOs: 356 and 357; SEQ ID NOs: 372 and 373; SEQ ID NOs: 388 and 389; and SEQ ID NOs: 394 and 395;
(v) SEQ ID NOs: 351 and 351; SEQ ID NOs: 354 and 355; SEQ ID NOs: 368 and 369; SEQ ID NOs: 372 and 373; SEQ ID NOs: 376 and 377; SEQ ID NOs: 386 and 387; SEQ ID NOs: 390 and 391; SEQ ID NOs: 396 and 397; and SEQ ID NOs: 398 and 399;
(vi) SEQ ID NOs: 352 and 353; SEQ ID NOs: 354 and 355; SEQ ID NOs: 370 and 371; SEQ ID NOs: 386 and 387; SEQ ID NOs: 388 and 389;
(vii) SEQ ID NOs: 350 and 351; SEQ ID NOs: 382 and 383; SEQ ID NOs: 388 and 389; and SEQ ID NOs: 392 and 393;
(viii) SEQ ID NOs: 350 and 351; SEQ ID NOs: 366 and 367; SEQ ID NOs: 374 and 375; SEQ ID NOs: 378 and 379; SEQ ID NOs: 382 and 383; and SEQ ID NOs: 384 and 385;
(ix) SEQ ID NOs: 352 and 353; SEQ ID NOs: 370 and 371; SEQ ID NOs: 380 and 381; SEQ ID NOs: 382 and 383; and SEQ ID NOs: 386 and 387;
(x) SEQ ID NOs: 352 and 353; SEQ ID NOs: 356 and 357; and SEQ ID NOs: 388 and 389;
(xi) SEQ ID NOs: 350 and 351; SEQ ID NOs: 354 and 355; SEQ ID NOs: 376 and 377; and SEQ ID NOs: 386 and 387;
(xii) SEQ ID NOs: 350 and 351;
(xiii) SEQ ID NOs: 352 and 353;
(xiv) SEQ ID NOs: 350 and 351 and SEQ ID NOs: 378 and 379; and
(xv) SEQ ID NOs: 352 and 353 and SEQ ID NOs: 382 and 383,
thereby identifying and/or selecting a drought tolerant maize plant or germplasm.

The presently disclosed subject matter also provides methods for producing a drought tolerant maize plant comprising detecting, in a maize germplasm, the presence of a marker associated with enhanced drought tolerance, wherein said marker comprises a plurality of alleles, which are detected using a plurality of probes selected from the group consisting of:
(i) SEQ ID NOs: 348 and 349; SEQ ID NOs: 350 and 351; SEQ ID NOs: 360 and 361; SEQ ID NOs: 372 and 373; SEQ ID NOs: 382 and 383; SEQ ID NOs: 388 and 389; SEQ ID NOs: 382 and 383; and SEQ ID NOs: 398 and 399;
(ii) SEQ ID NOs: 350 and 251; SEQ ID NOs: 356 and 357; SEQ ID NOs: 364 and 365; SEQ ID NOs: 366 and 367; SEQ ID NOs: 374 and 375; SEQ ID NOs: 378 and 379; SEQ ID NOs: 382 and 383; and SEQ ID NOs: 384 and 385;
(iii) SEQ ID NOs: 348 and 349; SEQ ID NOs: 352 and 353; SEQ ID NOs: 358 and 359; SEQ ID NOs: 362 and 363; SEQ ID NOs: 370 and 371; SEQ ID NOs: 374 and 375; SEQ ID NOs: 382 and 383; SEQ ID NOs: 386 and 387; and SEQ ID NOs: 394 and 395;
(iv) SEQ ID NOs: 346 and 347; SEQ ID NOs: 352 and 353; SEQ ID NOs: 356 and 357; SEQ ID NOs: 372 and 373; SEQ ID NOs: 388 and 389; and SEQ ID NOs: 394 and 395;
(v) SEQ ID NOs: 351 and 351; SEQ ID NOs: 354 and 355; SEQ ID NOs: 368 and 369; SEQ ID NOs: 372 and 373; SEQ ID NOs: 376 and 377; SEQ ID NOs: 386 and 387; SEQ ID NOs: 390 and 391; SEQ ID NOs: 396 and 397; and SEQ ID NOs: 398 and 399;
(vi) SEQ ID NOs: 352 and 353; SEQ ID NOs: 354 and 355; SEQ ID NOs: 370 and 371; SEQ ID NOs: 386 and 387; SEQ ID NOs: 388 and 389;
(vii) SEQ ID NOs: 350 and 351; SEQ ID NOs: 382 and 383; SEQ ID NOs: 388 and 389; and SEQ ID NOs: 392 and 393;

(viii) SEQ ID NOs: 350 and 351; SEQ ID NOs: 366 and 367; SEQ ID NOs: 374 and 375; SEQ ID NOs: 378 and 379; SEQ ID NOs: 382 and 383; and SEQ ID NOs: 384 and 385;

(ix) SEQ ID NOs: 352 and 353; SEQ ID NOs: 370 and 371; SEQ ID NOs: 380 and 381; SEQ ID NOs: 382 and 383; and SEQ ID NOs: 386 and 387;

(x) SEQ ID NOs: 352 and 353; SEQ ID NOs: 356 and 357; and SEQ ID NOs: 388 and 389;

(xi) SEQ ID NOs: 350 and 351; SEQ ID NOs: 354 and 355; SEQ ID NOs: 376 and 377; and SEQ ID NOs: 386 and 387;

(xii) SEQ ID NOs: 350 and 351;

(xiii) SEQ ID NOs: 352 and 353;

(xiv) SEQ ID NOs: 350 and 351 and SEQ ID NOs: 378 and 379; and (xv) SEQ ID NOs: 352 and 353 and SEQ ID NOs: 382 and 383, and producing a plant from said maize germplasm, thereby producing a drought tolerant maize plant.

In some embodiments of the presently disclosed methods, the maize plant or germplasm is of a non-naturally occurring variety of maize. In some embodiments, the genome of said maize plant or germplasm is at least 95% identical to that of NP2391.

The presently disclosed subject matter also provides in some embodiments methods for selecting a drought tolerant maize plant or germplasm. In some embodiments, the methods comprise crossing a first maize plant or germplasm with a second maize plant or germplasm, wherein said first maize plant or germplasm comprises within its genome a haplotype associated with enhanced drought tolerance, wherein said haplotype is selected from the group consisting of:

a G nucleotide at the position that corresponds to position 100 of SEQ ID NO: 2, an ACT trinucleotide at the position that corresponds to positions 4979-4981 of SEQ ID NO: 7, a G nucleotide at the position that corresponds to position 116 of SEQ ID NO: 23, an A nucleotide at the position that corresponds to position 391 of SEQ ID NO: 33, an A nucleotide at the position that corresponds to position 472 of SEQ ID NO: 48, an A nucleotide at the position that corresponds to position 237 of SEQ ID NO: 56, a T nucleotide at the position that corresponds to position 173 of SEQ ID NO: 57, and a G nucleotide at the position that corresponds to position 267 of SEQ ID NO: 60;

an ACT trinucleotide at the position that corresponds to positions 4979-4981 of SEQ ID NO: 7, an A nucleotide at the position that corresponds to position 309 of SEQ ID NO: 19, a G nucleotide at the position that corresponds to position 562 of SEQ ID NO: 25, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;

a G nucleotide at the position that corresponds to position 100, an A nucleotide at the position that corresponds to position 4641 of SEQ ID NO: 7, an A nucleotide at the position that corresponds to position 217 of SEQ ID NO: 23, a C nucleotide at the position that corresponds to position 746 of SEQ ID NO: 24, a C nucleotide at the position that corresponds to position 258 of SEQ ID NO: 29, an A nucleotide at the position that corresponds to position 266 of SEQ ID NO: 44, a G nucleotide at the position that corresponds to position 472 of SEQ ID NO: 48, a G nucleotide at the position that corresponds to position 193 of SEQ ID NO: 55, and a C nucleotide at the position that corresponds to position 486 of SEQ ID NO: 58;

a deletion at nucleotide at the position that corresponds to positions 264-271 of SEQ ID NO: 2, an A nucleotide at the position that corresponds to position 4641 of SEQ ID NO: 7, an A nucleotide at the position that corresponds to position 309 of SEQ ID NO: 19, an A nucleotide at the position that corresponds to position 391 of SEQ ID NO: 33, a G nucleotide at the position that corresponds to position 237 of SEQ ID NO: 56, and a C nucleotide at the position that corresponds to position 486 of SEQ ID NO: 58;

an ACT trinucleotide at the position that corresponds to positions 4979-4981 of SEQ ID NO: 7, a G nucleotide at the position that corresponds to position 463 of SEQ ID NO: 19, a C nucleotide at the position that corresponds to position 254 of SEQ ID NO: 27, an A nucleotide at the position that corresponds to position 391 of SEQ ID NO: 33, a T nucleotide at the position that corresponds to position 475 of SEQ ID NO: 45, a G nucleotide at the position that corresponds to position 193 of SEQ ID NO: 55, a C nucleotide at the position that corresponds to position 516 of SEQ ID NO: 56, a G nucleotide at the position that corresponds to position 729 of SEQ ID NO: 59, and a G nucleotide at the position that corresponds to position 267 of SEQ ID NO: 60;

an A nucleotide at the position that corresponds to position 4641 of SEQ ID NO: 7, a G nucleotide at the position that corresponds to position 463 of SEQ ID NO: 19, a C nucleotide at the position that corresponds to position 258 of SEQ ID NO: 29, a G nucleotide at the position that corresponds to position 193 of SEQ ID NO: 55, and a G nucleotide at the position that corresponds to position 237 of SEQ ID NO: 56;

an ACT trinucleotide at the position that corresponds to positions 4979-4981 of SEQ ID NO: 7, an A nucleotide at the position that corresponds to position 472 of SEQ ID NO: 48, an A nucleotide at the position that corresponds to position 237 of SEQ ID NO: 56, and a T nucleotide at the position that corresponds to position 173 of SEQ ID NO: 57;

an ACT trinucleotide at the position that corresponds to positions 4979-4981 of SEQ ID NO: 7, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;

an A nucleotide at the position that corresponds to position 4641 of SEQ ID NO: 7, a C nucleotide at the position that corresponds to position 258 of SEQ ID NO: 29, a G nucleotide at the position that corresponds to position 87 of SEQ ID NO: 47, a G nucleotide at the position that corresponds to position 472 of SEQ ID NO: 48, and a G nucleotide at the position that corresponds to position 193 of SEQ ID NO: 55;

an A nucleotide at the position that corresponds to position 4641 of SEQ ID NO: 7, an A nucleotide at the position that corresponds to position 309 of SEQ ID NO: 19, and a G nucleotide at the position that corresponds to position 237 of SEQ ID NO: 56;

an ACT trinucleotide at the position that corresponds to positions 4979-4981 of SEQ ID NO: 7, a G nucleotide at the position that corresponds to position 463 of SEQ ID NO: 19, a T nucleotide at the position that corresponds to position 475 of SEQ ID NO: 45, and a G nucleotide at the position that corresponds to position 193 of SEQ ID NO: 55;

an ACT trinucleotide at the position that corresponds to positions 4979-4981 of SEQ ID NO: 7;

an A nucleotide at the position that corresponds to position 4641 of SEQ ID NO: 7;

an ACT trinucleotide at the position that corresponds to positions 4979-4981 of SEQ ID NO: 7 and a C nucleotide at the position that corresponds to position 386 of SEQ ID NO: 46; and an A nucleotide at the position that corresponds to position 4641 of SEQ ID NO: 7 and a G nucleotide at the position that corresponds to position 472 of SEQ ID NO: 48, and combinations thereof; and selecting a progeny plant or germplasm that possesses said haplotype within its genome, thereby selecting a drought tolerant maize plant or germplasm. In some embodiments, either the first maize plant or germplasm or the second maize plant or germplasm, or both, is of a non-naturally occurring variety of maize. In some embodiments, the genome of said first maize plant or germplasm is at least 95% identical to that of CML333, CML322, Cateto SP VII, Confite Morocho AYA 38, or Tuxpeno VEN 692. In some embodiments, the first maize plant or germplasm is selected from the group consisting of CML333, CML322, Cateto SP VII, Confite Morocho AYA 38, and Tuxpeno VEN 692.

In some embodiments of the presently disclosed methods, the genome of said second maize plant or germplasm is at least 95% identical to that of an elite variety of maize. In some embodiments, the second maize plant or germplasm is of an elite variety of maize. In some embodiments, the elite variety of maize is NP2391.

IV. PRODUCTION OF IMPROVED TRAIT CARRYING MAIZE PLANTS BY TRANSGENIC METHODS

In some embodiments, the presently disclosed subject matter relates to the use of polymorphisms (including but not limited to SNPs) or trait-conferring parts for producing a trait carrying maize plant by introducing a nucleic acid sequence comprising a trait-associated allele and/or haplotype of the polymorphism into a recipient plant.

A donor plant, with the nucleic acid sequence that comprises a water optimization trait allele and/or haplotype can be transferred to the recipient plant lacking the allele and/or the haplotype. The nucleic acid sequence can be transferred by crossing a water optimization trait carrying donor plant with a non-trait carrying recipient plant (e.g., by introgression), by transformation, by protoplast transformation or fusion, by a doubled haploid technique, by embryo rescue, or by any other nucleic acid transfer system. Then, if desired, progeny plants comprising one or more of the presently disclosed water optimization trait alleles and/or haplotypes can be selected. A nucleic acid sequence comprising an water optimization trait allele and/or haplotype can be isolated from the donor plant using methods known in the art, and the isolated nucleic acid sequence can transform the recipient plant by transgenic methods. This can occur with a vector, in a gamete, or other suitable transfer element, such as a ballistic particle coated with the nucleic acid sequence.

Plant transformation generally involves the construction of an expression vector that will function in plant cells and includes nucleic acid sequence that comprises an allele and/or haplotype associated with the water optimization trait, which vector can comprise a water optimization trait-conferring gene. This gene usually is controlled or operatively linked to one or more regulatory element, such as a promoter. The expression vector can contain one or more such operably linked gene/regulatory element combinations, provided that at least one of the genes contained in the combinations encodes water optimization trait. The vector(s) can be in the form of a plasmid, and can be used, alone or in combination with other plasmids, to provide transgenic plants that are better water optimization plants, using transformation methods known in the art, such as the *Agrobacterium* transformation system.

Transformed cells often contain a selectable marker to allow transformation identification. The selectable marker is typically adapted to be recovered by negative selection (by inhibiting the growth of cells that do not contain the selectable marker gene), or by positive selection (by screening for the product encoded by the selectable marker gene). Many commonly used selectable marker genes for plant transformation are known in the art, and include, for example, genes that code for enzymes that metabolically detoxify a selective chemical agent that can be an antibiotic or a herbicide, or genes that encode an altered target which is insensitive to the inhibitor. Several positive selection methods are known in the art, such as mannose selection. Alternatively, marker-less transformation can be used to obtain plants without the aforementioned marker genes, the techniques for which are also known in the art.

V. DROUGHT TOLERANT MAIZE PLANTS AND GERMPLASMS

The presently disclosed subject matter provides drought tolerant maize plants and germplasms. As discussed above, the methods of the presently disclosed subject matter can be utilized to identify, produce and/or select a drought tolerant maize plant or germplasm. In addition to the methods described above, a drought tolerant maize plant or germplasm can be produced by any method whereby a marker associated with enhanced drought tolerance is introduced into the maize plant or germplasm, including, but not limited to, transformation, protoplast transformation or fusion, a double haploid technique, embryo rescue, or by any other nucleic acid transfer system.

In some embodiments, the maize plant or germplasm comprises a non-naturally occurring variety of maize. In some embodiments, the maize plant or germplasm is at least about 50%, 55%, 60%, 65%, 70%, 75%, 80%, 85%, 90%, 95%, 97%, 99% or 100% identical to that of an elite variety of maize. In some embodiments, the genome of said maize plant or germplasm is at least about 50%, 55%, 60%, 65%, 70%, 75%, 80%, 85%, 90%, 95%, 97%, 99% or 100%, identical to that of NP2391.

The maize plant or germplasm can be the progeny of a cross between an elite variety of maize and a variety of maize that comprises an allele associated with enhanced drought tolerance. In some embodiments, the elite variety of maize is NP2391. In some embodiments, the genome of the elite variety of maize is at least about 50%, 55%, 60%, 65%, 70%, 75%, 80%, 85%, 90%, 95%, 97%, 99% or 100% identical to that of NP2391. In some embodiments, the variety comprising an allele associated with enhanced drought tolerance is CML333, CML322, Cateto SP VII, Confite Morocho AYA 38, or Tuxpeno VEN 692. In some embodiments, the genome of the variety comprising an allele associated with enhanced drought tolerance is at least about 50%, 55%, 60%, 65%, 70%, 75%, 80%, 85%, 90%, 95%, 97%, 99% or 100% identical to that of CML333, CML322, Cateto SP VII, Confite Morocho AYA 38, or Tuxpeno VEN 692.

The maize plant or germplasm can be the progeny of an introgression wherein the recurrent parent is an elite variety of maize and the donor comprises an allele associated with enhanced drought tolerance. In some embodiments, the recurrent parent is NP2391. In some embodiments, the genome of the recurrent parent is at least about 50%, 55%, 60%, 65%, 70%, 75%, 80%, 85%, 90%, 95%, 97%, 99% or 100% identical to that of NP2391. In some embodiments, the donor is CML333, CML322, Cateto SP VII, Confite Morocho AYA 38, or Tuxpeno VEN 692. In some embodiments, the genome of the donor is at least about 50%, 55%, 60%, 65%, 70%, 75%, 80%, 85%, 90%, 95%, 97%, 99% or 100% identical to that of CML333, CML322, Cateto SP VII, Confite Morocho AYA 38, or Tuxpeno VEN 692.

The maize plant or germplasm can be the progeny of a cross between a first elite variety of maize (e.g., a tester line) and the progeny of a cross between a second elite variety of maize (e.g., a recurrent parent) and a variety of maize that comprises an allele associated with enhanced drought tolerance (e.g., a donor). In some embodiments, the first elite variety of maize is NP2460. In some embodiments, the genome of the first elite variety of maize is at least about 50%, 55%, 60%, 65%, 70%, 75%, 80%, 85%, 90%, 95%, 97%, 99% or 100% identical to that of NP2460. In some embodiments, the second elite variety of maize is NP2391. In some embodiments, the genome of the second elite variety of maize is at least about 50%, 55%, 60%, 65%, 70%, 75%, 80%, 85%, 90%, 95%, 97%, 99% or 100% identical to that of NP2391. In some embodiments, the variety comprising an allele associated with enhanced drought tolerance is CML333, CML322, Cateto SP VII, Confite Morocho AYA 38, or Tuxpeno VEN 692. In some embodiments, the genome of the variety comprising an allele associated with enhanced drought tolerance is at least about 50%, 55%, 60%, 65%, 70%, 75%, 80%, 85%, 90%, 95%, 97%, 99% or 100% identical to that of CML333, CML322, Cateto SP VII, Confite Morocho AYA 38, or Tuxpeno VEN 692.

The maize plant or germplasm can be the progeny of a cross between a first elite variety of maize and the progeny of an introgression wherein the recurrent parent is a second elite variety of maize and the donor comprises an allele associated with enhanced drought tolerance. In some embodiments, the first elite variety of maize is NP2460. In some embodiments, the genome of the first elite variety of maize is at least about 50%, 55%, 60%, 65%, 70%, 75%, 80%, 85%, 90%, 95%, 97%, 99% or 100% identical to that of NP2460. In some embodiments, the recurrent parent is NP2391. In some embodiments, the genome of the recurrent parent is at least about 50%, 55%, 60%, 65%, 70%, 75%, 80%, 85%, 90%, 95%, 97%, 99% or 100% identical to that of NP2391. In some embodiments, the donor is CML333, CML322, Cateto SP VII, Confite Morocho AYA 38, or Tuxpeno VEN 692. In some embodiments, the genome of the donor is at least about 50%, 55%, 60%, 65%, 70%, 75%, 80%, 85%, 90%, 95%, 97%, 99% or 100% identical to that of CML333, CML322, Cateto SP VII, Confite Morocho AYA 38, or Tuxpeno VEN 692.

Thus, the presently disclosed subject matter provides in some embodiments inbred Zea mays plants comprising one or more alleles associated with a desired water optimization trait. In some embodiments:

(i) the water optimization trait is grain yield at standard moisture percentage (YGSMN), and the favorable allele comprises a nucleotide sequence comprising an A at nucleotide position 270 of SEQ ID NO: 1; a G at nucleotide position 216 of SEQ ID NO: 3; an A at nucleotide position 503 of SEQ ID NO: 4; a CGCG tetranucleotide at nucleotide positions 818-821 of SEQ ID NO: 5; a G at nucleotide position 254 of SEQ ID NO: 6; a GA dinucleotide at nucleotide positions 4497-4498 of SEQ ID NO: 7; an A at nucleotide position 4641 of SEQ ID NO: 7; a C or a T at nucleotide position 4792 of SEQ ID NO: 7; a T at nucleotide position 4836 of SEQ ID NO: 7; an ACT or a TCC trinucleotide at nucleotide positions 4979-4981 of SEQ ID NO: 7; a C at nucleotide position 292 of SEQ ID NO: 9; an A at nucleotide position 166 of SEQ ID NO: 10; a C at nucleotide position 94 of SEQ ID NO: 12; a C at nucleotide position 86 of SEQ ID NO: 13; a G at nucleotide position 89 of SEQ ID NO: 13; an A at nucleotide position 753 of SEQ ID NO: 15; a G at nucleotide position 755 of SEQ ID NO: 16; a G at nucleotide position 431 of SEQ ID NO: 17; an A at nucleotide position 309 of SEQ ID NO: 19; a CTGG tetranucleotide at nucleotide positions 773-776 of SEQ ID NO: 20; a deletion of nucleotide positions 316-324 of SEQ ID NO: 21; a G at nucleotide position 562 of SEQ ID NO: 25; a T at nucleotide position 254 of SEQ ID NO: 27; a T at nucleotide position 496 of SEQ ID NO: 28; a G at nucleotide position 398 of SEQ ID NO: 30; a G at nucleotide position 239 of SEQ ID NO: 31; a G at nucleotide position 208 of SEQ ID NO: 32; a CA dinucleotide at the position that corresponds to positions 144-145 of SEQ ID NO: 34; a T nucleotide at the position that corresponds to position 169 of SEQ ID NO: 34; a G nucleotide at the position that corresponds to position 76 of SEQ ID NO: 35; a T nucleotide at the position that corresponds to position 698 of SEQ ID NO: 36; an A or a G nucleotide at the position that corresponds to position 386 of SEQ ID NO: 37; a G nucleotide at the position that corresponds to position 445 of SEQ ID NO: 39; an A nucleotide at the position that corresponds to position 602 of SEQ ID NO: 40; a G nucleotide at the position that corresponds to position 190 of SEQ ID NO: 41; a C nucleotide at the position that corresponds to position 580 of SEQ ID NO: 41; a TTG trinucleotide at the position that corresponds to positions 266-268 of SEQ ID NO: 42; an A nucleotide at the position that corresponds to position 708 of SEQ ID NO: 43; a G nucleotide at the position that corresponds to position 650 of SEQ ID NO: 49; an A or a T nucleotide at the position that corresponds to position 541 of SEQ ID NO: 50; a T nucleotide at the position that corresponds to position 428 of SEQ ID NO: 53; a C nucleotide at the position that corresponds to position 491 of SEQ ID NO: 53; and/or an A nucleotide at the position that corresponds to position 126 of SEQ ID NO: 54; and/or (ii) the water optimization trait is grain moisture at harvest (GMSTP), and the favorable allele comprises a nucleotide sequence comprising an A nucleotide at the position that corresponds to position 254 of SEQ ID NO: 6; an A nucleotide at the position that corresponds to position 217 of SEQ ID NO: 8; a C nucleotide at the position that corresponds to position 292 of SEQ ID NO: 9; an A nucleotide at the position that corresponds to position 166 of SEQ ID NO: 10; a G nucleotide at the position that corresponds to position 148 of SEQ ID NO: 11; an A nucleotide at the position that corresponds to position 35 of SEQ ID NO: 13; a G nucleotide at the position that corresponds to position 432 of SEQ ID NO: 14; a G nucleotide at the position that corresponds to position 518 of SEQ ID NO: 18; an A nucleotide at the position that corresponds to position 182 of SEQ ID NO: 19; a C nucleotide at the position that corresponds to position 463 of SEQ ID NO: 19; a CTGG tetranucleotide at the position that corresponds to positions 773-776 of SEQ ID NO: 20; a G nucleotide at the position that corresponds to position 211 of SEQ ID NO: 22; a G nucleotide at the position that corresponds to position 562 of SEQ ID NO: 25; a C nucleotide at the position that corresponds to position 254 of SEQ ID NO: 27; a G nucleotide at the position that corresponds to position 239 of SEQ ID NO: 31; a CA dinucleotide at the position that corresponds to positions 144-145 of SEQ ID NO: 34; an A nucleotide at the position that corresponds to position 537 of SEQ ID NO: 34; an A nucleotide at the position that corresponds to position 386 of SEQ ID NO: 37; a C nucleotide at the position that corresponds to position 309 of SEQ ID NO: 38; an A nucleotide at the position that corresponds to position 342 of SEQ ID NO: 38; a C nucleotide at the position that corresponds to position 445 of SEQ ID NO: 39; an A nucleotide at the position that corresponds to position 190 of SEQ ID NO: 41; a C nucleotide at the position that corresponds to position 708 of SEQ ID NO: 43; a G nucleotide at the position that corresponds to position 650 of SEQ ID NO: 49; a C nucleotide at the position that corresponds to position 428 of SEQ ID NO: 53; or a C nucleotide at the position that corresponds to position 491 of SEQ ID NO: 53; and/or (iii) the water optimization trait is grain weight per plot (GWTPN), and the favorable allele comprises a nucleotide sequence comprising a T at nucleotide position 518 of SEQ ID NO: 18.

The presently disclosed subject matter also provides in some embodiments Zea mays plants comprising at least one favorable allele contributing to water optimization, which allele is defined by at least one marker allele comprising a polymorphic site and characterized by a PCR amplification product obtainable in a PCR reaction using a PCR oligonucleotide primer or a plurality of oligonucleotide primers, particularly a pair of PCR oligonucleotide primers or a plurality of primer pairs, but especially a primer pair selected from the group consisting of primer pair 1 represented by a primer comprising SEQ ID NO: 118 and a primer comprising SEQ ID NO: 119; primer pair 2 represented by a primer comprising SEQ ID NO: 120 and a primer comprising SEQ ID NO: 121; primer pair 3 represented by a primer comprising SEQ ID NO: 122 and a primer comprising SEQ ID NO: 123; primer pair 4 represented by a primer comprising SEQ ID NO: 124 and a primer comprising SEQ ID NO: 125; primer pair 5 represented by a primer comprising SEQ ID NO: 126 and a primer comprising SEQ ID NO: 127; primer pair 6 represented by a primer comprising SEQ ID NO: 128 and a primer comprising SEQ ID NO: 129; primer pair 7 represented by a primer comprising SEQ ID NO: 130 and a primer comprising SEQ ID NO: 131; primer pair 8 represented by a primer comprising SEQ ID NO: 132 and a primer comprising SEQ ID NO: 133; primer pair 9 represented by a primer comprising SEQ ID NO: 134 and a primer comprising SEQ ID NO: 135; primer pair 10 represented by a primer comprising SEQ ID NO: 136 and a primer comprising SEQ ID NO: 137; primer pair 11 represented by a primer comprising SEQ ID NO: 138 and a primer comprising SEQ ID NO: 139; primer pair 12 represented by a primer comprising SEQ ID NO: 140 and a primer comprising SEQ ID NO: 141; primer pair 13 represented by a primer comprising SEQ ID NO: 142 and a primer comprising SEQ ID NO: 143; primer pair 14 represented by a primer comprising SEQ ID NO: 144 and a primer comprising SEQ ID NO: 145; primer pair 15 represented by a primer comprising SEQ ID NO: 146 and a primer comprising SEQ ID NO: 147; primer pair 16 represented by a primer comprising SEQ ID NO: 148 and a primer comprising SEQ ID NO: 149; primer pair 17 represented by a primer comprising SEQ ID NO: 150 and a primer comprising SEQ ID NO: 151; primer pair 18 represented by a primer comprising SEQ ID NO: 152 and a primer comprising SEQ ID NO: 153; primer pair 19 represented by a primer comprising SEQ ID NO: 154 and a primer comprising SEQ ID NO: 155; primer pair 20 represented by a primer comprising SEQ ID NO: 156 and a primer comprising SEQ ID NO: 157; primer pair 21 represented by a primer comprising SEQ ID NO: 158 and a primer comprising SEQ ID NO: 159; primer pair 22 represented by a primer comprising SEQ ID NO: 160 and a primer comprising SEQ ID NO: 161; primer pair 23 represented by a primer comprising SEQ ID NO: 162 and a primer comprising SEQ ID NO: 163; primer pair 24 represented by a primer comprising SEQ ID NO: 164 and a primer comprising SEQ ID NO: 165; primer pair 25 represented by a primer comprising SEQ ID NO: 166 and a primer comprising SEQ ID NO: 167; primer pair 26 represented by a primer comprising SEQ ID NO: 168 and a primer comprising SEQ ID NO: 169; primer pair 27 represented by a primer comprising SEQ ID NO: 170 and a primer comprising SEQ ID NO: 171; primer pair 28 represented by a primer comprising SEQ ID NO: 172 and a primer comprising SEQ ID NO: 173; primer pair 29 represented by a primer comprising SEQ ID NO: 174 and a primer comprising SEQ ID NO: 175; primer pair 30 represented by a primer comprising SEQ ID NO: 176 and a primer comprising SEQ ID NO: 177; primer pair 31 represented by a primer comprising SEQ ID NO: 178 and a primer comprising SEQ ID NO: 179; primer pair 32 represented by a primer comprising SEQ ID NO: 180 and a primer comprising SEQ ID NO: 181; primer pair 33 represented by a primer comprising SEQ ID NO: 182 and a primer comprising SEQ ID NO: 183; primer pair 34 represented by a primer comprising SEQ ID NO: 184 and a primer comprising SEQ ID NO: 185; primer pair 35 represented by a primer comprising SEQ ID NO: 186 and a primer comprising SEQ ID NO: 187; primer pair 36 represented by a primer comprising SEQ ID NO: 188 and a primer comprising SEQ ID NO: 189; primer pair 37 represented by a primer comprising SEQ ID NO: 190 and a primer comprising SEQ ID NO: 191; primer pair 38 represented by a primer comprising SEQ ID NO: 192 and a primer comprising SEQ ID NO: 193; primer pair 39 represented by a primer comprising SEQ ID NO: 194 and a primer comprising SEQ ID NO: 195; primer pair 40 represented by a primer comprising SEQ ID NO: 196 and a primer comprising SEQ ID NO: 197; primer pair 41 represented by a primer comprising SEQ ID NO: 198 and a primer comprising SEQ ID NO: 199; primer pair 42 represented by a primer comprising SEQ ID NO: 200 and a primer comprising SEQ ID NO: 201; primer pair 43 represented by a primer comprising SEQ ID NO: 202 and a primer comprising SEQ ID NO: 203; primer pair 44 represented by a primer comprising SEQ ID NO: 204 and a primer comprising SEQ ID NO: 205; primer pair 45 represented by a primer comprising SEQ ID NO: 206 and a primer comprising SEQ ID NO: 207; primer pair 46 represented by a primer comprising SEQ ID NO: 208 and a primer comprising SEQ ID NO: 209; primer pair 47 represented by a primer comprising SEQ ID NO: 210 and a primer comprising SEQ ID NO: 211; primer pair 48 represented by a primer comprising SEQ ID NO: 212 and a primer comprising SEQ ID NO: 213; primer pair 49 represented by a primer comprising SEQ ID NO: 214 and a primer comprising SEQ ID NO: 215; primer pair 50 represented by a primer comprising SEQ ID NO: 216 and a primer comprising SEQ ID NO: 217; primer pair 51 represented by a primer comprising SEQ ID NO: 218 and a primer comprising SEQ ID NO: 219; primer pair 52 represented by a primer comprising SEQ ID NO: 220 and a primer comprising SEQ ID NO: 221; primer pair 53 represented by a primer comprising SEQ ID NO: 222 and a primer comprising SEQ ID NO: 223; primer pair 54 represented by a primer comprising SEQ ID NO: 224 and a primer comprising SEQ ID NO: 225; primer pair 55 represented by a primer comprising SEQ ID NO: 226 and a primer comprising SEQ ID NO: 227; primer pair 56 represented by a primer comprising SEQ ID NO: 228 and a primer comprising SEQ ID NO: 229; and primer pair 57 represented by a primer comprising SEQ ID NO: 230 and a primer comprising SEQ ID NO: 231.

In some embodiments, the presently disclosed subject matter provides a non-naturally occurring maize plant or germplasm having in its genome a haplotype associated with enhanced drought tolerance. In some embodiments, wherein said haplotype is selected from the group consisting of:

- a G nucleotide at the position that corresponds to position 100 of SEQ ID NO: 2, an ACT trinucleotide at the position that corresponds to positions 4979-4981 of SEQ ID NO: 7, a G nucleotide at the position that corresponds to position 116 of SEQ ID NO: 23, an A nucleotide at the position that corresponds to position 391 of SEQ ID NO: 33, an A nucleotide at the position that corresponds to position 472 of SEQ ID NO: 48, an A nucleotide at the position that corresponds to position 237 of SEQ ID NO: 56, a T nucleotide at the position that corresponds to position 173 of SEQ ID NO: 57, and a G nucleotide at the position that corresponds to position 267 of SEQ ID NO: 60;
- an ACT trinucleotide at the position that corresponds to positions 4979-4981 of SEQ ID NO: 7, an A nucleotide at the position that corresponds to position 309 of SEQ ID NO: 19, a G nucleotide at the position that corresponds to position 562 of SEQ ID NO: 25, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;
- a G nucleotide at the position that corresponds to position 100, an A nucleotide at the position that corresponds to position 4641 of SEQ ID NO: 7, an A nucleotide at the position that corresponds to position 217 of SEQ ID NO: 23, a C nucleotide at the position that corresponds to position 746 of SEQ ID NO: 24, a C nucleotide at the position that corresponds to position 258 of SEQ ID NO: 29, an A nucleotide at the position that corresponds to position 266 of SEQ ID NO: 44, a G nucleotide at the position that corresponds to position 472 of SEQ ID NO: 48, a G nucleotide at the position that corresponds to position 193 of SEQ ID NO: 55, and a C nucleotide at the position that corresponds to position 486 of SEQ ID NO: 58;
- a deletion at nucleotide at the position that corresponds to positions 264-271 of SEQ ID NO: 2, an A nucleotide at the position that corresponds to position 4641 of SEQ ID NO: 7, an A nucleotide at the position that corresponds to position 309 of SEQ ID NO: 19, an A nucleotide at the position that corresponds to position 391 of SEQ ID NO: 33, a G nucleotide at the position that corresponds to position 237 of SEQ ID NO: 56, and a C nucleotide at the position that corresponds to position 486 of SEQ ID NO: 58;
- an ACT trinucleotide at the position that corresponds to positions 4979-4981 of SEQ ID NO: 7, a G nucleotide at the position that corresponds to position 463 of SEQ ID NO: 19, a C nucleotide at the position that corresponds to position 254 of SEQ ID NO: 27, an A nucleotide at the position that corresponds to position 391 of SEQ ID NO: 33, a T nucleotide at the position that corresponds to position 475 of SEQ ID NO: 45, a G nucleotide at the position that corresponds to position 193 of SEQ ID NO: 55, a C nucleotide at the position that corresponds to position 516 of SEQ ID NO: 56, a G nucleotide at the position that corresponds to position 729 of SEQ ID NO: 59, and a G nucleotide at the position that corresponds to position 267 of SEQ ID NO: 60;
- an A nucleotide at the position that corresponds to position 4641 of SEQ ID NO: 7, a G nucleotide at the position that corresponds to position 463 of SEQ ID NO: 19, a C nucleotide at the position that corresponds to position 258 of SEQ ID NO: 29, a G nucleotide at the position that corresponds to position 193 of SEQ ID NO: 55, and a G nucleotide at the position that corresponds to position 237 of SEQ ID NO: 56;
- an ACT trinucleotide at the position that corresponds to positions 4979-4981 of SEQ ID NO: 7, an A nucleotide at the position that corresponds to position 472 of SEQ ID NO: 48, an A nucleotide at the position that corresponds to position 237 of SEQ ID NO: 56, and a T nucleotide at the position that corresponds to position 173 of SEQ ID NO: 57;
- an ACT trinucleotide at the position that corresponds to positions 4979-4981 of SEQ ID NO: 7, a C nucleotide at the position that corresponds to position 1271 of SEQ ID NO: 26, an A nucleotide at the position that corresponds to position 266 of SEQ ID NO: 44, a C nucleotide at the position that corresponds to position 386 of SEQ ID NO: 46, an A nucleotide at the position that corresponds to position 472 of SEQ ID NO: 48, and a G nucleotide at the position that corresponds to position 111 of SEQ ID NO: 51;
- an A nucleotide at the position that corresponds to position 4641 of SEQ ID NO: 7, a C nucleotide at the position that corresponds to position 258 of SEQ ID NO: 29, a G nucleotide at the position that corresponds to position 87 of SEQ ID NO: 47, a G nucleotide at the position that corresponds to position 472 of SEQ ID NO: 48, and a G nucleotide at the position that corresponds to position 193 of SEQ ID NO: 55;
- an A nucleotide at the position that corresponds to position 4641 of SEQ ID NO: 7, an A nucleotide at the position that corresponds to position 309 of SEQ ID NO: 19, and a G nucleotide at the position that corresponds to position 237 of SEQ ID NO: 56;
- an ACT trinucleotide at the position that corresponds to positions 4979-4981 of SEQ ID NO: 7, a G nucleotide at the position that corresponds to position 463 of SEQ ID NO: 19, a T nucleotide at the position that corresponds to position 475 of SEQ ID NO: 45, and a G nucleotide at the position that corresponds to position 193 of SEQ ID NO: 55;
- an ACT trinucleotide at the position that corresponds to positions 4979-4981 of SEQ ID NO: 7;
- an A nucleotide at the position that corresponds to position 4641 of SEQ ID NO: 7;
- an ACT trinucleotide at the position that corresponds to positions 4979-4981 of SEQ ID NO: 7 and a C nucleotide at the position that corresponds to position 386 of SEQ ID NO: 46; and an A nucleotide at the position that corresponds to position 4641 of SEQ ID NO: 7 and a G nucleotide at the position that corresponds to position 472 of SEQ ID NO: 48, and combinations thereof.

In some embodiments, the genome of said maize plant or germplasm is at least 95% identical to that of an elite variety of maize. In some embodiments, the elite variety of maize is NP2391. In some embodiments, the maize plant or germplasm is derived from crossing an elite variety of maize with an exotic variety of maize. In some embodiments, the genome of said elite variety of maize is at least 95% identical to that of NP2391. In some embodiments, the elite variety of maize is NP2391.

In some embodiments, the genome of said exotic variety of maize is at least 95% identical to that of CML333, CML322, Cateto SP VII, Confite Morocho AYA 38, or Tuxpeno VEN 692. In some embodiments, 32. In some embodiments, said maize plant or germplasm is derived from crossing a first elite variety of maize with the progeny of a cross between a second elite variety of maize and an exotic variety of maize.

In some embodiments, the genome of said first elite variety of maize is at least 95% identical to that of NP2460. In some embodiments, the first elite variety of maize is NP2460.

In some embodiments, the genome of said second elite variety of maize is at least 95% identical to that of NP2391. In some embodiments, the second elite variety of maize is NP2391.

In some embodiments, the genome of said exotic variety of maize is at least 95% identical to CML333, CML322, Cateto SP VII, Confite Morocho AYA 38, or Tuxpeno VEN 692. In some embodiments, said exotic variety of maize is selected from the group consisting of CML333, CML322, Cateto SP VII, Confite Morocho AYA 38, and Tuxpeno VEN 692.

The presently disclosed subject matter also provides in some embodiments grain and/or kernels produced by from a maize plant described herein.

VI. OTHER COMPOSITIONS

In some embodiments, the presently disclosed subject matter also provides pairs of primers consisting of a forward primer and a reverse primer which primers are capable of amplifying in a PCR reaction a fragment of the marker allele, which is genetically linked to or identical with the favorable allele contributing to a water optimization phenotype, wherein said marker allele comprises a polymorphism, which polymorphism is diagnostic for the favorable allele. In some embodiments, the primer pairs are selected from the group consisting of primer pair 1 represented by a primer comprising SEQ ID NO: 118 and a primer comprising SEQ ID NO: 119; primer pair 2 represented by a primer comprising SEQ ID NO: 120 and a primer comprising SEQ ID NO: 121; primer pair 3 represented by a primer comprising SEQ ID NO: 122 and a primer comprising SEQ ID NO: 123; primer pair 4 represented by a primer comprising SEQ ID NO: 124 and a primer comprising SEQ ID NO: 125; primer pair 5 represented by a primer comprising SEQ ID NO: 126 and a primer comprising SEQ ID NO: 127; primer pair 6 represented by a primer comprising SEQ ID NO: 128 and a primer comprising SEQ ID NO: 129; primer pair 7 represented by a primer comprising SEQ ID NO: 130 and a primer comprising SEQ ID NO: 131; primer pair 8 represented by a primer comprising SEQ ID NO: 132 and a primer comprising SEQ ID NO: 133; primer pair 9 represented by a primer comprising SEQ ID NO: 134 and a primer comprising SEQ ID NO: 135; primer pair 10 represented by a primer comprising SEQ ID NO: 136 and a primer comprising SEQ ID NO: 137; primer pair 11 represented by a primer comprising SEQ ID NO: 138 and a primer comprising SEQ ID NO: 139; primer pair 12 represented by a primer comprising SEQ ID NO: 140 and a primer comprising SEQ ID NO: 141; primer pair 13 represented by a primer comprising SEQ ID NO: 142 and a primer comprising SEQ ID NO: 143; primer pair 14 represented by a primer comprising SEQ ID NO: 144 and a primer comprising SEQ ID NO: 145; primer pair 15 represented by a primer comprising SEQ ID NO: 146 and a primer comprising SEQ ID NO: 147; primer pair 16 represented by a primer comprising SEQ ID NO: 148 and a primer comprising SEQ ID NO: 149; primer pair 17 represented by a primer comprising SEQ ID NO: 150 and a primer comprising SEQ ID NO: 151; primer pair 18 represented by a primer comprising SEQ ID NO: 152 and a primer comprising SEQ ID NO: 153; primer pair 19 represented by a primer comprising SEQ ID NO: 154 and a primer comprising SEQ ID NO: 155; primer pair 20 represented by a primer comprising SEQ ID NO: 156 and a primer comprising SEQ ID NO: 157; primer pair 21 represented by a primer comprising SEQ ID NO: 158 and a primer comprising SEQ ID NO: 159; primer pair 22 represented by a primer comprising SEQ ID NO: 160 and a primer comprising SEQ ID NO: 161; primer pair 23 represented by a primer comprising SEQ ID NO: 162 and a primer comprising SEQ ID NO: 163; primer pair 24 represented by a primer comprising SEQ ID NO: 164 and a primer comprising SEQ ID NO: 165; primer pair 25 represented by a primer comprising SEQ ID NO: 166 and a primer comprising SEQ ID NO: 167; primer pair 26 represented by a primer comprising SEQ ID NO: 168 and a primer comprising SEQ ID NO: 169; primer pair 27 represented by a primer comprising SEQ ID NO: 170 and a primer comprising SEQ ID NO: 171; primer pair 28 represented by a primer comprising SEQ ID NO: 172 and a primer comprising SEQ ID NO: 173; primer pair 29 represented by a primer comprising SEQ ID NO: 174 and a primer comprising SEQ ID NO: 175; primer pair 30 represented by a primer comprising SEQ ID NO: 176 and a primer comprising SEQ ID NO: 177; primer pair 31 represented by a primer comprising SEQ ID NO: 178 and a primer comprising SEQ ID NO: 179; primer pair 32 represented by a primer comprising SEQ ID NO: 180 and a primer comprising SEQ ID NO: 181; primer pair 33 represented by a primer comprising SEQ ID NO: 182 and a primer comprising SEQ ID NO: 183; primer pair 34 represented by a primer comprising SEQ ID NO: 184 and a primer comprising SEQ ID NO: 185; primer pair 35 represented by a primer comprising SEQ ID NO: 186 and a primer comprising SEQ ID NO: 187; primer pair 36 represented by a primer comprising SEQ ID NO: 188 and a primer comprising SEQ ID NO: 189; primer pair 37 represented by a primer comprising SEQ ID NO: 190 and a primer comprising SEQ ID NO: 191; primer pair 38 represented by a primer comprising SEQ ID NO: 192 and a primer comprising SEQ ID NO: 193; primer pair 39 represented by a primer comprising SEQ ID NO: 194 and a primer comprising SEQ ID NO: 195; primer pair 40 represented by a primer comprising SEQ ID NO: 196 and a primer comprising SEQ ID NO: 197; primer pair 41 represented by a primer comprising SEQ ID NO: 198 and a primer comprising SEQ ID NO: 199; primer pair 42 represented by a primer comprising SEQ ID NO: 200 and a primer comprising SEQ ID NO: 201; primer pair 43 represented by a primer comprising SEQ ID NO: 202 and a primer comprising SEQ ID NO: 203; primer pair 44 represented by a primer comprising SEQ ID NO: 204 and a primer comprising SEQ ID NO: 205; primer pair 45 represented by a primer comprising SEQ ID NO: 206 and a primer comprising SEQ ID NO: 207; primer pair 46 represented by a primer comprising SEQ ID NO: 208 and a primer comprising SEQ ID NO: 209; primer pair 47 represented by a primer comprising SEQ ID NO: 210 and a primer comprising SEQ ID NO: 211; primer pair 48 represented by a primer comprising SEQ ID NO: 212 and a primer comprising SEQ ID NO: 213; primer pair 49 represented by a primer comprising SEQ ID NO: 214 and a primer comprising SEQ ID NO: 215; primer pair 50 represented by a primer comprising SEQ ID NO: 216 and a primer comprising SEQ ID NO: 217; primer pair 51 represented by a primer comprising SEQ ID NO: 218 and a primer comprising SEQ ID NO: 219; primer pair 52 represented by a primer comprising SEQ ID NO: 220 and a primer comprising SEQ ID NO: 221; primer pair 53 represented by a primer comprising SEQ ID NO: 222 and a primer comprising SEQ ID NO: 223; primer pair 54 represented by a primer comprising SEQ ID NO: 224 and a primer comprising SEQ ID NO: 225; primer pair 55 represented by a primer comprising SEQ ID NO: 226 and a primer comprising SEQ ID NO: 227; primer pair 56 represented by a primer comprising SEQ ID NO: 228 and a primer comprising SEQ ID NO: 229; and primer pair 57 represented by a primer comprising SEQ ID NO: 230 and a primer comprising SEQ ID NO: 231.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Introduction to the Examples

To assess the value of alleles under drought stress, diverse germplasm was screened in controlled field-experiments comprising a full irrigation control treatment and a limited irrigation treatment. The goal of the full irrigation treatment is to ensure water does not limit the productivity of the crop. In contrast, the goal of the limited irrigation treatment is to ensure that water becomes the major limiting constraint to grain yield. Main effects (e.g., treatment and genotype) and interactions (e.g., genotype×treatment) can be determined when the two treatments are applied adjacent to one another in the field. Moreover, drought related phenotypes can be quantified for each genotype in the panel thereby allowing for marker:trait associations to be conducted.

In practice, the method for the limited irrigation treatment can vary widely depending upon the germplasm being screened, the soil type, climatic conditions at the site, pre-season water supply, and in-season water supply, to name just a few. Initially, a site is identified where in-season precipitation is low (to minimize the chance of unintended water application) and is suitable for cropping. In addition, determining the timing of the stress can be important, such that a target is defined to ensure that year-to-year, or location-to-location, screening consistency is in place. An understanding of the treatment intensity, or in some cases the yield loss desired from the limited irrigation treatment, can also be considered. Selection of a treatment intensity that is too light can fail to reveal genotypic variation. Selection of a treatment intensity that is too heavy can create large experimental error. Once the timing of stress is identified and treatment intensity is described, irrigation can be managed in a manner that is consistent with these targets.

General methods for assessing and assessing drought tolerance can be found in Salekdeh et al., 2009 and in U.S. Pat. Nos. 6,635,803; 7,314,757; 7,332,651; and 7,432,416.

Example 1

Assessment of the Phenotypic Data

In order to identify alleles that were associated with water optimization, hybrids were grown in different stages at multiple locations and evaluated for water optimization. In this analysis, four traits were tested in stage 2-3: YGSMN (grain yield at standard moisture %), GMSTP (grain moisture at harvest), GWTPN (grain weight per plot), and PYREC (percentage yield recovery). The distribution of the phenotypic data of hybrids of the lines across locations and testers for YGSMN, GMSTP, GWTPN, and PYREC was determined. The mean values for YGSMN, GMSTP, and GWTPN were 165.41 bushels/acre, 18.94%, and 20.0 bushels/plot respectively. The phenotypic data for the selected trials included information from 4 locations. The number of observations in these locations ranged from 311 to 1456. A total of 575 inbreds were evaluated in crosses with up to 47 different inbred testers. The number of observations for inbred lines crossed to a particular tester ranged from 242 to 575 across all locations.

The testing for associations between potential markers and these three traits employed two analytical approaches: a Mixed Linear Models—(TASSEL) and a Quantitative Inbred Pedigree Disequilibrium Test (referred to herein as "QIPDT2").

Example 2

Phenotypic Adjustments

The use of stage 2-3 data for association mapping is not a traditional approach, and there are several aspects of its analysis that needed to be considered. Moreover, hybrids with various testers, instead of the lines per se, were employed for phenotyping, while both of the statistical approaches (TASSEL and QIPDT2) were designed for data on inbred lines which require a unique trait value for each line. To obtain a unique trait value for each inbred line that could be compared against its genotype, it was necessary to make phenotypic adjustments that help to control the effect of tester and/or location. Additional factors (e.g., maturity group) were not considered to avoid the further reduction of degrees of freedom or subsets sample sizes.

To do the phenotypic adjustments, mixed linear model analyses were performed in two different statistical packages, SAS/JMP and R, which were intended to ensure that the mixed-model approaches for the large data set were implemented correctly. Since approaches gave very close results, the SAS/JMP results were used for the downstream data analysis.

The "full model" analysis included effects of both locations and testers in the model as follows:

Phenotype=Location effect(random)+Line effect(random)+Tester effect(fixed)+error term The "by Location" model was used for each of the 4 selected locations as follows:

Phenotype=Line effect(random)+Tester effect(fixed)+ error term

The "by Tester" model was used for each of the 4 selected subsets of lines crossed to a particular tester as follows:

Phenotype=Location effect(random)+Line effect(random)+error term

The models were evaluated for convergence, estimation of covariance estimates, significance of fixed effects, etc. Best linear unbiased predictors (BLUPs) for line effects were used as adjusted genotypes. In some cases, the proposed mixed models did not converge or there was a problem with the estimation of line effects due to the lack of replications. For each such case, the effect of the line was removed from the model and the residuals were used as a rough method to capture line effects (additional replication was obtained later in the association analysis where each biallelic locus was represented by the total number of inbred lines of each group).

The solution for the lines random effects (BLUPs) were obtained from the mixed models that converged.

Example 3

Genotypic Data

A total of 2189 lines for which phenotypic data was collected in any of the selected trials were also genotyped. A total of 95 polymorphisms corresponding to about 57 candidate genes were scored in the inbred lines. After eliminating monomorphic assays and SNPs with allele frequencies less than 0.01, 85 candidate polymorphisms were tested for association in TASSEL. Besides, 153 random polymorphisms were genotyped in the inbred lines. After filtering, 149 random polymorphisms were also analyzed for association in TASSEL as anonymous candidates.

Example 4

Methodologies for Association Analysis

Association mapping (often referred as linkage disequilibrium mapping) has become a powerful tool to unveil the genetic control of complex traits. Association mapping relies on the large number of generations, and therefore recombination opportunities, in the history of a species, that allow the removal of association between a QTL and any marker not tightly linked to it (Jannink & Walsh, 2001). One of the most important steps in association mapping analysis is the control for population structure. Population structure can cause spurious correlations between markers and phenotypes, increasing the false-positive rate.

Kinship Analysis.

The method implemented in TASSEL uses a kinship matrix in the mixed-model approach for controlling genetic correlations among lines. Kinship analysis was done using genotypic data on the 153 random SNP assays. A method to estimate kinship relationships based on Zhao et al., 2007 was adopted. Scripts were created to calculate Kinship coefficients that were defined simply as the proportion of shared alleles for each pair of individuals (K pShared). Zhao et al. used the proportion of shared haplotypes as their kinship coefficients. The matrix of K coefficients was included for some association models in TASSEL to assess the control for spurious associations due to close interrelatedness of the lines in the panel.

Kinship Coefficient Matrix Calculator.

The K matrix was calculated for a set of inbred lines. The kinship coefficient $k_{ij}$ was calculated as proportion of shared alleles for all loci between two lines i and j, and $k_{ij}=k_{ji}$, $k_{ii}=1$.

Population Structure Analysis.

Analysis with the software program Structure (Pritchard et al., 2000) was done using genotypic data of the 153 random SNP assays.

A linkage model that incorporated population admixture and linkage between the markers was employed. The likelihoods of population structures ranging from k=1 to 15 subpopulations were determined using a burnin period of 50,000 followed by 50,000 MCMC reps. Four replications were run for each value of k. The estimated log probability of data Pr(X|K) for each value of k was plotted to choose an appropriate number of subpopulations to include in the covariance matrix.

The probability for a determinate k increased along with the number of k tested. k=10 was used as the number of subpopulations for association analysis. The inferred ancestry table containing the fraction of each subpopulation contributing to the ancestry of each inbred was used as a series of covariates in the association testing model.

Principal Component Analysis.

Principal Component Analysis (PCA) or "Eigen analysis" was used as an alternative to Structure for inferring population structure from genotypic data. PCA has some advantages over Structure such as the ability to handle large datasets in much shorter periods of time, and avoiding the need of selecting a specific number of sub-populations. PCA was performed using the software SMARTPCA that is part of Eigenstrat (Price et al., 2006). Ten Eigenvectors and their corresponding Eigenvalues for each of the lines were used as another covariate series for the association models of TASSEL.

Example 5

Association Analysis using TASSEL

Association Models in TASSEL.

The different models employed in TASSEL are shown in the Table 6. For the YGSMN and GMSTP phenotypes adjusted across locations and testers, the six (6) models were run and compared. Only Model 4 was run for all the sub-sets by location and by tester.

TABLE 6

Association Models Employed in TASSEL

| General Lineal Models | Mixed Lineal Models |
|---|---|
| 1) Adj. Phenotype = Marker | 4) Adj. Phenotype = Marker + K (pshared)* |
| 2) Adj. Phenotype = Marker + Q (Structure) | 5) Adj. Phenotype = Marker + K (pshared) + Q (Structure) |
| 3) Adj. Phenotype = Marker + PCA (Eigenvalues) | 6) Adj. Phenotype = Marker + K (pshared) + PCA (Eigenvalues) |

The GLM procedure in TASSEL employed an option to perform permutations to find out the experiment-wise error rate that corrected for accumulation of false positives when doing multiple comparisons. A total of 10,000 permutations were used for the water optimization data. The MLM procedure did not include correction for multiple testing. The Bonferroni correction was used a posteriori to avoid accumulation of false positives.

Example 6

Association Analysis Using QIPDT2

QIPDT2 (Quantitative Inbred Pedigree Disequilibrium Test 2) was used for association mapping that takes advantage of inbred pedigree information, which can give higher statistical power and lower false positive rates with a better control of population structure issue (Stich et al. 2006, TAG 113: 1121-1130). This is an extension of QIPDT originally developed for mapping human disease genes (Zhang et al., 2001. Genetic Epidemiol 21:370-375—see reference in Stich et al. 2006). An advantage of QIPDT2 is that this method can be more easily applied to materials from early breeding stages (e.g., stage 2 and 3) because phenotypic data on these materials have been collected for breeding purposes. Generally speaking, the materials from early breeding stages are similar to the lines in the well-known nested association populations (NAM), which was designed to use both linkage and linkage disequilibrium for mapping QTL.

The original QIPDT is a test statistic, T, which is calculated in the following way (Stich et al. 2006):

$$T = \frac{\sum_{k=1}^{P} D_k}{\sqrt{\sum_{k=1}^{P} D_k^2}},$$

following $N(0, 1)$ under $H_0$ $$D_k = \sum_{i=1}^{n_k} U_{jk},$$

$$E\left(\sum_{k=1}^{p} D_k\right) = 0 \text{ under } H_0$$

$$U_{jk} = \sum_{i=1}^{t_{jk}} (Y_{ijk} - \overline{Y}_k) X_{ijk}$$

$\overline{Y}_k$ – mean trait value for extended pedigree $k$ $X_{ijk}$ – marker value(−1, 0, 1)

In the general approach, a T value is calculated for each SNP, and its p value is found from standard normal distribution. While this approach is useful for testing the statistical significance of association, it does not provide an estimate of the magnitude of the SNP genetic effect, nor the relative genetic contribution to the total phenotypic variance.

Thus, the general QIPDT approach was improved using a regression model, which is referred to herein as "QIPDT2"; the original method is then called QIPDT1. The model for QIPDT2 can be written as:

$$y_{ki} = \beta_0 + \beta_1 x_{ki} + e_{ki},$$

where $y_{ki}$ is adjusted phenotypic value for individual i in pedigree k; $x_{ki}$ is coded marker genotypic value; $\beta_0$ is intercept; $\beta_1$ is regression coefficient, or genetic effect, of the SNP in question. Note that the methods for adjusting phenotypic values and coding marker genotypes are the same as used by Stich et al., 2006. With this model, both the genetic effect and $R^2$ for each SNP can be estimated. It is important to note that the phenotypic data were pre-adjusted for excluding effects from testers and/or locations before being further adjusted for pedigree structure; this adjustment was necessary to implement the complex model in QIPDT2. The methods for pre-adjustment were the same as described previously for the TASSEL analysis.

Association Models in QIPDT2.

Association results from both QIPDT1 and QIPDT2 for the whole data set and split subsets for locations and testers were generated. Like the analysis with TASSEL, the phenotypic data were adjusted for locations and/or testers, depending on which subset was used. This resulted in one adjusted phenotypic value (either BLUP line values or model residuals) for each inbred, which contains a combination of all genetic effects for the inbred and random residual only.

Before QIPDT analysis, all inbreds were grouped into different nuclear families, according to their parental lines. The use of nuclear families was expected to give better control of population structure than extended pedigrees that were used in Stich et al., 2006. For QIPDT1, a test statistic (Z value) and corresponding p value were estimated for each SNP; for QIPDT2, a test statistic (T value) and corresponding p value were derived from the simple regression model, along with R square, for each SNP. QIPDT2 was more powerful than QIPDT1, in terms of p values. Since QIPDT2 also gave estimates ($R^2$) for relative contribution for each SNP, QIPDT2 was used for reporting association results from the QIPDT approach.

Example 7

Significance and Contributions of Favorable Alleles to Water Optimization Phenotypes P values and contributions that each favorable allele was observed to have on the water optimization phenotypes YGSMN, GMSTP, and GWTPN were calculated. These values are summarized in Tables 7-9. In Tables 7-9, the term "contribution" refers to the contribution that the favorable allele was calculated to have with respect to the phenotype observed in view of the mean values of 201.68 bushels/acre, 18.95%, and 25.29 bushels/plot for YGSMN, GMSTP, and GWTPN, respectively. In Tables 7-9, the "contribution" is expressed in bushels/acre, percent, and bushels/plot for YGSMN, GMSTP, and GWTPN, respectively.

TABLE 7

Contributions of Favorable Alleles to Increased Water optimization Identified by Both TASSEL and QIPDT2

| SEQ ID NO. | SNP Position | F | U | Trait | Contribution | P Value |
|---|---|---|---|---|---|---|
| 12 | 292 | C | A | GMSTP | 0.973536 | 0.000509 |
| 37 | 145 | C | A | GMSTP | 0.2769 | 0.000315 |
| 39 | 169 | T | A | GMSTP | 0.2721405 | 0.00034675 |
| 42 | 386 | A | G | GMSTP | 0.379311 | 0.000192 |
| 51 | 708 | C | A | GMSTP | 0.31989 | 0.000287 |
| 55 | 491 | C | G | GMSTP | 0.544187 | 0.0001335 |
| 56 | 428 | G | A | GMSTP | 0.347253 | 0.000573 |

TABLE 8

Contributions of Favorable Alleles to Increased Water Optimization Identified by TASSEL

| SEQ ID NO. | SNP Position | F | U | Trait | P Value | Contribution |
|---|---|---|---|---|---|---|
| 1 | 428 | A | G | YGSMN | 0.0084 | 11.3070462 |
| 2 | 216 | G | T | YGSMN | 0.000054594 | 4.15 |
| 3 | 506 | A | G | YGSMN | 0.0005806 | 2.187 |
| 4 | 818-821 | — | CGCG | YGSMN | 0.0035 | 14.5878562 |
| 5 | 254 | G | A | YGSMN | 0.00022694 | 1.6857 |
|  |  | A | G | GMSTP | $5.62 \times 10^{-7}$ | 0.3725 |
| 6 | 186-188 | G | A | YGSMN | 0.007 | 6.8929277 |
| 7 | 526 | A | C | YGSMN | 0.000211972 | 3.3256 |
| 7* | 526 | A | C | YGSMN | 0.0026 | 7.3903226 |
| 8 | 615-616 | — | GA | YGSMN | 0.03 | 5.665 |
| 9 | 375 | A | G | YGSMN | 0.0143 | 6.5897654 |
| 10 | 331 | A | G | YGSMN | 0.000435023 | 3.01738 |
| 10* | 331 | A | G | YGSMN | 0.0026 | 7.3903226 |

TABLE 8-continued

Contributions of Favorable Alleles to Increased Water Optimization Identified by TASSEL

| SEQ ID NO. | SNP Position | F | U | Trait | P Value | Contribution |
|---|---|---|---|---|---|---|
| 11 | 210 | A | G | GMSTP | 0.2431269 | 0.599 |
| 12 | 292 | C | A | YGSMN | 0.0031 | 4.2222 |
| 13 | 166 | A | G | YGSMN | 0.0263 | 5.4031514 |
|  |  | A | G | GMSTP | 0.000204245 | 1.1278 |
| 15 | 94 | C | G | YGSMN | $4.38 \times 10^{-6}$ | 1.3181 |
| 15* | 94 | C | G | YGSMN | 0.0309 | 7.624524 |
| 16 | 35 | A | T | GMSTP | 0.00095646 | 0.086 |
| 17 | 146 | C | A | YGSMN | 0.0071 | 8.327576 |
| 18 | 149 | G | C | YGSMN | 0.000650794 | 1.312 |
| 19 | 432 | G | A | GMSTP | $5.47 \times 10^{-15}$ | 0.0393 |
| 20 | 753 | A | G | YGSMN | 0.0025 | 2.1981 |
| 21 | 755 | G | A | YGSMN | 0.000486298 | 2.2198 |
| 22 | 431 | G | C | GMSTP | $5.43 \times 10^{-6}$ | 0.4939 |
| 23 | 518 | G | T | GMSTP | $7.35 \times 10^{-5}$ | 1.2629 |
| 24 | 387 | C | G | GMSTP | 0.00039766 | 0.4522 |
| 25 | 660 | A | G | GMSTP | 0.00039306 | 0.4219 |
| 26 | 536 | T | C | YGSMN | 0.000740946 | 0.7923 |
| 27 | 773-776 | C | G | YGSMN | 0.000138841 | 0.9736 |
|  |  | C | G | GMSTP | 0.000124719 | 0.7974 |
| 28 | 310 | T | A | YGSMN | $1.87 \times 10^{-7}$ | 1.433 |
| 29 | 211 | G | A | GMSTP | 0.00034028 | 0.5831 |
| 30 | 401 | G | A | YGSMN | 0.0102 | 6.4804254 |
|  |  | G | A | GMSTP | 0.000177776 | 0.6844 |
| 31 | 254 | A | G | YGSMN | 0.0044 | 8.7386037 |
|  |  | G | A | GMSTP | 0.00125 | 1.8112 |
| 32 | 439 | A | G | YGSMN | 0.025 | 5.136 |
| 33 | 384 | G | A | YGSMN | 0.015 | 6.284 |
| 35 | 239 | G | A | YGSMN | 0.0495 | 4.6259439 |
|  |  | G | A | GMSTP | 0.000154145 | 1.4141 |
| 36 | 208 | G | A | YGSMN | 0.000249875 | 1.7148 |
| 37 | 145 | C | A | YGSMN | 0.00029249 | 3.16538 |
| 38 | 535 | A | T | GMSTP | 0.000180209 | 0.1236 |
| 39 | 169 | T | A | GMSTP | 0.000124333 | 1.2461 |
| 40 | 76 | G | A | YGSMN | 0.0012 | 11.9039947 |
| 41 | 724 | A | G | YGSMN | $2.71 \times 10^{-5}$ | 4.65472 |
| 42 | 386 | A | G | YGSMN | 0.0037 | 11.255257 |
| 43 | 375 | A | G | GMSTP | 0.000221511 | 0.6653 |
| 44 | 309 | C | G | GMSTP | 0.0011 | 0.1152 |
| 45 | 342 | A | C | GMSTP | 0.266801841 | 0.8445 |
| 46 | 445 | G | C | YGSMN | 0.000032821 | 1.6764 |
| 47 | 602 | A | T | YGSMN | 0.000769319 | 3.7163 |
| 48 | 190 | G | A | YGSMN | 0.000297308 | 3.369 |
| 48* | 190 | G | A | YGSMN | 0.0054 | 8.0700349 |
| 49 | 593 | C | G | YGSMN | 0.001142836 | 10.5852 |
| 49* | 593 | C | G | YGSMN | 0.0282 | 7.642183 |
| 50 | 266-267 | — | AA | YGSMN | 0.017 | 6.724 |
| 51 | 708 | A | C | YGSMN | 0.0054 | 7.3294598 |
|  |  | C | A | GMSTP | $2.42 \times 10^{-5}$ | 0.3221 |
| 52 | 648 | G | A | YGSMN | 0.0026 | 10.9837972 |
| 53 | 541 | A | T | YGSMN | 0.0003 | 10.3325637 |
| 54 | 442 | C | G | YGSMN | 0.000013938 | 11.0737 |
| 55 | 491 | C | G | YGSMN | 0.000238135 | 7.1354 |
| 55* | 491 | C | G | YGSMN | 0.0446 | 9.1504902 |
| 56 | 428 | A | G | YGSMN | 0.000578625 | 0.7024 |
| 57 | 126 | A | G | YGSMN | $6.83 \times 10^{-5}$ | 3.70653 |
|  |  | A | G | GMSTP | $6.19 \times 10^{-5}$ | 0.5342 |

*Values relate to tests of hybrids

TABLE 9

Contributions of Favorable Alleles to Increased Water Optimization Identified by QIPDT2

| SEQ ID NO. | SNP Position | F | U | Trait | Contribution | P Value |
|---|---|---|---|---|---|---|
| 12 | 292 | C | A | GMSTP | 0.973536 | 0.000509 |
| 14 | 148 | G | T | GMSTP | 0.739413 | 0.000003 |
| 23 | 518 | T | G | GWTPN | 3.438703 | 0.000198 |
| 37 | 145 | C | A | GMSTP | 0.2769 | 0.000315 |
| 39 | 169 | T | A | GMSTP | 0.2721405 | 0.00034675 |
| 42 | 386 | A | G | GMSTP | 0.379311 | 0.000192 |
| 46 | 445 | C | G | GMSTP | 0.777738 | 0.000547 |
| 48 | 190 | A | G | GMSTP | 1.47593 | 0.000274 |
| 51 | 708 | C | A | GMSTP | 0.31989 | 0.000287 |
| 52 | 648 | G | A | GMSTP | 0.450848 | 0.000111 |
| 55 | 491 | C | G | GMSTP | 0.544187 | 0.0001335 |
| 56 | 428 | G | A | GMSTP | 0.347253 | 0.000573 |

Materials and Methods Employed in Examples 8-12

NP2391 is an elite, non-Stiff Stalk variety of maize. NP2391 is described in U.S. Pat. No. 7,166,783. NP2391 comprises a G allele at position 87 of SEQ ID NO: 47, a G allele at position 386 of SEQ ID NO: 46, a G allele at positions 4979-4981 of SEQ ID NO: 7, a C allele at position 4641 of SEQ ID NO: 7, an A allele at position 472 of SEQ ID NO: 48, a G allele at position 237 of SEQ ID NO: 56, an A allele at position 516 of SEQ ID NO: 56, an A allele at position 266 of SEQ ID NO: 44, a T allele at position 475 of SEQ ID NO: 45, a T allele at position 173 of SEQ ID NO: 57, a C allele at position 746 of SEQ ID NO: 24, an A allele at position 391 of SEQ ID NO: 33, a C allele at position 258 of SEQ ID NO: 29, an A allele at position 217 of SEQ ID NO: 23, a G allele at position 116 of SEQ ID NO: 23, a G allele at position 463 of SEQ ID NO: 19, a T allele at position 309 of SEQ ID NO: 19, a D allele at positions 264-271 of SEQ ID NO: 2, an G allele at position 100 of SEQ ID NO: 2, a C allele at position 486 of SEQ ID NO: 58, a G allele at position 111 of SEQ ID NO: 51, a G allele at position 254 of SEQ ID NO: 27, a G allele at position 729 of SEQ ID NO: 59, a G allele at position 267 of SEQ ID NO: 60, a G allele at position 562 of SEQ ID NO: 25, a C allele at position 1271 of SEQ ID NO: 26 and a G allele at position 193 of SEQ ID NO: 55. See FIG. 1.

NP2460 is an elite, Stiff Stalk variety of maize. NP2460 is described in U.S. Pat. No. 7,122,726. NP2460 comprises a C allele at position 386 of SEQ ID NO: 46, an A allele at positions 4979-4981 of SEQ ID NO: 7, an A allele at position 4641 of SEQ ID NO: 7, a G allele at position 472 of SEQ ID NO: 48, a G allele at position 237 of SEQ ID NO: 56, a C allele at position 516 of SEQ ID NO: 56, a C allele at position 266 of SEQ ID NO: 44, a C allele at position 475 of SEQ ID NO: 45, a G allele at position 173 of SEQ ID NO: 57, a C allele at position 746 of SEQ ID NO: 24, an A allele at position 391 of SEQ ID NO: 33, a T allele at position 258 of SEQ ID NO: 29, an A allele at position 217 of SEQ ID NO: 23, a G allele at position 116 of SEQ ID NO: 23, a C allele at position 463 of SEQ ID NO: 19, a C allele at position 309 of SEQ ID NO: 19, a D allele at positions 264-271 of SEQ ID NO: 2, an G allele at position 100 of SEQ ID NO: 2, a C allele at position 486 of SEQ ID NO: 58, a G allele at position 254 of SEQ ID NO: 27, a G allele at position 729 of SEQ ID NO: 59, a G allele at position 267 of SEQ ID NO: 60, a G allele at position 562 of SEQ ID NO: 25, a C allele at position 1271 of SEQ ID NO: 26 and an A allele at position 193 of SEQ ID NO: 55. See FIG. 1.

CML333 is an exotic, inbred variety of maize from the International Maize and Wheat Improvement Center (CIMMYT) in Mexico. CML333 is known to be resistant to both southwestern corn borer and fall armyworm. CML333 comprises an A allele at positions 4979-4981 of SEQ ID NO: 7, a G allele at position 472 of SEQ ID NO: 48, a G allele at position 237 of SEQ ID NO: 56, a G allele at position 173 of SEQ ID NO: 57, a G allele at 0172A, an A allele at position 116 of SEQ ID NO: 23, an A allele at position 100 of SEQ ID NO: 2 and an A allele at position 267 of SEQ ID NO: 60. See FIG. 1.

CML322 is an exotic, inbred variety of maize from the International Maize and Wheat Improvement Center (CIMMYT) in Mexico. CML322 comprises a C allele at position 386 of SEQ ID NO: 46, an A allele at positions 4979-4981 of SEQ ID NO: 7, a G allele at position 472 of SEQ ID NO: 48, a C allele at position 266 of SEQ ID NO: 44, a C allele at position 309 of SEQ ID NO: 19, a C allele at position 111 of SEQ ID NO: 51, an A allele at position 562 of SEQ ID NO: 25 and an A allele at position 1271 of SEQ ID NO: 26. See FIG. 1.

Cateto SP VII is an exotic variety of maize that is native to Brazil. Although it demonstrates a high combining ability with many varieties of maize, it produces a relatively low yield. Cateto SP VII comprises an A allele at position 87 of SEQ ID NO: 47, an A allele at position 4641 of SEQ ID NO: 7, a G allele at position 472 of SEQ ID NO: 48, a C allele at position 266 of SEQ ID NO: 44, an A allele at position 746 of SEQ ID NO: 24, a T allele at position 258 of SEQ ID NO: 29, a G allele at position 217 of SEQ ID NO: 23, an A allele at position 100 of SEQ ID NO: 2, an A allele at position 486 of SEQ ID NO: 58 and an A allele at position 193 of SEQ ID NO: 55. See FIG. 1.

Confite Morocho AYA 38 is an exotic, variety of maize that is native to Peru. Although it is resistant to *Helminthosporium*, it is susceptible to rust. Confite morocho AYA 38 comprises an A allele at position 4641 of SEQ ID NO: 7, a C allele at position 237 of SEQ ID NO: 56, a G allele at position 391 of SEQ ID NO: 33, a C allele at position 309 of SEQ ID NO: 19, an insertion at positions 264-271 of SEQ ID NO: 2 and an A allele at position 486 of SEQ ID NO: 58. See FIG. 1.

Tuxpeno VEN 692 is an exotic, variety of maize that is native to Venezuela. It is highly resistant to both *Helminthosporium* and rust. Tuxpeno VEN 692 comprises an A allele at position 4641 of SEQ ID NO: 7, a C allele at position 237 of SEQ ID NO: 56, a G allele at position 258 of SEQ ID NO: 29, a C allele at position 463 of SEQ ID NO: 19 and an A allele at position 193 of SEQ ID NO: 55. See FIG. 1.

Maize plants of the NP2391 variety were crossed with 134 exotic varieties of maize, including CML333, CML322, Cateto SP VII, Confite Morocho AYA 38, and Tuxpeno VEN 692. The progeny of these crosses were backcrossed with NP2391 for five generations to create NP2391-exotic hybrids. Segmental introgressions of the shaggy kinase gene (GENBANK® Database Accession No. AY103545; incorporated by reference herein) were identified in NP2391-exotic hybrids representing 42 of the exotic donors (CML333, CML322, Cateto SP VII, Confite Morocho AYA 38, Tuxpeno VEN 692, CML69, HH5982, TLT0766, CML103, M37W, TLZ0845, AGG742, NC358, P39, Serrano GUA 3, Mochero LBQ 17, KXI0970, 6B209, Cholito BOV 705, CML228, Coroico Amarillo, 8B006, EE8001, Enano M.D.3, Perola BOV 711, Puya Grande SAN, XPRR001, B97, Cacao SAS 327, Tx303, Clavito ECU 366, Early Caribbean MAR 10, Patillo BOV 502, Rabo De Zorro ANC 325, Shajatu ANC 120, Shoe Peg P1269743, St. Croix IVC 2, Oh7B, Polio VEN 336, Tzi8 and Oh43). Each of the NP2391-exotic hybrids containing a segmental introgression in the shaggy kinase gene was selfed for two generations, selecting for progeny comprising the exotic donor genotype at positions 4979-4981 of SEQ ID NO: 7/position 4641 of SEQ ID NO: 7. Two lines were selected from the progeny of each NP2391-exotic hybrid selfing: one homozygous for the exotic donor genotype at positions 4979-4981 of SEQ ID NO: 7/position 4641 of SEQ ID NO: 7 and the other homozygous for the NP2391 genotype at positions 4979-4981 of SEQ ID NO: 7/position 4641 of SEQ ID NO: 7. Each of these lines was crossed with NP2460 to create an F1 hybrid line. In addition, NP2460 was crossed directly with NP2391 to create an F1 control hybrid.

The F1 hybrids were evaluated in four drought stress locations (La Salle, Colo., United States of America; Gilroy, Calif., United States of America; Los Andes, Chile and Granaros, Chile), with six treatment replications at each location using a restricted, randomized block design, as well as in twelve single-rep cornbelt locations. Drought stress treatments were imposed around the time of pollination and consisted of a period of water deficiency capable of decreasing grain yield by about 40-60%. The timing of each drought stress treatment was determined by soil type and local climate (from which water-holding capacity and the evapotranspiration rate (ET) were estimated or measured). Normal irrigation was stopped about 3-4 weeks before mid-shed to allow the soil moisture level to drop to a critical level, which level was reached approximately 7 days prior to pollination. Once the soil dried to the critical level, deficit irrigation was commenced (approximately 40% of ET). Drought stress treatments were continued for two weeks following mid-shed, at which time normal irrigation was resumed.

Drought tolerance was evaluated by measuring grain yield at standard moisture percentage (YGSMN) and grain moisture at harvest (GMSTP). The statistical data quality control was done by plotting the distribution of the data. Residuals were generated using the following model:

$$Y = \mu + \text{location} + \text{replications(location)} + \text{family} + \text{allele (family)},$$

wherein Y=dependent phenotype and $\mu$=phenotypic average; Location and replications(location) were random. Family and allele(family) were fixed. Residuals were analyzed across replications within a family and flagged according to specified criteria, which criteria depended upon the trait being evaluated. The final analysis was performed for both individual locations and for locations combined using the following model:

$$Y = \mu + \text{replications} + \text{family} + \text{allele(family)} + \text{replications} * \text{family},$$

wherein Y=dependent phenotype and $\mu$=phenotypic average. Replications were random. Family and allele(family) were fixed. Least squares means were calculated and student's T test was run for pairwise comparisons.

As shown in Table 10, six of the F1 hybrids derived from crossing NP2460 with a line homozygous for an exotic donor genotype at positions 4979-4981 of SEQ ID NO: 7/position 4641 of SEQ ID NO: 7 demonstrated enhanced drought tolerance.

TABLE 10

Comparisons of NP2460 Hybrids with respect to SEQ ID NO: 7

| F1 Hybrid | Yield (bu/ac) | | Difference under drought stress conditions (bu/ac) | |
|---|---|---|---|---|
| | Cornbelt | Drought Stress | vs. control hybrid | vs.-hybrid |
| Control | 180 | 162 | | |
| CML333+ | 184 | 176 | 14* | 11* |
| CML333− | 179 | 165 | | |
| CML322+ | 185 | 182 | 20* | 23* |

TABLE 10-continued

Comparisons of NP2460 Hybrids with respect to SEQ ID NO: 7

| F1 Hybrid | Yield (bu/ac) | | Difference under drought stress conditions (bu/ac) | |
|---|---|---|---|---|
| | Cornbelt | Drought Stress | vs. control hybrid | vs.-hybrid |
| CML322− | 183 | 159 | | |
| Cateto+ | 214 | 168 | 6* | 18* |
| Cateto− | 180 | 150 | | |
| Confite+ | 191 | 170 | 8* | 13* |
| Confite− | 189 | 157 | | |
| Tuxpeno+ | 195 | 175 | 13* | 10* |
| Tuxpeno− | 159 | 165 | | |

*indicates p value <0.05

Example 8

NP2460×(NP2391×CML333)

NP2391 was crossed with CML333, and progeny derived from that cross were backcrossed with NP2391 for five generations to create an NP2391×CML333 shaggy hybrid. The NP2391×CML333 shaggy hybrid was selfed for two generations, and two lines were selected based upon their genotype at positions 4979-4981 of SEQ ID NO: 7: one line homozygous for the CML333 genotype (AA) ("CML333 homozygous +") and the other homozygous for the NP2931 genotype (GG) ("CML333 homozygous −"). See FIG. 2. Each of these lines was crossed with NP2460 to create an F1 hybrid. See FIG. 2.

As shown in Table 2, the F1 hybrid line created by crossing NP2460 with the line comprising AA at positions 4979-4981 of SEQ ID NO: 7 ("CML333+") demonstrated enhanced drought tolerance as compared to both the control hybrid and the F1 hybrid derived by crossing NP2460 with the line comprising GG at positions 4979-4981 of SEQ ID NO: 7 ("CML333−"). Under drought stress treatment, the CML333+ hybrid demonstrated a significantly higher grain yield at standard moisture percentage (176 bu/ac) than both the control hybrid (162 bu/ac) and the CML333− hybrid (165 bu/ac).

Example 9

NP2460×(NP2391×CML322)

NP2391 was crossed with CML322, and progeny derived from that cross were backcrossed with NP2391 for five generations to create an NP2391×CML322 shaggy hybrid. The NP2391×CML322 shaggy hybrid was selfed for two generations, and two lines were selected based upon their genotype at positions 4979-4981 of SEQ ID NO: 7: one line homozygous for the CML322 genotype (AA) ("CML322 homozygous +") and the other homozygous for the NP2931 genotype (GG) ("CML322 homozygous −"). See FIG. 3. Each of these lines was crossed with NP2460 to create an F1 hybrid. See FIG. 3.

As shown in Table 2, the F1 hybrid line created by crossing NP2460 with the line comprising AA at positions 4979-4981 of SEQ ID NO: 7 ("CML322+") demonstrated enhanced drought tolerance as compared to both the control hybrid and the F1 hybrid derived by crossing NP2460 with the line comprising GG at positions 4979-4981 of SEQ ID NO: 7 ("CML322−"). Under drought stress treatment, the CML322+ hybrid demonstrated a significantly higher grain yield at standard moisture percentage (182 bu/ac) than both the control hybrid (162 bu/ac) and the CML322− hybrid (159 bu/ac). Notably, the grain yield of the CML322+ hybrid under drought stress conditions was nearly identical to its yield under cornbelt conditions.

Example 10

NP2460×(NP2391×Cateto SP VII)

NP2391 was crossed with Cateto SP VII, and progeny derived from that cross were backcrossed with NP2391 for five generations to create an NP2391×Cateto SP VII shaggy hybrid. The NP2391×Cateto SP VII shaggy hybrid was selfed for two generations, and two lines were selected based upon their genotype at position 4641 of SEQ ID NO: 7: one line homozygous for the Cateto SP VII genotype (AA) ("Cateto homozygous +") and the other homozygous for the NP2931 genotype (CC) ("Cateto homozygous −"). See FIG. 4. Each of these lines was crossed with NP2460 to create an F1 hybrid. See FIG. 4.

As shown in Table 2, the F1 hybrid line created by crossing NP2460 with the line comprising AA at position 4641 of SEQ ID NO: 7 ("Cateto+") demonstrated enhanced drought tolerance as compared to both the control hybrid and the F1 hybrid derived by crossing NP2460 with the line comprising CC at position 4641 of SEQ ID NO: 7 ("Cateto−"). Under drought stress treatment, the Cateto+ hybrid demonstrated a significantly higher grain yield at standard moisture percentage (168 bu/ac) than both the control hybrid (162 bu/ac) and the Cateto− hybrid (150 bu/ac).

Example 11

NP2460×(NP2391×Confite Morocho AYA 38)

NP2391 was crossed with Confite Morocho AYA 38, and progeny derived from that cross were backcrossed with NP2391 for five generations to create an NP2391×Confite Morocho AYA 38 shaggy hybrid. The NP2391×Confite Morocho AYA 38 shaggy hybrid was selfed for two generations, and two lines were selected based upon their genotype at position 4641 of SEQ ID NO: 7: one line homozygous for the Confite Morocho AYA 38 genotype (AA) ("Confite homozygous +") and the other homozygous for the NP2931 genotype (CC) ("Confite homozygous −"). See FIG. 5. Each of these lines was crossed with NP2460 to create an F1 hybrid. See FIG. 5.

As shown in Table 2, the F1 hybrid line created by crossing NP2460 with the line comprising AA at position 4641 of SEQ ID NO: 7 ("Confite+") demonstrated enhanced drought tolerance as compared to both the control hybrid and the F1 hybrid derived by crossing NP2460 with the line comprising CC at position 4641 of SEQ ID NO: 7 ("Confite−"). Under drought stress treatment, the Confite+ hybrid demonstrated a significantly higher grain yield at standard moisture percentage (170 bu/ac) than both the control hybrid (162 bu/ac) and the Cateto− hybrid (157 bu/ac).

Example 12

NP2460×(NP2391×Tuxpeno VEN 692)

NP2391 was crossed with Tuxpeno VEN 692, and progeny derived from that cross were backcrossed with NP2391 for five generations to create an NP2391×Tuxpeno VEN 692 shaggy hybrid. The NP2391×Tuxpeno VEN 692 shaggy hybrid was selfed for two generations, and two lines were selected based upon their genotype at position 4641 of SEQ ID NO: 7: one line homozygous for the Tuxpeno VEN 692 genotype (AA) ("Tuxpeno homozygous +") and the other homozygous for the NP2931 genotype (CC) ("Tuxpeno homozygous –"). See FIG. 7. Each of these lines was crossed with NP2460 to create an F1 hybrid. See FIG. 7.

As shown in Table 2, the F1 hybrid line created by crossing NP2460 with the line comprising AA at position 4641 of SEQ ID NO: 7 ("Tuxpeno+") demonstrated enhanced drought tolerance as compared to both the control hybrid and the F1 hybrid derived by crossing NP2460 with the line comprising CC at position 4641 of SEQ ID NO: 7 ("Tuxpeno–"). Under drought stress treatment, the Tuxpeno+ hybrid demonstrated a significantly higher grain yield at standard moisture percentage (175 bu/ac) than both the control hybrid (162 bu/ac) and the Tuxpeno– hybrid (165 bu/ac).

Example 13

Testing of Water Optimized Hybrids for Yield Gains 157 water optimized hybrids from 36 chassis were compared with base genetic (control) plant in 9-21 locations, each under four environment types: full irrigation, limited irrigation, non-irrigated (non-stress/receiving adequate rainfall), non-irrigated stress, dryland (low plant density; non-stress/receiving adequate rainfall) and dryland stress). As shown in Tables 11 and 12, water optimized hybrids outperformed closely related base hybrids under all conditions tested.

TABLE 11

Yields Under Full Irrigation Conditions

| WO Hybrid Haplotype* | Base Hybrid Haplotype | | WO Hybrid | Base Hybrid | Diff | P Value |
|---|---|---|---|---|---|---|
| ChIa | CI | | 219.8 | 205.4 | 14.3 | 0.108 |
| aCGhI | CGI | | 216.4 | 205.4 | 10.9 | 0.220 |
| bCdeghil | Cdeghi | | 224.5 | 213.5 | 11.0 | 0.048 |
| | | mean | 220.2 | 208.1 | 12.1 | |
| | | SD | 4.1 | 4.7 | 1.9 | |
| bCdefGhil | CdefGh[(1)] | | 241.0 | 226.8 | 14.2 | 0.005 |
| bCdefGhil | CdefGh[(2)] | | 238.0 | 226.8 | 11.2 | 0.030 |
| CefGh | cgi | | 204.4 | 192.1 | 12.3 | 0.077 |
| CefGh | cgi | | 211.2 | 192.1 | 19.2 | 0.018 |
| | | mean | 223.7 | 209.4 | 14.2 | |
| | | SD | 18.6 | 20.0 | 3.5 | |

*Haplotype designations refer to Haplotypes A-M as set forth hereinabove. Uppercase letters indicate that the hybrid was homozygous for the corresponding haplotype, and lowercase letters indicate the hybrid was heterozygous for the corresponding haplotype. The absence of a letter from A-M in the designation indicates that the hybrid did not have that haplotype.
[(1),(2)]indicate that these plants were derived from the same initial breeding but were distinct individuals.

TABLE 12

Yields Under Limited Irrigation Conditions

| WO Hybrid Haplotype* | Base Hybrid Haplotype | | WO Hybrid | Base Hybrid | Diff | P Value |
|---|---|---|---|---|---|---|
| ChIa | CI | | 138.3 | 132.6 | 5.9 | 0.371 |
| aCGhI | CGI | | 145.9 | 132.6 | 13.3 | 0.039 |
| bCdeghil | Cdeghi | | 149.2 | 142.1 | 7.2 | 0.266 |
| | | mean | 144.5 | 135.8 | 8.8 | |
| | | SD | 5.5 | 5.5 | 4.0 | |

*Haplotype designations are as in Table 11.

TABLE 13

Yields Under Dry Stress Conditions

| WO Hybrid Haplotype* | Base Hybrid Haplotype | | WO Hybrid | Base Hybrid | Diff | P Value |
|---|---|---|---|---|---|---|
| bCdgil | Cdgi | | 100.5 | 86.8 | 13.7 | 0.387 |
| aCeGHI | CeghI | | 107.5 | 88.5 | 19.0 | 0.178 |
| aCeGHI | CeghI | | 99.7 | 88.5 | 11.2 | 0.334 |
| cdefGhijkl | dfGh | | 109.3 | 90.9 | 18.4 | 0.157 |
| cdefghl | d | | 116.2 | 86.0 | 30.2 | 0.161 |
| acghi | cgi | | 102.2 | 81.5 | 20.7 | 0.066 |
| acghi | cgi | | 108.9 | 81.5 | 27.4 | 0.036 |
| cefGhi | cgi | | 96.9 | 77.7 | 19.2 | 0.100 |
| cdfghe | cd | | 95.2 | 81.6 | 13.6 | 0.201 |
| | | mean | 104.1 | 84.8 | 19.3 | |
| | | SD | 6.8 | 4.4 | 6.3 | |

*Haplotype designations are as in Table 11.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Altschul et al. (1990) J Mol Biol 215:403-410.
Altschul et al. (1997) Nucleic Acids Res 25:3389-3402.
Ausubel et al. (eds.) (1999) *Short Protocols in Molecular Biology* Wiley, New York, N.Y., United States of America.
Bradbury et al. (2007) Bioinformatics 23:2633-2635.
Camus-Kulandaivelu et al. (2007) Crop Science 47:887-890.
Close et al. (1989) Plant Mol Biol 13:95-108.
Dennis et al. (1984) Nucleic Acids Res 12:3983-4000.
Evanno et al. (2005) Molecular Ecology 14:2611-2620.
Falush et al. (2003) Genetics 164:1567-1587.
Fan et al. (2006) Nature Reviews Genetics 7:632-644.
Glick & Thompson (1993) *Methods in Plant Molecular Biology and Biotechnology*, CRC Press, Boca Raton. Fla., United States of America.
Guan & Scandalios (1993) Plant J 3:527-536.
Hannah et al. (2001) Plant Physiol 127:173-183.
Hardy & Vekemans (2002) Molecular Ecology Notes 2:618-620.
Jannink & Walsh (2002) in *Quantitative Genetics, Genomics and Plant Breeding*, Kang (ed.) CAB International Publishing, New York, N.Y., United States of America, pp. 59-68.
Liu & Muse (2005) Bioinformatics 21:2128-2129.
Loiselle et al. (2005) American Journal of Botany 82:1420-1425.
Morinaka et al. (2006) Plant Physiol 141:924-931.
Paterson (1996) in Paterson (ed.) *Genome Mapping in Plants*. R. G. Landes Company, Georgetown, Tex., United States of America, pages 41-54.
Patterson et al. (2006) PLoS Genetics 2:e190.
Perin et al. (2002) Theor Appl Genet 104:1017-1034.
Price et al. (2006) Nature Genetics 38:904-909.
Pritchard et al. (2000) Genetics 155:945-959.
Ritland (1996) Genetics Research 67:175-186.
Salekdeh et al. (2009) Trends in Plant Science 14:488-496.
Sambrook & Russell (2001). *Molecular Cloning: A Laboratory Manual, Third Edition*, Cold Spring Harbor Laboratory Press, Cold Spring Harbor, N.Y., United States of America.

Stich et al. (2006) Theoretical and Applied *Genetics* 113: 1121-1130.

Storey (2002) Journal of the Royal Statistical Society: Series B 64:479-498.

Tijssen (1993) *in Laboratory Techniques in Biochemistry and Molecular Biology*, Elsevier, New York, N.Y., United States of America.

U.S. Pat. Nos. 4,458,068; 6,635,803; 7,314,757; 7,332,651; 7,432,416.

Wu et al. (1994) Plant Physiol 106:1709-1710.

Zhang et al. (2001) Genetic Epidemiol 21:370-375.

Zhao et al. (2007) PLoS Genetics 3:e4.

Zietkiewicz et al. (1994) Genomics 20:176-183.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for producing a hybrid maize plant with enhanced water optimization, wherein enhanced water optimization is decreased grain moisture at harvest (GMSTP) and increased yield at standard moisture percentage (YGSMN), the method comprising:
   (a) identifying a first maize plant comprising a first genotype by identifying any one of haplotypes A-M, wherein the first maize plant comprises one or more of haplotypes A-M;
   (b) identifying a second maize plant comprising a second genotype by identifying any one of haplotypes A-M, wherein the second maize plant comprises one or more of haplotypes A-M wherein the second maize plant comprises at least one of haplotypes A-M that is not present in the first maize plant;
   (c) crossing the first maize plant and the second maize plant to produce an $F_1$ generation wherein the first maize plant or second maize plant comprise any one of haplotypes D or G; and
   (d) selecting one or more members of the $F_1$ generation that comprises a desired genotype comprising any combination of haplotypes A-M, wherein the desired genotype differs from both the first genotype of (a) and the second genotype of (b), whereby a hybrid maize plant with decreased GMSTP and increased YGSMN is produced.

2. The method of claim 1, wherein the first maize plant is a recurrent parent comprising at least one of haplotypes A-M and the second maize plant is a donor that comprises at least one of haplotypes A-M that is not present in the first maize plant.

3. The method of claim 2, wherein the first maize plant is homozygous for at least two, three, four, or five of haplotypes A-M.

4. The method of claim 1, wherein the hybrid maize plant comprises at least three, four, five, six, seven, eight, or nine of haplotypes A-M.

5. The method of claim 1, wherein the selecting comprises genotyping one or more members of an $F_1$ generation produced by crossing the first maize plant and the second maize plant with respect to each of the haplotypes A-M present in either the first plant or the second plant.

6. The method of claim 1, wherein enhanced water optimization confers increased or stabilized yield in water stressed environment as compared to a control plant.

7. The method of claim 1, wherein said maize hybrid with enhanced water optimization can be planted at a higher crop density.

8. The method of claim 1, wherein said maize hybrid with enhanced water optimization confers no yield drag when under favorable moisture levels.

9. The method of claim 1, wherein the maize hybrid comprises haplotypes G and D.

10. The method of claim 1, wherein the desired genotype further comprises a transgene that encodes a gene product that provides resistance to a herbicide selected from among the group consisting of glyphosate, Sulfonylurea, imidazolinione, dicamba, glufisinate, phenoxy proprionic acid, cycloshexome, traizine, benzonitrile, and broxynil.

11. The method of claim 1, wherein the selecting in step (d) comprises genotyping one or more F1 generation maize plants with at least one nucleic acid marker selected from among SEQ ID NOs: 1, 7-8, 19, 21, 21-28, 30, 36, 42 and 53.

* * * * *